(12) United States Patent
Adai et al.

(10) Patent No.: US 10,655,184 B2
(45) Date of Patent: *May 19, 2020

(54) METHODS AND COMPOSITIONS INVOLVING MIR-135B FOR DISTINGUISHING PANCREATIC CANCER FROM BENIGN PANCREATIC DISEASE

(71) Applicant: INTERPACE DIAGNOSTICS, LLC, Parsippany, NJ (US)

(72) Inventors: Alex Adai, Austin, TX (US); Anna Szafranska-Schwarzbach, Austin, TX (US); Bernard Andruss, Austin, TX (US); Stephan Albrecht Hahn, Bochum (DE)

(73) Assignee: INTERPACE DIAGNOSTICS, LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/491,399

(22) Filed: Apr. 19, 2017

(65) Prior Publication Data

US 2018/0066316 A1 Mar. 8, 2018

Related U.S. Application Data

(63) Continuation of application No. 13/615,066, filed on Sep. 13, 2012, now Pat. No. 9,644,241.

(60) Provisional application No. 61/536,486, filed on Sep. 19, 2011, provisional application No. 61/534,332, filed on Sep. 13, 2011.

(51) Int. Cl.
*C12Q 1/68* (2018.01)
*C12Q 1/6886* (2018.01)
*C12Q 1/6844* (2018.01)

(52) U.S. Cl.
CPC ......... *C12Q 1/6886* (2013.01); *C12Q 1/6844* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,876,187 A | 10/1989 | Duck et al. |
| 4,999,290 A | 3/1991 | Lee |
| 5,011,769 A | 4/1991 | Duck et al. |
| 5,188,934 A | 2/1993 | Menchen et al. |
| 5,256,555 A | 10/1993 | Milburn et al. |
| 5,260,191 A | 11/1993 | Yang |
| 5,262,311 A | 11/1993 | Pardee et al. |
| 5,366,860 A | 11/1994 | Bergot et al. |
| 5,432,272 A | 7/1995 | Benner |
| 5,486,603 A | 1/1996 | Buhr |
| 5,538,848 A | 7/1996 | Livak et al. |
| 5,543,296 A | 8/1996 | Sobol et al. |
| 5,545,522 A | 8/1996 | Van Gelder et al. |
| 5,660,988 A | 8/1997 | Duck et al. |
| 5,723,591 A | 3/1998 | Livak et al. |
| 5,739,169 A | 4/1998 | Ocain et al. |
| 5,766,888 A | 6/1998 | Sobol et al. |
| 5,800,996 A | 9/1998 | Lee et al. |
| 5,801,005 A | 9/1998 | Cheever et al. |
| 5,801,155 A | 9/1998 | Kutyavin et al. |
| 5,824,311 A | 10/1998 | Greene et al. |
| 5,830,880 A | 11/1998 | Sedlacek et al. |
| 5,847,162 A | 12/1998 | Lee et al. |
| 5,859,221 A | 1/1999 | Cook et al. |
| 5,861,245 A | 1/1999 | McClelland et al. |
| 5,863,727 A | 1/1999 | Lee et al. |
| 5,871,697 A | 2/1999 | Rothberg et al. |
| 5,898,031 A | 4/1999 | Crooke |
| 5,925,517 A | 7/1999 | Tyagi et al. |
| 5,936,087 A | 8/1999 | Benson et al. |
| 5,942,398 A | 8/1999 | Tartaglia et al. |
| 5,945,526 A | 8/1999 | Lee et al. |
| 5,965,364 A | 10/1999 | Benner |
| 5,976,567 A | 11/1999 | Wheeler et al. |
| 5,998,203 A | 12/1999 | Matulic-Adamic et al. |
| 6,001,983 A | 12/1999 | Benner |
| 6,004,755 A | 12/1999 | Wang |
| 6,008,379 A | 12/1999 | Benson et al. |
| 6,020,481 A | 2/2000 | Benson et al. |
| 6,037,129 A | 3/2000 | Cole et al. |
| 6,040,138 A | 3/2000 | Lockhart et al. |
| 6,051,719 A | 4/2000 | Benson et al. |
| 6,057,105 A | 5/2000 | Hoon et al. |

(Continued)

FOREIGN PATENT DOCUMENTS

| | | |
|---|---|---|
| EP | 0416817 A2 | 3/1991 |
| EP | 0870842 A2 | 10/1998 |

(Continued)

OTHER PUBLICATIONS

Yamato et al., "New highly potent and specific E6 and E7 siRNAs for treatment of HPV16 positive cervical cancer," Cancer Gene Therapy, 15:140-153, 2008.
Yanaihara et al., "Unique micro RNA molecular profiles in lung cancer diagnosis and prognosis," Cancer Cell, 9:189-198, 2006.
Yang et al., "Dicer is required for embryonic angiogenesis during mouse development," J Biol. Chem. 280(10):9330-9335, 2005.
Yang et al., "Differential expression of CCAA T /enhancer-binding protein-delta ( c/EBPdelta) in rat androgen-dependent tissues and human prostate cancer," J Androl., 22 (3): 471-480, 2001.
Yang et al., "Significance ofCD90+ cancer stem cells in human liver cancer," Cancer Cell, 13(2):153-66, 2008.
Yang et al., "Smad3 reduces susceptibility to hepatocarcinoma by sensitizing hepatocytes to apoptosis through dowmegulation ofBcl-2," Cancer Cell, 9(6):445-457, 2006.

(Continued)

*Primary Examiner* — Richard A Schnizer
(74) *Attorney, Agent, or Firm* — Pepper Hamilton LLP

(57) ABSTRACT

Provided are methods and compositions for identifying a miRNA profile for a particular condition, such as pancreatic disease, and using the profile in assessing the condition of a patient.

6 Claims, 20 Drawing Sheets

Specification includes a Sequence Listing.

(56) References Cited

U.S. PATENT DOCUMENTS

| | | | |
|---|---|---|---|
| 6,084,102 A | 7/2000 | Kutyavin et al. |
| 6,096,314 A | 8/2000 | Cohen et al. |
| 6,103,476 A | 8/2000 | Tyagi et al. |
| 6,107,094 A | 8/2000 | Crooke |
| 6,111,095 A | 8/2000 | Benseler et al. |
| 6,132,997 A | 10/2000 | Shannon |
| 6,140,054 A | 10/2000 | Wittwer et al. |
| 6,140,500 A | 10/2000 | Yan et al. |
| 6,150,097 A | 11/2000 | Tyagi et al. |
| 6,153,737 A | 11/2000 | Manoharan et al. |
| 6,174,670 B1 | 1/2001 | Wittwer et al. |
| 6,184,037 B1 | 2/2001 | Rolland et al. |
| 6,191,278 B1 | 2/2001 | Lee et al. |
| 6,232,066 B1 | 5/2001 | Felder et al. |
| 6,238,869 B1 | 5/2001 | Kris et al. |
| 6,287,792 B1 | 9/2001 | Pardridge et al. |
| 6,344,316 B1 | 2/2002 | Lockhart et al. |
| 6,355,421 B1 | 3/2002 | Coull et al. |
| 6,383,752 B1 | 5/2002 | Agrawal et al. |
| 6,418,382 B2 | 7/2002 | Rothberg et al. |
| 6,435,245 B1 | 8/2002 | Sette et al. |
| 6,458,382 B1 | 10/2002 | Herweijer et al. |
| 6,458,533 B1 | 10/2002 | Felder et al. |
| 6,476,205 B1 | 11/2002 | Buhr et al. |
| 6,485,901 B1 | 11/2002 | Gildea et al. |
| 6,506,559 B1 | 1/2003 | Fire et al. |
| 6,511,832 B1 | 1/2003 | Guarino et al. |
| 6,548,250 B1 | 4/2003 | Sorge |
| 6,573,048 B1 | 6/2003 | VanAtta et al. |
| 6,573,099 B2 | 6/2003 | Graham |
| 6,586,218 B2 | 7/2003 | Milburn et al. |
| 6,586,219 B2 | 7/2003 | Milburn et al. |
| 6,589,743 B2 | 7/2003 | Sorge |
| 6,590,091 B2 | 7/2003 | Albagli et al. |
| 6,593,091 B2 | 7/2003 | Keys et al. |
| 6,596,490 B2 | 7/2003 | Dattagupta |
| 6,706,480 B1 | 3/2004 | Armour |
| 6,720,138 B2 | 4/2004 | Sharma et al. |
| 6,723,509 B2 | 4/2004 | Ach |
| 6,730,477 B1 | 5/2004 | Sun et al. |
| 6,787,335 B2 | 9/2004 | Salceda et al. |
| 6,797,471 B2 | 9/2004 | Katz et al. |
| 6,815,432 B2 | 11/2004 | Wheeler et al. |
| 6,858,225 B2 | 2/2005 | Semple et al. |
| 6,964,847 B1 | 11/2005 | Englert |
| 6,967,016 B2 | 11/2005 | van Gemen et al. |
| 6,998,268 B2 | 2/2006 | Terada et al. |
| 7,001,724 B1 | 2/2006 | Greenfield |
| 7,005,261 B1 | 2/2006 | Lloyd et al. |
| 7,014,838 B2 | 3/2006 | Mueller et al. |
| 7,015,047 B2 | 3/2006 | Huang et al. |
| 7,056,704 B2 | 6/2006 | Tuschl et al. |
| 7,078,180 B2 | 7/2006 | Genetta |
| 7,078,196 B2 | 7/2006 | Tuschl et al. |
| 7,109,167 B2 | 9/2006 | Von Wronski et al. |
| 7,141,372 B2 | 11/2006 | Spivack et al. |
| 7,171,311 B2 | 1/2007 | Dai et al. |
| 7,192,586 B2 | 3/2007 | Bander |
| 7,205,105 B2 | 4/2007 | Afonina et al. |
| 7,232,806 B2 | 6/2007 | Tuschl et al. |
| 7,282,564 B2 | 10/2007 | Mello et al. |
| 7,297,480 B2 | 11/2007 | Vogt |
| 7,306,906 B2 | 12/2007 | Maruyama et al. |
| 7,307,067 B2 | 12/2007 | Sarnow et al. |
| 7,354,725 B2 | 4/2008 | Muraca |
| 7,365,058 B2 | 4/2008 | Stoffel et al. |
| 7,368,098 B2 | 5/2008 | Mueller et al. |
| 7,390,792 B2 | 6/2008 | Srivastava et al. |
| 7,402,389 B2 | 7/2008 | Mousses et al. |
| 7,452,987 B2 | 11/2008 | Giese et al. |
| 7,459,547 B2 | 12/2008 | Zamore et al. |
| 7,473,525 B2 | 1/2009 | Kreutzer et al. |
| 7,495,073 B2 | 2/2009 | Hsu et al. |
| 7,582,744 B2 | 9/2009 | Manoharan et al. |
| 7,592,441 B2 | 9/2009 | Bentwich et al. |
| 7,642,348 B2 | 1/2010 | Bentwich et al. |
| 7,655,785 B1 | 2/2010 | Bentwich |
| 7,683,036 B2 | 3/2010 | Esau et al. |
| 7,723,510 B1 | 5/2010 | Tuschl et al. |
| 7,888,010 B2 | 2/2011 | Brown et al. |
| 7,949,245 B2 | 5/2011 | Lvovsky et al. |
| 7,960,359 B2 | 6/2011 | Brown et al. |
| 8,003,320 B2 | 8/2011 | Brown et al. |
| 8,058,250 B2 | 11/2011 | Brown et al. |
| 8,173,611 B2 | 5/2012 | Brown et al. |
| 9,644,241 B2 * | 5/2017 | Adai .................. C12Q 1/6886 |
| 2002/0006630 A1 | 1/2002 | Sirbasku |
| 2002/0037540 A1 | 3/2002 | Ali et al. |
| 2002/0065396 A1 | 5/2002 | Yang et al. |
| 2002/0065406 A1 | 5/2002 | Meyers |
| 2002/0068307 A1 | 6/2002 | Pluta et al. |
| 2002/0086356 A1 | 7/2002 | Tuschl et al. |
| 2002/0094546 A1 | 7/2002 | Shimkets et al. |
| 2002/0119156 A1 | 8/2002 | Chen et al. |
| 2002/0165189 A1 | 11/2002 | Crooke |
| 2003/0009295 A1 | 1/2003 | Markowitz et al. |
| 2003/0027783 A1 | 2/2003 | Zernicka-Goetz et al. |
| 2003/0031678 A1 | 2/2003 | Ali et al. |
| 2003/0033614 A1 | 2/2003 | French et al. |
| 2003/0084471 A1 | 5/2003 | Beach et al. |
| 2003/0099976 A1 | 5/2003 | Chang |
| 2003/0108923 A1 | 6/2003 | Tuschl et al. |
| 2003/0124114 A1 | 7/2003 | McIntire et al. |
| 2003/0157030 A1 | 8/2003 | Davis et al. |
| 2003/0170623 A1 | 9/2003 | Chen et al. |
| 2003/0175768 A1 | 9/2003 | Carson et al. |
| 2003/0180298 A1 | 9/2003 | Old et al. |
| 2003/0204322 A1 | 10/2003 | Loehrlein et al. |
| 2003/0215842 A1 | 11/2003 | Sledziewski et al. |
| 2004/0001841 A1 | 1/2004 | Nagavarapu et al. |
| 2004/0010001 A1 | 1/2004 | Au et al. |
| 2004/0029121 A1 | 2/2004 | Cottrell et al. |
| 2004/0029128 A1 | 2/2004 | Cottrell et al. |
| 2004/0053411 A1 | 3/2004 | Cullen et al. |
| 2004/0058373 A1 | 3/2004 | Winkler et al. |
| 2004/0063197 A1 | 4/2004 | Tilles et al. |
| 2004/0063654 A1 | 4/2004 | Davis et al. |
| 2004/0072164 A1 | 4/2004 | Maruyama et al. |
| 2004/0086504 A1 | 5/2004 | Sampath et al. |
| 2004/0110191 A1 | 6/2004 | Winkler et al. |
| 2004/0114800 A1 | 6/2004 | Ponomarev et al. |
| 2004/0115630 A1 | 6/2004 | Olek et al. |
| 2004/0115671 A1 | 6/2004 | Zlokovic et al. |
| 2004/0147027 A1 | 7/2004 | Troy et al. |
| 2004/0152112 A1 | 8/2004 | Croce et al. |
| 2004/0166511 A1 | 8/2004 | Clasina Timmermans et al. |
| 2004/0175732 A1 | 9/2004 | Rana |
| 2004/0203145 A1 | 10/2004 | Zamore et al. |
| 2004/0214198 A1 | 10/2004 | Rana |
| 2004/0215651 A1 | 10/2004 | Markowitz et al. |
| 2004/0224337 A1 | 11/2004 | Foehr et al. |
| 2004/0229211 A1 | 11/2004 | Yeung |
| 2004/0236516 A1 | 11/2004 | Brandon |
| 2004/0243362 A1 | 12/2004 | Liebman |
| 2004/0259247 A1 | 12/2004 | Tuschl et al. |
| 2005/0020521 A1 | 1/2005 | Rana |
| 2005/0026278 A1 | 2/2005 | Tuschl et al. |
| 2005/0033030 A1 | 2/2005 | Lo et al. |
| 2005/0037362 A1 | 2/2005 | Remacle et al. |
| 2005/0059024 A1 | 3/2005 | Conrad |
| 2005/0065333 A1 | 3/2005 | Seth |
| 2005/0074788 A1 | 4/2005 | Dahlberg et al. |
| 2005/0075492 A1 | 4/2005 | Chen et al. |
| 2005/0095646 A1 | 5/2005 | Sherman |
| 2005/0112604 A1 | 5/2005 | Fujimoto et al. |
| 2005/0125161 A1 | 6/2005 | Cairney et al. |
| 2005/0130170 A1 | 6/2005 | Harvey et al. |
| 2005/0130172 A1 | 6/2005 | Beard et al. |
| 2005/0142556 A1 | 6/2005 | Hoon et al. |
| 2005/0153337 A1 | 7/2005 | Manoharan |
| 2005/0176018 A1 | 8/2005 | Thompson et al. |
| 2005/0181382 A1 | 8/2005 | Zamore et al. |
| 2005/0182005 A1 | 8/2005 | Tuschl et al. |
| 2005/0186018 A1 | 8/2005 | Byun |

(56) References Cited

U.S. PATENT DOCUMENTS

| | | |
|---|---|---|
| 2005/0186586 A1 | 8/2005 | Zamore et al. |
| 2005/0208493 A1 | 9/2005 | Alon |
| 2005/0234006 A1 | 10/2005 | Tuschl et al. |
| 2005/0234007 A1 | 10/2005 | Tuschl et al. |
| 2005/0261218 A1 | 11/2005 | Esau et al. |
| 2005/0266418 A1 | 12/2005 | Chen et al. |
| 2005/0287539 A1 | 12/2005 | Labourier et al. |
| 2006/0051768 A1 | 3/2006 | Hoon et al. |
| 2006/0078894 A1 | 4/2006 | Winkler et al. |
| 2006/0088521 A1 | 4/2006 | Mahadevan |
| 2006/0095980 A1 | 5/2006 | Petitte et al. |
| 2006/0105350 A1 | 5/2006 | Qiao et al. |
| 2006/0105360 A1 | 5/2006 | Croce et al. |
| 2006/0134639 A1 | 6/2006 | Huffel et al. |
| 2006/0134661 A1 | 6/2006 | Essner |
| 2006/0154275 A1 | 7/2006 | Sgarlato et al. |
| 2006/0165659 A1 | 7/2006 | Croce et al. |
| 2006/0183128 A1 | 8/2006 | Berlin et al. |
| 2006/0185026 A1 | 8/2006 | Sacktor et al. |
| 2006/0185027 A1 | 8/2006 | Bartel et al. |
| 2006/0189557 A1 | 8/2006 | Slack et al. |
| 2006/0195269 A1 | 8/2006 | Yeatman et al. |
| 2006/0210979 A1 | 9/2006 | Yang et al. |
| 2006/0247193 A1 | 11/2006 | Taira et al. |
| 2006/0252057 A1 | 11/2006 | Raponi et al. |
| 2006/0258566 A1 | 11/2006 | Von Wronski et al. |
| 2006/0271309 A1 | 11/2006 | Showe et al. |
| 2006/0292616 A1 | 12/2006 | Neely et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0009484 A1 | 1/2007 | Hunt et al. |
| 2007/0025997 A1 | 2/2007 | Nagavarapu et al. |
| 2007/0031840 A1 | 2/2007 | Klussmann et al. |
| 2007/0031873 A1 | 2/2007 | Wang et al. |
| 2007/0041934 A1 | 2/2007 | William et al. |
| 2007/0048758 A1 | 3/2007 | Lokhov et al. |
| 2007/0050146 A1 | 3/2007 | Bentwich et al. |
| 2007/0054287 A1 | 3/2007 | Bloch |
| 2007/0065844 A1 | 3/2007 | Golub et al. |
| 2007/0072204 A1 | 3/2007 | Hannon et al. |
| 2007/0093445 A1 | 4/2007 | Tuschl et al. |
| 2007/0099196 A1 | 5/2007 | Kauppinen et al. |
| 2007/0161004 A1 | 7/2007 | Brown et al. |
| 2007/0213292 A1 | 9/2007 | Stoffel et al. |
| 2007/0259827 A1 | 11/2007 | Aronin et al. |
| 2007/0287179 A1 | 12/2007 | Tuschl et al. |
| 2007/0299030 A1 | 12/2007 | Dmitrovsky et al. |
| 2008/0026951 A1 | 1/2008 | Brown et al. |
| 2008/0050744 A1 | 2/2008 | Brown et al. |
| 2008/0076674 A1 | 3/2008 | Litman et al. |
| 2008/0131878 A1 | 6/2008 | Latham et al. |
| 2008/0132461 A1 | 6/2008 | Tuschi et al. |
| 2008/0171667 A1 | 7/2008 | Brown et al. |
| 2008/0171715 A1 | 7/2008 | Brown et al. |
| 2008/0176766 A1 | 7/2008 | Brown et al. |
| 2008/0182237 A1 | 7/2008 | Bentwich et al. |
| 2008/0182245 A1 | 7/2008 | Brown et al. |
| 2008/0261908 A1 | 10/2008 | Croce et al. |
| 2008/0269147 A1 | 10/2008 | Tuschl et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0029932 A1 | 1/2009 | Voinnet et al. |
| 2009/0092974 A1 | 4/2009 | Davison et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0186353 A1 | 7/2009 | Aharonov et al. |
| 2009/0186843 A1 | 7/2009 | Tuschl et al. |
| 2010/0087507 A1 | 4/2010 | Ochiya et al. |
| 2010/0144850 A1 | 6/2010 | Croce |
| 2010/0203544 A1 | 8/2010 | Croce et al. |
| 2010/0234241 A1 | 9/2010 | Croce et al. |
| 2010/0257618 A1 | 10/2010 | Croce et al. |
| 2010/0286232 A1 | 11/2010 | Schmittgen et al. |
| 2011/0112173 A1 | 5/2011 | Brown et al. |
| 2011/0313025 A1 | 12/2011 | Brown et al. |
| 2012/0058481 A1* | 3/2012 | Ge .................. C12Q 1/6818 435/6.12 |
| 2012/0065248 A1 | 3/2012 | Brown et al. |
| 2012/0282696 A1 | 11/2012 | Johnson et al. |
| 2013/0017972 A1 | 1/2013 | Brown et al. |
| 2013/0310276 A1 | 11/2013 | Johansen et al. |

FOREIGN PATENT DOCUMENTS

| | | |
|---|---|---|
| EP | 0921195 A1 | 6/1999 |
| EP | 1352061 A2 | 10/2003 |
| EP | 1627925 A1 | 2/2006 |
| FR | 2877350 A1 | 5/2006 |
| JP | 2005/296014 A | 10/2005 |
| WO | 1993021329 A1 | 10/1993 |
| WO | 1997027317 A1 | 7/1997 |
| WO | 1997043450 A1 | 11/1997 |
| WO | 1997045539 A1 | 12/1997 |
| WO | 1998008973 A1 | 3/1998 |
| WO | 1999021881 A1 | 5/1999 |
| WO | 1999023256 A1 | 5/1999 |
| WO | 1999036760 A1 | 7/1999 |
| WO | 0005409 A1 | 2/2000 |
| WO | 0024939 A1 | 5/2000 |
| WO | 00044895 A1 | 8/2000 |
| WO | 0056748 A1 | 9/2000 |
| WO | 0066604 A2 | 11/2000 |
| WO | 0075356 A1 | 12/2000 |
| WO | 01068255 A2 | 9/2001 |
| WO | 01075164 A2 | 10/2001 |
| WO | 0200169 A2 | 1/2002 |
| WO | 0244321 A2 | 6/2002 |
| WO | 02064835 A2 | 8/2002 |
| WO | 03/020931 A2 | 3/2003 |
| WO | 03020898 A2 | 3/2003 |
| WO | 03022421 A2 | 3/2003 |
| WO | 03023058 A2 | 3/2003 |
| WO | 03029459 A2 | 4/2003 |
| WO | 03029485 A2 | 4/2003 |
| WO | 03040410 A1 | 5/2003 |
| WO | 03053586 A1 | 7/2003 |
| WO | 03066906 A2 | 8/2003 |
| WO | 03067217 A2 | 8/2003 |
| WO | 03076928 A1 | 9/2003 |
| WO | 03087297 A2 | 10/2003 |
| WO | 03091426 A1 | 11/2003 |
| WO | 03093810 A1 | 11/2003 |
| WO | 03100012 A2 | 12/2003 |
| WO | 03100448 A1 | 12/2003 |
| WO | 2004020085 A1 | 3/2004 |
| WO | 2004027093 A1 | 4/2004 |
| WO | 2004029212 A2 | 4/2004 |
| WO | 2004043387 A2 | 5/2004 |
| WO | 2004/050125 A1 | 6/2004 |
| WO | 2004046324 A2 | 6/2004 |
| WO | 2004/057017 A2 | 7/2004 |
| WO | 2004066183 A2 | 8/2004 |
| WO | 2004074509 A2 | 9/2004 |
| WO | 2004076622 A2 | 9/2004 |
| WO | 2005013901 A2 | 2/2005 |
| WO | 2005078139 A2 | 8/2005 |
| WO | 2005079397 A2 | 9/2005 |
| WO | 2005116261 A2 | 12/2005 |
| WO | 2005118806 A2 | 12/2005 |
| WO | 2006028967 A2 | 3/2006 |
| WO | 2006033928 A2 | 3/2006 |
| WO | 2006/101173 A1 | 9/2006 |
| WO | 2006/113679 A2 | 10/2006 |
| WO | 2006/119365 A2 | 11/2006 |
| WO | 2006/128245 A1 | 12/2006 |
| WO | 2006135765 A1 | 12/2006 |

(56) References Cited

FOREIGN PATENT DOCUMENTS

| WO | 2006137941 A2 | 12/2006 |
|---|---|---|
| WO | 2007/016548 A2 | 2/2007 |
| WO | 2007033023 A2 | 3/2007 |
| WO | 2007073737 A1 | 7/2007 |
| WO | 2007081720 A2 | 7/2007 |
| WO | 2007081740 A2 | 7/2007 |
| WO | 2007/087113 A2 | 8/2007 |
| WO | 2008014008 A2 | 1/2008 |
| WO | 2008095096 A2 | 8/2008 |
| WO | 2008/136971 A1 | 11/2008 |
| WO | 2008/137867 A2 | 11/2008 |

OTHER PUBLICATIONS

Yang et al., "Stromal expression of connective tissue growth factor promotes angiogenesis and prostate cancer tumorigenesis," Cancer Res., 65(19):8887-8895, 2005.
Yang et al., "The transformation suppressor Pdcd4 is a novel eukaryotic translation initiation factor 4A binding protein that inhibits translation," Mol. Cell Biol., 23(1):26-37, 2003.
Yang et al., "Tumorigenesis suppressor Pdcd4 down-regulates mitogen-activated protein kinase kinase kinase kinase 1 expression to suppress colon carcinoma cell invasion," Mol Cell Biol, 26(4):1297-1306, 2006.
Yao et al., "RhoC GTPase is required for PC-3 prostate cancer cell invasion but not motility," Oncogene, 25 (16):2285-2296, 2006.
Yeatman, "A renaissance for SRC," Nat Rev Cancer, 4(6):470-480, 2004.
Yi et al., "The association of the expression ofMTA1, nm23H1 with the invasion, metastasis of ovarian carcinoma," Chin Med Sci J, 18(2):87-92, 2003.
Yoon and De Micheli, "Prediction of regulatory modules comprising microRNAs and target genes," Bioinformatics, 21 (Suppl.2):ii93-ii100, 2005.
Yoshida et al., "The clinical significance ofCyclin B1 and Wee1 expression in non-small-cell lung cancer," Ann Oneal, 15(2):252-256, 2004.
Yoshimura et al., "Prognostic impact of hypoxia-inducible factors 1alpha and 2alpha in colorectal cancer patients: correlation with tumor angiogenesis and cyclooxygenase-2 expression," Clin. Cancer Res., 10(24):8554-8560, 2004.
Yoshioka et al,. "A role for LIM kinase in cancer invasion," Proc. Natl. Acad. Sci. USA, 100 (12): 7247-7252,2003.
Youssef et al., "Hypermethylation and silencing of the putative tumor suppressor, Tazaroteneinduced gene 1 in human cancers," Cancer Res., 64 (7): 2411-2417, 2004.
Yu et al,. "Global assessment of promoter methylation in a mouse model of cancer identifies ID4 as a putative tumor-suppressor gene in human leukemia," Nat. Genet., 37 (3): 265-274, 2005.
Yu et al., "Crosstalk between cancer and immune cells: role of STAT3 in the tumour microenvironment," Nat Rev / Immunol, 7(1):41-51, 2007.
Yu et al., "let-7 regulates self renewal and tumorigenicity of breast cancer cells," Cell, 131:1109-1123,2007.
Yu et al., Micro RNA alterations of pancreatic intraepithelial neoplasias, 2011, Clinical Cancer Research, vol. 18, pp. 981-992.
Zangemeister-Wittke and Huwiler, "Antisense targeting ofMcl-1 has therapeutic potential in gastric cancer," Cancer Biol. Ther., 5(10):1355-1356, 2006.
Zeng et al., "Both natural and designed micro RNAs can inhibit the expression of cognate mRNAs when expressed in human cells," Mol Cell. 9, 1327-33, 2002.
Zeng et al., "MicroRNAs and small interfering RNAs can inhibit mRNA expression by similar mechanisms," Proc. Natl. Acad. Sci. 100: 9779-9784, 2003.
Zhang et al., "Enhancement of hematopoietic stem cell repopulating capacity and self-renewal in the absence of the transcription factor C/EBP alpha," Immunity, 21(6):853-863, 2004.

Zhang et al., "Identification and characterization of ovarian cancer-initiating cells from primary human tumors," Cancer Res., 68 (11 ):4311-20, 2008.
Zhang et al., "Involvement of programmed cell death 4 in transforming growth factor-beta1-induced apoptosis in human hepatocellular carcinoma," Oncogene, 25(45):6101-6112, 2006.
Zhang et al., "Methylation of the retinoid response gene TIG1 in prostate cancer correlates with methylation of the retinoic acid receptor beta gene," Oncogene, 23 (12): 2241-2249, 2004.
Zhang et al., "microRNAs as oncogenes and tumor suppressors," Dev. Biol., 302(1):1-12, 2007.
Zhang et al., "NANOGP8 is a retrogene expressed in cancers," FEES J, 273(8): 1723-30, 2006.
Zhao et al., "CyclinG 1 has growth inhibitory activity linked to the ARF-Mdm2-p53 and pRb tumor suppressor pathways," Mol Cancer Res, 1(3):195-206, 2003.
Zhou et al., "Activation of the PTEN/mTOR/STAT3 pathway in breast cancer stem-like cells is required for viability and maintenance," Proc. Natl. Acad. Sci. USA, 104(41):16158-63, 2007.
Zhou et al., "The ABC transporter Bcrp1/ ABCG2 is expressed in a wide variety of stem cells and is a molecular determinant of the side-population phenotype," Nat. Med., 7(9): 1028-1034, 2001.
Zhu et al., "Epiregulin is Up-regulated in pancreatic cancer and stimulates pancreatic cancer cell growth," Biochem. Biophys. Res. Commun., 273 (3): 1019-1024, 2000.
Zhu et al., "MicroRNA-21 targets the tumor suppressor gene tropomyosin 1 (TIPM1)" The Journal of Biological Chemistry, 282(19):14328-14336, 2007.
Zimmerman et al., "Technical aspects of quantitative competitive PCR," Biotechniques, 21(2):268-270, 1996.
AMBION, "miRNA Research Guide," Technical Bulletin, pp. 1-17, 2005.
Ramaswamy et al. "Muticlass cancer diagnosis using tumor gene expression signatures." Proceedings of National Academy of Sciences 98.26 p. 15149-15154 (2001).
Office Communication in U.S. Appl. No. 12/281,194 dated Jan. 29, 2016.
Notice of Allowance dated Jan. 4, 2017 in U.S. Appl. No. 13/615,066.
Office Action issued in U.S. Appl. No. 11/857,948 dated Sep. 12, 2017.
Jansen et al., "Two umelated cell-derived sequences in the genome of avian leukemia and carcinoma inducing retrovirus MH2," Embo J, 2(11):1969-1975, 1983.
Jemal et al., "Cancer statistics, 2007," CA Cancer J Clin., 57:43-66, 2007.
Jemel, et al., Ca Cancer J Clin. 60:277-300, 2010.
Jemiellity et al., "Novel 'anti-reverse' cap analogs with superior translational properties," RNA, 9(9): 1108-1122, 2003.
Ji et al., "Restoration of tumor suppressor miR-34 inhibits human p53-mutant gastric cancer tumorspheres," BMC Cancer, 8:266, 2008.
Jiang et al., "Decreased expression of type II tumor suppressor gene RARRES3 in tissues of hepatocellular carcinoma and cholangiocarcinoma," World J Gastroenterol., 11: 948-953, 2005.
Jiang et al., "Real-time expression profiling ofmicroRNA precursors in human cancer cell lines," Nucleic Acids Research, 33(17):5394-5403, 2005.
Jiang et al., "RNA silencing of S-phase kinase-interacting protein 2 inhibits proliferation and centrosome amplification in lung cancer cells," Oncogene, 24(21):3409-3418, 2005.
Jin et al., "Tumorigenic transformation by CPI-17 through inhibition of a merlin phosphatase," Nature, 442 (7102): 576-579, 2006.
Jing et al., "Tazarotene-induced gene 1 (TIG1) expression in prostate carcinomas and its relationship to tumorigenicity," J. Natl. Cancer /nst., 94: 482-490, 2002.
John et al., "Human microRNA targets," PLOS Biology, 2(11):1862-1879, 2004.
Johnson et al., "RAS is regulated by the let-7 micro RNA family," Cell, 120:635-647, 2005.
Johnson et al., "The let-7 microRNA represses cell proliferation pathways in human cells," Cancer Res, 67(16):7713-7722, 2007.

(56) References Cited

OTHER PUBLICATIONS

Jonsson et al., "Loss of Wnt-5a protein is associated with early relapse in invasive ductal breast carcinomas," Cancer Res., 62 (2): 409-416, 2002.
Jopling et al., "Modulation of hepatitis C virus RNA abundance by a liver-specific MicroRNA," Science, 309(5740):1577-81, 2005.
Jubb et al., "EphB2 is a prognostic factor in colorectal cancer," Clin. Cancer Res., 11 (14): 5181-5187,2005.
Kabbarah et al., "Expression Profiling of Mouse Endometrial Cancers Microdissected from Ethanol-Fixed, Paraffin-Embedded Tissues," Am. J Pathology, 162:755-762, 2003.
Kalin et al., "Increased levels of the FoxM1 transcription factor accelerate development and progression of prostate carcinomas in both TRAMP and LADY transgenic mice," Cancer Res, 66(3):1712-1720, 2006.
Kalinichenko et al., "Foxm1b transcription factor is essential for development of hepatocellular carcinomas and is negatively regulated by the p19ARF tumor suppressor," Genes Dev, 18(7):830-850, 2004.
Kallay et al., "Vitamin D receptor activity and prevention of colonic hyperproliferation and oxidative stress," Food Chern. Toxicol., 40: 1191-1196,2002.
Kamata et al., "High expression of skp2 correlates with poor prognosis in endometrial endometrioid adenocarcinoma," J Cancer Res. Clin. Oneal., 131(9):591-596, 2005.
Kammula et al., "Serial follow-up and the prognostic significance of reverse transcriptase-polymerase chain reaction—staged sentinel lymph nodes from melanoma patients," J Clin. Oncol., 22:3989-3996, 2004.
Kapsimali et al., "MicroRNAs show a wide diversity of expression profiles in the developing and mature central nervous system," Genome Biol, 8(8):R173, 2007.
Karakaidos et al., "Overexpression of the replication licensing regulators hCdtI and hCdc6 characterizes a subset of non-small-celllung carcinomas: synergistic effect with mutant p53 on tumor growth and chromosomal instability—evidence of E2F-1 transcriptional control over hCdtI, "Am J Pathol, 165(4):1351-1365, 2004.
Karginov et al., "A biochemical approach to identifying microRNA targets," PNAS, 104(49):19291-19296, 2007.
Karhadkar et al. "Hedgehog signalling in prostate regeneration, neoplasia and metastasis," Nature, 431(7009):707-12, 2004.
Karin et al., "NF-kappaB in cancer: from innocent bystander to major culprit," Nat Rev Cancer, 2(4):301-310, 2002.
Kasashima et al., "Altered expression profiles of microRNAs during TP A-induced differentiation of HL-60 cells," Biochemical and Biophysical Research Communications, 322(2):403-410, 2004.
Kastan and Lim, "The many substrates and functions of ATM," Nat Rev Mol Cell Biol, 1(3):179-186, 2000.
Kato, "Adaptor-tagged competitive PCR: a novel method for measuring relative gene expression," Nucleic Acids Research, Oxford University Press, Surrey, GB, 25(22):4694-4696, 1997.
Kaufmann et al., "Elevated expression of the apoptotic regulator Mcl-1 at the time of leukemic relapse," Blood, 91(3):991-1000, 1998.
Kayed et al., Hedgehog signaling in the normal and diseased pancreas, 2006, Pancreas, vol. 32, pp. 119-129.
Keen and Taylor, "Aurora-kinase inhibitors as anticancer agents," Nat. Rev. Cancer, 4(12):927-936,2004.
Kern et al., "Application of a fed-batch system to produce RNA by in vitro transcription," Biotechnol. Prog., 15:174-184, 1999.
Kern et al., "Application of solution equilibrium analysis to in vitro RNA transcription," Biotechnol. Prog., 13:747-756, 1997.
Keshet et al., "MDR1 expression identifies human melanoma stem cells," Biochem. Biophys. Res. Commun., 368(4):930-6, 2008.
Kim et al., "Genomics of microRNA," Trends in Genetics, 22:165-173,2006.
Kim et al., "Identification of many microRNAs that copurify with polyribosomes in mammalian neurons," Proc. Natl. Acad. Sci., USA, 101:360-365, 2004.
Kim et al., "The Forkhead Box m1 transcription factor stimulates the proliferation of tumor cells during development of lung cancer," Cancer Res, 66(4):2153-2161, 2006.
Kiriakidou et al., "A combined computational-experimental approach predicts human microRNA targets," Genes Dev. 18(10):1165-78, 2004.
Kiriakidou et al., "An mRNA m7G cap binding-like motif within human Ago2 represses translation," Cell, 129(6):1141-1151, 2007.
Kirikoshi et al., "Up-regulation of Frizzled-7 (FZD7) in human gastric cancer," Int. J Oneal., 19 (1): 111-115,2001.
Kita et al., "Modulation of polygulutamine-induced cell death by genes identified by expression profiling," Human Molecular Genetics, 11(19):2279-2287, 2002.
Kitadai et al., "Expression of amphiregulin, a novel gene of the epidermal growth factor family, in human gastric carcinomas," Jpn. J Cancer Res., 84(8):879-884, 1993.
Kleer et al., "RhoC GTPase expression as a potential marker of lymph node metastasis in squamous cell carcinomas of the head and neck," Clin. Cancer Res., 12 (15): 4485-4490, 2006.
Kohno and Pouyssegur, "Pharmacological inhibitors of the ERK signaling pathway: application as anticancer drugs," Progress in Cell Cycle Research,. (Meijer, L., Jezequel, A., and Roberge, M., Eds), Chapter 22, vol. 5:219-224, 2003.
Koivunen et al., "Protein kinase C (PKC) family in cancer progression," Cancer Lett, 235(1):1-10, 2006.
Koivunen et al., "Protein kinase C alpha/beta inhibitor Go6976 promotes formation of cell junctions and inhibits invasion of urinary bladder carcinoma cells," Cancer Res, 64(16):5693-5701, 2004.
Kokko et al., "EPHB2 germline variants in patients with colorectal cancer or hyperplastic polyposis," BMC Cancer, 6:145, 2006.
Komatsu et al., "Increased expression of S 1 OOA6 (Calcyclin), a calcium-binding protein of the S100 family, in human colorectal adenocarcinomas," Clin. Cancer Res., 6: 172-177,2000.
Office Action issued in U.S. Appl. No. 12/125,412, dated Nov. 12, 2009.
Office Action issued in U.S. Appl. No. 12/125,675, dated Apr. 22, 2010.
Office Action issued in U.S. Appl. No. 12/125,675, dated Jan. 28, 2011.
Office Action issued in U.S. Appl. No. 12/125,675, dated Oct. 14, 2010.
Office Action issued in U.S. Appl. No. 12/125,675, dated Sep. 10, 2009.
Office Action issued in U.S. Appl. No. 12/134,932, dated Feb. 24, 2011.
Office Action issued in U.S. Appl. No. 12/134,932, dated Mar. 24, 2010.
Office Action issued in U.S. Appl. No. 12/134,932, dated Nov. 12, 2009.
Office Action issued in U.S. Appl. No. 12/134,932, dated Nov. 4, 2010.
Office Action issued in U.S. Appl. No. 12/167,492, dated Aug. 12, 2010.
Office Action issued in U.S. Appl. No. 12/167,492, dated Feb. 12, 2010.
Office Action issued in U.S. Appl. No. 12/167,492, dated Feb. 25, 2011.
Office Action issued in U.S. Appl. No. 12/167,492, dated Jun. 7, 2011.
Office Action issued in U.S. Appl. No. 12/209,822, dated Mar. 15, 2011.
Office Action issued in U.S. Appl. No. 12/253,718, dated Apr. 22, 2011.
Office Action issued in U.S. Appl. No. 12/253,718, dated Jun. 11, 2010.
Office Action issued in U.S. Appl. No. 12/253,718, dated Nov. 1, 2010.
Office Action issued in U.S. Appl. No. 12/325,917, dated Apr. 22, 2011.
Office Action issued in U.S. Appl. No. 12/325,917, dated Feb. 14, 2011.
Office Action issued in U.S. Appl. No. 12/325,917, dated Jul. 28, 2010.

(56) References Cited

OTHER PUBLICATIONS

Office Action issued in U.S. Appl. No. 12/325,917, dated May 3, 2010.
Office Action issued in U.S. Appl. No. 12/340,329, dated Sep. 28, 2010.
Office Action issued in U.S. Appl. No. 12/368,053, dated Aug. 19, 2010.
Office Action issued in U.S. Appl. No. 12/368,053, dated Dec. 21, 2010.
Office Action issued in U.S. Appl. No. 12/368,053, dated Jun. 22, 2011.
Office Action issued in U.S. Appl. No. 12/398,852, dated Aug. 11, 2011.
Office Action issued in U.S. Appl. No. 12/398,852, dated Mar. 7, 2011.
Office Action issued in U.S. Appl. No. 12/412,087, dated Apr. 22, 2011.
Office Action issued in U.S. Appl. No. 12/412,087, dated Aug. 18, 2011.
Office Action issued in U.S. Appl. No. 12/420,634, dated Apr. 29, 2011.
Office Action issued in U.S. Appl. No. 12/420,634, dated Aug. 30, 2010.
Office Action issued in U.S. Appl. No. 12/420,634, dated May 26, 2010.
Office Action issued in U.S. Appl. No. 12/437,899, dated Jun. 29, 2011.
Office Action issued in U.S. Appl. No. 12/437,899, dated Mar. 7, 2011.
Office Action issued in U.S. Appl. No. 12/616,616, dated Aug. 13, 2010.
Office Communication in Japanese Patent Application No. 2009/529373 dated Nov. 5, 2012.
Office Communication in U.S. Appl. No. 11/857,948 dated Aug. 24, 2010.
Office Communication in U.S. Appl. No. 11/857,948 dated Jan. 26, 2011.
Office Communication in U.S. Appl. No. 11/857,948 dated Jun. 5, 2009.
Office Communication in U.S. Appl. No. 11/857,948 dated Nov. 27, 2012.
Office Communication issued in International Application No. PCT/US2007/078936, dated Feb. 5, 2008.
Ohlsson et al., "Biomarker selection for detection of occult tumour cells in lymph nodes of colorectal cancer patients using real-time quantitative RT-PCR," Br. J Cancer, 95(2):218-225, 2006.
Ohsaki et al., "Antitumor activity of magainin analogues against human lung cancer cell lines," Cancer Res, 52(13):3534-3538, 1992.
Ollila et al., "Metastatic melanoma cells in the sentinel node cannot be ignored," JAm. Call. Surg., 208(5):924-929, 2009.
Olsen and Ambros, "The lin-4 regulatory RNA controls developmental timing in Caenorhabditis elegans by blocking LIN-14 protein synthesis after the initiation of translation," Dev. Biol., 216:671, 1999.
Opalinska and Gewirtz, "Nucleic-acid therapeutics: basic principles and recent applications," Nature Reviews, 1:503-514, 2002.
Ovcharenko et al., "High-throughput RNAi screening in vitro: from cell lines to primary cells," RNA, 11(6):985-93, 2005.
Ozaki et al., "Blockade of vascular endothelial cell growth factor receptor signaling is sufficient to completely prevent retinal neovascularization," Am. J Pathol., 156(2):697-707, 2000.
Paik et al., "FoxOs are lineage-restricted redundant tumor suppressors and regulate endothelial cell homeostasis," Cell, 128(2):309-323, 2007.
Palleres et al., "Structure of human carboxypeptidase A4: with its endogenous protein inhibitor, latexin," Proc. Natl. Acad. Sci. USA, 102:3978-3983,2005.
Walboomers et al., "Human papilloma virus is a necessary cause of invasive cervical cancer worldwide," J Pathol., 189(1):12-9, 1999.
Wang & Dick, "Cancer stem cells:lessons from leukemia", Trends Cell Biol., 15(9):494-501, 2005.
Wang and Wang, "Systematic identification of microRNA functions by combining target prediction and expression profiling," Nucleic Acids Research, 34(5): 1646-1652, 2006.
Wang et al., "Aberrant expression of oncogenic and tumor-suppressive microRNAs in cervical cancer is required for cancer cell growth;" PLoS One, 3(7):e2557, 2008.
Wang et al., "Identification of rat lung-specific microRNAs by micoRNA microarray: valuable discoveries for the facilitation of lung research," BMC Genomics, 8:29-42, 2007.
Wang et al., "Increased levels of forkhead box M1B transcription factor in transgenic mouse hepatocytes prevent age-related proliferation defects in regenerating liver," Proc Natl Acad Sci USA, 98(20):11468-11473, 2001.
Wang et al., "Oncogenic HPV infection interrupts the expression of tumor-suppressive miR-34a through viral oncoprotein E6," RNA, 15(4):637-647, 2009.
Wang et al., "Pten deletion leads to the expansion of a prostatic stem/progenitor cell subpopulation and tumor initiation," Proc. Natl. Acad. Sci. USA, 103(5):1480-1485, 2006.
Watabe et al., "Growth, regeneration, and tumorigenesis of the prostate activates the PSCA promoter," Proc Natl Acad Sci USA, 99(1):401-6, 2002.
Weeraratna et al., "Wnt5a signaling directly affects cell motility and invasion of metastatic melanoma," Cancer Cell, 1(3): 279-288, 2002.
Weidhaas et al., "MicroRNAs as potential agents to alter resistance to cytotoxic anticancer therapy," Cancer Res, 67(23):11111-11116, 2007.
Weil et al., "Targeting the kinesin Eg5 to monitor siRNA transfection in mammalian cells," Biotechniques, 33(6): 1244-1248, 2002.
Weinstein, "Disorders in cell circuitry during multistage carcinogenesis, the role of homeostasis," Carcinogenesis, 21(5): 857-864, 2000.
Weiss and Bohmann, "Deregulated repression of c-Jun provides a potential link to its role in tumorigenesis," Cell Cycle, 3 (2): 111-113,2004.
Welsh et al., "Fingerprinting genomes using PCR with arbitrary primers," Nucleic Acids Research, Oxford University Press, Surrey, GB, 18(24 ):7213-7218, 1990.
Welsh et al., "Nucleic acid fingerprinting by PCR-based methods: applications to problems in aging and mutagenesis," Mutation Research, 338(1-6):215-229, 1995.
Wheeler and Ridley, "Why three Rho proteins? RhoA, RhoB, RhoC, and cell motility," Exp. Cell. Res., 301 (1): 43-49, 2004.
Whitcombe et al., "A homogeneous fluorescence assay for PCR amplicons: its application to realtime, single-tube genotyping," Clin. Chem., 44(5):918-923, 1998.
Whitcombe et al., "Advances in approaches to DNA-based diagnostics," Curr. Opin. Biotechnol., 9(6):602-608, 1998.
White et al., "Treatment of pulmonary hemangiomatosis with recombinant interferon alfa-2a," N EnglJ Med 320:1197-1200, 1989.
Wiemer, "The role of microRNAs in cancer: no small matter," Eur. J Cancer, 43(10):1529-44, 2007.
Wikman et al., "Identification of differentially expressed genes in pulmonary adenocarcinoma by using cDNA array," Oncogene, 21(37):5804-5813, 2002.
Willert et al., "Wnt proteins are lipid-modified and can act as stem cell growth factors," Nature, 423(6938):448-52, 2003.
Wilson and Laimins, "Differentiation of HPV-containing cells using organotypic "raft" culture or methylcellulose," Methods Mol. Med., 119:157-69, 2005.
Wong et al., "Number of nodes examined and staging accuracy in colorectal carcinoma," J Clin. Oneal., 17(9):2896-2900, 1999.
Wood et al., "DNA microarray analysis of vitamin D-induced gene expression in a human colon carcinoma cell line," Physiol. Genomics, 17 (2): 122-129,2004.
Wood et al., "One hundred consecutive cases of sentinel lymph node mapping in early colorectal carcinoma: detection of missed micrometastases," J Gastrointest Surg., 6(3):322-330, 2002.
Wooster and Weber, "Breast and ovarian cancer," N Engl. J Med., 348(23):2339-2347, 2003.

(56) References Cited

OTHER PUBLICATIONS

Wu et al., "Expression ofEphb2 and Ephb4 in breast carcinoma," Pathol. Oneal. Res., 10 (1): 26-33, 2004.
Wu et al., "MicroRNA and cancer: current status and prospective," International Journal of Cancer, 120:953-960, 2006.
Wu et al., "p107 Expression in colorectal tumours rises during carcinogenesis and falls during invasion," EurJ Cancer, 38(14):1838-1848,2002.
Wu et al., "RARRES1 expression is significantly related to tumour differentiation and staging in colorectal adenocarcinoma," Eur. J Cancer, 42(4):557-565, 2006.
Wu et al., "RhoC induces differential expression of genes involved in invasion and metastasis in MCF10A breast cells," Breast Cancer Res., Treat., 84 (1); 3-12, 2004.
Wu et al., "The prognostic impact ofEphB2/B4 expression on patients with advanced ovarian carcinoma," Gynecol. Oneal., 102 (1): 15-21, 2006.
Wu, et al., Sci Trans! Med. 3(92):92ra66, 2011.
Wyatt et al., "Synthesis and purification of large amounts of RNA oligonucleotides," Biotechniques, 11(6):764-769, 1991.
Wyttenbach et al., "Polyglutamine expansions cause decreased CRE-mediated transcription and early gene expression changes prior to cell death in an inducible cell model of Huntington's disease," Human Molecular Genetics, 10(17):1829-1845, 2001.
Xi a et al., "Regulation of vascular endothelial growth factor transcription by endothelial PAS domain protein 1 (EP AS 1) and possible involvement of EP AS 1 in the angiogenesis of renal cell carcinoma," Cancer, 91(8):1429-1436, 2001.
Xi et al., "A combination of molecular markers accurately detects lymph node metastasis in non-small cell lung cancer patients," Clin. Cancer Res., 12:2484-2491,2006.
Xi et al., "Differentially regulated micro-RNAs and actively translated messenger RNA transcripts by tumor suppressor p53 in colon cancer," Clin Cancer Res., 12:2014-2024, 2006b.
Xi et al., "Identification of mRNA markers for molecular staging of lymph nodes in colorectal cancer," Clin. Chem., 52 (3):520-523, 2006.
Xi et al., "Molecular staging oflymph nodes from patients with esophageal adenocarcinoma," Clin. Cancer Res., 11:1099-1109,2005.
Xi et al., "Prognostic Values of microRNAs in Colorectal Cancer," Biomark Insights, 2:113-121, 2006a.
Xia et al., "Positive expression ofHIF-2alpha/EPAS1 in invasive bladder cancer," Urology, 59(5):774-778, 2002.
Xia et al., "The Src-suppressed C kinase substrate, SSeCKS, is a potential metastasis inhibitor in prostate cancer," Cancer Res, 61(14):5644-5651, 2001.
Xie et al., "Negative feedback regulation ofDicer-Like1 in *Arabidopsis* by microRNA-guided mRNA degradation," Current Biology, 13:784-789, 2003.
Xie, et al., "Systematic discovery of regulatory motifs in human promoters and 3' UTRs by comparison of several mammals," Nature, 434(7031 ):338-345, 2005.
Xu et al., "The *Drosophila* microRNA Mir-14 suppresses cell death and is required for normal fat metabolism," Curr. Biol., 13:790-795, 2003.
Yamamoto et al., "Cdk2/cdc2 expression in colon carcinogenesis and effects of cdk2/cdc2 inhibitor in colon cancer cells," /nt J Oneal, 13(2):233-239, 1998.
Komiya et al., "PRLTS gene alterations in human prostate cancer," Jpn. J Cancer Res., 88(4):389-393, 1997.
Konopleva et al., "Mechanisms of apoptosis sensitivity and resistance to the BH3 mimetic ABT-737 in acute myeloid leukemia," Cancer Cell, 10(5):375-88, 2006.
Kops et al., "On the road to cancer: aneuploidy and the mitotic checkpoint," Nat Rev Cancer, 5(1 0):773-785. 2005.
Krek et al., "Combinatorial microRNA target predictions," Nature Genet., 37:495-500, 2005.

Krichevsky et al., "A micro RNA array reveals extensive regulation of microRNAs during brain development," RNA, 9(10):1274-1281, 2003.
Kristjansd6ttir and Rudolph, "Cdc25 phosphatases and cancer," Chem Biol, 11(8): 1043-1051, 2004.
Kubista et al., "Light-up probe based real-time Q-PCR," SPIE, 4264:53-58, 2007.
Kuehbacher et al., "Targeting microRNA expression to regulate angiogenesis," Trends Pharmacal Sci., 29(1):12-15, 2008.
Kuhajda, "Fatty acid synthase and cancer: new application of an old pathway," Cancer Res, 66(12):5977-5980, 2006.
Kumar et al., "Suppression of non-small cell lung tumor development by the let-7 micro RNA family," PNAS, 105(10):3903-3908, 2008.
Kutay Ruban et al., "Dowmegulation ofmiR-122 in the rodent and human hepatocellular carcinomas", Journal of Cellular Biochemistry, vol. 99, No. 3, pp. 671-678, Oct. 15, 2006.
Kwak et al., "VEGF is major stimulator in model of choroidal neovascularization," Invest. Ophthalmol. Vis. Sci., 41(10):3158-3164, 2000.
Kwong et al., "Silencing of the retinoid response gene TIG1 by promoter hypermethylation in nasopharyngeal carcinoma," Int. J Cancer, 113 (3): 386-392, 2005.
L'hote and Knowles, "Cell responses to FGFR3 signalling: growth, differentiation and apoptosis," Exp. Cell. Res., 304(2): 417-431, 2005.
Labourier et al., "Improving in vitro transcription for large scale sytnthesis of human quality capped RNA," Ambion Diagnostics, RNA Healthcare Solutions, Eukaryotic mRNA Processing meeting, Cold Spring Harbor Laboratory, Cold Spring Harbor, NY, Aug. 2003.
Lagos-Quintana et al., "Identification of novel genes coding for small expressed RNAs," Science, 294(5543):853-858, 2001.
Lagos-Quintana et al., "Identification oftissue-specific microRNAs from mouse," Current Biology, 12:735-739, 2002.
Lagos-Quintana et al., "New microRNAs from mouse and human," RNA, 9(2):175-179, 2003.
Lam et al., "Expression ofp19INK4d, CDK4, CDK6 in glioblastoma multiforme," BrJ Neurosurg, 14(1):28-32, 2000.
Lanza et al., "mRNA/microRNA gene expression profile in microsatellite unstable colorectal cancer," Malec Cancer, 6:54, 2007.
Lanza, et al., Molecular Cancer. 6:54, 2007.
Lao et al., "Multiplexing RT-PCR for the detection of multiple miRNA species in small samples," Biochemical and Biophysical Research Communications, 343:85-89, 2006.
Lau et al., "An abundant class of tiny RNAs with probable regulatory roles in Caenorhabditis elegans," Science, 294(5543):858-862, 2001.
Lecellier et al., "A cellular microRNA mediates antiviral defense in human cells," Science, 308(5721):557-60, 2005.
Lechner et al., "Nestin-positive progenitor cells derived from adult human pancreatic islets of Langerhans contain side population (SP) cells defined by expression ofthe ABCG2 (BCRP1) ATP-binding cassette transporter," Biochem. Biophys. Res. Commun., 293(2):670-674, 2002.
Lee and Ambros, "An extensive class of small RNAs in Caenorhabditis elegans," Science, 294(5543):862-864, 2001.
Lee et al., "A protein reacted with anti-vitronectin antibody accumulates in tumors derived from BI6F10 melanoma cells," Cell Struct. Funct., 23 (4): 193-199, 1998.
Lee et al., "Altered microRNA expression in cervical carcinomas," Clin Cancer Res, 14(9):2535-2542, 2008.
Lee et al., "Ectopic expression of neutrophil gelatinase-associated lipocalin suppresses the invasion and liver metastasis of colon cancer cells," Int. J Cancer, 118(10):2490-2497, 2006.
Lee et al., "Expression profiling identifies stroma- and tumor-related microRNAs in pancreatic cancer," 97th Annual AACR, Washington D.C., Abstract No. 5725, 2006.
Lee et al., "Micro RNA maturation: stepwise processing and subcellular localization," EMBO J., 21(17):4663-4670, 2002.
Lee et al., "The *C. elegans* heterochronic gene lin-4 encodes small RNAs with antisense complementarity to lin-14," Cell, 75(5):843-854, 1993.

(56) References Cited

OTHER PUBLICATIONS

Lee et al., "The nuclear RNase III Drosha initiates microRNA processing," Nature, 425(6956):415-419, 2003.
Leong and Gao, "The Notch pathway in prostate development and cancer," Differentiation, 76(6): 699-716,2008.
Leprince et al., "A putative second cell-derived oncogene of the avian leukaemia retrovirus E26," Nature, 306 (5941):395-397, 1983.
Leris et al., "WNT5A expression in human breast cancer," Anticancer Res., 25 (2a): 731-734, 2005.
Lessard and Sauvageau, "Bmi-1 determines the proliferative capacity of normal and leukaemic stem cells," Nature, 423(6937):255-60, 2003.
Lewis et al., "Conserved seed pairing, often flanked by adenosines, indicates that thousands of human genes are microRNA targets," Cell, 120:15-20, 2005.
Lewis et al., "Prediction of mammalian micro RNA targets," Cell, 115(7):787-798, 2003.
Li et al., "Apoptosis of non-small-celllung cancer cell lines after paclitaxel treatment involves the BH3-only proapoptotic protein Bim," Cell Death Differ, 12(3):292-303, 2005.
Li et al., "Evidence that transgenes encoding components of the Wnt signaling pathway preferentially induce mammary cancers from progenitor cells," Proc Natl Arad Sci USA, 100(26):15853-8, 2003.
Li et al., "Intrinsic resistance of tumorigenic breast cancer cells to chemotherapy," J Natl. Cancer /nst., 100(9):672-9, 2008.
Li et al., "Mutant TNFalpha negatively regulates human breast cancer stem cells from MCF7 in vitro," Cancer Biol. Ther., 6(9):1480-9, 2007.
Li et al., "Overexpression ofETS2 in human esophageal squamous cell carcinoma," World J Gastroenterol., 9 (2):205-208, 2003.
Li et al., "PDGF-D is a potent transforming and angiogenic growth factor," Oncogene, 22(10):1501-1510, 2003.
Liang et al., "Chacterization ofmicroRNA expression profiles in normal human tissues," BMC Genomics, 8:166,2007.
Lilja et al., "Prostate-specific antigen and prostate cancer: prediction, detection and monitoring," Nat. Rev. Cancer, 8(4):268-278, 2008.
Lim et al., "Microarray analysis shows that some microRNAs dowmegulate large numbers of target mRNAs," Nature, 433(7027):769-773, 2005.
Lim et al., "The microRNAs ofCaenorhabditis elegans," Genes and Development, 17:991-1008,2003.
Lima e Silva et al., "The SDF-I/CXCR4 ligand/receptor pair is an important contributor to several types of ocular neovascularization," FASEB J, 21(12):3219-3230, 2007.
"Human miRNA targets," for "mmu-miR-126-3p" Apr. 2005 version, accessed and retrieved from miRanda webserver at www.microma.org and http:/ /cbio.mskcc.org/cgi-bin/mimaviewer, on Dec. 31, 2009. p. 1 of the 23 print-out pages included.
"Poster Abstracts," Annals of Surgical Oncology, 15(Suppl1):33-64, 2008.
Aaboe et al., "Vitronectin in human breast carcinomas," Biochem. Biophys. Acta., 1638 (1): 72-82, 2003.
Aagaard et al., "An inflammatory role for the mammalian carboxypeptidase inhibitor latexin: relationship to cystatins and the tumor suppressor TIG1," Structure (Camb), 13: 309-317,2005.
Abuharbeid et al., "The fibroblast growth factor-binding protein FGF-BP," Int. J Biochem. Cell Biol., 38(9):1463-1468, 2006.
Adams et al., "Infrequent mutation of TRAIL receptor 2 (TRAIL-R2/DR5) in transitional cell carcinoma of the bladder with 8p21loss of heterozygosity," Cancer Lett. 220 (2): 137-144, 2005.
Afanasyeva et al., "New miRNAs cloned from neuroblastoma," BMC Genomics, 9(1 ):52, 2008.
Agrawal and Kandimalla, "Antisense therapeutics: is it as simple as complementary base recognition," Molecular Medicine Today, 6:72-81, 2000.
Agrawal and Syngal, "Colon cancer screening strategies," Curr Opin Gastroenterol, 21(1):59-63, 2005.
Aiello et al., "Suppression of retinal neovascularization in vivo by inhibition of vascular endothelial growth factor (VEGF) using soluble VEGF-receptor chimeric proteins," Proc. Natl. Acad. Sci. USA. 92(23):10457-10461, 1995.
Akao et al., "Iet-7 micro RNA functions as a potential growth suppressor in human colon cancer cells," Biol. Pharm. Bull, 29(5):903-906, 2006.
Akao et al., "MicroRNAs 143 and 145 are possible common onco-microRNAs in human cancers," Oncology Reports, 16:845-850, 2006.
Akiba et al., "Expression and function of interleukin-8 in human hepatocellular carcinoma," Int. J Oncol., 18 (2): 257-264,2001.
Ai-Hajj et al., "Prospective identification of tumorigenic breast cancer cells," Proc. Natl. Acad. Sci. USA, 100(7):3983-8, 2003.
Alevizos et al., "Oral cancer in vivo gene expression profiling assisted by laser capture microdissection and microarray analysis," Oncogene, 20(43):6196-6204, 2001.
Ali, et al., Am J Trans! Res. 3(1):28-47, 2011.
Allawi et al., "Quantitation of MicroRNAs using a modified Invader assay," RNA, 10:1153-1161, 2004.
Altucci and Gronemeyer, "The promise of retinoids to fight against cancer," Nat. Rev. Cancer, 1:181-193, 2001.
Altucci and Gronomeyer, "Retinoids and TRAIL: two cooperating actors to fight against cancer," Vitam. Harm., 67:319-345, 2004.
Ambros et al., "A uniform system for microRNA annotation," RNA, 9(3):277-279, 2003.
Ambros, "microRNAs: tiny regulators with great potential," Cell, 107(7):823-826, 2001.
Anatharaman and Aravind, "Evolutionary history, structural features and biochemical diversity ofthe N1pC/P60 superfamily of enzymes," Genome Biol., 4: RII, 2003.
Ando et al., "Polo-like kinase 1 (P1k1) inhibits p53 function by physical interaction and phosphorylation," J Biol. Chern., 279 (24): 25549-25561, 2004.
Aoki et al., "Proteasomal degradation of the Fox01 transcriptional regulator in cells transformed by the P3k and Akt oncoproteins," Proc Natl Arad Sci US A, 101(37):13613-13617, 2004.
Armour et al., "Measurement of locus copy number by hybridisation with amplifiable probes," Nucleic Acids Research, 28(2):605-609, 2000.
Association of Directors of Anatomic and Surgical Pathology, "Recommendations for the reporting of resected large intestinal carcinomas. Association of directors of anatomic and surgical pathology," Am. J Clin. Pathol., 106 (1): 12-15, 1996.
Astler and Caller, "The prognostic significance of direct extension of carcinoma of the colon and rectum," Ann. Surg., 139: 846-852, 1954.
Asuragen, Inc. website, "Asuragen's DiscovArray miRNA Expression Profiling Service," located at http:/ /www.asuragen.com/Services/solutions/discovarray.aspx, printed Mar. 6, 2009.
Austin and Cook, "Increased expression of Mcl-1 is required for protection against serum starvation in phosphatase and tensin homologue on chromosome 10 null mouse embryonic fibroblasts, but repression ofBim is favored in human glioblastomas," J Biol Chem, 280(39):33280-33288, 2005.
Azuma, et al. Int J Cancer. 67: 492-497, 1996.
Baba et al., "Involvement of deregulated epiregulin expression in tumorigenesis in vivo through activated Ki-Ras signaling pathway in human colon cancer cells," Cancer Res, 60(24):6886-6889,2000.
Bader and Vogt, "An essential role for protein synthesis in oncogenic cellular transformation," Oncogene, 23(18):3145-3150, 2004.
Bader et al.,"Oncogenic PI3K deregulates transcription and translation," Nat Rev Cancer, 5(12):921-929, 2005.
Bae et al., "MCL-1S, a splicing variant ofthe antiapoptotic BCL-2 family member MCL-1, encodes a proapoptotic protein possessing only the BH3 domain," J Biol. Chern., 275(33):25255-61, 2000.
Baffa et al., "Micro RNA expression profiling of human metastatic cancers identifies cancer gene targets," J Pathol., Epub Ahead of Print, 2009.
Bagga et al., "Regulation by let-7 and lin-4 miRNAs results in target mRNA degradation," Cell, 122( 4):553-563, 2005.

(56) References Cited

OTHER PUBLICATIONS

Bai et al., "Downregulation of selective microRNAs in trigeminal ganglion neurons following inflammatory muscle pain," Mol Pain, 3:15, 2007.
Bandres et al., "Identification by Real-time PCR of 13 mature microRNAs differentially expressed in colorectal cancer and non-tumoral tissues," Mol. Cancer, 5:29, 2006.
Bangoura et al., "Expression of HIF-2alpha/EPAS1 in hepatocellular carcinoma," World J Gastroenterol., 10(4):525-530, 2004.
Sao et al., "Glioma stem cells promote radioresistance by preferential activation of the DNA damage response," Nature, 444(7120):756-60, 2006.
Barnetson et al., "Genetic analysis of multiple sporadic colon carcinomas from a single patient," Int J Colorectal Dis, 15:83-86, 2000.
Bartel et al., "Alternative and aberrant splicing of MDM2 mRNA in human cancer," Cancer Cell, 2(1):9-15, 2002.
Bartel, "MicroRNAs: genomics, biogenesis, mechanism, and function," Cell, 116:281-297, 2004.
Bartlett and Davis, "Effect of siRNA nuclease stability on the in vitro and in vivo kinetics of siRNA-mediated gene silencing," Biotechnol. Bioeng., 97(4): 909-921, 2007.
Bartlett et al., "Impact of tumor-specific targeting on the biodistribution and efficacy of siRNA nanoparticles measured by multimodality in vivo imaging," 104(39): 15549-15554, 2007.
Bartlett et al., "Insights into the kinetics of siRNA-mediated gene silencing from live-cell and live-animal bioluminescent imaging," Nucleic Acids Research, 34(1):322-333, 2006.
Barton et al., "Angiogenic protein expression in advanced epithelial ovarian cancer," Clin. Cancer Res., 3 (9): 1579-1586, 1997.
Basturk et al., "MicroRNA expression in androgen independent and metastatic prostate cancer," Modern Pathology, Abstract No. 669, 21(Suppl. 1):148A, 2008.
Bedell et al., "Amplification of human papillomavirus genomes in vitro is dependent on epithelial differentiation," J Virol., 65(5):2254-60, 1991.
Beeram et al. "Raf: a strategic target for therapeutic development against cancer," J Clin Oncol, 23(27):6771-6790, 2005.
PCT International Search Report and Written Opinion issued in International Application No. PCT/US2009/064015, dated May 11, 2010.
PCT International Search Report and Written Opinion, issued in International Application No. PCT/US2005/022710, dated Oct. 7, 2005.
PCT International Search Report and Written Opinion, issued in International Application No. PCT/US2005/036799, dated Jun. 22, 2006.
PCT International Search Report and Written Opinion, issued in International Application No. PCT/US2005/041162, dated Nov. 16, 2007.
PCT International Search Report and Written Opinion, issued in International Application No. PCT/US2007/078859, dated Mar. 25, 2008.
PCT International Search Report and Written Opinion, issued in International Application No. PCT/US2007/078894, dated Apr. 14, 2008.
PCT International Search Report and Written Opinion, issued in International Application No. PCT/US2007/086396, dated May 30, 2008.
PCT International Search Report and Written Opinion, issued in International Application No. PCT/US2007/087021, dated Sep. 3, 2008.
PCT International Search Report and Written Opinion, issued in International Application No. PCT/US2007/087029, dated Jan. 13, 2009.
PCT International Search Report and Written Opinion, issued in International Application No. PCT/US2007/087031, dated Jan. 13, 2009.
PCT International Search Report and Written Opinion, issued in International Application No. PCT/US2007/087033, dated Jan. 13, 2009.
PCT International Search Report and Written Opinion, issued in International Application No. PCT/US2007/087037, dated Jan. 12, 2009.
PCT International Search Report and Written Opinion, issued in International Application No. PCT/US2007/087038, dated Oct. 17, 2008.
PCT International Search Report and Written Opinion, issued in International Application No. PCT/US2007/089206, dated Aug. 26, 2008.
PCT International Search Report and Written Opinion, issued in International Application No. PCT/US2008/076246, dated Feb. 27, 2009.
PCT International Search Report and Written Opinion, issued in International Application No. PCT/US2008/080318, dated Feb. 9, 2009.
PCT International Search Report and Written Opinion, issued in International Application No. PCT/US2008/085178, dated Aug. 21, 2009.
PCT International Search Report and Written Opinion, issued in International Application No. PCT/US2009/033556, dated Aug. 4, 2009.
PCT International Search Report, issued in International Application No. PCT/US2002/003169, dated Feb. 17, 2003.
PCT Invitation to Pay Additional Fees and Partial International Search, issued in PCT/US2007/078952, dated Sep. 22, 2009.
PCT Invitation to Pay Additional Fees and Partial International Search, issued in International Application No. PCT/US2005/018826, dated Mar. 20, 2006.
PCT Invitation to Pay Additional Fees and Partial International Search, issued in International Application No. PCT/US2005/041162, dated Aug. 31, 2007.
PCT Invitation to Pay Additional Fees and Partial International Search, issued in International Application No. PCT/US2007/078859, dated Jan. 28, 2008.
PCT Invitation to Pay Additional Fees and Partial International Search, issued in International Application No. PCT/US2007/078894, dated Feb. 11, 2008.
PCT Invitation to Pay Additional Fees and Partial International Search, issued in International Application No. PCT/US2007/087021, dated Jul. 10, 2008.
PCT Invitation to Pay Additional Fees and Partial International Search, issued in International Application No. PCT/US2007/087029, dated Sep. 10, 2008.
PCT Invitation to Pay Additional Fees and Partial International Search, issued in International Application No. PCT/US2007/087031, dated Sep. 10, 2008.
PCT Invitation to Pay Additional Fees and Partial International Search, issued in International Application No. PCT/US2007/087033, dated Sep. 5, 2008.
PCT Invitation to Pay Additional Fees and Partial International Search, issued in International Application No. PCT/US2007/087037, dated Aug. 25, 2008.
PCT Invitation to Pay Additional Fees and Partial International Search, issued in International Application No. PCT/US2007/087038, dated Jul. 16, 2008.
PCT Invitation to Pay Additional Fees and Partial International Search, issued in International Application No. PCT/US2007/089206, dated Jul. 7, 2008.
PCT Invitation to Pay Additional Fees and Partial International Search, issued in International Application No. PCT/US2008/076246, dated Dec. 30, 2008.
PCT Invitation to Pay Additional Fees and Partial International Search, issued in International Application No. PCT/US2008/085178, dated May 8, 2009.
PCT Invitation to Pay Additional Fees and Partial International Search, issued in International Application No. PCT/US2009/033556, dated Jun. 5, 2009.
PCT Invitation to Pay Additional Fees and Partial International Search, issued in International Application No. PCT/US2009/036195, dated Jul. 2, 2009.

(56) References Cited

OTHER PUBLICATIONS

PCT Invitation to Pay Additional Fees and Partial International Search, issued in International Application No. PCT/US2009/043361, dated Jul. 22, 2009.
PCT Invitation to Pay Additional Fees issued in International Application No. PCT/US2007/078952, dated Sep. 22, 2009.
PCT Invitation to Pay Additional Fees issued in International Application No. PCT/US2008/087762, dated Nov. 9, 2009.
Peacock et al., "Hedgehog signaling maintains a tumor stem cell compartment in multiple myeloma," Proc. Natl. Acad. Sci. USA, 104(10):4048-53, 2007.
Pendas et al., "Worldwide experience with lymphatic mapping for invasive breast cancer," Semin. Oneal., 31(3):318-323, 2004.
Peng et al., "Overexpression of micro RNA let-7c in prostate cancer," Modern Pathology, Abstract No. 788,20 (Suppl. 2):169A, 2007.
Peracchi, "Prospects for antiviral ribozymes and deoxyribozymes," Rev. Med. Viral., 14:47-64, 2004.
Petit et al., "LHFP, a novel translocation partner gene ofHMGIC in a lipoma, is a member of a new family ofLHFP-like genes," Genomics, 57(3): 438-441, 1999.
Phan et al., "Sentinel lymph node biopsy for melanoma: indications and rationale," Cancer Control, 16(3):234-239, 2009.
Phillips et al., "Antisense RNA amplification: A linear amplification method for analyzing the mRNA populaion," Methods, a Companion to Methods in Enzymology, 10(3):283-288, 1996.
Pietras et al., "PDGF receptors as cancer drug targets," Cancer Cell, 3(5):439-443, 2003.
Poliseno et al., "MicroRNAs modulate the angiogenic properties ofHUVECs," Blood 108(9):3068-3071, 2006.
Meng et al., "Involvement of human micro-ma in growth and response to chemotherapy in human cholangiocarcinoma cell lines," Gastroenterology, 130(7):2113-2129, 2006.
Merle et al., "Functional consequences of frizzled-7 receptor overexpression in human hepatocellular carcinoma," Gastroenterology, 127 ( 4): 110-1122, 2004.
Mestdagh, et al., Nuc Acid Res. 36(21):e143, 2008.
Metzler et al., "High Expression of Precursor MicroRNA-155/B/C RNA in Children with Burkitt Lymphoma," Genes, Chromosomes, & Cancer 39:167-169; 2004.
Mi et al., "Micro RNA expression signatures accurately discriminate acute lymphoblastic leukemia from acute myeloid leukemia," PNAS, 104(50):19971-19976, 2007.
Michael and Oren, "The p53-Mdm2 module and the ubiquitin system," Semin. Cancer Biol. 13:49-58, 2003.
Michael et al., "Reduced accumulation of specific micrornas in colorectal neoplasia," Molecular Cancer Research, 1(12):882-891, 2003.
Michael, et al., Mol Cancer Res. 1:882-91, 2003.
Miki & Rhim, "Prostate cell cultures as in vitro models for the study of normal stem cells and cancer stem cells", Prost. Can. Prost. Dis., 11:32-39,2008.
Miki et al., "Identification of putative stem cell markers, CD133 and CXCR4, in hTERTimmortalized primary nonmalignant and malignant tumor-derived human prostate epithelial cell lines and in prostate cancer specimens," Cancer Res., 67(7):3153-61, 2007.
Miller et al., "Vascular endothelial growth factor/vascular permeability factor is temporally and spatially correlated with ocular angiogenesis in a primate mode," Am. J Pathol., 145(3):574-584, 1994.
Minakuchi et al., "Atelocollagen-mediated synthetic small interfering RNA delivery for effective gene silencing in vitro and in vivo," Nucleic Acids Research, 32(13):e109, 2004.
Mishima et al., "RT-PCR-based analysis ofmicroRNA (miR-1 and -124) expression in mouse CNS," Brain Res, 1131(1):37-43, Epub Dec. 19, 2006.2007.
Miyake et al., "Increased angiogenin expression in the tumor tissue and serum ofurothelial carcinoma patients is -elated to disease progression and recurrence," Cancer, 86 (2): 316-324, 1999.

Mizunuma et al., "The LIM-only protein, LM04, and the LIM domain-binding protein, LDB1, expression in squamous cell carcinomas of the oral cavity," Br J Cancer, 88(1 0): 1543-1548, 2003.
Mohanty and Kushner, "Polynucleotide phosphorylase functions both as a 3'-5' exonuclease and a poly( A) polymerase in *Escherichia coli*," PNAS, 97: 11966-11971; 2000.
Moller et al., "Expression of APO-1 (CD95), a member ofthe NGF/TNF receptor superfamily, in normal and neoplastic colon epithelium," /nt J Cancer, 57(3):371-377, 1994.
Momand et al., "The MDM2 gene amplification database," Nucleic Acids Res, 26(15):3453-3459, 1998.
Montero et al., "Angiogenin expression and prognosis in primary breast carcinoma," Clin. Cancer Res., 4 (9): 2161-2168, 1998.
Mori et al., "A genome-wide search identifies epigenetic silencing of somatostatin, tachykinin-1, and 5 other genes in colon cancer," Gastroenterology, 131(3):797-808, 2006.
Morton et al., "Sentinel-node biopsy or nodal observation in melanoma," N Engl. J Med., 355(13):1307-1317, 2006.
Morton et al., "Technical details of intraoperative lymphatic mapping for early stage melanoma," Arch Surg, 127(4):392-399, 1992.
Mourelatos et al., "miRNPs: a novel class of ribonucleoproteins containing numerous microRNAs," Genes & Development, 16:720-728, 2002.
Mrozek et al., "Clinical relevance of mutations and gene-expression changes in adult acute myeloid leukemia with normal cytogenetics: are we ready for a prognostically prioritized molecular classification?," Blood, 109:431-448, 2007.
Munding et al., Global microRNA expression profiling of microdissected tissues identifies miR-135b as a novel biomarker for pancreatic ductal adenocarcinoma, 2012, International Journal of Cancer, vol. 131, pp. E86-E95.
Mundt et al., "On the regulation and function of human polo-like kinase 1 (PLK1 ): effects of overexpression on cell cycle progression," Biochem Biophys Res Commun, 239(2):377-385, 1997.
Muralidhar et al., "Global microRNA profiles in cervical squamous cell carcinoma depend on Drosha expression levels," J Pathol., 212:368-377, 2007.
Murphy et al., "p16INK4A, CDC6, and MCM5: predictive biomarkers in cervical preinvasive neoplasia and cervical cancer," J Clin Pathol, 58(5):525-534, 2005.
Nagpal et al., "Tazarotone-induced gen 1 (TIG1), a novel retinoic acid receptor-responsive gene in skin," J Invest. Dermatol.,. 106 (2): 269-274, 1996.
Nakada et al., "The phosphorylation ofEphB2 receptor regulates migration and invasion of human glioma cells," Cancer Res., 64 (9): 3179-3185, 2004.
Nakamura et al., "MARCH-II is a syntaxin-6-binding protein involved in endosomal trafficking," Molecular Biology of the Cell, 16(4):1696-1710, 2005.
Nauert et al., "Gravin, an autoantigen recognized by serum from myasthenia gravis patients, is a kinase scaffold protein," Curr Biol, 7(1):52-62, 1997.
Nelson et al., "Microarray-based, high-throughput gene expression profiling ofmicroRNAs," Nature Methods, 1(2):1-7, 2004.
Nerlov, "C/EBPalpha mutations in acute myeloid leukaemias," Nat Rev Cancer, 4(5):394-400, 2004.
Nesbit et al. "MYC oncogenes and human neoplastic disease," Oncogene, 18 (19): 3004-3016, 1999.
Ngan et al., "Quantitative evaluation ofvimentin expression in tumour stroma of colorectal cancer," Br J Cancer, 96(6):986-992, 2007.
Nikiforova et al., "MicroRNA expression profiling ofthyroid tumors: biological significance and diagnostic utility," 93 (5);1600-1608, 2008.
Nordgard et al., "Quantitative RT-PCR detection oftumor cells in sentinel lymph nodes isolated from colon cancer patients with an ex vivo approach," Annals of Surgery, 249( 4):602-607,2009.
Notice of Allowance issued in U.S. Appl. No. 11/141,707, dated Oct. 4, 2010.
Notice of Allowance issued in U.S. Appl. No. 11/837,490, dated Apr. 2011.
Notice of Allowance issued in U.S. Appl. No. 11/837,495, dated Dec. 2, 2010.

(56) References Cited

OTHER PUBLICATIONS

Nykanen et al., "ATP requirements and small interfering RNA structure in the RNA interference pathway," Cell, 107:309-321,2001.
O'Connor et al., "Bim: a novel member of the Bcl-2 family that promotes apoptosis," Embo J, 17(2):384-395, 1998.
O'Donnel et al., "c-Myc-regulated microRNA's modulcate E2F1 expression," Nature, 435(7043):839-4843, 2005.
Oberg et al., "Detection of occult tumour cells in lymph nodes of colorectal cancer patients using real-time quantitative RT-PCR for CEA and CK20 mRNAS," Int. J Cancer, 111(1): 101-110, 2004.
Office Action issued in Australian Application No. 2005250432, dated Aug. 25, 2010.
Office Action issued in Australian Application No. 2005250432, dated Dec. 1, 2009.
Office Action issued in Australian Application No. 2005250432, dated Jun. 10, 2011.
Office Action issued in Australian Application No. 2005250432, dated Mar. 29, 2011.
Cox et al., "Significance of sentinel lymph node micrometastases in human breast cancer," J Am. Call. Surg., 206(2):261-268, 2008.
Cox, "Epidemiology and natural history ofHPV," J Fam. Pract., Suppl:3-9, 2006.
Crnogorac-Jurcevic et al., Proteomic analysis of chronic pancreatitis and pancreatic adenocarcinoma, 2005, Gastroenterology, vol. 129, pp. 1454-1463.
Croci et al., "Inhibition of connective tissue growth factor (CTGF/CCN2) expression decreases the survival and myogenic differentiation ofhuman rhabdomyosarcoma cells," Cancer Res.,64(5): 1730-1736, 2004.
Crooke, "Progress in antisense technology," Annu. Rev. Med., 55:61-95, 2004.
Cross et al., "25-Hydroxyvitamin D (3)-1alpha-hydroxylase and vitamin D receptor gene expression in human colonic mucosa is elevated during early cancerogenesis," Steroids, 66:287-292, 2001.
Cully et al., "Transforming acidic coiled coil 1 promotes transformation and mammary tumorigenesis," Cancer Res., 65(22):10363-10370, 2005.
Cummins and Velculescu, "Implications of micro-RNA profiling for cancer diagnosis, " Oncogene, 25(46):6220-6227, 2006.
Cummins et al., "The colorectal microRNAome," Proc. Natl. Acad. Sci. USA, 103(10):3687-3692,2006.
D'Antonio et al., "Transforming growth factor alpha, amphiregulin and cripto-1 are frequently expressed in advanced human ovarian carcinomas," Int. J Oneal., 21(5):941-948, 2002.
D'Cunha et al., "Poor correspondence between clinical and pathologic staging in stage 1 nonsmall cell lung cancer: results from CALGB 9761, a prospective trial," Lung Cancer, 48:241-246,2005.
D'Souza et al., "Case-control study of human papillomavirus and oropharyngeal cancer," New Engl. J Med., 356:1944-1956,2007.
Dahl et al., "Identification of sentinel nodes in patients with colon cancer," Eur. J Surg. Oneal., 31(4):381-385, 2005.
Dai et al., "Prostate cancer induces bone metastasis through Wnt-induced bone morphogenetic protein-dependent and independent mechanisms," Cancer Res., 68(14): 5785-94, 2008.
Danilkovitch-Miagkova and Zbar, "Dysregulation of Met receptor tyrosine kinase activity in invasive tumors," J Clin Invest, 109(7):863-867, 2002.
Database EMBL, "Human DNA related to regulating mammalian cells using miRNAs Seq 471," EBI Database Accession No. ADR83569, Dec. 2, 2004.
Davalos et al., "High EPHB2 mutation rate in gastric but not endometrial tumors with microsatellite instability," Oncogene, 26 (2): 308-311, 2006.
Davis et al., "Modeling of repeated-batch transcription for production of RNA," Journal of Biotechnology, 71:25-37,.
Davison et al., "Analyzing micro-RNA expression using microarrays," Meth. Enzymol., 411: 14-34,2006.
De Boer et al., "Micrometastases and isolated tumor cells: relevant and robust or rubbish? (MIRROR): preliminary results of the Mirror study from the Dutch breast cancer trialists' group (BOOG)," San Antonio Breast Cancer Symposium, Abstract 23, 2008.
De Candia et al., "Id4 messenger RNA and estrogen receptor expression: inverse correlation in human normal breast epithelium and carcinoma," Hum. Pathol., 37 (8): 1032-1041, 2006.
Dean et al., "The human met oncogene is related to the tyrosine kinase oncogenes," Nature, 318(6044):385-388, 1985.
Decision on Appeal, Appeal2008-002253, issued in U.S. Appl. No. 10/880,350, filed May 29, 2009.
Declaration of Dr. David P. Bartel under 37 C.F.R. 1.132, submitted in U.S. Appl. No. 10/913,288, 2009.
DeNigris et al., "Induction ofETS-1 and ETS-2 transcription factors is required for thyroid cell transformation," Cancer Res., 61 (5): 2267-2275, 2001.
Denli and Hannon. "RNAi: an ever-growing puzzle," Trends Biochem. Sci., 28:196,2003.
Devine et al., "Serum markers CASA, CEA, CYFRA, TPS, and NSE in lung cancer," Lung Cancer, Abstract, 11:37, 1994.
Dews et al., "Augmentation oftumor angiogenesis by a Myc-activated microRNA cluster," Nat. Genet., 3 8(9): 1060-1065, 2006.
Didenko, Biotechniques. 31(5): 1106-21, 200t.
Diederichs and Haber, "Sequence variations of microRNAs in human cancer: Alterations in predicted secondary structure do not affect processing," Cancer Res., 66(12):6097-6104, 2006.
Dillon et al., "An April to remember: novel TNF ligands as therapeutic targets," Nat Rev Drug Discov, 5(3):235-246, 2006.
DiSepio et al., "Identification and characterization of a retinoid-induced class II tumor suppressor/growth regulatory gene," Proc. Natl. Acad. Sci. USA, 95: 14811-14815, 1998.
Dittmer, "The biology of the Ets1 proto-oncogene," Mol Cancer, 2:29, 2003.
Doench and Sharp, "Specificity of micro RNA target selection in translational repression," Genes Dev, 18(5):504-11, 2004.
Doench et al., "siRNAs can function as miRNAs," Genes & Dev, 17:438-442, 2003.
Doleshal, et al., J Mol Diagnos. 10(3): 201,11,2008.
Dong et al., "Telomerase: regulation, function and transformation," Crit Rev Oneal Hematol. 54(2):85-93, 2005.
Donnellan and Chetty, "Cyclin D1 and human neoplasia," Mol Pathol, 51(1):1-7, 1998.
Dontu et al., "In vitro propagation and transcriptional profiling of human mammary stem/progenitor cells," Genes Dev., 17:1253-70, 2003.
Dostie et al. "Numerous microRNPs in neuronal cells containing novel microRNAs," RNA, 9:180-186; 2003.
Doyle and Ross, "Multidrug resistance mediated by the breast cancer resistance protein BCRP (ABCG2)," Oncogene, 22(47):7340-58, 2003.
Droge and Davey, "Do cells let-7 determine sternness?" Cell Stem Cell, 2(1):8-9, 2008.
Duvic et al., "Expression of a retinoid-inducible tumor suppressor, tazarotene-inducible gene-3 is decreased in psoriasis and skin cancer," Clin. Cancer Res., 6 (8): 3249-3259, 2000.
Duvic et al., "Tazarotene-induced gene 3 is suppressed in basal cell carcinomas and reversed in vivo by tazarotene application," J Invest. Dermatol., 121: 902-909, 2003.
Dyer and Bremner, "The search for the retinoblastoma cell of origin," Nat Rev Cancer, 5(2):91-101,2005.
Dylla et al., "Colorectal cancer stem cells are emiched in xenogeneic tumors following chemotherapy," PLoS One, 3(6): e2428, 13 pages, 2008.
Ebert et al., "Induction and expression of amphiregulin in human pancreatic cancer," Cancer Res., 54(15):3959-3962, 1994.
Eferl et al., "Liver tumor development. c-Jun antagonizes the proapoptotic activity of p53," Cell, 112 (2): 181-192,2003.
Egle et al., "Bim is a suppressor ofMyc-induced mouse B cell leukemia," Proc Natl Acad Sci USA, 101(16):6164-6169, 2004.
Egloff et al., "Cyclin B1 and other cyclins as tumor antigens in immunosurveillance and immunotherapy of cancer," Cancer Res, 66(1 ):6-9, 2006.
Calin et al., "Micro RNA profiling reveals distinct signatures in B cell chronic lymphocytic leukemias," Proc Natl Acad Sci USA, 101(32):11755-11760.

(56) References Cited

OTHER PUBLICATIONS

Campochiaro and Hackett, "Ocular neovascularization: a valuable model system," Oncogene, 22(42):6537-6548, 2003.
Cao et al., "A functional study of miR-124 in the developing neural tube," Genes & Development, 21(5):531-536, 2007.
Carrano et al., "SKP2 is required for ubiquitin-mediated degradation of the CDK inhibitor p27," Nat Cell. Biol., 1 (4): 193-199, 1999.
Carreiras et al., "Expression and localization of alpha v integrins and their ligand vitronectin in normal ovarian apithelium and in ovarian carcinoma," Gynecol. Oneal., 62 (2): 260-267, 1996.
Carreiras et al., "Human ovarian adenocarcinoma cells synthesize vitronectin and use It to organize their adhesion," Gynecol. Oneal., 72 (3): 312-322, 1999.
Carrington and Ambros, "Role of MicroRNAs in Plant and Animal Development Science," 301:336-338; 2003.
Carter and Brunet, "FOXO transcription factors," Curr Biol, 17(4):R113-114, 2007.
Casanova et al., "The class II trumor-suppressor gene RARRES3 is expressed in B cell lymphocytic leukemias and down-regulated with disease progression," Leukemia, 15 (10): 1521-1526, 2001.
Caselitz et al., "Malignant melanomas contain only the vim en tin type of intermediate filaments," Virchows Arch A Pathol Anat Histopathol, 400(1):43-51, 1983.
Castillo et al., "Amphiregulin contributes to the transformed phenotype of human hepatocellular carcinoma cells," Cancer Res., 66(12):6129-6138, 2006.
Caudy et al., "Fragile X-related protein and VIG associate with the RNA interference machinery," Genes & Development, 16:2491-2496; 2002.
Chan et al., "Downregulation of ID4 by promoter hypermethylation in gastric adenocarcinoma," Oncogene, 22 (44): 6946-6953, 2003.
Chan et al., "MicroRNA-21 is an antiapoptotic factor in human glioblastoma cells," Cancer Res., 65(14):6029-6033, 2005.
Chan, et al., Anticancer Res. 28:907-912, 2008.
Chandler et al., "Prevalent expression of fibroblast growth factor (FGF) receptors and FGF2 in human tumor cell lines," Int. J Cancer, 81(3):451-458, 1999.
Chang et al., "Elevated circulating level of osteopontin is associated with advanced disease state of non-small cell lung cancer," Lung Cancer, 57(3):373-380, 2007.
Chang et al., "MicroRNAs act sequentially and asymmetrically to control chemosensory laterality in the nematode," Nature, 430(7001):785-789, 2004.
Chang et al., "Transactivation of miR-34a by p53 broadly influences gene expression and promotes apoptosis," Mol. Cell., 26(5):745-752, 2007.
Chen et al., "Identification of trophinin as an enhancer for cell invasion and a prognostic factor for early stage lung cancer," European Journal of Cancer, 43( 4):782-790, 2007.
Chen et al., "Loss of PDCD4 expression in human lung cancer correlates with tumour progression and prognosis," J Pathol, 200(5):640-646, 2003.
Chen et al., "MicroRNAs modulate hematopoietic lineage differentiation," Science, 303(5654):83-86, 2004.
Chen et al., "Real-time quanithcation of microRNAs by stem-loop RT-PCR," Nucleic Acids Research, 33(20): e179 (13 printed pages), 2005.
Chen, et al., BMC Genomics. 10:407,2009.
Chendrimada et al., "MicroRNA silencing through RISC recruitment of eiF6," Nature, 447(7146):823-828, 2007.
Cheng et al., "Antisense inhibition of human miRNAs and indications for an involvement of miRNA in cell growth and apoptosis," Nucleic Acids Res., 33(4):1290-1297, 2005.
Chiaretti et al., "Gene expression profiling identifies a subset of adult T-cell acute lymphoblastic leukemia with myeloid-like gene features and over-expression of miR-223," Haematologica, 95(7):1114-1121, 2010.

Chieffi et al., "Aurora B expression directly correlates with prostate cancer malignancy and influence prostate cell proliferation," Prostate, 66(3):326-333, 2006.
Chirila et al., "The use of synthetic polymers for delivery of therapeutic antisense oligodeoxynucleotides," Biomaterials, 23:321-342, 2002.
Chmielarz et al., "Prognostic factors for the time of occurrence and dynamics of distant metastases and local recurrences after radical treatment in patients with rectal cancer," Med Sci Manit., 7(6):1263-1269, 2001.
Choi et al., "AKAP12/Gravin is inactivated by epigenetic mechanism in human gastric carcinoma and shows growth suppressor activity," Oncogene, 23(42):7095-7103, 2004.
Churg, "Immunohistochemical staining for vimentin and keratin in malignant mesothelioma," Am J Surg Pathol, 9(5):360-365, 1985.
Ciafre et al., "Extensive modulation of a set of microRNAs in primary glioblastoma," Biochem. Biophys. Res. Commun., 334(4):1351-1358, 2005.
Cimmino et al., "miR-15 and miR-16 induce apoptosis by targeting BCL2;" Proceedings of the National Academy of Sciences of the USA, 102(39):13944-13949, 2005.
Ciocca et al., "Heat shock portein hsp70 in patients with axillary lymph node-negative breast cancer: Prognostic implications," Journal of the National Cancer Institute, 85(7):570-574, 1993.
Cipriano and Chen, "Insensitivity to growth inhibition by TGF-beta1 correlates with a lack of inhibition of the CDK2 activity in prostate carcinoma cells," Oncogene, 17 ( 12): 1549-1556, 1998.
Claudio et al., "Expression of cell-cycle-regulated proteins pRb2/p 130, p 107, p2 7 (kip 1 ), p53, mdm-2, and Ki-67 (Mib-1) in prostatic gland adenocarcinoma," Clin Cancer Res, 8( 6): 1808-1815, 2002.
Clement et al., "HEDGEHOG-GLil signaling regulates human glioma growth, cancer stem cell self-renewal, and tumorigenicity," Curr. Biol., 17(2): 165-72, 2007.
Clifford et al., "Human papillomavirus types in invasive cervical cancer worldwide: a metaanalysis," Br. J Cancer, 88(1):63-73, 2003.
Coello et al. "Prognostic significance of micrometastasis in non-small-celllung cancer," Clin. Lung Cancer, 5:214-225, 2004.
Cogliano et al., "Carcinogenicity of human papillomaviruses," Lancet Oneal., 6(4):204, 2005.
Cohen et al., "Expression of a down-regulated target, SSeCKS, reverses v-Jun-induced transformation of 10TI/2 murine fibroblasts," Oncogene, 20(2):141-146, 2001.
Cohen et al., "Prognosis of node-positive colon cancer," Cancer, 67(7):1859-1861, 1991.
Coleman et al., "Superior 5' homogeneity of RNA from ATP-initiated transcription under T7 <1>2.5 promoter," Nucleic Acids Research, 32(1):e14, 2004.
Collet al., "Molecular cloning of the avian acute transforming retrovirus MH2 reveals a novel cell-derived sequence (v-mil) in addition to the myc oncogene," Embo J, 2(12):2189-2194, 1983.
Collins et al., "Prospective identification of tumorigenic prostate cancer stem cells," Cancer Res., 65(23):10946-51, 2005.
Conaco et al., "Reciprocal actions of REST and a microRNA promote neuronal identity," PNAS, 103(7):2422-2427, 2006.
Cooper et al., "Molecular cloning of a new transforming gene from a chemically transformed human cell line," Nature, 311(5981):29-33,1984.
Costello et al., "Cyclin-dependent kinase 6 (CDK6) amplification in human gliomas identified using two-dimensional separation of genomic DNA," Cancer Res, 57 (7): 1250-1254, 1997.
Costinean et al., "Pre-B cell proliferation and lymphoblastic leukemia/ high-grade lymphoma in EJ..L-miR155 transgenic mice," Proc. Natl. A cad. Sci. USA, 1 03(18):7024-7029, 2006.
Gao et al., "Frequent loss of PDCD4 expression in human glioma: possible role in the tumorigenesis of glioma," Oneal. Rep., 17(1):123-128, 2007.
Garzon et al., "Micro RNA signatures associated with cytogenetics and outcome in acute myeloid leukemia. Session Type: Oral Session," Blood, 108(11): 49A, Abstract #151, 2006.
Garzon et al., "MicroRNA fingerprints during human megakaryocytopoiesis," Proc. Natl. Acad. Sci. USA, 103(13):5078-5083, 2006.

(56) References Cited

OTHER PUBLICATIONS

Gerald and Haber, "The EWS-WTI gene fusion in desmoplastic small round cell tumor," Semin Cancer Biol, 15(3):197-205, 2005.
Giannakakis et al., "mlRNA genetic alterations in human cacners," Expert opinion on biological therapy, 7(9):1375-1386, 2007.
Gillam et al., Nuc Acid Res. 6(9): 2973-85, 1979.
Gillam, et al., J Biol Chern. 253(8):2532-2539, 1978.
Gillanders et al., "Molecular detection ofmicrometastatic breast cancer in histopathologynegative axillary lymph nodes correlates with traditional predictors of prognosis: an interim analysis of a prospective multi-institutional cohort study," Ann. Surg., 239:828-840, 2004.
Gilles et al., "Vimentin expression in cervical carcinomas: association with invasive and migratory potential," J Pathol, 180(2):175-180, 1996.
Ginestier et al., "ALDH1 is a marker of normal and malignant human mammary stem cells and a predictor of poor clinical outcome," Cell Stem Cell, 1(5):555-567, 2007.
Giovannetti, et al., Cancer Res. Doi:10.1158/0008-5472.CAN-09-4467, 2010.
Gipponi et al., "Sentinel lymph node as a new marker for therapeutic planning in breast cancer patients," J Surg. Oneal., 85(3):102-111, 2004.
Gironella, et al., PNAS USA. 104(41):16170-5, 2007.
Goke et al., "Programmed cell death protein 4 suppresses CDK1/cdc2 via induction of p21(Wafl/Cip1)," Am. J Physiol. Cell Physiol., 287(6):C1541-6, 2004.
Gomez-Bougie et al., "The imbalance between Bim and Mcl-1 expression controls the survival of human myeloma cells," Eur J /mmunol, 34(11):3156-3164, 2004.
Gonzalez et al., "Oncogenic activity ofCdc6 through repression of the INK4/ARF locus," Nature, 440(7084):702-706, 2006.
Goodell et al., "Isolation and functional properties of murine hematopoietic stem cells that are replicating in vivo," J Exp. Med., 183(4):1797-806, 1996.
Goyns et al., "The c-ets-1 proto-oncogene is rearranged in some cases of acute lymphoblastic leukaemia," BrJCancer, 56(5):611-613, 1987.
Grandori et al., "The Myc/Max/Mad network and the transcriptional control of cell behavior," Annu. Rev. Cell. Dev. Biol., 16: 653-699, 2000.
Grenier et al., "Cyfra 21-1, a new marker for lung cancer," Nucl. Med. Biol., 21(3):471-476,1994.
Griffiths-Janes et al., "miRBase: microRNA sequences, targets and gene nomenclature," Nucleic Acids Res., 34 (Database Issue):D140-D144, 2006.
Griffiths-Janes et al., "miRBase: tools for microRNA genomics," Nucl. Acids Res., 36 (Database Issue):D154-D158, 2008.
Grimwade, "The clinical significance of cytogenetic abnormalities in acute myeloid leukaemia," Best. Pract. Res. Clin. Haematol., 14:497-529, 2001.
Grishok et al., "Genes and mechanisms related to RNA interference regulate expression of the small temporal RNAs that control C. elegans developmental timing," Cell, 106:23-34, 2001.
Grosshans et al., "The temporal patterning micro RNA let-7 regulates several transcription factors at the larval to adult transition in C. elegans," Dev. Cell, 8(3):321-330, 2005.
Gstaiger et al., "Skp2 is oncogenic and overexpressed in human cancers," Proc. Natl. Acad. Sci. USA, 98(9):5043-5048, 2001.
Gu et al., "Prostate cancer cells with stem cell characteristics reconstitute the original human tumor in vivo," Cancer Res., 67(10):4807-15, 2007.
Guda and Subramaniam, "TARGET: a new method for predicting protein subcellular localization in eukaryotes," Bioinformatics, 21: 3963-3969, 2005.
Guo et al., "Reduced expression of EphB2 that parallels invasion and metastasis in colorectal tumours," Carcinogenesis, 27(3):454-464, 2006.
Gurevich, "Preparative in vitro mRNA synthesis using SP6 and T7 RNA polymerases," Anal Biochem., 195(2):207-213, 1991.
Ha et al., "A bulged lin-4/lin-14 RNA duplex is sufficient for Caenorhabditis elegans lin-14 temporal gradient formation," Genes Dev., 10, 3041-3050, 1996.
Habbe, et al., Cancer Biol Ther. 8(4):340-6, 2009.
Hajnal et al., "Subtaction cloning ofH-rev107, a gene specifically expressed in H-ras resistant fibroblasts," Oncogene, 9:479-490, 1994.
Hamamura et al., "Ganglioside GD3 promotes cell growth and invasion through p130Cas and paxillin in malignant melanoma cells," Proc Natl Arad Sci US A, 102(31): 11041-11046, 2005.
Hambardzumyan et al., "PBK pathway regulates survival of cancer stem cells residing in the perivascular niche following radiation in medulloblastoma in vivo," Genes Dev., 22(4):436-48, 2008.
Han et al., "Cyclin D I expression in human prostate carcinoma cell lines and primary tumors," The Prostate, 35:95-101, 1998.
Hanahan and Weinberg, "The hallmarks of cancer," Cell, 100(1):57-70, 2000.
Hannigan et al., "Integrin-linked kinase: a cancer therapeutic target unique among its ILK," Nat Rev Cancer, 5(1):51-63, 2005.
Hardenbol et al., "Multiplexed genotyping with sequence-tagged molecular inversion probes," Nat Biotechnol, 21(6):673-678, 2003.
Harfe, "MicroRNAs in vertebrate development," Curr. Opin. Genet. Dev., 15(4):410-5, 2005.
Hartmann et al., "Hypoxia-iinduced up-regulation of angiogenin in human malignant melanoma," Cancer Res., 59 (7):1578-1583, 1999.
Hayashita et al., "A polycistronic micro RNA cluster, miR-17-92, is overexpressed in human lung cancers and anhances cell proliferation," Cancer Res., 65(21):9628-9632, 2005.
Hayette et al., "In B-cell chronic lymphocytic leukemias, 7q21 translocations lead to overexpression ofthe CDK6 gene," Blood, 102(4):1549-1550, 2003.
He et al., "A micro RNA component of the p53 tumour suppressor network," Nature, 447(7148):1130-1134, 2007.
He et al., "A micro RNA polycistron as a potential human oncogene," Nature, 435(7043):828-833, 2005.
He et al., "The role of micro RNA genes in papillary thyroid carcinoma," Proc. Natl. Acad. Sci.USA, 102 (52):19075-19080, 2005.
He, et al., PNAS USA. 102(52):19075-80, 2005.
Hermann et al., "Distinct populations of cancer stem cells determine tumor growth and metastatic activity in human pancreatic cancer," Cell Stem Cell, 1(3):313-23, 2007.
Hermeking, "p53 enters the microRNA world," Cancer Cell, 12(5):414-418, 2007.
Hirschmann-Jax et al., "A distinct "side population" of cells with high drug efflux capacity in human tumor cells," Proc. Natl. Acad. Sci. USA, 101:14228-33,2004.
Toh et al., "Overexpression of the MTA1 gene in gastrointestinal carcinomas: correlation with invasion and metastasis," /nt J Cancer, 74(4):459-463, 1997.
Tomasini-Johansson et al., "Vitronectin in colorectal adenocarcinoma—synthesis by stromal cells in culture," Exp. Cell. Res., 214 (1): 303-312, 1994.
Torring et al., "Increased expression of heparin binding EGF (HB-EGF), amphiregulin, TGF alpha and epiregulin in androgen-independent prostate cancer cell lines," Anticancer Res., 20 (1a): 91-95,2000.
Toyoda et al., "Distribution of mRNA for human epiregulin, a differentially expressed member of the epidermal growth factor family," Biochem J, 326 (Pt 1):69-75, 1997.
Trang et al., "Regression of murine lung tumors by the let-7 micro RNA," Oncogene, 29(11):1580-1587, Epub 2009.
Traub et al., "Prognostic impact of Skp2 and p27 in human breast cancer.," Breast Cancer Res. Treat., 99 (2):185-191,2006.
Tricoli et al., "MicroRNA: potential for cancer detection, diagnosis, and prognosis," Cancer Res., 67(10):4553-4555, 2007.
Tsai et al., "Correlation of intrinsic chemoresistance ofnon-small-celllung cancer cell lines with HER-2/neu gene expression but not with ras gene mutations," J Natl Cancer /nst, 85(11):897-901, 1993.
Tsai et al., "RIG 1 inhibits the Ras/mitogen-activated protein kinase pathway by suppressing the activation of Ras.," Cell Signal, 18 (3): 349-358, 2006.

(56) References Cited

OTHER PUBLICATIONS

Turner et al., "Hallmarks of BRCAness' in sporadic cancers," Nat Rev Cancer, 4(10):814-819, 2004.
Tuveson et al., "BRAF as a potential therapeutic target in melanoma and other malignancies," Cancer Cell, 4(2):95-98, 2003.
Uhm et al., "Vitronectin, a glioma-derived extracellular matrix protein, protects tumor cells from apoptotic death," Clin. Cancer Res., 5 (6): 1587-1594, 1999.
Ulisse et al., "Expression of Aurora kinases in human thyroid carcinoma cell lines and tissues," Int. J Cancer, 119 (2): 275-282, 2006.
Upton et al., "Expression of vimentin in surgically resected adenocarcinomas and large cell carcinomas of lung," Am J Surg Pathol, 10(8):560-567, 1986.
Vanhaesebroeck et al., "Phosphoinositide 3-kinases: a conserved family of signal transducers," Trends Biochem Sci, 22(7):267-272, 1997.
Vargas-Roig et al., "Heat shock protein expression and drug resistance in breast cancer patients treated with induction chemotherapy," Cancer Detection and Prevention, 21(5):441-451, 1997.
Vella et al., "Architecture of a validated microRNA::target interaction," Chem. Biol., 11(12):1619-1623, 2004.
Vella et al., "The C. elegans micro RNA let-7 binds to imperfect let-7 complementary sites from the lin-41 3'UTR," Genes Dev., 18(2):132-7, 2004.
Vermeulen et al., "Single-cell cloning of colon cancer stem cells reveals a multi-lineage differentiation capacity," PNAS, 105(360):13427-13432, 2008.
Vezina & Bushman, "Hedgehog signaling in prostate growth and benign prostate hyperplasia," Curr. Ural. Rep., 8(4):275-80, 2007.
Visvader et al., "The LIM domain gene LM04 inhibits differentiation of mammary epithelial cells in vitro and is overexpressed in breast cancer," Proc Natl A cad Sci US A, 98(25): 14452-14457, 2001.
Visvanathan et al., "The microRNA miR-124 antagonizes the antineural REST/SCP1 pathway during embryonic CNS development," Genes &Development, 21(7):744-749, 2007.
Vogt et al., "Triple layer control: phosphorylation, acetylation and ubiquitination of FOXO proteins," Cell Cycle, 4(7):908-913, 2005.
Volinia et al., "A microRNA expression signature of human solid tumors defines cancer gene targets," Proc. Natl. Acad. Sci. USA, 103(7):2257-2261, 2006.
Volloch and Sherman, "Oncogenic potential of Hsp72," Oncogene, 18(24):3648-3651, 1999.
Voorhoeve et al., "A genetic screen implicates miRNA-372 and miRNA-373 as oncogenes in testicular germ cell tumors," Cell, 124(6):1169-1181, 2006.
Vos et al., "RASSF2 is a novel K-Ras-specific effector and potential tumor suppressor," J Biol Chern, 278 (30):28045-28051, 2003.
Wade, "Transcriptional control at regulatory checkpoints by histone deacetylases: molecular connections between cancer and chromatin," Hum. Mol. Genet., 10(7):693-698, 2001.
Wagner and Sondak, "The sentinel lymph node: more than just another blue lymph node," Cancer, 97(8):1821-1823, 2003.
Paramo et al., "Validation of sentinel node mapping in patients with colon cancer," Ann Surg Oneal, 9(6):550-554, 2002.
Parkin et al. "Global cancer statistics, 2002," CA Cancer J Clin., 55(2):74-1 08, 2005.
Pasquinelli and Ruvkun, "Control of developmental timing by micromas and their targets," Ann. Rev. Cell Dev. Biol., 18:495-513, 2002.
Pasquinelli et al., "Reverse 5' caps in RNAs made in vitro by phage RNA polymerases," RNA, 1:957-967, 1995.
Patrawala et al., "Hierarchical organization of prostate cancer cells in xenograft tumors: the CD44+alpha2beta1 +cell population is emiched in tumor-initiating cells," Cancer Res., 67(14):6796-805, 2007.
Patrawala et al., "Highly purified CD44+ prostate cancer cells from xenograft human tumors are emiched in tumorigenic and metastatic progenitor cells," Oncogene, 25(12): 1696-708, 2006.

Patrawala et al., "MicroRNAs in prostate cancer stem cells", AACR Cancer Stem Cell Special Conference—Los Angeles, Feb. 12-15, 2008.
Patrawala et al., "Side population is emiched in tumorigenic, stem-like cancer cells, whereas ABCG2+ and ABCG2– cancer cells are similarly tumorigenic," Cancer Res., 65(14):6207-19, 2005.
Patwa, et al. Anal Chern. 78: 6411-6421, 2006.
Payton and Coats, "Cyclin E2, the cycle continues," /nt J Biochem Cell Biol, 34(4):315-320, 2002.
Payton et al., "Deregulation of cyclin E2 expression and associated kinase activity in primary breast tumors," Oncogene, 21(55):8529-8534, 2002.
PCT International Preliminary Report on Patentability and Written Opinion issued in International Application No. PCT/US2008/080318, dated Apr. 29, 2010.
PCT International Preliminary Report on Patentability and Written Opinion issued in International Application No. PCT/US2008/085178, dated Jun. 10, 2010.
PCT International Preliminary Report on Patentability and Written Opinion issued in International Application No. PCT/US2008/087762, dated Jul. 1, 2010.
PCT International Preliminary Report on Patentability and Written Opinion issued in International Application No. PCT/US2005/018826, dated Dec. 7, 2006.
PCT International Preliminary Report on Patentability and Written Opinion issued in International Application No. PCT/US2005/022710, dated Jan. 18, 2007.
PCT International Preliminary Report on Patentability and Written Opinion issued in International Application No. PCT/US2005/036799, dated Apr. 26, 2007.
PCT International Preliminary Report on Patentability and Written Opinion issued in International Application No. PCT/US2005/041162, dated Dec. 6, 2007.
PCT International Preliminary Report on Patentability and Written Opinion issued in International Application No. PCT/US2007/086396, dated Jun. 18, 2009.
PCT International Preliminary Report on Patentability and Written Opinion issued in International Application No. PCT/US2007/087021, dated Jun. 18, 2009.
PCT International Preliminary Report on Patentability and Written Opinion issued in International Application No. PCT/US2007/087029, dated Jun. 18, 2009.
PCT International Preliminary Report on Patentability and Written Opinion issued in International Application No. PCT/US2007/087031, dated Jun. 18, 2009.
PCT International Preliminary Report on Patentability and Written Opinion issued in International Application No. PCT/US2007/087033, dated Jun. 18, 2009.
PCT International Preliminary Report on Patentability and Written Opinion issued in International Application No. PCT/US2007/087037, dated Jun. 18, 2009.
PCT International Preliminary Report on Patentability and Written Opinion issued in International Application No. PCT/US2007/087038, dated Jun. 18, 2009.
PCT International Preliminary Report on Patentability and Written Opinion issued in International Application No. PCT/US2007/089206, dated Jun. 18, 2009.
PCT International Preliminary Report on Patentability issued in International Application No. PCT/US2007/078952, dated Feb. 11, 2010.
PCT International Preliminary Report on Patentability issued in International Application No. PCT/US2008/066025, dated Dec. 23, 2009.
PCT International Preliminary Report on Patentability issued in International Application No. PCT/US2008/076246, dated Mar. 16, 2010.
PCT International Preliminary Report on Patentability issued in International Application No. PCT/US2009/033556, dated Aug. 19, 2010.
PCT International Preliminary Report on Patentability issued in International Application No. PCT/US2009/036195, dated Sep. 16, 2010.

(56) References Cited

OTHER PUBLICATIONS

PCT International Preliminary Report on Patentability issued in International Application No. PCT/US2009/038399, dated Oct. 7, 2010.
PCT International Preliminary Report on Patentability issued in International Application No. PCT/US2009/039935, dated Oct. 21, 2010.
PCT International Preliminary Report on Patentability issued in International Application No. PCT/US2009/043361, dated Nov. 18, 2010.
PCT International Preliminary Report on Patentability, issued in International Application No. PCT/US2007/078859, dated Apr. 2, 2009.
PCT International Preliminary Report on Patentability, issued in International Application No. PCT/US2007/078894, dated Apr. 2, 2009.
PCT International Preliminary Report on Patentability, issued in International Application No. PCT/US2007/078936, dated Apr. 2, 2009.
PCT International Search Report and Written Opinion issued in International Application No. PCT/US2009/064015, dated Jul. 26, 2010.
PCT International Search Report and Written Opinion issued in International Application No. PCT/US2008/066025, dated Sep. 16, 2009.
PCT International Search Report and Written Opinion issued in International Application No. PCT/US2009/036195, dated Sep. 4, 2009.
PCT International Search Report and Written Opinion issued in International Application No. PCT/US2009/039935, dated Sep. 17, 2009.
PCT International Search Report and Written Opinion issued in International Application No. PCT/US2009/043361, dated Nov. 4, 2009.
PCT International Search Report and Written Opinion issued in International Application No. PCT/US2007/078952, dated Jan. 26, 2010.
PCT International Search Report and Written Opinion issued in International Application No. PCT/US2008/087762, dated Mar. 16, 2010.
PCT International Search Report and Written Opinion issued in International Application No. PCT/US2009/038399, dated Mar. 3, 2010.
Beier et al., "CD133(+) and CD133(−) glioblastoma-derived cancer stem cells show differential growth characteristics and molecular profiles," Cancer Res., 67(9):4010-5, 2007.
Bell and Dutta, "DNA replication in eukaryotic cells," Annu Rev Biochem, 71:333-374,2002.
Bell et al., "Androgen responsive adult human prostatic epithelial cell lines immortalized by humanpapillomavirus 18," Carcinogenesis, 18(6):1215-1223, 1997.
Bellovin et al., "Reciprocal regulation of RhoA and RhoC characterizes the EMT and identifies RhoC as a prognostic marker of colon carcinoma," Oncogene, 25 (52): 6959-6967, 2006.
Ben-Porath et al., "An embryonic stem cell-like gene expression signature in poorly differentiated aggressive human tumors," Nat. Genet., 40(5):499-507, 2008.
Bendtsen et al., "Feature-based prediction of non-classical and leaderless protein secretion," Protein Eng. Des. Sel., 17: 349-356, 2004.
Benlloch et al., "Role ofCEA, PLUNC and CK19 mRNA expression in lymph nodes from resected stage I non-small cell lung cancer (NSCLC) patients as markers of occult micrometastasis: A pilot study," Lung Cancer, Abstract No. P-649, 49(1):S289, 2005.
Bentwich et al., "Identification of hundreds of conserved and nonconserved human microRNAs," Nat Genet., 37(7):766-770, 2005.
Berezikov et al, Cell, "Phylogenetic shadowing and computational identification of human microRNA genes," 120(1):21-24, 2005.

Berman et al., "Medulloblastoma growth inhibition by hedgehog pathway blockade," Science, 297(5586): 1559-61, 2002.
Bertagnolli et al., "Sentinel node staging of resectable colon cancer: results of a multicenter study," Ann. Surg., 240(4):624-630, 2004.
Billottet et al., "A selective inhibitor of the p110delta isoform of PI 3-kinase inhibits AML cell proliferation and survival and increases the cytotoxic effects ofVP16," Oncogene, 25 (50):6648-6659, 2006.
Birchmeier et al., "Met, metastasis, motility and more," Nat Rev Mol Cell Biol, 4(12):915-925, 2003.
Birnie et al., "Gene expression profiling of human prostate cancer stem cells reveals a proinflammatory phenotype and the importance of extracellular matrix interactions," Genome Biol., 9(5):R83. [Epub ahead of print], 2008.
Biswas et al., "Transforming growth factor beta receptor type II inactivation promotes the establishment and progression of colon cancer," Cancer Res., 64 (14): 4687-4692, 2004.
Bitomsky et al., "Transformation suppressor protein Pdcd4 interferes with JNK-mediated phosphorylation of c-Jun and recruitment of the coactivator p300 by c-Jun," Oncogene, 23(45):7484-93, 2004.
Black et al., "Expression of cyclin D1, cyclin E, EGFR, UBE1L and K167 in paired benign and malignant lung tissues," Lung Cancer, 49:S289, Abstract P-650, 2005.
Blanc et al., "Wnt-5a gene expression in malignant human neuroblasts," Cancer Lett., 228 (1-2): 117-123,2005.
Blobe et al., "Functional roles for the cytoplasmic domain of the type III transforming growth factor beta receptor in regulating transforming growth factor beta signaling," J Biol Chem, 276(27):24627-24637, 2001.
Blower et al., "MicroRNAs modualte the chemosensitivity of tumor cells," Mol Cancer Ther, 7(1):1-9, 2008.
Boccaccio and Comoglio, "Invasive growth: a MET-driven genetic programme for cancer and stem cells," Nat Rev Cancer, 6(8):637-645, 2006.
Bodner-Adler et al., "Serum levels of angiogenin (ANG) in invasive cervical cancer and in cervical intraepithelial neoplasia (CIN)," Anticancer Res., 21 (1B): 809-812, 2001.
Bommer et al., "p53-mediated activation ofmiRNA34 candidate tumor-suppressor genes," Current Biology, 17:1298-1307, mailed 2007.
Bonci et al., "The miR-15A/miR-16-I cluster controls prostate cancer progression by targeting multiple oncogenic activities," European Urology Supplements, Abstract No. 802, 7(3):271, 2008.
Bonci et al., "The miR-15a-miR-16-1 cluster controls prostate cancer by targeting multiple oncogenic activities," Nature Medicine, 14(11):1271-1277, 2008.
Bosch and de Sanjose, "The epidemiology of human papillomavirus infection and cervical cancer," Dis Markers., 23(4):213-27, 2007.
Bostwick et al., "Amphiregulin expression in prostatic intraepithelial neoplasia and adenocarcinoma: a study of93 cases," Prostate, 58(2):164-168, 2004.
Bottoni et al., "miR-15a and miR-16-1 Down-Regulation in Pituitary Adenomas," J Cell. Physiol., 204:280-285, 2005.
Boultwood et al., "Low expression of the putative tumour suppressor gene gravin in chronic myeloid leukaemia, myelodysplastic syndromes and acute myeloid leukaemia," Br J Haematol, 126( 4):508-511, 2004.
Bourguignon et al., "Hyaluronan-CD44 interaction activates stem cell marker Nanog, Stat-3-mediated MDR1 gene expression, and ankyrin-regulated multidrug efflux in breast and ovarian tumor cells," J Biol. Chem., 283(25):17635-51,2008.
Braasch et al., "RNA interference in mammalian cells by chemically-modified RNA," Biochemistry, 42:7967-7975,2003.
Brazma and Vilo, "Gene expression data analysis," FEES Letters, 480:17-24, 2000.
Brennecke et al., "Bantam encodes a developmentally regulated micro RNA that controls cell proliferation and regulates the proapoptotic gene hid in *Drosophila*," Cell, 113:25-36, 2003.
Brioschi et al., "Down-regulated ofmicroRNAs 222/221 in acute myelogenous leukemia with deranged core-binding factor subunits," Neoplasia, 12(11):866-876, 2010.

(56) References Cited

OTHER PUBLICATIONS

Brothman et al., "Metastatic properties of the human prostatic cell line, PPC-1, in a thymic nude mice," JUral., 145(5):1088-1091, 1991.

Brown and Regillo, "Anti-VEGF agents in the treatment of neovascular age-related macular degeneration: applying clinical trial results to the treatment of everyday patients," Am J Ophthalmol., 144(4):627-637, 2007.

Bullinger et al., "Gene expression profiling in acute myeloid leukemia," Journal of Clinical Oncology, 23(26):6296-6305, 2005.

Burdy et al., "Identifying patients with T3-T4 node-negative colon cancer at high risk of recurrence," Dis Colon Rectum, 44:1682-1688,2001.

Burmistrova et al., "MicroRNA in schizophrenia: Genetic and expression analysis ofmiR-1300b (22q 11)", Biochemistry, vol. 72, No. 5, pp. 578-582, May 2007.

Bussing et al., "let-7 microRNAs in development, stem cells and cancer," Trends in Molecular Medicine, 14(9):400-409, 2008.

Bustin et al., "Real-time reverse transcription PCR (qRT-PCR) and its potential use in clinical diagnosis," Clinical Science, 109:365-379,2005.

Byrd et al., "Pretreatment cytogenetic abnormalities are predictive of induction success, cumulative incidence of relapse, and overall survival in adult patients with de novo acute myeloid leukemia: results from Cancer and Leukemia Group B (CALGB 8461)" Blood,100:4325-4336, 2002.

Cai et al., "Human papilloma virus genotype 31 does not express detectable micro RNA levels during latent or productive virus replication," J Viral., 80(21 ): 10890-3, 2006.

Calin and Croce, "Genomics of chronic lymphocytic leukemia microRNAs as new players with clinical significance," Seminars in Oncology, 33(2): 167-173, 2006.

Calin and Croce, "MicroRNA signatures in human cancers," Nat Rev Cancer, 6(11):857-866, 2006.

Calin and Croce, "MicroRNA-cancer connection: the beginning of a new tale," Cancer Res., 66 (15):7390-7394, 2006.

Calin and Croce, "MicroRNAs and chromosomal abnormalities in cancer cells," Oncogene, 25 ( 46):6202-621 0, 2006.

Calin et al., "A Micro RNA signature associated with prognosis and progression in chronic lymphocytic leukemia," New England Journal of Medicine, 353(17):1793-1801, 2005.

Calin et al., "Frequent deletions and down-regulation of micro-RNA genes miR15 and miR16 at 13q14 in chronic lymphocytic leukemia," Proc. Natl. Acad. Sci. USA, 99:15524-15529,2002.

Calin et al., "Human micro RNA genes are frequently located at fragile sites and genomic regions involved in cancers," PNAS, 101(9):2999-3004, 2004.

Schwarz et al., "Asymmetry in the assembly of the RNAi enzyme complex," Cell, 115:199-208, 2003.

Scoggins et al., "Prospective multi-institutional study of reverse transcriptase polymerase chain reaction for molecular staging of melanoma," J Cliin. Oneal., 24:2849-2857,2006.

Scott et al., "BCL2 antisense reduces prostate cancer cell survival following irradiation," Cancer Biotherapy & Radiopharmaceuticals, 17(6):647-656, 2002.

Search Report and Written Opinion in PCT/US2012/055255 dated May 7, 2013.

Search Report and Written Opinion in PCT/US2012/062295 dated Mar. 22, 2013.

Segal et al., "A module map showing conditional activity of expression modules in cancer," Nature Genetics, 36 (10):1090-1098, 2004.

Seggerson et al., "Two genetic circuits repress the *Caenorhabditis elegans* heterochronic gene lin-28 after translation initiation," Dev. Biol., 243:215, 2002.

Sellner et al., "Reverse transcriptase inhibits Taq polymerase activity," Nucleic Acids Research, 20(7):1487-1490, 1992.

Sementchenko et al, "ETS2 function is required to maintain the transformed state of human prostate cancer cells," Oncogene, 17 (22): 2883-2888, 1998.

Semple and Duncker, "ORC-associated replication factors as biomarkers for cancer," Biotechnol Adv, 22(8):621-631, 2004.

Sevignani et al., "Mammalian microRNAs: a small world for fine-tuning gene expression," Mamm. Genome, 17 (3):189-202, 2006.

Shah, et al., "FGFR4 overexpression in pancreaticc cancer is mediated by an intronic enhancer activated by HNF1alpha," Oncogene, 21 (54): 8251-8261,2002.

Shelly et al., "Epiregulin is a potent pan-ErbB ligand that preferentially activates heterodimeric receptor complexes," J Biol. Chem., 273 (17): 10496-10505, 1998.

Shelton et al., "MicroRNAs and Human Cancer," Abstract submitted for a Cold Spring Symposium in early Jun. 2006—71 st Symposium: Regulatory RNAs.

Shen et al., "MicroRNAs regulate ocular neovascularization," Molecular Therapy, 16(7): 1208-1216, 2008.

Shen et al., "Oxidative damage in age-related macular degeneration," Histol. Histopathol. 22(12):1301-1308, 2007.

Shen et al., "Suppression of ocular neovascularization with siRNA targeting VEGF receptor 1," Gene Therapy, 13:225-234, 2006.

Shepherd et al., "Expression profiling ofCD133+ and CD133−epithelial cells from human prostate," Prostate, 68(9):1007-1024, 2008.

Sherr and McCormick, "The RB and p53 pathways in cancer," Cancer Cell, 2(2): 103-112, 2002.

Sherr and Roberts, "CDK inhibitors: positive and negative regulators ofG1-phase progression," Genes Dev, 13(12):1501-1512, 1999.

Shi et al., "Facile means for quantifYing micro RNA expression by real-time PCR," BioTechniques, 39(4):519-524, 2005.

Shibahara et al., "Down-regulation of Skp2 is correlated with p2 7-associated cell cycle arrest induced by phenylacetate in human prostate cancer cells," Anticancer Res., 25 (3b): 1881-1888, 2005.

Shigemasa et al., "Increased MCL-1 expression is associated with poor prognosis in ovarian carcinomas," Jpn. J Cancer Res., 93(5):542-550, 2002.

Shimo et al., "Connective tissue growth factor as a major angiogenic agent that is induced by hypoxia in a human breast cancer cell line," Cancer Lett., 174(1):57-64, 2001.

Shimoyama et al., "Increased serum angiogenin concentration in colorectal cancer is correlated with cancer progression," Clin. Cancer Res., 5 (5): 1125-1130, 1999.

Shingara et al., "An optimized isolation and labeling platform for accurate microRNA expression profiling," RNA, 11:1461-1470,2005.

Shipitsin et al., "Molecular definition of breast tumor heterogeneity," Cancer Cell, 11(3):259-73, 2007.

Shuldiner et al., "RNA template-specific polymerase chain reaction RS-PCR a novel strategy to reduce dramatically false positives," Gene, 91(1):139-142, 1990.

Shyu et al., "RARRES3 expression positively correlated to tumour differentation in tissues of colorectal adenocarcinoma," Br. J Cancer, 89 (1): 146-151,2003.

Si et al., "miR-21-mediated tumor growth," Oncogene, 1-5, 2006.
Si et al., "miR-21-mediated tumor growth," Oncogene, 26(19):2799-2803, 2007.

Simpson et al., "Altered expression of Erg and Ets-2 transcription factors is associated with genetic changes at 21q22.2-22.3 in immortal and cervical carcinoma cell lines," Oncogene, 14 (18): 2149-2157, 1997.

Singh et al., "Identification of a cancer stem cell in human brain tumors," Cancer Res., 63(18):5821-8, 2003.

Singh et al., "Overexpression ofvimentin: role in the invasive phenotype in an androgenindependent model of prostate cancer," Cancer Res, 63 (9):23 06-2311, 2003.

Sinner et al., "Sox17 and Sox4 differentially regulate beta-catenin/T-cell factor activity and proliferation of colon carcinoma cells," Mol. Cell Biol., 27(22):7802-15, 2007.

Sirera et al., "The analysis of serum DNA concentration by means of hTER T quantification: A useful prognostic factor in advanced non-small cell lung cancer (NSCLC)," Lung Cancer, 49:S74, Abstract PD-026, 2005.

(56) References Cited

OTHER PUBLICATIONS

Skotzko et al., "Retroviral vector-mediated gene transfer of antisense cyclinG 1 (CYCG 1) inhibits proliferation of human osteogenic sarcoma cells," Cancer Res., 55 (23): 5493-5498, 1995.
Slaby et al., "Altered expression ofmiR-21, miR-31, miR-143 and miR-145 is related to clinicopathologic features of colorectal cancer," Oncology, 72(5-6):397-402, 2007.
Slack et al., "The lin-41 RBCC gene acts in the C. elegans heterochronic pathway between the let-7 regulatory RNA and the LIN-29 transcription factor," Malec. Cell, 5( 4):659-669, 2000.
Slack, "Control of Development by microRNAs," believed at the time of the filing of this form to have been presented by Frank Slack at Keystone miRNAs on Apr. 15, 2005.
Slack, "Control of Development by microRNAs," believed at the time of the filing of this form to have been presented by Frank Slack at liT Bombay on Jan. 28, 2004.
Slack, "Control of Development by microRNAs," believed at the time of the filing of this form to have been presented by Frank Slack at UCT on Feb. 17, 2004.
Slack, "Control of Development by microRNAs," believed at the time of the filing of this form to have been presented by Frank Slack at UNMC on Mar. 29, 2004.
Slack, "Control of developmental timing by microRNAs," believed at the time of the filing of this form to have been presented by Frank Slack at Santa Cruz in Aug. 2004.
Slack, "MicroRNA control of oncogene expression," believed at the time of the filing of this form to have been presented by Frank Slack at Slack GTBIO on Nov. 8, 2004.
Slack, "MicroRNAs and cancer," believed at the time of the filing of this form to have been presented by Frank Slack at University of Puerto Rico Bayamon on Sep. 22, 2004.
Slack, "Multiple, dynamic microRNA ribonucleoprotein complexes with select microRNA cargos in C. elegans," believed at the time of the filing of this form to have been presented by Frank Slack at Gordon on Jun. 8, 2004.
Slack, "Small RNA genes as potential causes and treatments of cancer," believed at the time of the filing of this form to have been presented by Frank Slack at Jaslok on Feb. 1, 2004.
Slack, "Temporal patterning and biological timing," believed at the time of the filing of this form to have been presented by Frank Slack at Dartmouth on Mar. 19, 2004.
Smirnova et al., "Regulation of miRNA expression during neural cell specification," Eur J Neurosci, 21(6):1469-1477, 2005.
Smith et al., "Exclusive amplification of eDNA template (EXACT) RT-PCR to avoid amplifying contaminating genomic pseudo genes," BioTechniques, 31( 4): 776-778, 780, 782, 2001.
Smith et al., "Human papilloma virus type distribution in invasive cervical cancer and highgrade cervical lesions: a meta-analysis update," Int. J Cancer, 121(3):621-32, 2007.
Smith et al., "Malignant transformation of mammalian cells initiated by constitutive expression ofthe polo-like kinase," Biachem Biaphys Res Cammun, 234(2):397-405, 1997.
Smith et al., "Overexpression of aurora B kinase (AURKB) in primary non-small cell lung carcinoma is frequent, generally driven from one allele, and correlates with the level of genetic instability," Br J Cancer, 93(6):719-729, 2005.
Smith et al., "Oxygen-induced retinopathy in the mouse," Invest. Ophthalmol. Vis. Sci. 35(1):101-111, 1994.
Sommers et al., "Loss of epithelial markers and acquisition ofvimentin expression in adriamycin- and vinblastine-resistant human breast cancer cell lines," Cancer Res, 52(19):5190-5197, 1992.
Sparmann and Bar-Sagi, "Ras-induced interleukin-8 expression plays a critical role in tumor growth and angiogenesis," Cancer Cell, 6(5):447-458, 2004.
Stehelin et al., "DNA related to the transforming gene( s) of avian sarcoma viruses is present in normal avian DNA," Nature, 260(5547): 170-173, 1976.
Stepinski et al., "Synthesis and properties ofmRNAs containing the novel 'anti-reverse' cap analogs 7-methyl(3'0-methyl)GpppG and 7-methyl(e'-deoxy)GpppG," RNA, 7:1486-1495, 2001.

Stone et al., "Isolation of a human prostate carcinoma cell line (DU 145)," Int. J Cancer, 21 (3): 274-281, 1978.
Strebhardt and Ullrich, "Targeting polo-like kinase 1 for cancer therapy," Nat Rev. Cancer, 6 (4): 321-330, 2006.
Sturniolo et al., "A novel tumor suppressor protein promotes keratinocyte terminal differentiation via activation oftype I transglutaminase," J Bial. Chem., 278 (48): 48066-48073, 2003.
Sueoka et al., "Detection of plasma hnRNP B 1 mRNA, a new cancer biomarker, in lung cancer patients by quantitative real-time polymerase chain reaction," Lung Cancer, 48(1):77-83, 2005.
Suh et al., "Human embryonic stem cells express a unique set of microRNAs," Developmental Biology, 270:488-498, 2004.
Sui et al., "Clinical significance of Skp2 expression, alone and combined with Jab 1 and p2 7 in epithelial ovarian tumors," Oneal. Rep., 15 (4): 765-771,2006.
Sum et al., "Overexpression ofLM04 induces mammary hyperplasia, promotes cell invasion, and is a predictor of poor outcome in breast cancer," Prac Natl Acad Sci US A, 1 02(21 ):7659-7664,2005.
Sum et al., "The LIM domain protein LM04 interacts with the cofactor CtiP and the tumor suppressor BRCA1 and inhibits BRCA1 activity," J Bial Chern, 277(1 0):7849-7856, 2002.
Sun et al., "Development of a micro-array to detect human and mouse microRNAs and characterization of expression in human organs," Nucleic Acids Research, 32(22):e188, 2004.
Sun et al., "Dowmegulation ofCCND1 and CDK6 by miR-34a induces cell cycle arrest," FEES Letters, 582:1564-1568,2008.
Sunpaweravong et al., "Epidermal growth factor receptor and cyclin D 1 are independently amplified and overexpressed in esophageal squamous cell carcinoma," J Cancer Res Clin Oneal, 131(2):111-119, 2005.
Swanson et al., "The prognosis of T3NO colon cancer is dependent on the number of lymph nodes examined," Ann. Surg. Oneal., 10(1):65-71, 2003.
Szafranska et al., "A unique micro RNA molecular signature for pancreatic carcinoma," AACRPancreatic Cancer: Early Detection and Novel Therapeutics, Chapel Hill, NC, Jun. 26-27, 2006.
Szafranska et al., "MicroRNA expression alterations are linked to tumorigenesis and nonneoplastic processes in pancreatic ductal adenocarcinoma", Oncogene, vol. 26, No. 30, pp. 4442-4452, Jun. 28, 2007.
Szafranska, et al., J Mol Diag. 1 0(5), 2008.
Tagawa et al., "Genome-wide array-based CGH for mantle cell lymphoma: identification of homozygous deletions ofthe proapoptotic gene BIM," Oncogene, 24(8):348-1358, 2005.
Takamizawa et al., "Reduced expression of the let-7 microRNAs in human lung cancers in association with shortened postoperative survival," Cancer Research, 64:3753-3756, 2004.
Takanami, "The prognostic value of overexpression of Skp2 mRNA in non-small cell lung cancer.," Oneal. Rep., 13 (4): 727-731,2005.
Takei et al., "A small interfering RNA targeting vascular endothelial growth factor as cancer therapeutics," Cancer Research, 64:3365-3370, 2004.
Takeshita et al., "Efficient delivery of small interfering RNA to bone-metastatic tumors by using atelocollagen in vivo," PNAS, 102(34): 12177-12182, 2005.
Takeshita et al., "Systemic delivery of synthetic microRNA-16 inhibits the growth of metastatic prostate tumors via dowmegulation of multiple cell-cycle genes," Molecular Therapy, 18(1):181-187, 2010.
Takeuchi et al., "Prognostic significance of molecular upstaging of paraffin-embedded sentinel lymph nodes in melanoma patients," J Clin. Oneal., 22:2671-2680, 2004.
Takimoto et al., "Genetic alterations in the retinoblastoma protein-related p107 gene in human hematologic malignancies," Biochem Biophys Res Commun, 251(1):264-268, 1998.
Tanaka et al., "A novel frizzled gene identified in human esophageal carcinoma mediates APC/beta-catenin signals," Proc. Natl. Acad. Sci. USA, 95 (17): 10164-10169, 1998.
Tang et al., "Prostate cancer stem/progenitor cells: identification, characterization, and implications," Mol. Carcinog., 46(1):1-14, 2007.

(56) References Cited

OTHER PUBLICATIONS

Tang et al., "PS 7-2 microma expression profile in cervical cancer and its derived cell lines," 23rd International Papillomavirus Conference and Clinical Workshop, Prague, Czech Republic, Sep. 1-7, 2006.
Tang et al., "Transforming growth factor-beta can suppress tumorigenesis through effects on the putative cancer stem or early progenitor cell and committed progeny in a breast cancer xenograft model;" Cancer Res., 67(18):8643-52, 2007.
Taniwaki et al., "Gene expression profiles of small-celllung cancers: molecular signatures of lung cancer," /nt J Oneal, 29(3):567-575, 2006.
Tassi et al., "Enhancement of fibroblast growth factor (FGF) activity by an FGF-binding protein," J Biol. Chem., 276(43):40247-40253, 2001.
Tazawa et al., "Tumor-suppressive miR-34a induces senescence-like growth arrest through modulation of the E2F pathway in human colon cancer cells," PNAS, 104(39): 15472-15477, 2007.
Thügersen et al., "A subclass of HER1 ligands are prognostic markers for survival in bladder cancer patients," Cancer Res., 61 (16): 6227-6233, 2001.
The Japanese Journal of Clinical and Experimental Medicine. 72(1): 224-228, 1995.
Thiyagarajan et al., "Role ofGLl2 transcription factor in growth and tumorigenicity of prostate cells," Cancer Res., 67(22):10642-6, 2007.
Tijsterman and Plasterk, "Dicers at RISC: the mechanism of RNAi," Cell, 117:1-4, 2004.
Tockman et al., "Considerations in bringing a cancer biomarker to clinical application," Cancer Research, 52:2711s-2718s, 1992.
Toh et al., "A novel candidate metastasis-associated gene, mta1, differentially expressed in highly metastatic mammary adenocarcinoma cell lines. eDNA cloning, expression, and protein analyses," J Biol Chem, 269(37):22958-22963, 1994.
Toh et al., "Overexpression of metastasis-associated MTA1 mRNA in invasive oesophageal carcinomas," BrJCancer, 79(11-12):1723-1726, 1999.
Einama et al., "High-level Skp2 expression in pancreatic ductal adenocarcinoma: correlation with the extent of lymph node metastasis, higher histological grade, and poorer patient outcome," Pancreas, 32(4):376-381, 2006.
Engelmann et al., "MCF7 side population cells with characteristics of cancer stem/progenitor cells express the tumor antigen MUC1," Cancer Res., 68(7):2419-26, 2008.
Esau et al., "MicroRNA-143 regulates adipocyte differentiation," Journal of Biological Chemistry, 279(50):52361-52365, 2004.
Esquela-Kerscher and Slack, "Oncomirs- microRNAs with a role in cancer," Nat Rev Cancer, 6(4):259-269, 2006.
Esquela-Kerscher et al., "The let-7 microRNA reduces tumor growth in mouse models oflung cancer," Cell Cycle, 7(6):759-764, 2008.
Esser et al., "The role of sentinel lymph node mapping in staging of colon and rectal cancer," Dis Colon Rectum, 44(6):850-856, 2001.
European Search Report issued in European Application No. 09154092.2, dated Aug. 12, 2009.
Extended European Search Report issued in European Application No. 10181713.8, dated Jun. 24, 2011.
Extended European Search Report issued in European Application No. 10181728.6, dated Jul. 8, 2011.
Extended European Search Report issued in European Application No. 10181821.9, dated Jul. 29, 2011.
Extended European Search Report issued in European Application No. 10183451.3, dated Jan. 12, 2011.
Extended European Search Report issued in European Application No. 10183456.2, dated Jan. 12, 2011.
Extended European Search Report issued in European Application No. 10183462.0, dated Feb. 4, 2011.
Extended European Search Report issued in European Application No. 10183470.3, dated Feb. 3, 2011.
Extended European Search Report issued in European Application No. 10183481.0, dated Jan. 7, 2011.
Extended European Search Report issued in European Application No. 10183490.1, dated Feb. 4, 2011.
Extended European Search Report issued in European Application No. 10183515.5, dated Feb. 7, 2011.
Extended European Search Report issued in European Application No. 10183525.4, dated Feb. 7, 2011.
Extended European Search Report issued in European Application No. 10183534.5, dated Feb. 15, 2011.
Extended European Search Report issued in European Application No. 10183538.7, dated Jan. 12, 2011.
Extended European Search Report issued in European Application No. 10183543.7, dated Feb. 4, 2011.
Extended European Search Report issued in European Application No. 10183560.1, dated Jan. 7, 2011.
Extended European Search Report issued in European Application No. 10183567.6, dated Jan. 7, 2011.
Extended European Search Report issued in European Application No. 10183577.5, dated Feb. 14, 2011.
Extended European Search Report issued in European Application No. 10183589.0, dated Jan. 7, 2011.
Extended European Search Report issued in European Application No. 10183596.5, dated Feb. 14, 2011.
Extended European Search Report issued in European Application No. 10183611.2, dated Jan. 7, 2011.
Extended European Search Report issued in European Application No. 10183639.3, dated Mar. 2, 2011.
Extended European Search Report issued in European Patent Application No. 12159733.0, dated Jul. 18, 2012.
Ezzat et al., "Dual inhibition of RET and FGFR4 restrains medullary thyroid cancer cell growth," Clin. Cancer Res., 11(3): 1336-1341,2005.
Fakharzadeh et al., "Tumorigenic potential associated with enhanced expression of a gene that is amplified in a mouse tumor cell line," Embo J, 10(6):1565-1569, 1991.
Fan et al., "Hedgehog signaling promotes prostate xenograft tumor growth," Endocrinology, 145:3961-3970,2004.
Fan et al., "Notch pathway inhibition depletes stem-like cells and blocks engraftment in embryonal brain tumors," Cancer Res., 66(15): 7445-52, 2006.
Faried et al., "RhoA and RhoC proteins promote both cell proliferation and cell invasion of human oesophageal squamous cell carcinoma cell lines in vitro and in vivo," Eur. J Cancer, 42 (10): 1455-1465, 2006.
Fay et al., "Analysis of CUL-5 expression in breast epithelial cells, breast cancer cell lines, normal tissues and tumor tissues," Mol. Cancer, 2:40, 2003.
Fazi et al., "A minicircuitry comprised ofmicroRNA-223 and transcription factors NFI-A and C/EBPa regulates human granulopoiesis," Cell, 123:819-831, 2005.
Feldman and Feldman, "The development of androgen-independent prostate cancer," Nat. Rev. Cancer, 1(1):34-45, 2001.
Fernandez et al., "The matrix metalloproteinase-9/neutrophil gelatinase-associated lipocalin complex plays a role in breast tumor growth and is present in the urine of breast cancer patients," Clin. Cancer Res., 11(15):5390-5395, 2005.
Ferris et al., "Molecular staging of cervical lymph nodes in squamous cell carcinoma of the head and neck," Cancer Res., 65:2147-2156, 2005.
Fesik, "Promoting apoptosis as a strategy for cancer drug discovery," Nat Rev Cancer, 5(11 ):876-885, 2005.
Firth and Baxter, "Cellular actions of the insulin-like growth factor binding proteins," Endocrin. Rev., 23 (6): 824-854, 2002.
Folkman, "Successful treatment of an angiogenic disease," N Engl J Med 320:1211-1212, 1989.
Fontana et al, "MicroRNA's 17-5p-20a-106a control monocytopeiesis through AML1 targeting and M-CSF receptor upregulation," Nature Cell Biology, 9(7):775-787, 2007.
Francipane et al., "Crucial role of interleukin-4 in the survival of colon cancer stem cells," Cancer Res., 68(11):4022-4025, 2008.

(56) References Cited

OTHER PUBLICATIONS

Freelove and Walling, "Pancreatic cancer: diagnosis and management," Am. Fam. Physician, 73(3):485-492, 2006.
Froehler, et al., Nuc Acid Res. 14(13): 5399-5407, 1986.
Fujiwara et al., "Isolation of a candidate tumor suppressor gene on chromosome 8p21.3-p22 that is homologous to an extracellular domain of the PDGF receptor beta gene," Oncogene, 1 0(5):891-895, 1995.
Galardi et al., "miR-221 and miR-222 expression affects the proliferation potential of human prostate carcinoma cell lines by targeting p27Kip1," J Biol. Chem, 282(32):23716-23724, 2007.
Office Action issued in Australian Application No. 2005333165, dated Feb. 7, 2011.
Office Action issued in Chinese Application No. 200780050263.1, dated Mar. 28, 2011.
Office Action issued in European Application No. 02720894.1, dated Jul. 11, 2007.
Office Action issued in European Application No. 05804851.3, dated Dec. 21, 2007.
Office Action issued in European Application No. 05804851.3, dated Jul. 30, 2008.
Office Action issued in European Application No. 05815286.9, dated Apr. 3, 2008.
Office Action issued in European Application No. 05858321.2, dated Apr. 11, 2008.
Office Action issued in European Application No. 05858321.2., dated Apr. 16, 2010.
Office Action issued in European Application No. 07 814 937.4, dated Apr. 8, 2011.
Office Action issued in European Application No. 07 871 691.7, dated Oct. 28, 2010.
Office Action issued in European Application No. 07 871 693.3, dated Oct. 18, 2010.
Office Action issued in European Application No. 07871689.1, dated Dec. 15, 2009.
Office Action issued in European Application No. 07871690.9, dated Dec. 14, 2009.
Office Action issued in European Application No. 07871691.7, dated Dec. 14, 2009.
Office Action issued in European Application No. 07871693.3, dated Dec. 9, 2009.
Office Action issued in European Application No. 07871694.1, dated Dec. 10, 2009.
Office Action issued in European Application No. 07871756.8, dated Jun. 30, 2010.
Office Action issued in European Application No. 07871756.8, dated Oct. 20, 2009.
Office Action issued in European Application No. 08 831 073.5, dated Aug. 16, 2010.
Office Action issued in European Application No. 08770269.2, dated Jul. 30, 2010.
Office Action issued in European Application No. 08831073.5, dated Feb. 25, 2011.
Office Action issued in European Application No. 09 154 092.2, dated Mar. 30, 2011.
Office Action issued in European Application No. 09 154 092.2, dated Nov. 10, 2010.
Office Action issued in European Application No. 09154092.2, dated Apr. 2010.
Office Action issued in European Application No. 09717913.9, dated Mar. 7, 2011.
Office Action issued in Japanese Application No. 2007-515415, dated Jan. 26, 2011 (and English language translation thereof).
Office Action issued in Japanese Application No. 2007-541398, dated Mar. 28, 2011.
Office Action issued in U.S. Appl. No. 09154092.2, dated May 7, 2009.
Office Action issued in U.S. Appl. No. 10/632,534, dated Jul. 11, 2006.
Office Action issued in U.S. Appl. No. 10/632,534, dated Mar. 24, 2006.
Office Action issued in U.S. Appl. No. 10/632,534, dated Mar. 29, 2007.
Office Action issued in U.S. Appl. No. 10/632,539, dated Apr. 17, 2007.
Office Action issued in U.S. Appl. No. 10/632,539, dated Jul. 27, 2006.
Office Action issued in U.S. Appl. No. 10/632,539, dated Mar. 27, 2006.
Office Action issued in U.S. Appl. No. 10/880,350, dated Feb. 21, 2006.
Office Action issued in U.S. Appl. No. 10/880,350, dated Oct. 4, 2006.
Office Action issued in U.S. Appl. No. 10/880,350, dated Sep. 10, 2007.
Office Action issued in U.S. Appl. No. 10/963,415, dated Apr. 13, 2007.
Office Action issued in U.S. Appl. No. 10/963,415, dated Aug. 2, 2007.
Office Action issued in U.S. Appl. No. 10/963,415, dated Mar. 17, 2008.
Office Action issued in U.S. Appl. No. 10/963,415, dated Mar. 9, 2009.
Office Action issued in U.S. Appl. No. 11/141,707, dated Feb. 9, 2009.
Office Action issued in U.S. Appl. No. 11/141,707, dated Jan. 6, 2010.
Office Action issued in U.S. Appl. No. 11/141,707, dated Jul. 17, 2008.
Office Action issued in U.S. Appl. No. 11/141,707, dated Jun. 19, 2009.
Office Action issued in U.S. Appl. No. 11/141,707, dated Mar. 11, 2010.
Office Action issued in U.S. Appl. No. 11/141,707, dated May 15, 2007.
Office Action issued in U.S. Appl. No. 11/141,707, dated Oct. 17, 2007.
Office Action issued in U.S. Appl. No. 11/141,707, dated Sep. 2, 2010.
Hishikawa et al., "Connective tissue growth factor induces apoptosis in human breast cancer cell line MCF-7," J Biol. Chern., 274(52):37461-37466, 1999.
Ho et al., "Quantification of colorectal cancer micrometastases in lymph nodes by nested and real-time reverse transcriptase-PCR analysis for carcinoembryonic antigen," Clin. Cancer Res., 10(17):5777-5784, 2004.
Hodge et al., "The role ofiL-6 and STAT3 in inflammation and cancer," Eur J Cancer, 41(16):2502-2512, 2005.
Hoeflich et al., "Insulin-like growth factor-binding protein 2 in tumorigenesis: protector or promoter?" Cancer Res, 61(24):8601-8610, 2001.
Hofer et al., "The role of metastasis-associated protein 1 in prostate cancer progression," Cancer Res, 64(3):825-829, 2004.
Holmquist-Mengelbier et al., "Recruitment ofHIF-1alpha and HIF-2alpha to common target genes is differentially regulated in neuroblastoma: HIF-2alpha promotes an aggressive phenotype," Cancer Cell, 10(5):413-423, 2006.
Honma et al., "The role of atelocollagen-based cell transfection array in high-throughput screening of gene functions and in drug discovery," Current Drug Discovery Technologies, 1(4):287-294, 2004.
Hornstein et al., The microRNA miR-196 acts upstream of Hoxb8 and Shh in limb development, 2005, Nature, vol. 438, pp. 671-674.
Horoszewicz et al., "The LNCaP cell line—a new model for studies on human prostatic carcinoma," Prog Clin Biol Res., 37:115-32, 1980.
Houbaviy et al., "Embryonic stem cell-specific micro-RNAs," Developmental Cell, 5:351-358, 2003.
Houston and O'Connell, "The Fas signalling pathway and its role in the pathogenesis of cancer," Curr Opin Pharmacal, 4(4):321-326,2004.

(56) References Cited

OTHER PUBLICATIONS

Houvenaeghel et al., "Micrometastases in sentinel lymph node in a multicentric study: predictive factors of nonsentinellymph node involvement—Groupe des Chirurgiens de la Federation des Centres de Lutte Contre le Cancer," J Clin. Oneal., 24:1814-1822,2006.
Hsu et al., "BOD (Bcl-2-related ovarian death gene) is an ovarian BH3 domain-containing proapoptotic Bcl-2 protein capable of dimerization with diverse antiapoptotic Bcl-2 members," Mol Endocrinol, 12(9):1432-1440, 1998.
Hu, et al., IntJ Cancer. 128(1): 132-143, 2011.
Huang et al., "Cloning and characterization of a novel retinoid-inducible gene 1 (RIG 1) deriving from human gastric cancer cells," Mol. Cell. Endocrinol., 159: 15-24, 2000.
Huang et al., "Skp2 inhibits FOX01 in tumor suppression through ubiquitin-mediated degradation," Proc. Natl. Acad. Sci. USA, 102(5):1649-1654, 2005.
Huang et al., "Skp2 overexpression is highly representative of intrinsic biological aggressiveness and independently associated with poor prognosis in primary localized myxofibrosarcomas," Clin. Cancer Res., 12 (2): 487-498, 2006.
Huang et al., "The retinoid-inducible gene I: effect on apoptosis and mitogen-activated kinase signal pathways," Anticancer Res., 22: 799-804, 2002.
Huang et al., "Wnt5a expression is associated with the tumor proliferation and the stromal vascular endothelial growth factor—an expression in non-small-celllung cancer," J Clin. Oneal., 23 (34): 8765-8773, 2005.
Huber et al., "Variance stabilization applied to microarray data calibration and to the quantification of differential expression," Bioinformatics, 18: Suppl 1: S96-1 04, 2002.
Hughes et al., "A rapid, fully automated, molecular-based assay accurately analyzes sentinel lymph nodes for the presence of metastatic breast cancer," Ann. Surg., 243:389-398,2006.
Hummel et al., "Differentiation-induced and constitutive transcription of human papilloma virus type 31b in cell lines containing viral episomes," J Viral., 66(10):6070-80, 1992.
Hurt et al., "CD44+ CD24(–) prostate cells are early cancer progenitor/stem cells that provide a model for patients with poor prognosis," Br. J Cancer, 98( 4):756-65, 2008.
Hutvagner and Zamore, "A microRNA in a multiple-turnover RNAi enzyme complex," Science, 297(5589):2056-2060, 2002.
Hutvagner et al. "Sequence-specific inhibition of small RNA function," PLoS Biol. 2( 4):E98, 2004.
Huusko et al, "Nonsense-mediated decay microarray analysis identifies mutations ofEPHB2 in human prostate cancer," Nat. Genet., 36 (9): 979-983, 2004.
Hynes and Lane, "ERBB receptors and cancer: the complexity of targeted inhibitors," Nat Rev Cancer, 5(5):341-354, 2005.
Ibarra et al., "A role for microRNAs in maintenance of mouse mammary epithelial progenitor cells", Genes Dev., 21(24)3238-3243, 2007.
Illmer et al., "MiRNA expression signatures in actue myeloid leukemia are predictors for patient outcome. Session Type: Oral Session," Blood, 108(11): 49A, Abstract #152, 2006.
International Search Report and Written Opinion issued in International Application No. PCT/US2007/078936, dated Apr. 14, 2008.
Iorio et al., "MicroRNA gene expression deregulation in human breast cancer," Cancer Res, 65(16):7065-7070, 2005.
Iorio, et al., Cancer Res. DOI: 10.1158/0008-5472.CAN-05-1783, 2005.
Isbarn et al., "Association of numerous micro-RNAs (J..LRNAs) with prostate cancer initiation and progression," European Urology Supplements, Abstract No. 429, 6(2): 130, 2007.
Ishikawa et al., "Increases of amphiregulin and transforming growth factor-alpha in serum as predictors of poor response to gefitinib amoung patients with advanced non-small cell lung cancers," Cancer Res., 65(20):9176-9184, 2005.
Islam et al., "Vimentin expression in human squamous carcinoma cells: relationship with phenotypic changes and adherin-based cell adhesion," J Cell Biochem, 78(1 ): 141-150, 2000.

Itakura, et al., J Biolog Chern. 250(12):4592-600, 1975.
Ito et al., "Decreased expression of cyclin G2 is significantly linked to the malignant transformation of papillary carcinoma ofthe thyroid," Anticancer Res., 23(3B):2335-2338, 2003.
Ito et al., "Decreased expression of p 107 is correlated with anaplastic transformation in papillary carcinoma of the thyroid," Anticancer Res., 23(5A):3819-3824, 2003.
Ito et al., "Expression of ets-1 and ets-2 in colonic neoplasms," Anticancer Res., 22 (3): 1581-1584, 2002.
Ito et al., "Expression of p8 protein in medullary thyroid carcinoma," Anticancer Res., 25 (5): 3419-3423, 2005.
Jaakkola et al., "Amplification offgfr4 gene in human breast and gynecological cancers," Int. J Cancer, 54 (3): 378-382, 1993.
Jaattela, "Over-expression ofhsp70 confers tumorigenicity to mouse fibrosarcoma cells," Int. J Cancer, 60(5):689-693, 1995.
Jackson and Foster, "The enigmatic protein kinase Cdelta: complex roles in cell proliferation and survival," Faseb J, 18(6):627-636, 2004.
Jamieson et al., "Granulocyte-macrophage progenitors as candidate leukemic stem cells in blast-crisis CML," N En5;I. J Med., 351(7):657-67, 2004.
Jang et al., "Gene delivery from polymer scaffolds for tissue engineering," Expert Rev. Medical Devices, 1(1):127-138, 2004.
Jang et al., "MTA1 overexpression correlates significantly with tumor grade and angiogenesis in human breast cancers," Cancer Sci, 97(5):374-379, 2006.
Janknecht, "EWS-ETS oncoproteins: the linchpins ofEwing tumors," Gene, 363:1-14,2005.
Jansen et al., "Characterization of programmed cell death 4 in multiple human cancers reveals a novel enhancer of drug sensitivity," Mol. Cancer Ther., 3(2):103-110, 2004.
Jansen et al., "Epidermal expression of the translation inhibitor programmed cell death 4 suppresses tumorigenesis," Cancer Res., 65(14):6034-41, 2005.
Office Action issued in U.S. Appl. No. 11/273,640, dated Jul. 26, 2011.
Office Action issued in U.S. Appl. No. 11/273,640, dated Jun. 26, 2009.
Office Action issued in U.S. Appl. No. 11/273,640, dated May 5, 2010.
Office Action issued in U.S. Appl. No. 11/273,640, dated Nov. 20, 2009.
Office Action issued in U.S. Appl. No. 11/567,082, dated Jan. 27, 2009.
Office Action issued in U.S. Appl. No. 11/567,082, dated Jul. 21, 2008.
Office Action issued in U.S. Appl. No. 11/567,082, dated Jul. 3, 2007.
Office Action issued in U.S. Appl. No. 11/567,082, dated Nov. 13, 2007.
Office Action issued in U.S. Appl. No. 11/567,082, dated Sep. 30, 2009.
Office Action issued in U.S. Appl. No. 11/837,487, dated Mar. 25, 2009.
Office Action issued in U.S. Appl. No. 11/837,487, dated May 28, 2010.
Office Action issued in U.S. Appl. No. 11/837,487, dated Nov. 22, 2010.
Office Action issued in U.S. Appl. No. 11/837,487, dated Sep. 15, 2009.
Office Action issued in U.S. Appl. No. 11/837,488, dated Feb. 15, 2011.
Office Action issued in U.S. Appl. No. 11/837,488, dated Feb. 19, 2010.
Office Action issued in U.S. Appl. No. 11/837,490, dated Apr. 9, 2010.
Office Action issued in U.S. Appl. No. 11/837,490, dated Aug. 18, 2009.
Office Action issued in U.S. Appl. No. 11/837,490, dated Aug. 6, 2008.
Office Action issued in U.S. Appl. No. 11/837,490, dated Jan. 13, 2009.

(56) References Cited

OTHER PUBLICATIONS

Office Action issued in U.S. Appl. No. 11/837,494, dated Dec. 9, 2010.
Office Action issued in U.S. Appl. No. 11/837,494, dated Jan. 15, 2009.
Office Action issued in U.S. Appl. No. 11/837,494, dated Jan. 5, 2010.
Office Action issued in U.S. Appl. No. 11/837,494, dated Mar. 5, 2009.
Office Action issued in U.S. Appl. No. 11/837,494, dated Oct. 30, 2008.
Office Action issued in U.S. Appl. No. 11/837,495, dated Jan. 5, 2010.
Office Action issued in U.S. Appl. No. 11/837,495, dated Mar. 5, 2009.
Office Action issued in U.S. Appl. No. 11/837,495, dated Oct. 30, 2008.
Office Action issued in U.S. Appl. No. 11/837,495, dated Sep. 2, 2010.
Office Action issued in U.S. Appl. No. 11/837,498, dated Apr. 30, 2009.
Office Action issued in U.S. Appl. No. 11/837,498, dated Jan. 15, 2009.
Office Action issued in U.S. Appl. No. 11/837,498, dated May 7, 2010.
Office Action issued in U.S. Appl. No. 11/837,498, dated Nov. 20, 2009.
Office Action issued in U.S. Appl. No. 11/837,498, dated Oct. 29, 2008.
Office Action issued in U.S. Appl. No. 11/953,606, dated Aug. 10, 2009.
Office Action issued in U.S. Appl. No. 11/953,606, dated Jan. 8, 2010.
Office Action issued in U.S. Appl. No. 11/953,606, dated Jul. 1, 2010.
Office Action issued in U.S. Appl. No. 11/953,606, dated Oct. 1, 2010.
Office Action issued in U.S. Appl. No. 11/967,639, dated Mar. 13, 2009.
Office Action issued in U.S. Appl. No. 11/967,639, dated Mar. 24, 2010.
Office Action issued in U.S. Appl. No. 11/967,639, dated May 14, 2009.
Office Action issued in U.S. Appl. No. 11/967,639, dated May 14, 2010.
Office Action issued in U.S. Appl. No. 11/967,663, dated Feb. 12, 2010.
Office Action issued in U.S. Appl. No. 11/967,663, dated Oct. 1, 2009.
Office Action issued in U.S. Appl. No. 12/112,291, dated Mar. 1, 2010.
Office Action issued in U.S. Appl. No. 12/112,291, dated Nov. 16, 2009.
Office Action issued in U.S. Appl. No. 12/120,388, dated Feb. 19, 2010.
Office Action issued in U.S. Appl. No. 12/120,388, dated Jul. 21, 2010.
Office Action issued in U.S. Appl. No. 12/124,394, dated Feb. 5, 2010.
Office Action issued in U.S. Appl. No. 12/124,394, dated Nov. 6, 2009.
Office Action issued in U.S. Appl. No. 12/125,412, dated Feb. 16, 2010.
Porkka et al., "MicroRNA expression profiling in prostate cancer," Cancer Res., 67(13):6130-6135, 2007.
Pretlow et al., "K-ras mutations in putative preneoplastic lesions in human colon," J Natl Cancer /nst., 85(24):2004-2007, 1993.

Qian et al., "Expression profiling of CD34+ hematopoietic stem/progenitor cells reveals distinct subtypes of therapy-related acute myeloid leukemia," Proc Natl Acad Sci US A, 99(23): 14925-14930, 2002.
Quan et al., "The evolution oflymph node assessment in breast cancer," Journal of Surgical Oncology, 2008.
Rader et al., "In vitro differentiation of epithelial cells from cervical neoplasias resembles in vivo lesions," Oncogene, 5(4):571-6, 1990.
Rapp et al., "Structure and biological activity ofv-raf, a unique oncogene transduced by a retrovirus," Proc Natl Acad Sci US A, 80(14):4218-4222, 1983.
Raval, et al., Modern Path. 23:1467-76,2010.
Redston et al., "Analysis of micrometastatic disease in sentinel lymph nodes from resectable colon cancer: results of Cancer and Leukemia Group B Trial80001," J Clin. Oneal., 24(6):878-883, 2006.
Ree et al., "Expression of a novel factor in human breast cancer cells with metastatic potential," Cancer Res., 59 (18): 4675-4680, 1999.
Reimer et al., "Altered regulation of cyclinG in human breast cancer and its specific localization at replication foci in response to DNA damage in p53+/+ cells," J Biol. Chem., 274 (16): 11022-11029, 1999.
Reinhart et al. "The 21-nucleotide let-7 RNA regulates developmental timing in Caenorhabditis elegans," Nature, 403:901-906,2000.
Reintgen et al., "Sentinel Node Biopsy in Breast Cancer: An Overview," Breast J, 6(5):299-305, 2000.
Reiter and Sawyers, "Xenograft models and the molecular biology of human prostate cancer," In :Prostate Cancer: Biology, Genetics, and the New Therapeutics, Totowa, NJ, 163-173, 2001.
Reshmi and Pillai, "Beyond HPV: oncomirs as new players in cervical cancer," FEES Letters, 582:4113-4116, 2008.
Richardson et al., "CD133, a novel marker for human prostatic epithelial stem cells," J Cell Sci., 117(Pt 16):3539-45, 2004.
Rickert et al., "Multiplexed Real-Time PCR Using Universal Reporters," Clin. Chem., 50(9):1680-1683, 2004.
Roberts et al., "Interpretive disparity among pathologists in breast sentinel lymph node evaluation," Am. J Surg., 186:324-329,2003.
Roldo et al., J Clin Oncol 2006 24(29):4677-84.
Rosenfeld et al., "Ranibizumab: Phase III clinical trial results," Ophthalmol. Clin. North Am. 19(3):361-372, 2006.
Rosenkilde and Schwartz, "The chemokine system—a major regulator of angiogenesis in health and disease," Apmis, 112(7-8):481-495, 2004.
Rossi et al., "Identification of inactivating mutations in the JAK1, SYNJ2, and CLPTM1 genes in prostate cancer cells using inhibition of nonsense-mediated decay and microarray analysis," Cancer Genet. Cytogenet., 161 (2): 97-103,2005.
Rous, "A sarcoma of the fowl transmissible by an agent separable from the tumor cells," J Exp Med, 13:397-411, 1911.
Rubin and Gutmann, "Neurofibromatosis type 1—a model for nervous system tumour formation?," Nat Rev Cancer, 5(7):557-564, 2005.
Ruth et al., "RhoC promotes human melanoma invasion in a PBK/AKT-dependent pathway," J Invest. Dermatol., 126(4):862-868, 2006.
Ryan et al., "MicroRNAs of the mammalian eye display distinct and overlapping tissue specificity," Molecular Vision, 12:1175-1184, 2006.
Ryu, et al., Pancreatology. 10:66-73,2010.
Sacchi et al., "Hu-ets-1 and Hu-ets-2 genes are transposed in acute leukemias with (4;11) and (8;21) translocations," Science, 231 (4736): 379-382, 1986.
Saha et al., "Historical review oflymphatic mapping in gastrointestinal malignancies," Ann Surg Oneal, 11(3 Suppl):245S-249S, 2004.
Saha et al., "Ultrastaging of colorectal cancer by sentinel lymph node mapping technique—a multicenter trial," Ann. Surg. Oneal., 8(9 Suppl):94S-98S, 2001.
Saigusa et al., "Overexpressed Skp2 within 5p amplification detected by array-based comparative genomic hybridization is associated with poor prognosis of glioblastomas," Cancer Sci, 96(1 0):676-683, 2005.

(56) References Cited

OTHER PUBLICATIONS

Saitoh et al., "Frequent up-regulation of WNT5A mRNA in primary gastric cancer," Int. J Mol. Med., 9 (5):515-519,2002.
Saiz et al., "MicroRNA expression profiling in acute myelogenous leukemia," Blood, ASH Annual Meeting Abstracts, 104:320a, Abstract No. 1131, Poster board number session 285-I, 2004.
Sakai et al., "Microarray hybridization with fractionated eDNA: enhanced identification of differentially expressed genes," Analytical Biochemistry, 287(1):32-37, 2000.
Sampson and Uhlenbeck, "Bichemical and physical characterization of an unmodified yeast phenylalanine transfer RNA transcribed in vitro," Proc. Natl. Acad. Sci., USA, 85(4):1033-1037, 1988.
Sanger Institute, "miRBase" miRBase Sequence Database, located at http://microma.sanger.ac.uk/, printed Jan. 21, 2009.
Sanger Institute, miRBase::Sequences—Stem-loop sequence MI0000268, Sep. 2008, located at http://microRNA.sanger.ac.ukm, printed on Dec. 23, 2008.
Sasaki et al., "Expression of the MTA1 mRNA in advanced lung cancer," Lung Cancer, 35(2):149-154, 2002.
Scaria et al. "Host-virus genome interactions: macro roles for microRNAs," Cell Microbial., (12):2784-94 2007.
Scaria et al. "Host-virus interaction: a new role for microRNAs," Retrovirology, 3:68, 2006.
Schenbom and Stecha, "Ribo m7G cap analog: A reagent for preparing in vitro capped transcripts", PromegaNotes, 74:18-20,2000.
Schepeler et al., "Diagnostic and prognostic microRNAs in stage II colon cancer," Cancer Research, 68(15):6416-6424, 2008.
Scherer and Rossi, "Approaches for the sequence-specific knock-down of mRNA," Nat. Biotechnol., 21(12):1457-1465, 2003.
Scherr et al., "Lentivirus-mediated antagomir expression for specific inhibition of miRNA function," Nucleic Acids Research, 35(22):e149, 2007.
Scherr et al., "Modulation of gene expression by lentiviral-mediated delivery of small interfering RNA," Cell Cycle, 2(3):251-257, 2003.
Schetter et al., "MicroRNA expression profiles associated with prognosis and therapeutic outcome in colon adenocarcinoma," JAMA, 299(4):425-436, 2008.
Schmittgen, etal., Methods. 44(1):31-38, 2008.
Schouten et al., "Relative quantification of 40 nucleic acid sequences by multiplex ligationdependent probe amplification," Nucleic Acids Research, 30(12):e57, 2002.
Schulze-Bergkamen et al., "Suppression of Mcl-1 via RNA interference sensitizes human hepatocellular carcinoma cells towards apoptosis induction," BMC Cancer, 6:232, 2006.
Schurr et al., "Lymphatic spread and microinvolvement in adenocarcinoma of the esophagogastric junction," J Surg. Oneal., 94:307-315,2006.
Schuster and Porse, "C/EBPalpha: a tumour suppressor in multiple tissues?" Biochim Biophys Acta, 1766(1):88-103, 2006.
Lin and Gelman, "Reexpression of the major protein kinase C substrate, SSeCKS, suppresses vsrc-induced morphological transformation and tumorigenesis," Cancer Res, 57(11 ):2304-2312, 1997.
Lin et al., "Connective tissue growth factor inhibits metastasis and acts as an independent prognostic marker in colorectal cancer," Gastroenterology, 128(1):9-23, 2005.
Lin et al., "The C. elegans hunchback homolog, hbl-1, controls temporal patterning and is a probable microRNA target," Dev. Cell, 4(5):639-650, 2003.
Linsley et al., "Transcripts targeted by the microRNA-16 family cooperatively regulate cell cycle progression," Molecular and Cellular Biology, 27(6):2240-2252, 2007.
Liu and Erikson, "Polo-like kinase (Plk)1 depletion induces apoptosis in cancer cells," Proc Natl Acad Sci US A, 100(10):5789-5794, 2003.
Liu and Matsuura, "Inhibition of Smad antiproliferative function by CDK phosphorylation," Cell Cycle, 4(1):63-66, 2005.
Liu et al., "An oligonucleotide microchip for genome-wide micronRNA profiling in human and mouse tissue," Proc. Nat. Acad. Sci. USA, 101:9740-9744,2004.
Liu et al., "CpG island methylation and expression of the secreted frizzled-related protein gene family in chronic lymphocytic leukemia," Cancer Res., 66 (2): 653-658, 2006.
Liu et al., "FoxM1B is overexpressed in human glioblastomas and critically regulates the tumorigenicity of glioma cells," Cancer Res., 66 (7): 3593-3602, 2006.
Liu et al., "Functional studies of BCLIIA: characterization of the conserved BCLIIA-XL splice variant and its interaction with BCL6 in nuclear paraspeckles of germinal center B cells," Mol. Cancer, 5:18,2006.
Liu et al., "Hedgehog signaling and Bmi-1 regulate self-renewal of normal and malignant human mammary stem cells," Cancer Res., 66(12):6063-71, 2006.
Liu et al., "Sex-determining region Y box 4 is a transforming oncogene in human prostate cancer cells," Cancer Res., 66(8):4011-9, 2006.
Liu et al., "The prognosticrole of a gene signature from tumorigenic breast-cancer cells," N Engl. J Med., 356(3):217-26, 2007.
Lo et al., "High resolution allelotype of microdissected primary nasopharyngeal carcinoma," Cancer Res., 60: 3348-3353, 2000.
Lo Vasco et al., "Inositide-specific phospholipase c beta1 gene deletion in the progression of myelodysplastic syndrome to acute myeloid leukemia," Leukemia, 18 (6): 1122-1126,2004.
Logsdon et al., Molecular profiling of pancreatic adenocarcinoma and chronic pancreatitis identifies multiple genes differentially regulated in pancreatic cancer, 2003, Cancer Research, vol. 63, pp. 2649-2657.
Lu et al., "Defined culture conditions of human embryonic stem cells,"Proc. Natl. Acad. Sci. USA, 103(15): 5688-93, 2006.
Lu et al., "MicroRNA expression profiles classify human cancers," Nature, 435(7043):834-838, 2005.
Lucke et al., "Inhibiting mutations in the transforming growth factor beta type 2 receptor in recurrent human breast cancer," Cancer Res, 61(2):482-485, 2001.
Lui et al., "Patterns ofknown and novel small RNAs in human cervical cancer," Cancer Res., 67(13):6031-6043, 2007.
Lujambio et al., "Genetic unmasking of an epigenetically silenced micro RNA in human cancer cells," Cancer Research, 67(4):1424-1429, 2007.
Lukiw, "Micro-RNA speciation in fetal, adult and Alzheimer's disease hippocampus," Neuroreport, 18(3):297-300, 2007.
Ma et al., "Tumour invasion and metastasis initiated by microRNA-1 Ob in breast cancer," Nature, 449(7163):682-688, 2007.
Mahato et al., "Modulation of gene expression by antisense and antigene oligodeoxynucleotides and small interfering RNA," Expert Opinion on Drug Delivery, 2(1):3-28, 2005.
Maitland & Collins, "Prostate cancer stem cells: a new target for therapy", J Clin Oneal., 26(17):2862-70, 2008. (Abstract).
Makeyev et al., "The microRNA miR-124 promotes neuronal differentiation by triggering brain-specific alternative pre-mRNA splicing," Molecular Cell, 27(3):435-448, 2007.
Maki et al., "Avian sarcoma virus 17 carries the jun oncogene," Proc. Natl. Acad. Sci. USA, 84 (9): 2848-2852, 1987.
Malanchi et al., "Cutaneous cancer stem cell maintenance is dependent on beta-catenin signalling," Nature, 452(7187):650-3, 2008.
Malumbres and Barbacid, "To cycle or not to cycle: a critical decision in cancer," Nat Rev Cancer, 1(3):222-231, 2001.
Mammalian Gene Collection (MGC) Program Team, "Generation and initial analysis of more than 15,000 full-length human and mouse eDNA sequences," PNAS, 99(26): 16899-16903, 2002.
Manion and Hockenbery, "Targeting Bcl-2-related proteins in cancer therapy," Cancer Biol Ther, 2(4 Suppl1):S105-114, 2003.
Mansfield et al., "MicroRNA-responsive 'sensor' transgenes uncover Hox-like and other developmentally regulated patterns of vertebrate microRNA expression," Nature Genetics, 36(10):1079-1083, 2004.
Marcucci et al., "Prognostic factors and outcome of core binding factor acute myeloid leukemia patients with t(8;21) differ from those of patients with inv(16): a Cancer and Leukemia Group B study," JClin.Oncol., 23:5705-5717, 2005.

(56) References Cited

OTHER PUBLICATIONS

Markowitz et al., "Inactivation of the type II TGF-beta receptor in colon cancer cells with microsatellite instability," Science, 268(5215):1336-1338, 1995.

Markowitz, "TGF-beta receptors and DNA repair genes, coupled targets in a pathway of human colon carcinogenesis," Biochim. Biophys. Acta., 1470 (1): M13-20, 2000.

Marks, "Thioredoxin in cancer—role of histone deacetylase inhibitors," Semin. Cancer Biol., 16(6):436-443, 2006.

Marone et al., "Analysis of cyclin E and CDK2 in ovarian cancer: gene amplification and RNA overexpression," /nt J Cancer, 75(1):34-39, 1998.

Martello et al., "MicroRNA control of nodal signaling," Nature, 449(7159):183-188, 2007.

Martin and Keller, "Tailing and 3'-end labeling of RNA with yeast poly(A) polymerase and various nucleotides," RNA, 4(2):226-230, 1998.

Martinet al., "Molecular profiling of cervical neoplasia," Expert Review of Molecular Diagnostics, 6(2):217-229, 2006.

Martinez et al., "Human papillomavirus type 16 reduces the expression ofmicroRNA-218 in cervical carcinoma cells," Oncogene, 27:2575-2582, 2008.

Martinez, "Identification of differentially expressed genes in HPV associated cancers using gene expression, tissue, and microRNA microarrays," Dissertation Abstract, University of Pittsburg, 2007.

Massague et al. "TGFbeta signaling in growth control, cancer, and heritable disorders," Cell, 103 (2): 295-309, 2000.

Matoba et al., "Gene expression in mouse cerebellum during its development," Gene, 241:125-131,2000.

Matoba et al., "Gene expression profiling of mouse postnatal cerebellar development Physiol.Genomics," 4:155-164,2000.

Mattie et al., "Optimized high-throughput micro RNA expression profiling provides novel biomarker assessment of clinical prostate and breast cancer biopsies," Mol. Cancer, 5:24, 2006.

Mcinroy and Maatta, "Down-regulation ofvimentin expression inhibits carcinoma cell migration and adhesion," Biochem Biophys Res Commun, 360(1):109-114, 2007.

McManus, "MicroRNAs and cancer," Seminars in Cancer Biology, 13:253-258, 2003.

Meister et al., "Sequence-specific inhibition ofmicroRNA- and siRNA-induced RNA silencing," RNA, 10(3):544-50, 2004.

Mendrzyk et al., "Genomic and protein expression profiling identifies CDK6 as novel independent prognostic marker in medulloblastoma," J Clin Oneal, 23(34):8853-8862, 2005.

* cited by examiner

| Model | TrainAUC | Metric | MetricEstimate |
|---|---|---|---|
| LDA+ModT+6 | 0.978 | MCC | 0.883 |
| LDA+ModT+6 | 0.978 | Sens | 0.955 |
| LDA+ModT+6 | 0.978 | Spec | 0.927 |
| LDA+ModT+6 | 0.978 | Youden | 0.882 |
| LDA+ModT+7 | 0.978 | MCC | 0.831 |
| LDA+ModT+7 | 0.978 | Sens | 0.913 |
| LDA+ModT+7 | 0.978 | Spec | 0.919 |
| LDA+ModT+7 | 0.978 | Youden | 0.833 |
| LDA+ModT+5 | 0.976 | MCC | 0.879 |
| LDA+ModT+5 | 0.976 | Sens | 0.940 |
| LDA+ModT+5 | 0.976 | Spec | 0.940 |
| LDA+ModT+5 | 0.976 | Youden | 0.880 |
| LDA+ModT+4 | 0.975 | MCC | 0.835 |
| LDA+ModT+4 | 0.975 | Sens | 0.902 |
| LDA+ModT+4 | 0.975 | Spec | 0.936 |
| LDA+ModT+4 | 0.975 | Youden | 0.837 |
| PLS+ModT+6 | 0.975 | MCC | 0.856 |
| PLS+ModT+6 | 0.975 | Sens | 0.942 |
| PLS+ModT+6 | 0.975 | Spec | 0.912 |
| PLS+ModT+6 | 0.975 | Youden | 0.854 |

TrainAUC = AUC on FFPE; MCC = Matthew's correlation coefficient; Sens = sensitivity; Spec = specificity; Youden = Sens+Spec-1

FIG. 1

LDA+ModT+6 (7 miRNAs)

| Metric | Estimate% | Lower95% | Upper95% |
|---|---|---|---|
| Sens | 89.68 | 83.00 | 94.39 |
| Spec | 91.18 | 76.32 | 98.14 |
| PPV | 97.41 | 92.63 | 99.47 |
| NPV | 70.45 | 54.80 | 83.24 |

| (N=160) | True PDAC | True CP |
|---|---|---|
| Predicted PDAC | 113 | 3 |
| Predicted CP | 13 | 31 |

AUC = 0.904 / Threshold = 0.5

Simple Model (miR-135b and miR-24)

| Metric | Estimate% | Lower95% | Upper95% |
|---|---|---|---|
| Sens | 82.68 | 74.96 | 88.81 |
| Spec | 91.18 | 76.32 | 98.14 |
| PPV | 97.22 | 92.10 | 99.42 |
| NPV | 58.49 | 44.13 | 71.86 |

| (N=161) | True PDAC | True CP |
|---|---|---|
| Predicted PDAC | 105 | 3 |
| Predicted CP | 22 | 31 |

AUC = 0.885 / Threshold = -5.14

Sens = sensitivity / Spec = specificity / PPV = positive predictive value / NPV = negative predictive value

FIG. 3

```
          Estimate     Lower      Upper
Sens    0.8170732   0.7492756  0.8730456
Spec    0.9500000   0.7512672  0.9987349
PPV     0.9925926   0.9584206  0.9998125
NPV     0.3877551   0.2519745  0.5376145

Truth
Predicted  PDAC   Benign
  PDAC     134       1
  Benign    30      19

Overall accuracy: 83.152 %
Overall AUC: 0.900
```

FIG. 6

| DiffPair<LowerThreshold | | |
|---|---|---|
| | Truth | |
| Predicted | PDAC | Benign |
| PDAC | 16 | 1 |
| Benign | 21 | 4 |

| DiffPair>=LowerThreshold | | |
|---|---|---|
| | Truth | |
| Predicted | PDAC | Benign |
| PDAC | 118 | 0 |
| Benign | 9 | 16 |

| DiffPair<UpperThreshold | | |
|---|---|---|
| | Truth | |
| Predicted | PDAC | Benign |
| PDAC | 23 | 1 |
| Benign | 23 | 6 |

| DiffPair>=UpperThreshold | | |
|---|---|---|
| | Truth | |
| Predicted | PDAC | Benign |
| PDAC | 111 | 0 |
| Benign | 7 | 14 |

FIG. 9

```
                Estimate      Lower       Upper
Sens           0.9024390   0.8464038   0.9432009
Spec           0.6500000   0.4078115   0.8460908
PPV            0.9548387   0.9091661   0.9816527
NPV            0.4482759   0.2644553   0.6430613

Truth
Predicted  PDAC  Benign
    PDAC    148       7
    Benign   16      13

Overall accuracy: 87.500 %
```

FIG. 10

```
Consistent=TRUE
           Truth
Predicted  PDAC  Benign
    PDAC    148       5
    Benign    7      13
``` miRinform Pancreas Performance
With Consistent Reflex Metric Calls

|  | Estimate | Lower | Upper |
|---|---|---|---|
| Sens | 0.8947368 | 0.7519506 | 0.9705655 |
| Spec | 0.6500000 | 0.4078115 | 0.8460908 |
| PPV | 0.8292683 | 0.6794391 | 0.9284847 |
| NPV | 0.7647059 | 0.5010067 | 0.9318923 |

|  | Truth | |
|---|---|---|
| Predicted | PDAC | Benign |
| PDAC | 34 | 7 |
| Benign | 4 | 13 |

Accuracy: 81.034% miRinform Pancreas Performance
No Reflex Metric

|  | Estimate | Lower | Upper |
|---|---|---|---|
| Sens | 0.6052632 | 0.4338615 | 0.7596121 |
| Spec | 0.9500000 | 0.7512672 | 0.9987349 |
| PPV | 0.9583333 | 0.7887983 | 0.9989456 |
| NPV | 0.5588235 | 0.3788576 | 0.7281498 |

|  | Truth | |
|---|---|---|
| Predicted | PDAC | Benign |
| PDAC | 23 | 1 |
| Benign | 15 | 19 |

Accuracy: 72.414%

FIG. 11 miRinform Pancreas Performance
With Consistent Reflex Metric Calls

```
        Estimate      Lower      Upper
Sens  0.9545455   0.7715556  0.9988499
Spec  0.6500000   0.4078115  0.8460908
PPV   0.7500000   0.5512845  0.8930920
NPV   0.9285714   0.6613155  0.9981932
```

```
              Truth
Predicted  PDAC  Benign
    PDAC     21       7
  Benign      1      13
```

Accuracy: 80.952 % miRinform Pancreas Performance
No Reflex Metric

```
        Estimate      Lower      Upper
Sens  0.5454545   0.3221048  0.7561381
Spec  0.9500000   0.7512672  0.9987349
PPV   0.9230769   0.6397026  0.9980544
NPV   0.6551724   0.4566943  0.8206164
```

```
              Truth
Predicted  PDAC  Benign
    PDAC     12       1
  Benign     10      19
```

Accuracy: 73.810 %

FIG. 12

```
miRInform Pancreas Performance
With Consistent Reflex Metric Calls
-------------------------------------------
          Estimate   Lower      Upper
Sens      0.9756098  0.9387311  0.9933154
Spec      0.6500000  0.4078115  0.8460908
PPV       0.9580838  0.9155460  0.9829840
NPV       0.7647059  0.5010067  0.9318923

Truth
Predicted  PDAC  Benign
  PDAC     160    7
  Benign     4   13

Accuracy: 94.022%
```

```
miRInform Pancreas Performance
No Reflex Metric
-------------------------------------------
          Estimate   Lower      Upper
Sens      0.9085366  0.8536337  0.9479015
Spec      0.9500000  0.7512672  0.9987349
PPV       0.9933333  0.9634168  0.9998312
NPV       0.5588235  0.3788576  0.7281498

Truth
Predicted  PDAC  Benign
  PDAC     149    1
  Benign    15   19

Accuracy: 91.304 %
```

FIG. 13

METHODS AND COMPOSITIONS INVOLVING MIR-135B FOR DISTINGUISHING PANCREATIC CANCER FROM BENIGN PANCREATIC DISEASE

This application is a continuation application of U.S. patent application Ser. No. 13/615,066, filed Sep. 13, 2012, now U.S. Pat. No. 9,644,241, which claims priority to U.S. Provisional Application Ser. No. 61/534,332, filed Sep. 13, 2011, and U.S. Provisional Application Ser. No. 61/536,486, filed Sep. 19, 2011, each of which is incorporated by reference in their entirety.

The invention was made with government support under Grant No. P50CA062924 awarded by the National Institutes of Health and Grant No. R44CA118785 from the National Institutes of Health and the National Cancer Institute. The government has certain rights in the invention.

BACKGROUND OF THE INVENTION

I. Field of the Invention

The invention relates generally to the field of molecular biology. More particularly, it concerns methods and compositions involving microRNA molecules (miRNAs). Certain aspects of the invention include applications for miRNAs in diagnostics, therapeutics, and prognostics for pancreatic cancer.

II. Background

In 2001, several groups used a cloning method to isolate and identify a large group of "microRNAs" (miRNAs) from *C. elegans, Drosophila*, and human s (Lagos-Quintana et al., 2001; Lau et al., 2001; Lee and Ambros, 2001). Several hundreds of miRNAs have been identified in plants and animals—including humans—which do not appear to have endogenous siRNAs. Thus, while similar to siRNAs, miRNAs are nonetheless distinct.

miRNAs thus far observed have been approximately 21-22 nucleotides in length and arise from longer precursors, which are transcribed from non-protein-encoding genes. See review of Carrington et al. (2003). The precursors form structures that fold back on themselves in self-complementary regions; they are then processed by the nuclease Dicer in animals or DCL1 in plants. miRNA molecules interrupt translation through precise or imprecise base-pairing with their targets.

Many miRNAs are conserved among diverse organisms, and this has led to the suggestion that miRNAs are involved in essential biological processes throughout the life span of an organism (Esquela-Kerscher and Slack, 2006). In particular, miRNAs have been implicated in regulating cell growth and cell and tissue differentiation, cellular processes that are associated with the development of cancer. For instance, lin-4 and let-7 both regulate passage from one larval state to another during *C. elegans* development (Ambros, 2001). miR-14 and bantam are *Drosophila* miRNAs that regulate cell death, apparently by regulating the expression of genes involved in apoptosis (Brennecke et al., 2003, Xu et al., 2003).

Research on miRNAs is increasing as scientists are beginning to appreciate the broad role that these molecules play in the regulation of eukaryotic gene expression. In particular, several recent studies have shown that expression levels of numerous miRNAs are associated with various cancers (reviewed in Esquela-Kerscher and Slack, 2006). Reduced expression of two miRNAs correlates strongly with chronic lymphocytic leukemia in human s, providing a possible link between miRNAs and cancer (Calin et al., 2002). Others have evaluated the expression patterns of large numbers of miRNAs in multiple human cancers and observed differential expression of almost all miRNAs across numerous cancer types (Lu et al., 2005). Most such studies link miRNAs to cancer only by indirect evidence. In contrast, a single study has provided more direct evidence that miRNAs may contribute directly to causing cancer. By forcing the over-expression of six miRNAs in mice, He et al. (2005) demonstrated a significant increase in B cell lymphomas.

Pancreatic cancer is a particularly challenging disease to diagnose and treat. Each year about 33,000 people in the United States are diagnosed with adenocarcinoma of the pancreas, and about 32,000 people the each year from pancreatic cancer (Jemal et al., 2006). Pancreatic carcinoma ranks as the fourth leading cause of cancer deaths in the United Stales, and the five year survival rate (~4%) is the lowest among all cancers (Jemal et al., 2006).

Most pancreatic cancers are adenocarcinomas of the ductal epithelium (Freelove and Walling. 2006)—or pancreatic ductal adenocarcinomas (PDAC). PDAC is characterized by its late clinical presentation, early and aggressive local invasion and high metastatic potential. The lack of sensitive early detection strategies and its strong resistance to chemotherapy and radiation therapy compounds the overall very poor prognosis of PDAC, which has a median survival time following diagnosis of 3-5 months. Currently, effective diagnostic methods and/or treatments for pancreatic cancer are lacking (Monti et al., 2004). Surgery is still the only effective treatment option, improving the median survival time to 10-20 months; however, at the time of diagnosis only 20% of PDACs are amenable to surgery and cure is rarely achieved (See Yeo et al., 2002). Thus, improved early diagnosis modalities as well as new therapeutic targets for the development of effective treatment strategies are urgently needed to improve the dismal prognosis of PDAC.

Distinguishing between chronic pancreatitis and pancreatic cancer can be extremely difficult Symptoms are frequently non-specific and limited to jaundice, weight loss and bruising. Many patients with chronic pancreatitis (non-cancerous condition) exhibit the same symptoms as patients with PDAC. Serum levels of certain proteins may be suggestive of pancreatic adenocarcinoma but are not diagnostic; and the serum tumor marker CA19-9 can help confirm pancreatic cancer diagnosis, but is ineffective as a patient screening tool (Freelove and Walling, 2006). A need exists for additional diagnostic assays that can assess the condition of the pancreas in general and distinguish a patient with PDAC from a patient suffering from chronic pancreatitis or a patient with a healthy pancreas.

SUMMARY OF THE INVENTION

The disclosed methods and compositions overcome these problems in the art by providing ways to use the expression of different miRNAs as biomarkers to distinguish between abnormal pancreatic cells. Embodiments concern differentiating diseased, normal, cancerous, and/or abnormal tissues, including but not limited to normal pancreas, non-cancerous diseased pancreas such as pancreatitis, and pancreatic cancer (e.g., pancreatic ductal adenocarcinomas (PDAC)). Further, method are provided for diagnosing diseased, normal, cancerous, and/or abnormal tissues, including but not limited to pancreatic cancer and chronic pancreatitis that is based on determining expression levels of selected miRNAs In patient-derived samples that contain pancreatic cells. Additional methods provide information for assessing whether a patient with abnormal or aberrant pancreatic cells has PDAC.

Disclosed herein are methods for evaluating pancreatic cells from a patient to determine whether cells are cancerous or non-cancerous, whether cells are PDAC cells or CP cells, or whether cells are PDAC cells or normal cells or benign cells. This provides a clinician with information useful for diagnosis and/or treatment options. It may also confirm an assessment based on the cytology of the patient's pancreas cells or on the patient's medical history or on the patient's symptoms or on some other test.

Methods involve obtaining information about the levels of expression of certain microRNAs or miRNAs whose expression levels differ in different types of pancreatic cysts. In some embodiments, differences in miRNA expression between or among different types of pancreas cells depends on whether the cells are PDAC cells or are not PDAC cells. Such differences are highlighted when expression levels are first compared among two or more miRNAs and those differential values are compared to or contrasted with the differential values of PDAC cells or either pancreatitis cells or normal pancreatic cells. Embodiments concern methods and compositions that can be used for evaluating pancreas cells or a pancreas sample, differentiating PDAC cells, distinguishing PDAC from chronic pancreatitis, identifying a patient with PDAC or a patient with chronic pancreatitis, identifying PDAC cells as a target for surgical resection, determining PDAC cells should not be surgically resected, categorizing abnormal pancreatic cells, diagnosing PDAC or diagnosing benign pancreas cells or diagnosis pancreatitis, providing a prognosis to a patient regarding abnormal pancreatic cells or symptoms of pancreatitis and/or PDAC, evaluating treatment options for PDAC, or treating a patient with PDAC. These methods can be implemented involving steps and compositions described below in different embodiments.

In some embodiments, methods involve measuring from a pancreatic sample from the patient the level of expression of at least one, two, three, four, five, six or seven of the following miRNAs: miR-135b, miR-148a, miR-24, miR-196a, miR-130b, miR-375, and/or miR-96. In certain embodiments, the level of expression of 1, 2, 3, 4, 5, 6, or 7 of the following miRNAs, which may or may not be a diff pair miRNA, may be measured: miR-135b, miR-148a, miR-24, miR-196a, miR-130b, miR-375, and/or miR-96. In curtain embodiments, methods involve measuring from a pancreas sample from the patient the level of expression of al least one of the following diff pair miRNAs: miR-135b, miR-148a, miR-24, miR-196a, miR-130b, miR-375, and/or miR-96, wherein at least one of the miRNAs is a biomarker miRNA. The term "diff pair miRNA" refers to a miRNA that is one member of a pair of miRNAs where the expression level of one miRNA of the diff pair in a sample is compared to the expression level of the other miRNA of the diff pair in the same sample. The expression levels of two diff pair miRNAs may be evaluated with respect to each other, i.e., compared, which includes but is not limited to subtracting, dividing, multiplying or adding values representing the expression levels of the two diff pair miRNAs. The term "biomarker miRNA" refers to a miRNA whose expression level is indicative of a particular disease or condition. A biomarker miRNA may be a diff pair miRNA in certain embodiments. As part of a diff pair, the level of expression of a biomarker miRNA may highlight or emphasize differences in miRNA expression between different populations, such as PDAC cells from CP cells or from benign or normal pancreas cells. In some embodiments, when miRNA expression is different in a particular population relative to another population, differences between miRNA expression levels can be increased, highlighted, emphasized, or otherwise more readily observed in the context of a diff pair. It will be understood that the terms "diff pair miRNA," "biomarker miRNA," and "comparative miRNA" are used for convenience and that embodiments discussed herein may or may not refer to miRNAs using these terms. Regardless of whether the terms are used, the implementation of methods, kits, and other embodiments remains essentially the same.

In further embodiments, methods involve comparing levels of expression of different miRNAs in the pancreatic sample to each other or to expression levels of other biomarkers, which occurs after a level of expression is measured or obtained. In certain embodiments, miRNA expression levels are compared to each other. In some embodiments, methods involve comparing the level of expression of the at least one biomarker miRNA to the level of expression of a comparative microRNA to determine a biomarker diff pair value. A "comparative miRNA" refers to a miRNA whose expression level is used to evaluate the level of another miRNA in the sample; in some embodiments, the expression level of a comparative microRNA is used to evaluate a biomarker miRNA expression level. For example, a differential value between the biomarker miRNA and the comparative miRNA can be calculated or determined or evaluated; this value is a number that is referred to as a "diff pair value" when it is based on the expression level of two miRNAs. A diff pair value can be calculated, determined or evaluated using one or mom mathematical formulas or algorithms. In some embodiments, the value is calculated, determined or evaluated using computer software. Moreover, it is readily apparent that the miRNA used as a biomarker and the miRNA used as the comparative miRNA may be switched, and that any calculated value can be evaluated accordingly by a person of ordinary skill in the art. However, a person of ordinary skill in the art understands that different pair analysis may be adjusted, particular with respect to altering the comparative miRNA in a pair without affecting the concept of the embodiments discussed herein.

A comparative miRNA may be any miRNA, but in some embodiments, the comparative miRNA is chosen because it allows a statistically significant and/or relatively large difference in expression to be detected or highlighted between expression levels of the biomarker in one pancreatic cyst population as compared to a different pancreatic cyst population. Furthermore, a particular comparative miRNA in a diff pair may serve to increase any difference observed between diff pair values of different pancreated cyst populations, for example, a PDAC cell population compared to a CP cell population. In further embodiments, the comparative miRNA expression level serves as an internal control for expression levels. In some embodiments, the comparative miRNA is one that allows the relative or differential level of expression of a biomarker miRNA to be distinguishable from the relative or differential level of expression of that same biomarker in a different pancreatic cyst population. In some embodiments, the expression level of a comparative miRNA is a normalized level of expression for the different pancreatic cyst populations, while in other embodiments, the comparative miRNA level is not normalized. In some embodiments, there are methods for distinguishing or identifying pancreatic cancer cells in a patient comprising determining the level of expression of one or more miRNAs in a biological sample that contains pancreatic cells from the patient.

Methods may involve determining the level of expression of one or more of miR-135b, miR-148a, miR-24, miR-196a, miR-130b, miR-375, and/or miR-96. It will be understood that "determining the level of expression" refers to measuring or assaying for expression of the recited microRNA using a probe that is at least 98% complementary to the entire length of the mature human miRNA sequence, which will involve performing one or more chemical reactions. In some embodiments, a probe that is at least 99% or 100% complementary to the sequence of the entire length of the most predominant mature human miRNA sequence is used to implement embodiments discussed herein. It is contemplated that while additional miRNAs that are nearly identical to the recited miRNA may be measured in embodiments, the recited miRNA whose expression is being evaluated is at least one of the miRNAs whose expression is being measured in embodiments. These different recited human miRNA sequences are provided in SEQ ID NOs: 1-12. Mature miRNAs may be indirectly determined by directly measuring precursor microRNA molecules; in some embodiments, this Is done using the same probe that is used for measuring mature miRNAs.

In some embodiments, there are methods for determining whether a patient has pancreatic ductal carcinoma comprising: a) measuring from a pancreatic sample from the patient the level of expression of at least two of the following diff pair miRNAs: miR-135b, miR148a, miR-130b, miR-196a, miR-24, miR-375, miR-96, miR-155, miR-21, miR-24, miR-210, miR-217, miR-223, and miR-375, wherein at least one of the miRNAs is a biomarker miRNA and one is a comparative miRNA; b) determining at least one biomarker diff pair value based on the level of expression of the biomarker miRNA compared to the level of expression of the comparative miRNA; and, c) evaluating whether the pancreatic sample comprises pancreatic ductal adenocarcinoma (PDAC) cells based on the biomarker diff pair value(s). In certain embodiments, the level of at least 3, 4, 5, 6, 7, 8, 9, 10, 11, or 12 of the diff pair miRNAs are measured.

Embodiments involve 1, 2, 3, 4, 5, 6, 7, 8, 9, 10, 11, or 12 probes that are at least 90, 9, 92, 93, 94, 95, 96, 97, 98, 99, 01 100% identical or complementary to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12, depending on which miRNA is being measured (see Table 1).

In other embodiments, methods involve measuring the level of miR-135b expression in a pancreatic sample from a patient having aberrant or abnormal pancreatic cells; comparing the level of miR-135b expression to the level of expression of miR-24 in the pancreatic sample; and providing a score that provides information about the likelihood that the patient has pancreatic cancer cells. In further embodiments, methods involve measuring the level of miR-148a expression in a pancreatic sample from a patient having aberrant or abnormal pancreatic cells; comparing the level of miR-148a expression to the level of expression of miR-135b in the pancreatic sample; and providing a score that provides information about the likelihood that the patient has pancreatic cancer cells. In certain embodiments, methods are combined to evaluate different miRNA pairs.

Some embodiments concern diagnosing a patient with PDAC after generating an miRNA profile for a patient suspected of having or at risk for PDAC, wherein the miRNA profile comprises the level of expression of one or more of miR-135b, miR-148a, miR-24, miR-196a, miR-130b, miR-375, and/or miR-96. In other embodiments, an miRNA profile alternatively or additionally comprises the level of expression of one or more of miR-155, miR-223, miR-217, miR-210 and/or miR-21. Such miRNAs may be referred to as a "diff pair miRNA." In some embodiments, the miRNA is a biomarker miRNA. In further embodiments, the miRNA is a comparative miRNA.

In some embodiments, the level of miR-135b expression in a pancreatic sample from a patient is measured or assayed. In other embodiments, the level of miR-148a expression in a pancreatic sample from a patient is measured or assayed, which may be in addition to measuring or assaying for miR-135b. In further embodiments, the level of miR-24 expression in a pancreatic sample from a patient is measured or assayed. In additional embodiments, the level of miR-196a expression in a pancreatic sample from a patient is measured or assayed. In some embodiments, the level of miR-375 expression in a pancreatic sample from a patient is measured or assayed. In additional embodiments, the level of miR-96 expression in a pancreatic sample from a patient is measured or assayed. It is contemplated that methods may involve determining the level of 1, 2, 3, 4, 5, 6, 7, 8, 9, 10, 11 or 12 different miRNAs or at least 1, 2, 3, 4, 5, 6, 7, 8, 9, 10, 11, or 12 different miRNAs, and any range derivable therein. In specific embodiments, methods involve determining the level of expression of at least or at most the following miRNAs: miR-135b, miR-148a, miR-24, miR-130b, and miR-196a. In further embodiments, methods involve determining the level of expression of at least or at most the following miRNAs; miR-135b, miR-148a, miR-24. Alternatively or additionally, methods involve determining the level of expression of one or more of miR-155, miR-223, miR-217, miR-210 and/or miR-21. Methods may or may not involve determining the amount or level of expression of a non-miRNA nucleic acid in sample.

Moreover, in some embodiments, methods involve evaluating a differential pair analysis factor that involves one or more of the following pairs of miRNAs (the miRNA after the slash (/) is the reference miRNA): miR-135b/miR-24; miR-130b/miR-135b; miR135b/miR-148a; miR-375/miR-135b; miR-135b/miR-96; and miR-148a/miR-196a. In a specific embodiment, methods involve evaluating at least or at most the following differential pair analysis factors: miR-135b/miR-24; miR-130b/miR-135b; miR135b/miR-148a; miR-375/miR-135b; miR-135b/miR-96; and miR-148a/miR-196a; such pairs of miRNAs may also be referred to as "diff pairs" In a different specific embodiment, methods involve evaluating at least or at most the following differential pair analysis factors: 125b/miR-24; miR-130b/miR-135b; miR-135b/miR-96; and miR-148a/miR-196a. In further embodiments, methods involve evaluating at least or at most one or more of the following diff pairs: miR-155/miR-21, and/or miR-130b/miR-24. However, a person of ordinary skill in the art understands that different pair analysis factors may be used, particular with respect to altering the reference miRNA in a pair without affecting the concept of the embodiments discussed herein. In some methods, the following six diff pairs are evaluated: miR-135b/miR-24; miR-130b/miR-135b; miR-135b/miR-148a; miR-148a/miR-196a; miR-375/miR-135b; and miR-135b/miR-96. In further embodiments, these six diff pairs are evaluated, and further information about false positives or false negatives is provided by evaluating the following diff pairs: miR-155/miR-21 and/or miR-130b/miR-24.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-21/miR-24; miR-21/miR-96; miR-21/miR-130b; miR-21/miR-135b; miR-21/miR-148a; miR-21/miR-155; miR-21/miR-196a; miR-21/miR-210; miR-21/miR-217; miR-21/miR-223; and/or miR-21/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

In certain embodiments, a sample is first evaluated using cytology, and only if the sample is not characterized as PDAC by cytology is the sample then evaluated with respect to the level of expression of one or more miRNAs, as discussed herein. In some cases, if the sample is characterized as benign, uncertain, pancreatitis or something other than PDAC then the sample is evaluated for miRNA expression levels.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-24/miR-21; miR-24/miR-96; miR-24/miR-130b; miR-24/miR-135b; miR-24/miR-148a; miR-24/miR-155; miR-24/miR-196a; miR-24/miR-210; miR-24/miR-217; miR-24/miR-223; and/or miR-24/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysts, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-96/miR-21; miR-96/miR-24; miR-96/miR-130b; miR-96/miR-135b; miR-96/miR-148a; miR-96/miR-155; miR-96/miR-196a; miR-96/miR-210; 217; miR-96/miR-223; and/or miR-96/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-130b/miR-21; miR-130b/miR-24; miR-130b/miR-96; miR-130b/miR-135b; miR-130b/miR-148a; miR-130b/miR-155; miR-130b/miR-196a; miR-130b/miR-210; miR-130b/miR-217; miR-130b/miR-223; and/or miR-130b/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-135b/miR-21; miR-135b/miR-24; miR-135b/miR-96; miR-135b/miR-130b; miR-135b/miR-148a; miR-135b/miR-155; miR-135b/miR-196a; miR-135b/miR-210; miR-135b/miR-217; miR-135b/miR-223; and/or miR-135b/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-148a/miR-21; miR-148a/miR-24; miR-148a/miR-96; miR-148a/miR-130b; miR-148a/miR-135b; miR-148a/miR-155; miR-148a/miR-196a; miR-148a/miR-210; miR-148a/miR-217; miR-148a/miR-223 and/or miR-148a/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor miR-155/miR-21; miR-155/miR-24; miR-155/miR-96; miR-155/miR-130b; miR-155/miR-135b; miR-155/miR-148a; miR-155/miR-196a; miR-155/miR-210; miR-155/miR-217; miR-155/miR-223 and/or miR-155/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-196a/miR-21; miR-196a/miR-24; miR-196a/miR-96; miR-196a/miR-130b; miR-196a/miR-135b; miR-196a/miR-148a; miR-196a/miR-155; miR-196a/miR-210; miR-196a/miR-217; miR-196a/miR-223 and/or miR-196a/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-210/miR-21; miR-210/miR-24; miR-210/miR-96; miR-210/miR-130b; miR-210/miR-135b; miR-210/miR-148a; miR-210/miR-155; miR-210/miR-196a; miR-210/miR-217; miR-210/miR-223 and/or miR-210/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-217/miR-21; miR-217/miR-24; miR-217/miR-96; miR-217/miR-130b; miR-217/miR-135b; miR-217/miR-148a; miR-217/miR-155; miR-217/miR-196a; miR-217/miR-210; miR-217/miR-223 and/or miR-217/miR-375. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-223/miR-21; miR-223/miR-24; miR-223/miR-96; miR-223/miR-130b; miR-223/miR-135b; miR-223/miR-148a; miR-223/miR-155; miR-223/miR-196a; miR-223/miR-210; miR-223/miR-217 and/or miR-223/miR-375. At least 1, 2, 3, 4, 5, 6, 7, 8, 9, 10, or 11 of these cliff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

It is contemplated that 1, 2, 3, 4, 5, 6, 7, 8, 9, 10, or 11 (or any range derivable therein) of the following diff pairs may be evaluated and used in any embodiments discussed herein, including any method, any computer readable medium, any kit, or any computer processor: miR-375/miR-21; miR-375/miR-24; miR-375/miR-96; miR-375/miR-130b; miR-375/miR-135b; miR-375/miR-148a; miR-375/miR-155; miR-375/miR-196a; miR-375/miR-210; miR-375/miR-217; and/or miR-375/miR-223. At least 1, 2, 3, 4, 5, 6, 7, 8, 9, 10, or 11 of these diff pairs (or any range derivable therein) may be used to evaluate a first risk score and/or they may be used to evaluate a second risk score, which may or may not be a reflex test. Such risk scores may be part of a linear analysis, a non-linear analysis or a tree-based algorithm.

In certain embodiments, miR-135b expression levels are used to calculate 1, 2, 3, 4, 5, 6, 7 or more differential pair analysis factors (or any range derivable therein). In specific embodiments, miR-135b expression levels are used to calculate up to five differential pair analysis factors. In further embodiments, miR-148a expression levels are used to calculate 1, 2, 3, 4, 5, 6, 7 or more differential pair analysis factors (or any range derivable therein). In specific embodiments, miR-148a expression levels are used to calculate up to two differential pair analysis factors. In certain embodiments, miR-130b expression levels are used to calculate 1, 2, 3, 4, 5, 6, 7 or more differential pair analysis factors (or any range derivable therein). In certain embodiments. miR-196a expression levels are used to calculate 1, 2, 3, 4, 5, 6, 7 or more differential pair analysis factors (or any range derivable therein). In certain embodiments, miR-24 expression levels are used to calculate 1, 2, 3, 4, 5, 6, 7 or more differential pair analysis factors (or any range derivable therein). In certain embodiments, miR-375 expression levels are used to calculate 1, 2, 3, 4, 5, 6, 7 or more differential pair analysis factors (or any range derivable therein). In certain embodiments, miR-96 expression levels are used to calculate 1, 2, 3, 4, 5, 6, 7 or more differential pair analysis factors (or any range derivable therein).

The level of expression of any of these microRNAs may be used to calculate or assess its relative or differential level of expression as a biomarker for PDAC by comparing its level of expression to the level of expression of a reference miRNA. A reference miRNA may be any miRNA, but in some embodiments, the reference miRNA is one that allows a statistically significant and/or relatively large difference in expression to be detected between expression levels of the biomarker in one pancreatic cell population as compared to a different pancreatic cell population. In further embodiments, the reference miRNA expression level serves as an internal control for expression levels. In some embodiments, the reference miRNA is one that allows the relative or differential level of expression of a PDAC biomarker to be distinguishable from the relative or differential level of expression of that same biomarker in a non-PDAC pancreatic cell. In some embodiments, the expression level of a reference miRNA is a normalized level of expression for the different pancreatic cell populations, while in other embodiments, the reference miRNA level is not normalized.

In some embodiments, an miRNA whose expression is used as a biomarker may also be used as a reference miRNA. Therefore, in certain embodiments, the level of expression each of these microRNAs (miR-135b, miR-148a, miR-24, miR-196a, miR-130b, miR-375, miR-96, miR-21, miR-155, miR-210, miR-217, miR-223, and miR-375) may be used instead of or also as a reference level of expression that can be used to calculate or assess a relative or differential level of expression. For example, in some embodiments, miR-135b is used a reference miRNA against which the relative or differential level of expression of a different miRNA is determined.

Some methods are provided for determining whether a patient has pancreatic ductal carcinoma comprising: a) measuring from a pancreatic sample from the patient the level of expression of at least one of the following diff pair miRNAs: miR-135b, miR148a, miR-130b, miR-196a, miR-24, miR-375, or miR-96, wherein at least one of the miRNAs is a biomarker miRNA; b) comparing the level of expression of the at least one biomarker miRNA to the level of expression of at least one comparative microRNA to calculate at least one biomarker diff pair value; and, c) determining the pancreatic sample comprises pancreatic ductal adenocarcinoma (PDAC) cells based on the biomarker diff pair value(s).

Other embodiments concern methods for evaluating a pancreatic sample from a patient comprising: a) measuring from the pancreatic sample from the patient the level of expression of at least miR-135b and at least one comparative miRNA; b) comparing the level of expression between miR-135b and the second microRNA to calculate a miR-135b diff pair value; and, c) calculating the patient's risk of having pancreatic ductal carcinoma using the miR-135b diff pair value.

Further embodiments involve methods for evaluating a pancreatic sample from a patient comprising: a) from the sample, measuring the level of expression of miRNAs from at least two diff pairs selected from the group consisting of miR-135b/miR-24; miR-130b/miR-135b; miR-135b/miR-148a; miR-148a/miR-196a; miR-375/miR-135b; miR-135b/miR-96; miR-155/miR-21 and miR-130b/miR-24; b) determining diff pair values for the at least two diff pairs; and, c) calculating a risk score for pancreatic ductal adenocarcinoma for the patient.

In further embodiments, methods involve calculating a differential or relative value of the expression level of a particular miRNA and the level of expression of a reference miRNA in the sample, wherein the differential or relative value is a factor, termed differential pair analysis factor, that may be evaluated with one or more other differential pair analysis factors (i.e., involving different pairwise comparisons). In some embodiments, methods include evaluating one or more differential pair analysis factors using a scoring algorithm to generate a risk score for the presence of pancreatic cancer cells in the pancreatic sample, wherein the patient is identified as having or as not having pancreatic cancer cells based on the score. It is understood by those of skill in the art that the score is a predictive value about whether the patient does or docs not pancreatic cells. In some embodiments, a report is generated and/or provided that identifies the risk score.

Additionally, some methods involve evaluating or determining a first risk score, and then in some embodiments, evaluating or determining a second, third and/or fourth risk score. The first and additional risk scores may be evaluated or determined at the same time, or the first score may be determined or evaluated first, and then one or more other scores may be determined or evaluated. In some embodiments, a subsequent score is determined or evaluated depending on the first risk score. For instance, in some embodiments, a first risk score may indicate that the patient is positive for PDAC, and then subsequently or concurrently, a second risk score may be evaluated based on one or more miRNA expression levels and/or diff pairs or diff pair values discussed herein to determined whether the first risk score reflects a true positive or a false positive. In some embodiments, more than one risk score is evaluated. In certain cases, at least one risk score is determined or evaluated. In further embodiments, there is a second risk score that is based on the expression level of miR-135b, miR-148a, miR-24, miR-196a, miR-130b, miR-375, and/or miR-96 alone or as a diff pair along with the expression of a different miRNA that is chosen from miR-135b, miR-148a, miR-24, miR-196a, miR-130b, miR-375, and/or miR-96. In some embodiments, a second risk score involves measuring the level of expression of one or more of miR-155, miR-223, miR-217, miR-210 and/or miR-21. In some embodiments, false negatives and/or false positives are further evaluated using a reflex test. Alternatively or additional, risk scores relating to false positives and/or false negatives may be part of a linear analysis, a non-linear analysis or a tree-based algorithm.

In some embodiments, a cut-off score is employed to characterize a sample as likely having PDAC cells or not having PDAC cells. In some embodiments, the risk score for the patient is compared to a cut-off score to characterize the biological sample from the patient with respect to the presence of PDAC cells.

In some embodiments, the level of expression of an miRNA biomarker such as miR-1235b, miR148, miR130b, miR-196a, miR-24, miR-375, or miR-96 may be discussed as being upregulated or downregulated in a PDAC cell compared to a non-pDAC cell, however, a person of ordinary skill in the art will understand that the embodiments herein focus on relative pairwise values in order to provide increased clarity for differential expression between pancreatic cancer cells and non-cancer pancreatic cells. Nonetheless, embodiments may be implemented with respect to a 1, 2, 3, 4, 5, 6, 7, 8, 9, or 10-fold difference (increase or decrease, as seen in the Examples) between PDAC cells and pancreatitis or non-PDAC cells.

In some embodiments, methods further comprise one or more of the following: comparing the level of miR-135b to the level of miR-148a expression in the biological sample; comparing the level of miR-135b to the level of miR-96 expression in the biological sample; comparing the level of miR-135b to the level of miR-96 expression in the biological sample; comparing the level of miR-130b to the level of miR-135b expression in the biological sample; comparing the level of miR-375 to the level of miR-135b expression in the biological sample; or comparing the level of miR-148a to the level of miR-196a expression in the biological sample. In certain embodiments, the level of miR-210 expression is not determined or the level of miR-196a expression is not compared to the level of miR-135b expression in the biological sample.

In certain methods, the patient has already been identified as possibly having pancreatic cancer based on the detection or observation of aberrant pancreatic cells. Thus, in some embodiments, a biological sample comprising pancreatic cells has already been obtained directly from the patient. In additional embodiments, methods involve obtaining from the patient, e.g., retrieving from the patient, a biological sample that contains pancreatic cells ("pancreatic biological sample" or "pancreatic sample"). In some embodiments, a first, second, or third biological sample comprising pancreatic cells is obtained directly or retrieved from the patient. In further embodiments, methods involve obtaining a patient's biological sample, which may or may not involve retrieving the sample from the patient. For example, a clinician may directly obtain (or retrieve) the sample from the patient. An entity that will assay the sample may obtain the patient's sample from the clinician who retrieved the patient's sample.

The biological sample used in embodiments is obtained so as to retrieve from the patient pancreatic cells. In some embodiments, the biological sample is a microdissected sample, while in other embodiments, the biological sample is a macrodissected sample. In certain embodiments, methods involve obtaining a biological sample with a fine needle aspirate (FNA). Alternatively, methods may involve a biological sample retrieved from a biopsy, such as a fine needle aspiration biopsy (FNAB) or needle aspiration biopsy (NAB). In certain embodiments, methods involve a biological sample that is a formalin-fixed paraffin embedded (PPFE) sample.

Some embodiments further involve isolating ribonucleic or RNA from a biological sample. Other steps may or may not include amplifying a nucleic acid in a sample and/or hybridizing one or more probes to an amplified or non-amplified nucleic acid. In certain embodiments, a microarray may be used to measure or assay the level of miRNA expression in a sample.

The term "miRNA" is used according to its ordinary and plain meaning and refers to a microRNA molecule found in eukaryotes that is involved in RNA-based gene regulation. See, e.g., Carrington et al., 2003, which is hereby incorporated by reference. The term will be used to refer to the single-stranded RNA molecule processed from a precursor. Individual miRNAs have been identified and sequenced in different organisms, and they have been given names. Names of miRNAs that are related to the disclosed methods and compositions, as well as their sequences, are provided herein. The name of the miRNAs that are used in methods and compositions refers to an miRNA that is at least 90% identical to the named miRNA based on its matured sequence listed herein and that is capable of being detected under the conditions described herein using the designated ABI part number for the probe. In most embodiments, the sequence provided herein is the sequence that is being measured in methods described herein. In some methods, a step may involving using a nucleic acid with the sequence comprising or consisting of any of SEQ ID NOs:1-11 to measure expression of a miRNA in the sample. In some embodiments, a complement of SEQ ID NO:1 (UAGGUAGUUUCAUGUUGUUGG) is used to measure expression of naturally occurring miR-196a in a sample. In other embodiments, a complement of SEQ ID NO:2 (CUGUGCGUGUGACAGCGGCUGA) is used to measure expression of naturally occurring miR-210 in a sample. In further embodiments, a complement of SEQ ID NO:3 (UACUGCAUCAGGAACUGAUUGGA) is used to measure expression of naturally occurring miR-217. In further embodiments, a complement of SEQ ID NO:4 (UUUGUUCGUUCGGCUCGCGUGA) is used to measure expression of naturally occurring miR-375. In other embodiments, a complement of SEQ ID NO:5 (CAGUGCAAUGAUGAAAGGGCAU) is used to measure expression of naturally occurring miR-130. In some embodiments, a complement of SEQ ID NO:6 (UAUGGCUUUUCAUUCCUAUGUG) is used to measure expression of naturally occurring miR-135b. In other embodiments, a complement of SEQ ID NO:7 (UCAGUGCACUACAGAACUUUGU) is used to measure expression of naturally occurring miR148a. In additional embodiments, a complement of SEQ ID NO:8 (UUAAUGCUAAUCGUGAUAGGGG) is used to measure expression of naturally occurring miR-155. In further embodiments, a complement of SEQ ID NO:9 (UGUCAGUUUGUCAAAUACCCC) is used to measure the expression of naturally occurring miR-223. In other embodiments, a complement of SEQ ID NO:10 (UUUGGCACUAGCACAUUUUUGC) is used to measure the expression of naturally occurring miR-96. In certain embodiments, a complement of SEQ ID NO:11 (UGGCUCAGUUCAGCAGGAACAG) is used to measure the expression of naturally occurring miR-24. In other embodiments, a complement of SEQ ID NO:12 (UAGCUUAUCAGACUGAUGUUGA) is used to measure the expression of naturally occurring miR-21.

The term "naturally occurring" refers to something found in an organism without any intervention by a person; it could refer to a naturally-occurring wildtype or mutant molecule. In some embodiments a synthetic miRNA molecule, such as a probe or primer, does not have the sequence of a naturally occurring miRNA molecule. In other embodiments, a synthetic miRNA molecule may have the sequence of a naturally occurring miRNA molecule, but the chemical structure of the molecule that Is unrelated specifically to the precise sequence (i.e., non-sequence chemical structure) differs from chemical structure of the naturally occurring miRNA molecule with that sequence. Corresponding miRNA sequences that can be used in the context of five the disclosed methods and compositions include, but are not limited to, all or a portion of those sequences in the SEQ ID NOs disclosed herein, as well as any other miRNA sequence, miRNA precursor sequence, or any sequence complementary thereof. In some embodiments, the sequence is or is derived from or contains all or part of a sequence identified herein to target a particular miRNA (or set of miRNAs) that can be used with that sequence.

In some embodiments, it may be useful to know whether a cell expresses a particular miRNA endogenously or whether such expression is affected under particular conditions or when the organism is in a particular disease state. Thus, in some embodiments, methods include assaying a cell or a sample containing a cell for the presence of one or more miRNAs. Consequently, in some embodiments, methods include a step of generating a miRNA profile for a sample. The term "miRNA profile" refers to a set of data regarding the expression pattern for a plurality of miRNAs (e.g., one or more miRNAs disclosed herein) in the sample; it is contemplated that the miRNA profile can be obtained using a set of miRNAs, using for example nucleic acid amplification or hybridization techniques well know to one of ordinary skill in the art.

In some embodiments, a miRNA profile is generated by steps that include: (a) labeling miRNA in the sample; b) hybridizing miRNA to a number of probes, or amplifying a number of miRNAs, and c) determining miRNA hybridization to the probes or detection of miRNA amplification products, wherein a miRNA profile is generated. See, e.g., U.S. Provisional Patent Application No. 60/575,743; U.S. Provisional Patent Application No. 60/649,584; and U.S. patent application Ser. No. 11/141,707, all of which are hereby incorporated by reference. One miRNA may be evaluated at a time or measurements may be done simultaneously. In some embodiments, reactions are multiplexed in order to measure the level of expression of more than one miRNA.

Some methods involve diagnosing a patient based on a miRNA expression profile. In certain embodiments, the elevation or reduction in the level of expression of a particular miRNA or set of miRNAs in a cell is correlated with a disease state, as compared to the expression level of that miRNA or set of miRNAs in a normal cell. This correlation allows for diagnostic methods to be carried out when that the expression level of a miRNA is measured in a biological sample and then compared to the expression level of a normal sample. Similarly, a set of miRNAs may be measured in a biological sample and then compared to the expression levels of those miRNAs in a normal sample. Also, a ratio (or ratios) or one or more miRNAs as compared to one or more other microRNAs may be determined in a biological sample and then compared to the corresponding ratio (or ratios) determined for a normal sample. It is specifically contemplated that miRNA profiles for patients, particularly those suspected of having a disease or condition such as pancreatitis or pancreatic cancer, can be generated by evaluating any of or sets of the miRNAs discussed in this disclosure. The miRNA profile that is generated from the patient will be one that provides information regarding the particular disease or condition. In many embodiments, the miRNA profile is generated using miRNA hybridization or amplification, (e.g., array hybridization or RT-PCR). In certain aspects, a miRNA profile can be used in conjunction with other diagnostic tests, such as protein profiles in the serum or cytopathology examination.

Embodiments include methods for diagnosing and/or assessing a condition in a patient comprising measuring an expression profile of one or more miRNAs in a sample from the patient. The difference in the expression profile in the sample from the patient and a reference expression profile (such as an expression profile from a normal, non-pathologic, non-cancerous sample) is indicative of a pathologic, disease, or cancerous condition. A miRNA or probe set comprising or identifying a segment of a corresponding miRNA can include all or part of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 125, 150, 175, 200, 250, 300, 350, or any integer or range derivable there between, of a miRNA or a probe disclosed herein. It is contemplated that methods may involve a microarray or that compositions may involve a microarray comprising one or more miRNA probe sets discussed herein.

A sample may be taken from a patient having or suspected of having a disease or pathological condition. In certain aspects, the sample can be, but is not limited to a tissue (e.g., biopsy, such as fine needle biopsy), blood, serum, plasma, or pancreatic juice sample. The sample may be fresh, frozen, fixed (e.g., formalin fixed), or embedded (e.g., paraffin embedded). In a particular aspect, the sample can be a pancreatic sample.

The disclosed methods can be used to diagnose or assess a pathological condition. In a certain aspect, the condition is a non-cancerous condition, such as pancreatitis or chronic pancreatitis. In other aspects, the condition is a cancerous condition, such as pancreatic cancer, and in particular aspects, the cancerous condition is pancreatic ductal adenocarcinoma (PDAC).

Certain embodiments include determining the expression of one or more miRNAs by using an amplification assay or a hybridization assay, a variety of which are well known to one of ordinary skill in the art. In certain aspects, an amplification assay can be a quantitative amplification assay, such as quantitative RT-PCR or the like. In still further aspects, a hybridization assay can include array hybridization assays or solution hybridization assays.

In certain aspects, methods and compositions are provided to diagnose or assess a patient's condition. For example, the methods can be used to screen for a pathological condition, assess prognosis of a pathological condition, stage a pathological condition, or assess response of a pathological condition to therapy. In further embodiments, methods include identifying or selecting a pattern for treatment of PDAC or treating a patient for PDAC. Additional steps include monitoring a patient or not treating a patient for PDAC. In specific embodiments, a patient is determined not to have or be at risk for PDAC, in which case the patient is not treated for cancer but monitored for changes in non-cancer status.

Some embodiments concern nucleic acids that, when introduced into cells, perform the activities of or inhibit endogenous miRNAs. In certain aspects, nucleic acids are synthetic or non-synthetic miRNAs. Sequence-specific miRNA inhibitors can be used to inhibit the activities of one or more endogenous miRNAs in cells, as well those genes and associated pathways modulated by the endogenous miRNA. Such miRNAs may be used sequentially or in combination. When miRNAs are used to inhibit activities of endogenous miRNAs, the inhibition of such activities may be sequential or in combination.

In some embodiments, short nucleic acid molecules function as miRNAs or as inhibitors of miRNAs in a cell. The term "short" refers to a length of a single polynucleotide that is 25, 50, 100, or 150 nucleotides or fewer, including all integers or ranges derivable there between.

Such nucleic acid molecules may be synthetic and isolated. While in some embodiments, nucleic acids do not have an entire sequence that is identical to a sequence of a naturally-occurring nucleic acid, such molecules may encompass all or part of a naturally-occurring sequence. It is contemplated, however, that a synthetic nucleic acid administered to a cell may subsequently be modified or altered in the cell such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA. Nucleic acid molecules are "isolated" when the nucleic acid molecules are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments, a nucleic acid is isolated by virtue of it having been synthesized in vitro separate from endogenous nucleic acids in a cell, it will be understood, however, that isolated nucleic acids may be subsequently mixed or pooled together.

In some embodiments, there is a synthetic miRNA having a length of between 17 and 130 residues. The disclosed methods and compositions may concern synthetic miRNA molecules that are, are al least, or are at most 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 145, 150, 160, 170, 180, 190, 200 or more residues in length, including any integer or any range derivable therein.

In certain embodiments, synthetic miRNAs used as probes have a "complementary region" having a sequence from 5' to 3' is between 60% and 100% complementary to the miRNA sequence. In certain embodiments, these synthetic miRNAs are also isolated, as defined above. The term "complementary region" refers to a region of a synthetic miRNA that is or is al least 60% complementary to a particular mature, naturally occurring miRNA sequence. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein. In some embodiments, there may be a hairpin loop structure.

Furthermore, any method articulating a list of miRNAs using Markush group language may be articulated without the Markush group language and a disjunctive article (i.e., or) instead, and vice versa.

The methods may further comprise administering an anticancer therapy after a patient is determined to have a risk score that indicates a significant likelihood that the patient has pancreatic cancer. This may be done in conjunction with a cytopathology analysis or evaluation that indicates or confirms the patient has or likely has pancreatic cancer. The anticancer therapy can be, but is not limited to, chemotherapy, radiotherapy, surgery, or immunotherapy. A person of ordinary skill in the art would know the appropriate therapy for PDAC. In other embodiments, a patient is determined not to have PDAC. In some cases, the patient is determined to instead have chronic pancreatitis (CP), which may be subsequently treated. Therefore, in some embodiments a patient is treated for chronic pancreatitis after miRNAs have been measured and analyzed as discussed herein.

In some embodiments, a score involves weighting the a diff pair value. In some embodiments, one or more of the following diff pairs is erighted in order to increase or decrease the significance of that diff pair in calculating a risk score: miR-135b/miR-24; miR-130b/miR-135b; miR-135b/miR-148a; miR-148a/miR-196a; miR-375/miR-135b; miR-135b/miR-96; miR-155/miR-21 or miR-130b/miR-24. In certain embodiments, the weighting ranges from the following numbers or is at least or at most 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or any range derivable therein.

It will be understood that the term "providing" an agent is used to include "administering" the agent to a patient.

Also provided are kits containing the disclosed compositions or compositions used to implement the disclosed methods. In some embodiments, kits can be used to evaluate one or more miRNA molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more, or any range and combination derivable therein, of miRNA probes, synthetic miRNA molecules, or miRNA inhibitors. In some embodiments, there are kits for evaluating miRNA activity in a cell.

Kits may comprise components, which may be individually packaged or placed in a container, such as a tube, bottle, vial, syringe, or other suitable container.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more, or any range derivable therein.

Kits for using miRNA probes, synthetic miRNAs, non-synthetic miRNAs, and/or miRNA inhibitors for therapeutic, prognostic, or diagnostic applications are provided. Specifically contemplated are any such molecules corresponding to any miRNA reported to influence biological activity, such as those discussed herein.

In certain aspects, negative and/or positive control synthetic miRNAs and/or miRNA inhibitors are included in some kit embodiments. Such control molecules can be used, for example, to verify transfection efficiency and/or control for transfection-induced changes in cells.

It is contemplated that any method or composition described herein can be implemented with respect to any other method or composition described herein, and that different embodiments may be combined. It is specifically contemplated that any methods and compositions discussed herein with respect to miRNA molecules may be implemented with respect to synthetic miRNAs to the extent the synthetic miRNA is exposed to the proper conditions to allow it to become a mature miRNA under physiological circumstances.

Any embodiment involving specific miRNAs is contemplated also to cover embodiments involving miRNAs whose sequences are at least 80, 81, 82, 83, 84, 85, 86, 87, 88, 89, 90, 91, 92, 93, 94, 95, 96, 97, 98, 99% identical to the mature sequence of the specified miRNA or to involve 1, 2, 3, 4, 5, 6, 7, 8, 9, 10, 11, or 12 or more (or any range derivable therein) miRNA probes whose sequences are at least 80, 81, 82, 83, 84, 85, 86, 87, 88, 89, 90, 91, 92, 93, 94, 95, 96, 97, 98, 99% complementary to the mature sequence of the specified miRNA. In other embodiments, embodiments may involve 1, 2, 3, 4, 5, 6, 7, 8, 9, 10, 11, or 12 or more (or any range derivable therein) miRNA probes, which may be capable of specifically detecting any of the following miRNAs: miR-196a, miR-210, miR-217, miR-375, miR-130, miR-135b, miR-148a, miR-155, miR-223, miR-96, miR-24, and/or miR-21.

In some embodiments, methods will involve determining or calculating a diagnostic or risk score based on data concerning the expression level of one or more miRNAs, meaning that the expression level of the one or more miRNAs is at least one of the factors on which the score is based. A diagnostic or risk score will provide information about the biological sample, such as the general probability that the pancreatic sample contains PDAC cells or that the pancreatic sample does not contain PDAC cells. In some embodiments, the diagnostic or risk score represents the probability that the patient is more likely than not to have PDAC. In other embodiments, the diagnostic or risk score represents the probability that the patient has benign cells or chronic pancreatic cells or non-PDAC cancer cells. In certain embodiments, a probability value is expressed as a numerical integer that represents a probability of 0% likelihood to 100% likelihood that a patient has PDAC or does not have PDAC (or has benign cells or normal cells or CP cells or some other type of cancer cells). In some embodiments, the probability value is expressed as a numerical integer that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has PDAC or something other than PDAC.

In some embodiments, methods include evaluating one or more differential pair values using a scoring algorithm to generate a diagnostic or risk score for having PDAC, wherein the patient is identified as having or as not having such a based on the score. It is understood by those of skill in the art that the score is a predictive value about whether the patient does or does not s have PDAC. In some embodiments, a report is generated and/or provided that identifies the diagnostic score or the values that factor into such a score. In some embodiments, a cut-off score is employed to characterize a sample as likely having PDAC (or alternatively not having PDAC). In some embodiments, the risk score for the patient is compared to a cut-off score to characterize the biological sample from the patient with respect to whether they are likely to have or not to have PDAC.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to a level of expression in a pancreatic or pancreas sample from a patient of at least one, two, or three of the following miRNAs: miR-135b, miR-148a, miR-24, miR-196a, miR-130b, miR-375, and/or miR-96; and b) determining a biomarker diff pair value using information corresponding to the at least one biomarker miRNA and information corresponding to the level of expression of a comparative miRNA. The diff pair value or a combination of diff pair values provide information that allows a risk score for PDAC to be determined. In some embodiments, receiving information comprises receiving from a tangible data storage device information corresponding to a level of expression in a pancreatic sample from a patient of at least two of the following diff pair miRNAs: miR-135b, miR- 148a, miR-130b, miR-196a, miR-24, miR-375, or miR-96, wherein at least one of the miRNAs is a biomarker miRNA. In additional embodiments the medium further comprises computer-readable code that, when executed by a computer, causes the computer to perform one or more additional operations comprising: sending information corresponding to the biomarker diff pair value to a tangible data storage device. In specific embodiments, it further comprises computer-readable code that, when executed by a computer, causes the computer to perform one or more additional operations comprising: sending information corresponding to the biomarker diff pair value to a tangible data storage device. In certain embodiments, receiving information comprises receiving from a tangible data storage device information corresponding to a level of expression in a pancreatic sample from a patient of at least two of the following diff pair miRNAs: miR-135b, miR-148a, miR-130b, miR-196a, miR-24, miR-375, or miR-96, wherein at least one of the miRNAs is a biomarker miRNA. In even further embodiments, the tangible computer-readable medium has computer-readable code that, when executed by a computer, causes the computer to perform operations further comprising: c) calculating a risk score for the pancreatic sample, wherein the risk score is indicative of the probability that the pancreatic sample contains PDAC cells or that the patient has PDAC. In particular embodiments, methods or computer readable code allow the implementation of one or more scoring algorithms. In some cases, the scoring algorithm comprises a method selected from the group consisting of: Linear Discriminate Analysis (LDA), Significance Analysis of Microarrays, Tree Harvesting, CART, MARS, Self Organizing Maps, Frequent Item Set, Bayesian networks, Prediction Analysis of Microarray (PAM), SMO, Simple Logistic Regression, Logistic Regression, Multilayer Perceptron, Bayes Net, Naive Bayes, Naive Bayes Simple, Naive Bayes Up, IB1, lbk, Kstar, LWL, AdaBoost, ClassViaRegression, Decorate, Multiclass Classifier, Random Committee, J48, LMT, NBTree, Part, Random Forest, Ordinal Classifier, Sparse Linear Programming (SPLP), Sparse Logistic Regression (SPLR), Elastic NET, Support Vector Machine, Prediction of Residual Error Sum of Squares (PRESS), and combinations thereof.

A processor or processors can be used in performance of the operations driven by the example tangible computer-readable media disclosed herein. Alternatively, the processor or processors can perform those operations under hardware control, or under a combination of hardware and software control. For example, the processor may be a processor specifically configured to carry out one or more those operations, such as an application specific integrated circuit (ASIC) or a field programmable gate array (FPGA). The use of a processor or processors allows for the processing of information (e.g., data) that is not possible without the aid of a processor or processors, or at least not at the speed achievable with a processor or processors. Some embodiments of the performance of such operations may be achieved within a certain amount of time, such as an amount of time less than what it would take to perform the operations without the use of a computer system, processor, or processors, including no more than one hour, no more than 30 minutes, no more than 15 minutes, no more than 10 minutes, no more than one minute, no more than one second, and no more than every time interval in seconds between one second and one hour.

Some embodiments of the present tangible computer-readable media may be, for example, a CD-ROM, a DVD-ROM, a flash drive, a hard drive, or any other physical storage device. Some embodiments of the present methods may include recording a tangible computer-readable medium with computer-readable code that, when executed by a computer, causes the computer to perform any of the operations discussed herein, including those associated with the present tangible computer-readable media. Recording the tangible computer-readable medium may include, for example, burning data onto a CD-ROM or a DVD-ROM, or otherwise populating a physical storage device with the data. Expression data, diff pair values, sealing matrix values, and/or risk scores may be stored or processed according to embodiments discussed herein.

Other embodiments are discussed throughout this disclosure, such as in the provided detailed description of the embodiments and the examples. Any embodiment discussed with respect to one aspect applies to other aspects as well, and vice versa.

The terms "inhibiting," "reducing," or "preventing," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any disclosed method or composition, and vice versa. Any embodiment discussed with respect to a particular pancreatic disorder can be applied or implemented with respect to a different pancreatic disorder. Furthermore, the disclosed compositions and kits can be used to achieve the disclosed methods.

Throughout this application, the term "about" is used to indicate that a value includes the standard deviation of error for the device or method being employed to determine the value.

The use of the term "or" in the claims is used to mean "and/or" unless explicitly indicated to refer to alternatives only, or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. However, for a claim using any of these terms, embodiments are also contemplated where the claim is closed and does exclude additional, unrecited elements or method steps.

Other objects, features and advantages of the invention will be apparent from the following detailed description. It should be understood, however, that the detailed description and the specific examples, while indicating specific embodiments, are given by way of illustration only, because various changes and modifications within the spirit and scope of the invention will be apparent to those skilled in the art from this detailed description.

DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

FIG. 1. Assessing the ability of different models to distinguish between PDAC and CP samples using a training set of specimens. PDAC and CP formalin-fixed, paraffin-embedded (FFPE) samples were obtained and used to evaluate different models for the ability to distinguish between PDAC and CP samples.

FIG. 3. Evaluation of the LDA+ModT+6 model as compared to a Simple Model that uses only one miRNA DiffPair to distinguish between PDAC and CP samples.

FIG. 6. This top table captures the performance of MP without adjustment by a reflex test or additional QC procedures. The middle 2×2 table (confusion matrix) captures the raw results of calls by MP (Predicted) versus final diagnosis (Truth). Also included are overall accuracy derived from the 2×2 table and the area under the receiver operating characteristic curve (AUC).

FIG. 9. The figure captures classification results of MP stratified by Diff(miR-130b, miR-24) using the lower (left panel) and upper (right panel) thresholds. See main text for more information.

FIG. 10. The left panel shows the results of calls from Diff)miR-130b, miR-24) outside of 95% of the thresholds tend to be very good at classifying PDAC (increasing sensitivity) with an expected drop in accuracy classifying Benign (decreasing specificity). The calls in this panel are consistent from all replications of cross-validation. Calls that were inconsistent on the reflex metric were set to incorrect predictions. The right panel shows the results of applying Diff(miR-130b, miR-24) to all 184 samples in the FNA validation study. As expected the overall accuracy increases because sensitivity increases.

FIG. 11. The figure shows the results of the FNA validation study with samples PDAC by cytology excluded from analysis. Samples consistently called PDAC by the reflex metric were set to PDAC, while samples with inconsistent reflex calls were set to opposite of Truth (classified incorrectly). Of particular importance is the sum of the lower bounds of the 95% CI for Sens+Spec and PPV+NPV are comparable across panels. In other words, the reflex test essentially reflects a trade-off of sensitivity and specificity.

FIG. 12. The figure shows the results of the FNA validation study with samples PDAC and Suspicions by cytology excluded from analysis. The assumptions and analysis presented here is comparable to that described in FIG. 11 and the main text.

FIG. 13. The figure shows the results of the FNA validation study where outcome is determined by either Cytology or MP. Essentially, if either Cytology or MP predicts a specimen as PDAC, the specimen is classified as PDAC. Otherwise, the sample is classified as Benign. The assumptions and analysis presented here is comparable to that described in FIG. 11 and the main text. Again, notice the sum of the lower bounds of the 95% CI for Sens+Spec and PPV+NPV. The reflex test again favors sensitivity at the cost specificity.

DETAILED DESCRIPTION OF THE INVENTION

Figure 2:
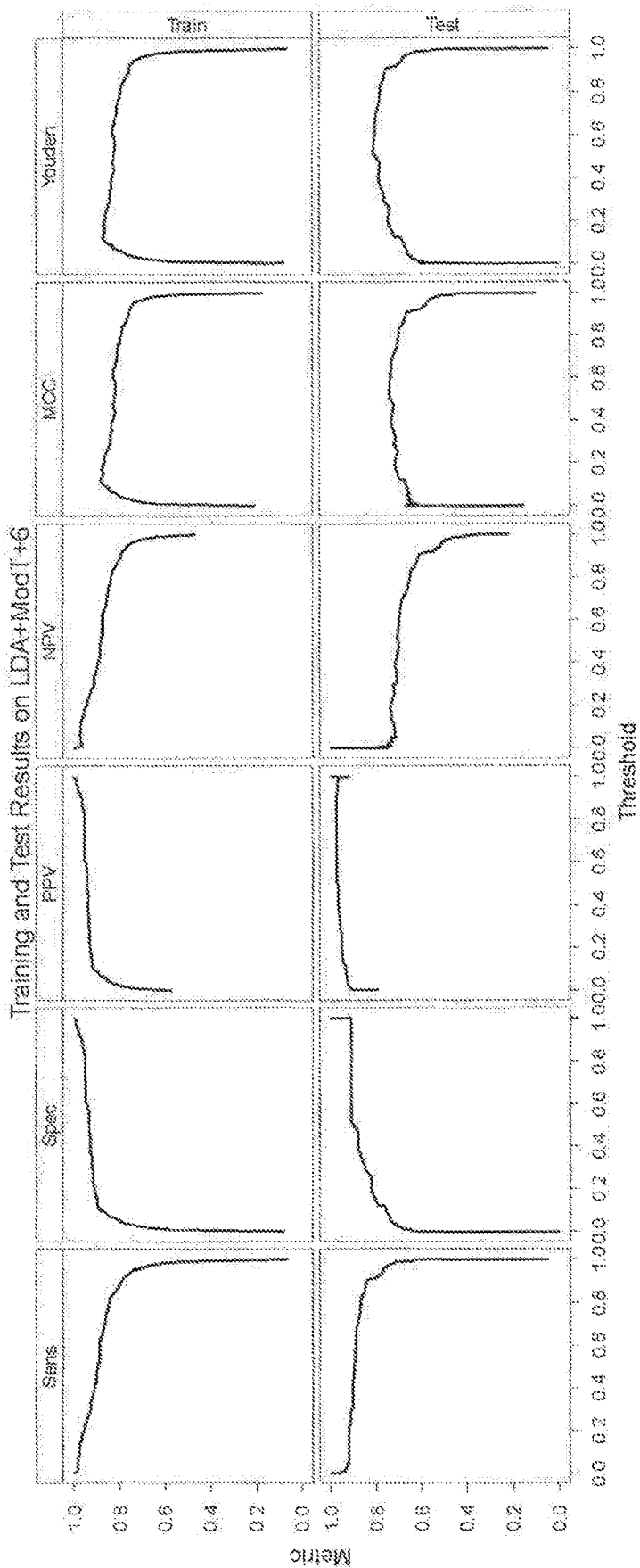
FIG. 2. The LDA+ModT+6 model effectively distinguishes between PDAC and CP samples using a test set of specimens. PDAC and CP fine needle aspirate (FNA) samples were obtained and used to evaluate the LDA+ModT+6 model for the ability to distinguish between PDAC and CP samples.

Certain embodiments are directed to compositions and methods relating to preparation and characterization of miRNAs, as well as use of miRNAs for therapeutic, prognostic, and diagnostic applications, particularly those methods and compositions related to assessing and/or identifying pancreatic disease.

I. miRNA MOLECULES

MicroRNA molecules ("miRNAs") are generally 21 to 22 nucleotides in length, though lengths of 19 and up to 23 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enable them to form a stem-loop- or fold-back-like structure, which is cleaved in animals by a ribonuclease III-like nuclease enzyme called Dicer. The processed miRNA is typically a portion of the stem.

The processed miRNA (also referred to as "mature miRNA") becomes part of a large complex to down-regulate a particular target gene. Examples of animal miRNAs include those that imperfectly basepair with the target, which halts translation of the target (Olsen et al., 1999; Seggerson et al., 2002). siRNA molecules also are processed by Dicer, but from a long, double-stranded RNA molecule. siRNAs are not naturally found in animal cells, but they can direct the sequence-specific cleavage of an mRNA target through an RNA-induced silencing complex (RISC) (Denli et al., 2003).

A. Nucleic Acids

In the disclosed compositions and methods miRNAs can be labeled, used in array analysis, or employed in diagnostic, therapeutic, or prognostic applications, particularly those related to pathological conditions of the pancreas. The RNA may have been endogenously produced by a cell, or been synthesized or produced chemically or recombinantly. They may be isolated and/or purified. The term "miRNA," unless otherwise indicated, refers to the processed RNA, after it has been cleaved from its precursor. The name of the miRNA is often abbreviated and referred to without a hsa-, mmu-, or mo-prefix and will be understood as such, depending on the context. Unless otherwise indicated, miRNAs referred to are human sequences identified as miR-X or let-X, where X is a number and/or letter.

In certain experiments, a miRNA probe designated by a suffix "5P" or "3P" can be used. "5P" indicates that the mature miRNA derives from the 5' end of the precursor and a corresponding "3P" indicates that it derives from the 3' end of the precursor, as described on the World Wide Web at sanger.ac.ak. Moreover, in some embodiments, a miRNA probe is used that does not correspond to a known human miRNA. It is contemplated that these non-human miRNA probes may be used in embodiments or that there may exist a human miRNA that is homologous to the non-human miRNA. While the methods and compositions are not limited to human miRNA, in certain embodiments, miRNA from human cells or a human biological sample is used or evaluated. In other embodiments, any mammalian miRNA or cell biological sample, or preparation thereof may be employed.

In some embodiments, methods and compositions involving miRNA may concern miRNA and/or other nucleic acids. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, miRNA probes, precursor miRNA, miRNA containing vectors, control nucleic acids, and other probes and primers. In many embodiments, miRNAs are 19-24 nucleotides in length, while miRNA probes are 19-35 nucleotides in length, depending on the length of the processed miRNA and any flanking regions added. miRNA precursors are generally between 62 and 110 nucleotides in humans.

Nucleic acids used in methods and compositions disclosed herein may have regions of identity or complementarity to another nucleic acid. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, or any range derivable therein, contiguous nucleotides. It is further understood that the length of complementarity within a precursor miRNA or between a miRNA probe and a miRNA or a miRNA gene are such lengths. Moreover, the complementarity may be expressed as a percentage, meaning that the complementarity between a probe and its target is 90% or greater over the length of the probe. In some embodiments, complementarity is or is at least 90%, 95% or 100%. In particular, such lengths may be applied to any nucleic acid comprising a nucleic acid sequence identified in any of the SEQ ID NOs disclosed herein. The commonly used name of the miRNA is given (with its identifying source in the prefix, for example, "hsa" for human sequences) and the processed miRNA sequence. Unless otherwise indicated, a. miRNA without a prefix will be understood to refer to a human miRNA. A miRNA designated, for example, as miR-1-2 in the application will be understood to refer to hsa-miR-1-2. Moreover, a lower-case letter in the name of a miRNA may or may not be lowercase; for example, hsa-miR-130b can also be referred to as miR-130B. In addition, miRNA sequences with a "mu" or "mmu" sequence will be understood to refer to a mouse miRNA and miRNA sequences with a "mo" sequence will be understood to refer to a rat miRNA. The term "miRNA probe" refers to a nucleic acid probe that can identify a particular miRNA or structurally related miRNAs.

It is understood that a miRNA is derived from genomic sequences or a gene. In this respect, the term "gene" is used for simplicity to refer to the genomic sequence encoding the precursor miRNA for a given miRNA. However, embodiments may involve genomic sequences of a miRNA that are involved in its expression, such as a promoter or other regulatory sequences.

The term "recombinant" generally refers to a molecule that has been manipulated in vitro or that is a replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide" each as a subgenus of the term "nucleic acid."

The term "miRNA" generally refers to a single-stranded molecule, but in specific embodiments, molecules will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary. miRNA probes or nucleic acids can include, can be, or can be at least 60, 65, 70, 75, 80, 85, 90, 95, 96, 97, 98, 99 or 100% complementary to their target.

As used herein, "hybridization", "hybridizes" or "capable of hybridizing" is understood to mean the forming of a double or triple stranded molecule or a molecule with partial double or triple stranded nature. The term "anneal" is synonymous with "hybridize." The term "hybridization", "hybridize(s)" or "capable of hybridizing" encompasses the terms "stringent conditions)" or "high stringency" and the terms "low stringency" or "low stringency condition(s)."

As used herein, "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvents) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or Isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of such include hybridization performed at about 0.15 M to about 0.9 M NaCl at a temperature range of about 20° C. to about 50° C. Of course, it is within the skill of one in the art to further modify the low or high stringency conditions to suite a particular application.

1. Nuclcobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those with a purine or pyrimidine substituted by one or more of an alkyl, caboxyalkyl, amino, hydroxyl, halogen (i.e., fluoro, chloro, bromo, or iodo), thiol or alkylthiol moiety. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such a nucleobase may be labeled or may be part of a molecule that is labeled and contains the nucleobase.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2-fluoro-2'-deoxyribose or a carbocyclic sugar where a carbon is substituted for an oxygen atom in the sugar ring.

Different types of covalent attachments) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used therein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods disclosed herein. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside, and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acid probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602.240, which describe oligonucleotides with three or four atom linker moiety replacing phosphodiester backbone moiety used for improved nuclease resistance, cellular uptake, and regulating RNA expression; U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'deoxyguanosine nucleotides and nucleic acid analogs thereof).

5. Modified Nucleotides

Labeling methods and kits may use nucleotides that are both modified for attachment of a label and can be incorporated into a miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the methods and compositions are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in some embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, etc. Functional groups may be prepared according to ways known to those of skill in the art, including the representative information found in U.S. Pat. Nos. 4,404,289; 4,405,711; 4,337,063 and 5,268,486, and U.K. Patent 1,529,202, which are all incorporated by reference.

Amine-modified nucleotides are used in some embodiments. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino)butyl-dATP; N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargylamino-dCTP, and 5-propargylamino-dUTP. Such nucleotides can be prepared according to methods known, to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

B. Preparation of Nucleic Acids

A nucleic acid may be made by any technique known to one of ordinary skill in the art, such as for example, chemical synthesis, enzymatic production, or biological production, it is specifically contemplated that miRNA probes are chemically synthesized.

In some embodiments, miRNAs are recovered or isolated from a biological sample. The miRNA may be recombinant or it may be natural or endogenous to the cell (produced from the cell's genome). It is contemplated that a biological sample may be treated in a way so as to enhance the recovery of small RNA molecules such as miRNA. U.S. patent application Ser. No. 10/667,126 describes such methods and is specifically incorporated herein by reference. Generally, methods involve lysing cells with a solution having guanidinium and a detergent.

Alternatively, nucleic acid synthesis is performed according to standard methods. See, for example, Itakura and Riggs (1980). Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide) include a nucleic acid made by in vitro chemical synthesis using phosphotriester, phosphite, or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In some methods, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide as described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 2001, incorporated heroin by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method, polynucleotide phosphorylase method, and by solid-phase chemistry. The diester method was the first to be developed to a usable slate, primarily by Khorana and co-workers. (Khorana, 1979). The basic step is the joining of two suitably protected deoxynucleotides to form a dideoxynucleotide containing a phosphodiester bond.

The main difference between the diester and triester methods is the presence in the latter of an extra protecting group on the phosphate atoms of the reactants and products (Itakura et al., 1975). Purifications are typically done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method is an enzymatic method of DNA synthesis that can be used to synthesize many useful oligonucleotides (Gillam et al., 1978; Gillam et al., 1979). Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods draw on technology developed for the solid-phase synthesis of polypeptides. It has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become the most widely used coupling chemistry for the synthesis of oligonucleotides. Phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used hi the context of a cell free system so long as the reagents for generating the RNA molecule are present. Such methods include those described in Sambrook, 2003, Sambrook, 2001 and Sambrook, 1989, which are hereby incorporated by reference.

In certain embodiments, nucleic acid molecules are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

C. Isolation of Nucleic Acids

Nucleic acids may be isolated using techniques well known to those of skill in the art, though in particular embodiments, methods for isolating small nucleic acid molecules, and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased.

Methods may involve the use of organic solvents and/or alcohol to isolate nucleic acids, particularly miRNA used in methods and compositions disclosed herein. Some embodiments are described in U.S. patent application Ser. No. 10/667,126, which is hereby incorporated by reference. Generally, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column may work particularly well for such Isolation procedures.

In specific embodiments, miRNA isolation processes include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for forming a lysate/alcohol mixture, wherein the concentration of alcohol in the mixture is between about 35% to about 70%; d) applying the lysate/alcohol mixture to a solid support; e) eluting the miRNA molecules from the solid support with an tonic solution; and, f) capturing the miRNA molecules. Typically the sample is dried down and resuspended in a liquid and volume appropriate for subsequent manipulation.

II. LABELS AND LABELING TECHNIQUES

In some embodiments, miRNAs are labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In particular embodiments, the label is non-radioactive. Generally, nucleic acids may be labeled by adding labeled nucleotides (one-step process) or adding nucleotides and labeling the added nucleotides (two-step process).

A. Labeling Techniques

In some embodiments, nucleic acids are labeled by catalytically adding to the nucleic acid an already labeled nucleotide or nucleotides. One or more labeled nucleotides can be added to miRNA molecules. Sec U.S. Pat. No. 6,723,509, which is hereby incorporated by reference.

In other embodiments, an unlabeled nucleotide(s) is catalytically added to a miRNA, and the unlabeled nucleotide is modified with a chemical moiety that enables it to be subsequently labeled. In some embodiments, the chemical moiety is a reactive amine such that the nucleotide is an amine-modified nucleotide. Examples of amine-modified nucleotides are well known to those of skill in the art, many being commercially available.

In contrast to labeling of cDNA during its synthesis, the issue for labeling miRNA is how to label the already existing molecule. Some aspects concern the use of an enzyme capable of using a di- or tri-phosphate ribonucleotide or deoxyribonucleotide as a substrate for its addition to a miRNA. Moreover, in specific embodiments, a modified di- or tri-phosphate ribonucleotide is added to the 3' end of a miRNA. The source of the enzyme is not limiting. Examples of sources for the enzymes include yeast, gram-negative bacteria such as *E. coli, Lactococcus lactis*, and sheep pox virus.

Enzymes capable of adding such nucleotides include, but are not limited to, poly(A) polymerase, terminal transferase, and polynucleotide phosphorylase. In specific embodiments, a ligase is contemplated as not being the enzyme used to add the label, and instead, a non-ligase enzyme is employed.

Terminal transferase may catalyze the addition of nucleotides to the 3' terminus of a nucleic acid. Polynucleotide phosphorylase can polymerize nucleotide diphosphates without the need for a primer.

B. Labels

Labels on miRNA or miRNA probes may be colorimetric (includes visible and UV spectrum, including fluorescent), luminescent, enzymatic, or positron emitting (including radioactive). The label may be detected directly or indirectly. Radioactive labels include $^{125}$I, $^{32}$P, $^{33}$P, and $^{35}$S. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; cosins and erythrosins; fluorescein and its derivatives, such as fluorescein isothiocyanate: macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR: Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides include Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides include Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, and Alexa Fluor 647-12-OBEA-dCTP.

It is contemplated that nucleic acids may be labeled with two different labels. Furthermore, fluorescence resonance energy transfer (FRET) may be employed in disclosed methods (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and other ligands, include ligands for an antibody.

C. Visualization Techniques

A number of techniques for visualizing or detecting labeled nucleic acids are readily available. Such techniques include, microscopy, arrays, fluorometry, light cyclers or other real time PCR machines, FACS analysis, scintillation counters, phosphoimagers, Geiger counters, MRI, CAT, antibody-based detection methods (Westerns, immunofluorescence, immunohistochemistry), histochemical techniques, HPLC (Griffey et al., 1997), spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize association of one or more nucleic acids. Furthermore, a person of ordinary skill in the art is well aware of ways of visualizing, identifying, and characterizing labeled nucleic acids, and accordingly, such protocols may be used. Examples of tools that may be used also include fluorescent microscopy, a Bio-Analyzer, a plate reader, Storm (Molecular Dynamics), Array Scanner, FACS (fluorescent activated cell sorter), or any instrument that has the ability to excite and detect a fluorescent molecule.

III. ARRAY PREPARATION AND SCREENING

A. Array Preparation

Some embodiments involve the preparation and use of miRNA arrays or miRNA probe arrays, which are ordered macroarrays or microarrays of nucleic acid molecules (probes) that are fully or nearly complementary or identical to a plurality of miRNA molecules or precursor miRNA molecules and that are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array-devices in which a plurality of distinct nucleic acid probes are stably associated with the surface of a solid support are known to those of skill in the art. Useful substrates for arrays include nylon, glass, metal, plastic, and silicon. Such arrays may vary in a number of different ways, including average probe length, sequence or types of probes, nature of bond between the probe and the array surface, e.g. covalent or non-covalent, and the like. The labeling and screening methods are not limited by with respect to any parameter except that the probes detect miRNA; consequently, methods and compositions may be used with a variety of different types of miRNA arrays.

Representative methods and apparatuses for preparing a microarray have been described, for example, in U.S. Pat. Nos. 5,143,854; 5,202,231; 5,242,974; 5,288,644; 5,324, 633; 5,384,261; 5,405,783; 5,412,087; 5,424,186; 5,429, 807; 5,432,049; 5,436,327; 5,445,934; 5,468,613; 5,470, 710; 5,472,672; 5,492,806; 5,525,464; 5,503,980; 5,510, 270; 5,525,464; 5,527,681; 5,529,756; 5,532,128; 5,545, 531; 5,547,839; 5,554,501; 5,556,752; 5,561,071; 5,571, 639; 5,580,726; 5,580,732; 5,593,839; 5,599,695; 5,599, 672; 5,610; 287; 5,624,711; 5,631,134; 5,639,603; 5,654, 413; 5,658,734; 5,661,028; 5,665,547; 5,667,972; 5,695, 940; 5,700,637; 5,744,305; 5,800,992; 5,807,522; 5,830, 645; 5,837,196; 5,871,928; 5,847,219; 5,876,932; 5,919, 626; 6,004,755; 6,087,102; 6,368,799; 6,383,749; 6,617, 112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000, which are each herein incorporated by reference.

It is contemplated that the arrays can be high density arrays, such that they contain 2, 20, 25, 50, 80, 100, or more, or any integer derivable therein, different probes. It is contemplated that they may contain 1000, 16,000, 65,000, 250,000 or 1,000,000 or more, or any interger or range derivable therein, different probes. The probes can be directed to targets in one or more different organisms or cell types. In some embodiments, the oligonucleotide probes may range from 5 to 50, 5 to 45, 10 to 40, 9 to 34, or 15 to 40 nucleotides in length. In certain embodiments, the oligonucleotide probes are 5, 10, 15, 20, 25, 30, 35, 40 nucleotides in length, including all integers and ranges there between.

Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed herein or may be found in, for example, WO 9743450; WO 03023058; WO 03022421; WO 03029485; WO 03067217; WO 03066906; WO 03076928; WO 03093810; WO 03100448A1, all of which are specifically incorporated by reference.

B. Sample Preparation

It is contemplated that the miRNA of a wide variety of samples can be analyzed using arrays, miRNA probes, or array technology. While endogenous miRNA is contemplated for use with compositions and methods disclosed herein, recombinant miRNA—including nucleic acids that are complementary or identical to endogenous miRNA or precursor miRNA—can also be handled and analyzed as described herein. Samples may be biological samples, in which case, they can be from biopsy, fine needle aspirates, exfoliates, blood, tissue, organs, semen, saliva, tears, other bodily fluid, hair follicles, skin, or any sample containing or constituting biological cells. In certain embodiments, samples may be, but are not limited to, fresh, frozen, fixed, formalin fixed, paraffin embedded, or formalin fixed and paraffin embedded. Alternatively, the sample may not be a biological sample, but a chemical mixture, such as a cell-free reaction mixture (which may contain one or more biological enzymes).

C. Hybridization

After an array or a set of miRNA probes is prepared and the miRNA in the sample is labeled, the population of target nucleic acids is contacted with the array or probes under hybridization conditions, where such conditions can be adjusted, as desired, to provide for an optimum level of specificity in view of the particular assay being performed. Suitable hybridization conditions are well known to those of skill in the art and reviewed in Sambrook et al. (2001) and WO 95/21944. Of particular interest in embodiments is the use of stringent conditions during hybridization. Stringent conditions are known to those of skill in the art.

It is specifically contemplated that a single array or set of probes may be contacted with multiple samples. The samples may be labeled with different labels to distinguish the samples. For example, a single array can be contacted with a tumor tissue sample labeled with Cy3, and normal tissue sample labeled with Cy5. Differences between the samples for particular miRNAs corresponding to probes on the array can be readily ascertained and quantified.

The small surface area of the array permits uniform hybridization conditions, such as temperature regulation and salt content. Moreover, because of the small area occupied by the high density arrays, hybridization may be carried out in extremely small fluid volumes (e.g., about 250 µl or less, including volumes of about or less than about 5, 10, 25, 50, 60, 70, 80, 90, 100 µl, or any range derivable therein). In small volumes, hybridization may proceed very rapidly.

D. Differential Expression Analyses

Arrays can be used to detect differences between two samples. Specifically contemplated applications include identifying and/or quantifying differences between miRNA from a sample that is normal and from a sample that is not normal, between a cancerous condition and a non-cancerous condition, or between two differently treated samples. Also, miRNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. These arrays may generally be produced using mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. No. 5,384,261, incorporated herein by reference in its entirety. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate (see U.S. Pat. Nos. 5,770,358, 5,789,162, 5,708,153, 6,040,193 and 5,800,992, each of which is hereby incorporated in its entirety). Arrays may be packaged in such a manner as to allow for diagnostics or other manipulation of an all inclusive device (see for example, U.S. Pat. Nos. 5,856,174 and 5,922,591, each incorporated in its entirety by reference). See also U.S. patent application Ser. No. 09/545,207, filed Apr. 7, 2000, which is incorporated by reference in its entirety for additional information concerning arrays, their manufacture, and their characteristics.

Particularly, arrays can be used to evaluate samples with respect to diseases or conditions that include, but are not limited to: chronic pancreatitis; pancreatic cancer; AIDS, autoimmune diseases (rheumatoid arthritis, multiple sclerosis, diabetes-insulin-dependent and non-independent, systemic lupus erythematosus and Graves disease); cancer (e.g., malignant, benign, metastatic, precancer); cardiovascular diseases (heart disease or coronary artery disease, stroke-ischemic and hemorrhagic, and rheumatic heart disease); diseases of the nervous system; and infection by pathogenic microorganisms (Athlete's Foot, Chickenpox, Common cold, Diarrheal diseases. Flu, Genital herpes, Malaria, Meningitis, Pneumonia, Sinusitis, Skin diseases, Strep throat. Tuberculosis, Urinary tract infections, Vaginal infections, Viral hepatitis); inflammation (allergy, asthma); prion diseases (e.g., CJD, kuru, GSS, FFI).

Moreover, miRNAs can be evaluated with respect to the following diseases, conditions, and disorders: pancreatitis, chronic pancreatitis, and/or pancreatic cancer.

Cancers that may be evaluated by the disclosed methods and compositions include cancer cells particularly from the pancreas, including pancreatic ductal adenocarcinoma (PDAC), but may also include cells and cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma: endometroid carcinoma; skin appendage carcinoma; apocrine adenocarcinoma; sebaceous adenocarcinoma; ceruminous adenocarcinoma; mucocpidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant: myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxlacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia: megakaryoblastic leukemia; myeloid sarcoma; and hairy cell leukemia. Moreover, miRNAs can be evaluated in precancers, such as metaplasia, dysplasia, and hyperplasia.

It is specifically contemplated that the disclosed methods and compositions can be used to evaluate differences between stages of disease, such as between hyperplasia, neoplasia, pre-cancer and cancer, or between a primary tumor and a metastasized tumor.

Moreover, it is contemplated that samples that have differences in the activity of certain pathways may also be compared. These pathways include the following and those involving the following factors: antibody response, apoptosis, calcium/NFAT signaling, cell cycle, cell migration, cell adhesion, cell division, cytokines and cytokine receptors, drug metabolism, growth factors and growth factor receptors, inflammatory response, insulin signaling, NFk-B signaling, angiogenesis, adipogenesis, cell adhesion, viral infect on, bacterial infection, senescence, motility, glucose transport, stress response, oxidation, aging, telomere extension, telomere shortening, neural transmission, blood clotting, stem cell differentiation, G-Protein Coupled Receptor (GPCR) signaling, and p53 activation.

Cellular pathways that may be profiled also include but are not limited to the following: any adhesion or motility pathway including but not limited to those involving cyclic AMP, protein kinase A, G-protein couple receptors, adenylyl cyclase, L-selectin, E-selectin, PECAM, VCAM-1, α-actinin, paxillin, cadherins, AKT, integrin-α, integrin-β, RAF-1, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, RhoA, RAC1, myosin light chain kinase, platelet-derived growth factor receptor or ezrin: any apoptosis pathway including but not limited to those involving AKT, Fas ligand, NFκB, caspase-9, PI3 kinase, caspase-3, caspase-7, ICAD, CAD, EndoG, Granzyme B, Bad, Bax, Bid, Bak, APAF-1, cytochrome C, p53, ATM, Bel-2, PARP, Chk1, Chk2, p21, c-Jun, p73, Rad51, Mdm2, Rad50, c-Ab1, BRCA-1, perforin, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, $H_2O_2$, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RIP, cyclin-D1, PCNA, Bcl-XL, PIP2, PIP3, PTEN, ATM, Cdc2, protein kinase C, calcineurin, IKKα, IKKβ, IKKγ, SOS-1, c-FOS, Traf-1, Traf-2, IKBβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p16, p34, p20, PP2A, angiotensin, angiotensin-converting enzyme, protease-activated receptor-1, protease-activated receptor-4, Ras, RAF-1, PLCβ, PLCγ, COX-1, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCC1, CD40, CD40 ligand, p38, IKKα, IKKβ, NFκB, TRAF2, TRAF3, TRAF5, TRAF6, IL-4, IL-4 receptor, CDK5, AP-1 transcription factor, CD45, CD4, T cell receptors, MAP kinase, nerve growth factor, nerve growth factor receptor, c-Jun, c-Fos, Jun kinase, GRB2, SOS-1, ERK-1, ERK, JAK2, STAT4, IL-12, IL-12 receptor, nitric oxide synthase, TYK2, IFNγ, clastase, IL-8, epithclins, IL-2, IL-2 receptor, CD28, SMAD3, SMAD4, TGFβ or TGFβ receptor; any cell cycle regulation, signaling or differentiation pathway including tail not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-1, BRCA-2, SKP1, the proteasome, CUL1, E2F, p107, steroid hormones, steroid hormone receptors, IκBα, IκBβ, Sin3A, heat shock proteins, Ras, Rho, ERKs, IKKs, PI3 kinase, Bel-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCC1, Sonic Hedgehog, Crm1, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, IKβ, NFκB, RAC1, RAF1, EPO, diacylglycerol, c-Jun, c-Fos, Jun kinase, hypoxia-inducible factors, GATA4, β-catenin, α-catenin, calcium, arrestin, surviyin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-1 receptor, the urea cycle, vesicular transport, or salvage pathways. It is further contemplated that the disclosed nucleic acids molecules can be employed in diagnostic and therapeutic methods with respect to any of the above pathways or factors. Thus, in some embodiments, a miRNA may be differentially expressed with respect to one or more of the above pathways or factors.

Phenotypic traits also include characteristics such as longevity, morbidity, appearance (e.g., baldness, obesity), strength, speed, endurance, fertility, susceptibility or receptivity to particular drugs or therapeutic treatments (drug efficacy), and risk of drug toxicity. Samples that differ in these phenotypic traits may also be evaluated using the arrays and methods described.

In certain embodiments, miRNA profiles may be generated to evaluate and correlate those profiles with pharmacokinetics. For example, miRNA profiles may be created and evaluated for patient tumor and blood samples prior to the patient being treated or during treatment to determine if there are miRNAs whose expression correlates with the outcome of the patient. Identification of differential miRNAs can lead to a diagnostic assay involving them that can be used to evaluate tumor and/or blood samples to determine what drug regimen the patient should be provided. In addition, identification of differential miRNAs can be used to identify or select patients suitable for a particular clinical trial. If a miRNA profile is determined to be correlated with drug efficacy or drug toxicity, such may be relevant to whether that patient is an appropriate patient for receiving a drug or for a particular dosage of a drug.

In addition to the above prognostic assays, blood samples from patients with a variety of diseases can be evaluated to determine if different diseases can be identified based on blood miRNA levels. A diagnostic assay can be created based on the profiles that doctors can use to identify individuals with a disease or who are at risk to develop a disease. Alternatively, treatments can be designed based on miRNA profiling. Examples of such methods awl compositions are described in the U.S. Provisional Patent Application entitled "Methods and Compositions Involving miRNA and miRNA Inhibitor Molecules" filed on May 23, 2005, in the names of David Brown, Lance Ford, Angie Cheng and Rich Jarvis, which is hereby incorporated by reference in its entirety.

E. Other Assays

In addition to the use of arrays and microarrays, it is contemplated that a number of different assays amid be employed to analyze miRNAs, their activities, and their effects. Such assays include, but are not limited to, nucleic acid amplification, polymerase chain reaction, quantitative PCR, RT-PCR, in situ hybridization, Northern hybridization, hybridization protection assay (HPA), branched DNA (bDNA) assay, rolling circle amplification (RCA), single molecule hybridization detection, Invader assay, and/or Bridge Litigation Assay.

F. Evaluation of Expression Levels and Diff Pair Values

A variety of different models can be employed to evaluate expression levels and/or other comparative values based on expression levels of miRNAs (or their precursors or targets). One model is a logistic regression model (see the Wikipedia entry on the World Wide Web at en.wikipedia.com).

Start by computing the weighted sum of the DiffPair values:

$$z = \beta_0 + \beta_1 * Diff(miR_{1a}, miR_{1b}) + \beta_2 * Diff(miR_{2a}, miR_{2b}) + \ldots$$

where the $\beta_0$ is the (Intercept) term identified in the spreadsheets, while the remaining $\beta_1$ are the weights corresponding to the various DiffPairs in the model in question. Once z is computed, the score $p_{malignant}$ (which may be interpreted as predicted probability of malignancy) is calculated as $$p_{malignant} = \frac{1}{1 + \exp(-z)}$$

This functions to turn the number z, which may be any value from negative infinity to positive infinity, into a number between 0 and 1, with negative values for z becoming scores/probabilities of less than 50% and positive values for z becoming scores/probabilities of greater than 50%.

Other examples of models include but are not limited to Decision Tree, Linear Disciminant Analysis, Neural Network, Support Vector Machine, and k-Nearest Neighbor Classifier. In certain embodiments, scoring algorithm comprises a method selected from the group consisting of: Linear Discriminate Analysis (LDA), Significance Analysis of Microarrays, Tree Harvesting, CART, MARS, Self Organizing Maps, Frequent Item Set, Bayesian networks, Prediction Analysis of Microarray (PAM), SMO, Simple Logistic Regression, Logistic Regression, Multilayer Perception, Bayes Net, Naive Bayes, Naive Bayes Simple, Naive Bayes Up, IB1, Ibk, Kstar, LWL, AdaBoost, ClassViaRegression, Decorate, Multiclass Classifier, Random Committee, j48, LMT, NBTrce, Part, Random Forest, Ordinal Classifier, Sparse Linear Programming (SPLP), Sparse Logistic Regression (SPLR), Elastic NET, Support Vector Machine, Prediction of Residual Error Sum of Squares (PRESS), and combinations thereof. A person of ordinary skill in the art could use these different models to evaluate expression level data and comparative data involving expression levels of one or more miRs (or their precursors or their targets). In some embodiments, the underlying classification algorithm is linear discriminate analysis (LDA). LDA has been extensively studied in the machine learning literature, for example, Hastie et al. (2009) and Venables & Ripley (2002), which are both incorporated by reference.

Models may take into account one or more diff pair values or they may also take into account differential expression of one or more miRNAs not specifically as part of a diff pair. A diagnostic or risk score may be based on 1, 2, 3, 4, 5, 6, 7, 8 or more diff pair values (or any range derivable therein), but in some embodiments, it takes into account additionally or alternatively, 1, 2, 3, 4, 5, 6, 7, 8, 9, 10 or more miRNA expression levels (or any range derivable therein), wherein the miRNA expression level detectably differs between PDAC cells and cells that are not PDAC.

In some embodiments, a score is prepared. The score may involve numbers such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, (or any range or a subset therein) in some embodiments.

IV. KITS

Any of the compositions described herein may be comprised in a kit. In a non-limiting example, reagents for isolating miRNA, labeling miRNA, and/or evaluating a miRNA population using an array, nucleic acid amplification, and/or hybridization can be included in a kit, as well as reagents for preparation of samples from pancreatic samples. The kit may further include reagents for creating or synthesizing miRNA probes. Such kits may thus comprise, in suitable container means, an enzyme for labeling the miRNA by incorporating labeled nucleotides or unlabeled nucleotides that are subsequently labeled. In certain aspects, the kit can include amplification reagents. In other aspects, the kit may include various supports, such as glass, nylon, polymeric beads, and the like, and/or reagents for coupling any probes and/or target nucleic acids. Kits may also include one or more buffers, such as a reaction buffer, labeling buffer, washing buffer, or hybridization buffer, compounds for preparing the miRNA probes, and components for isolating miRNAs. Other kits may include components for making a nucleic acid array comprising miRNAs, and thus, may include, for example, a solid support.

Kits for implementing methods described herein are specifically contemplated. In some embodiments, there are kits for preparing miRNAs for multi-labeling and kits for preparing miRNA probes and/or miRNA arrays. In such embodiments, kits comprise, in suitable container means, 1, 2, 3, 4, 5, 6, 7, 8, 9, 10, 11, 12 or more of the following: 1) poly(A) polymerase; 2) unmodified nucleotides (G, A, T, C, and/or U); 3) a modified nucleotide (labeled or unlabeled); 4) poly(A) polymerase buffer; 5) at least one microfilter; 6) label that can be attached to a nucleotide; 7) at least one miRNA probe; 8) reaction buffer; 9) a miRNA array or components for making such an array; 10) acetic acid; 11) alcohol; 12) solutions for preparing, isolating, enriching, and purifying miRNAs or miRNA probes or arrays. Other reagents include those generally used for manipulating RNA, such as formamide, loading dye, ribonuclease inhibitors, and DNase.

In specific embodiments, kits include an array containing miRNA probes, as described in the application. An array may have probes corresponding to all known miRNAs of an organism or a particular tissue or organ in particular conditions, or to a subset of such probes. The subset of probes on arrays may be or include those identified as relevant to a particular diagnostic, therapeutic, or prognostic application. For example, the array may contain one or more probes that are indicative or suggestive of 1) a disease or condition (chronic pancreatitis and/or pancreatic cancer), 2) susceptibility or resistance to a particular drug or treatment; 3) susceptibility to toxicity from a drug or substance; 4) the stage of development or severity of a disease or condition (prognosis); and 5) genetic predisposition to a disease or condition.

For any kit embodiment, including an array, there can be nucleic acid molecules that contain or can be used to amplify a sequence that is a variant of, identical to, or complementary to all or part of any of the SEQ ID NOs disclosed herein. In certain embodiments, a kit or array can contain one or more probes for the miRNAs identified by SEQ ID NOs disclosed herein. Any nucleic acid discussed above may be implemented as part of a kit.

Components of kits may be packaged either in aqueous media or in lyophilized form. The container means of the kits will generally include at least one vial, test tube, flask, bottle, syringe, or other container means, into which a component may be placed, and preferably, suitably aliquotted. Where there is more than one component in the kit (e.g., labeling reagent and label may be packaged together), the kit also will generally contain a second, third, or other additional container into which the additional components may be separately placed. However, various combinations of components may be comprised in a vial. The kits also may include a means for containing the nucleic acids, and any other reagent containers in close confinement for commercial sale. Such containers may include injection or blow molded plastic containers into which the desired vials are retained.

When the components of a kit are provided in one and/or more liquid solutions, the liquid solution may be an aqueous solution, with a sterile aqueous solution being particularly preferred.

However, the components of a kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg, or at least or at most those amounts, of dried dye are provided in kits. The dye may then be resuspended in any suitable solvent, such as DMSO.

The container means will generally include at least one vial, test tube, flask, bottle, syringe and/or other container means, into which the nucleic acid formulations are placed, for example, suitably allocated. Kits may also comprise a second container means for containing a sterile, pharmaceutically acceptable buffer and/or other diluent.

Kits may include a means for containing the vials in close confinement for commercial sale, such as, e.g., injection and/or blow-molded plastic containers into which the desired vials are retained.

Such kits may also include components that facilitate isolation of the labeled miRNA. It may also include components that preserve or maintain the miRNA or that protect against its degradation. Such components may be RNAse-free or protect against RNAses. Such kits generally will comprise, in suitable means, distinct containers for each individual reagent or solution.

A kit may also include instructions for employing the kit components as well the use of any other reagent not included in the kit Instructions may include variations that can be implemented.

Kits may also include one or more of the following: control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors.

It is contemplated that such reagents are embodiments of kits. Such kits, however, are not limited to the particular items identified above and may include any reagent used for the manipulation or characterization of miRNA.

V. EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art will, in light of the present disclosure, appreciate that many changes can be made in the specific embodiments that are disclosed and still obtain a like or similar result without departing from the spirit and scope of the invention.

Example 1

A panel of 95 formalin-fixed, paraffin-embedded (FFPE) tissue specimens (52 pancreatic ductal adenocarcinoma (PDAC) samples and 43 chronic pancreatitis (CP) samples) was used as a training set for building a model that can distinguish between PDAC samples and CP samples. A model is a classifier trained on a number of miRNA DiffPairs to predict whether a specimen is a PDAC specimen. The variables (factors) for the model are: the classification algorithm (e.g., Linear Discriminate Analysis (LDA), Partial Least Squares (PLS), and Logistic Regression); the number of miRNA DiffPairs included in the analysis; the method to select the number of miRNA DiffPairs (e.g., Wilcox-test, RankProduct, and Moderated t-test). All such methods are probabilistic in nature and provide the posterior probability of a sample being PDAC, so all scores are 0 to 1 inclusive. Models were evaluated and ranked based on estimates of area under the receiver operating characteristic curve (AUC) as determined from nested and replicated 5-fold cross-validation. Additional performance metrics such as Matthew's correlation coefficient and Youden's index were also considered.

Table 1 provides representative miRNAs that may be included in a miRNA DiffPair. Sequences and ABI pan numbers (ABI, Foster City, Calif.) are provided.

TABLE 1

Representative miRNAs

| miRNA | ABI Part No. | Sequence | SEQ ID NO. |
|---|---|---|---|
| miR-196a | 000495 | UAGGUAGUUUCAUGUUGUUGG | 1 |
| miR-210 | 000512 | CUGUGCGUGUGACAGCGGCUGA | 2 |
| miR-217 | 002337 | UACUGCAUCAGGAACUGAUUGGA | 3 |
| miR-375 | 000564 | UUUGUUCGUUCGGCUCGCGUGA | 4 |
| miR-130 | 000456 | CAGUGCAAUGAUGAAAGGGCAU | 5 |
| miR-135b | 000461 | UAUGGCUUUUCAUUCCUAUGUG | 6 |
| miR-148a | 000470 | UCAGUGCACUACAGAACUUUGU | 7 |
| miR-155 | 000479 | UUAAUGCUAAUCGUGAUAGGGG | 8 |
| miR-223 | 000526 | UGUCAGUUUGUCAAAUACCCC | 9 |
| miR-96 | 000434 | UUUGGCACUAGCACAUUUUUGC | 10 |
| miR-24 | 000402 | UGGCUCAGUUCAGCAGGAACAG | 11 |
| miR-21 | 000397 | UAGCUUAUCAGACUGAUGUUGA | 12 |

Based on the ranking from the AUC estimate, a single model was selected for validation on 162 annotated FNA samples. These FNA samples were collected from eight independent sites in North America and Europe. Samples were collected by performing Endoscopic Ultrasound Guided Fine Needle Aspiration (EUS-FNA) in patients showing evidence of solid pancreatic lesions that were referred for cytological evaluation due to suspicion of pancreatic ductal adenocarcinoma. Patients were informed of the study, given the opportunity to participate in the study, and completed informed consent forms. The study and consent forms were approved by each institution's Institutional Review Board or Ethics Committee.

Patients were selected for inclusion in this study based on the following criteria: (a) pancreatic EUS-FNA is indicated for diagnostic workup based on standard of care and determined to be essential for the patient's clinical care by the Gastroenterologist taking care of the patient; (b) the patient is age 18 or older; and (c) the patient may be any gender or ethnicity to be included in the study. Patients were excluded from the study based on the following criteria: (a) evidence of other active primary cancer (non-pancreatic); (b) the patient is under 18 years of age; or (c) the study physicians determined that sufficient EUS-FNA material cannot be obtained.

After collection of the diagnostic FNA for cytology evaluation, each participant had one to three additional FNAs collected and deposited into Asuragen's RNARetain® pre-analytical RNA Stabilization Solution. Samples were stored in RNARetain overnight at 4° C. and then stored at −80° C. and shipped to Asuragen on dry ice in batches, where they were stored at −80 until processing for RNA isolation.

RNA isolation was performed using a modified procedure based on the mirVana PARIS kit (Ambion), and reverse transcription was performed. For each sample, 30 ng of RNA per RT reaction per miRNA was used as input, and each sample was performed in triplicate if sufficient total RNA was available. Sample RNA concentration was adjusted to 7.5 ng/uL. RT Master Mix was prepared using TaqMan MicroRNA RT master kit components and individual TaqMan Assay RT primers. Following reverse transcription, quantitative PCR (qPCR) was performed to assess the expression levels of the miRNAs listed in Table 1.

The model that provided the best overall performance in terms of its ability to distinguish between PDAC and CP samples was the LDA+ModT+6 model and included 6 miRNA DiffPairs: Diff(miR-135b-miR-24); Diff(miR-130b, miR-135b); Diff(miR-135b, miR-148a); Diff(miR-375, miR-135b); Diff(miR-135b, miR-96); and Diff(miR-145a, miR-196a). As explained above, a miRNA DiffPair is a biomarker that is a self-normalizing combination of two miRNAs with expression values from one miRNA subtracted from expression values of another miRNA. The combination could involve one miRNA as an actual predictor and another as a normalize, or the combination could involve two anti-correlated predictor miRNAs.

Expression values were integrated using Linear Discriminate Analysis (LDA). The implementation of this algorithm is known to those of skill in the art and is, for example, described in "Modern Applied Statistics with S" by Venables and Ripley. The source code used in the analysis is also known to those of skill in the art and was adopted from the MASS package in the R programming language, which is available on the World Wide Web at cran.r-project.org/web/packages/MASS/index.html.

LDA integrates the expression values obtained into a single score that makes the classification decision (PDAC vs CP (called "Benign")). The score represents the probability of a sample being PDAC based on the expression data of the diff pairs. Because it is a probability, the score is 0 to 1 inclusive. The score is dichotomized in order to make a clinical call of a diagnostic positive (predicted PDAC) or a diagnostic negative (predicted Benign).

As shown in FIG. 1, the LDA+ModT+6 model provided the highest AUC value in the training exercise using the FFPE samples. The different models were ranked by the estimated AUC from cross-validation based on the 95 FFPE training samples. The performance metrics from all of the top models were similar. However, the LDA+ModT+6 model had nominally higher AUC and MCC estimates (including ties) and a strong Youden index. Specifically, as shown in FIG. 1, that model provided an AUC estimate of 0.978; sensitivity of 0.95 (sensitivity=# true positives/(# true positives+# false negatives)); specificity of 0.93 (specificity=# of true negatives/(# true negatives+# false positives)); and a Youden's index of 0.88 (Youden's index=(sensitivity+specificity)−1). Negative control models (models based on random chance) were also used in the analysis, and the performance of those models had AUC estimates around 0.5 as expected (data not shown).

The LDA+ModT+6 model was then used to evaluate an independent panel of fine needs aspirate (FNA) specimens. The 162 FNA samples (128 PDAC and 34 CP from multiple sites) are referred to as the test set, and no samples from the test set were used to optimize (train) the final model. On the test set, the LDA+ModT+6 model provided an AUC of 0.90 with sensitivity and specificity at 0.89 and 0.91, respectively. The results are shown in FIG. 2.

In FIG. 2, panels are stratified horizontally by performance metrics of LDA+ModT+6, while panels are stratified vertically by data sets (Train=FFPE sample assessment and Test=FNA sample assessment). The LDA+ModT+6 model shows relatively robust performance estimates across a range of thresholds (x-axis in all plots), for most performance metrics. This suggests that performance is stable and unlikely to be greatly affected by threshold estimates. Because the model calculates the posterior probability of being PDAC, the thresholds range from 0 to 1 inclusive. The results shown in FIG. 2 confirm that it is possible to set the threshold value for distinguishing between a PDAC and Benign sample over a broad range, and the threshold value can be adjusted to provide increased sensitivity or specificity as needed. For example, the threshold may be 0.5, where a sample is a diagnostic positive if the score is greater than or equal to 0.5, and the sample is a diagnostic negative if the score is less than 0.5. This 0.5 threshold was used to evaluate the ability of the LDA+ModT+6 model, as well as other models, to correctly distinguish between PDAC and CP samples.

Although the LDA+ModT+6 model (also called the "Full Model" or "miRInform" herein and in the drawings) provided improved sensitivity as compared to other models, two other models were also able to distinguish between PDAC and CP samples. The "Simple Model" evaluated only one miRNA DiffPair: miR-135b and miR-24. The "Reduced Model" evaluated four miRNA DiffPairs: Diff(miR-135b, miR-24); Diff(miR-130b, miR-135b); Diff(miR-135b, miR-148a); and Diff(miR-148a, miR-196a).

The Simple Model provided adequate specificity and sensitivity, as shown in FIG. 3. In FIG. 3, the differences in the number of samples available for classification are due to the handling of missing data. The more complex model (LDA+ModT+6) is more sensitive to missing data—particularly 196a and 96. In this case, any measurable Ct less than or equal to 45 was set to 40 Ct. Ct values greater than 45 were non-determined. The sensitivity for the LDA+ModT+6 is statistically better than the sensitivity value for the Simple Model, suggesting that the LDA+ModT+6 model maintains high specificity while improving on sensitivity as compared to the Simple Model.

Figure 4:
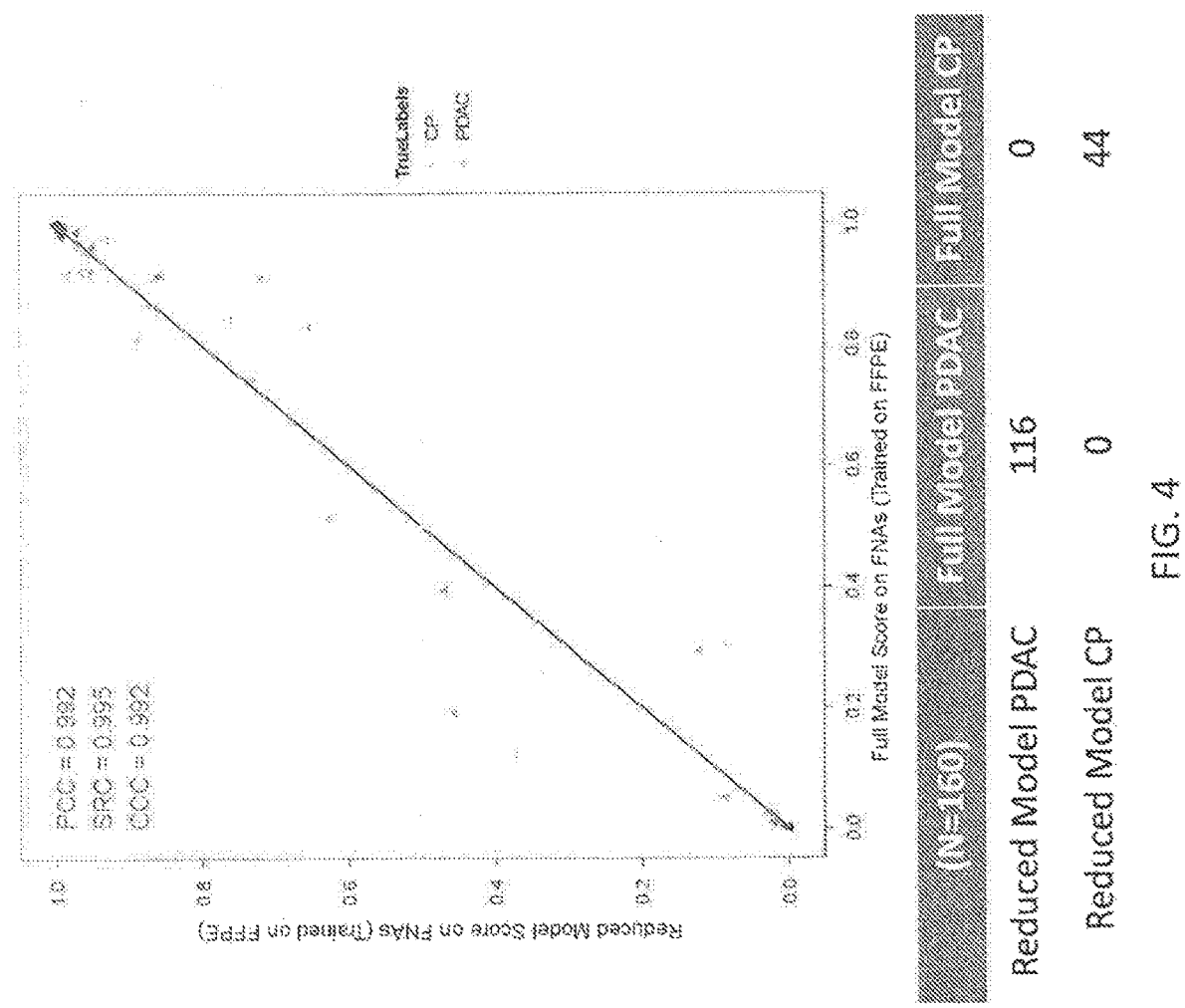
FIG. 4. Post-hoc comparison of the LDA+ModT+6 model to the Reduced Model in terms of ability to distinguish between PDAC and CP samples. The Reduced Model includes four miRNA DiffPairs: Diff(miR-135b, miR-24); Diff(miR-130b, miR-135b); Diff(miR-135b, miR-148a); and Diff(miR-148a, miR-196a).

A post-hoc analysis was performed to evaluate the equivalence between the Reduced Model based on 4 miRNA DiffPairs, and the LDA+ModT+6 model (also called the "Full Model"). As shown in FIG. 4, the Reduced Model maintained high performance, indicating that fewer than 6 miRNA DiffPairs are sufficient to distinguish between PDAC and CP samples. The Reduced Model was trained on the same 95 FFPE sample training set as was used for the LDA+ModT+6 model. Both the Full and Reduced models were individually trained on FFPE samples and tested on FNA samples. The Pearson correlation coefficient (PCC), Spearman rank correlation (SRC) and the concordance correlation coefficient (CCC) are all strong and close to the maximum value of 1, indicating that both models performed at a high level. In fact, there was a 100% overall agreement between the calls made by the Reduced Model and those made by the Full Model.

Figure 5:
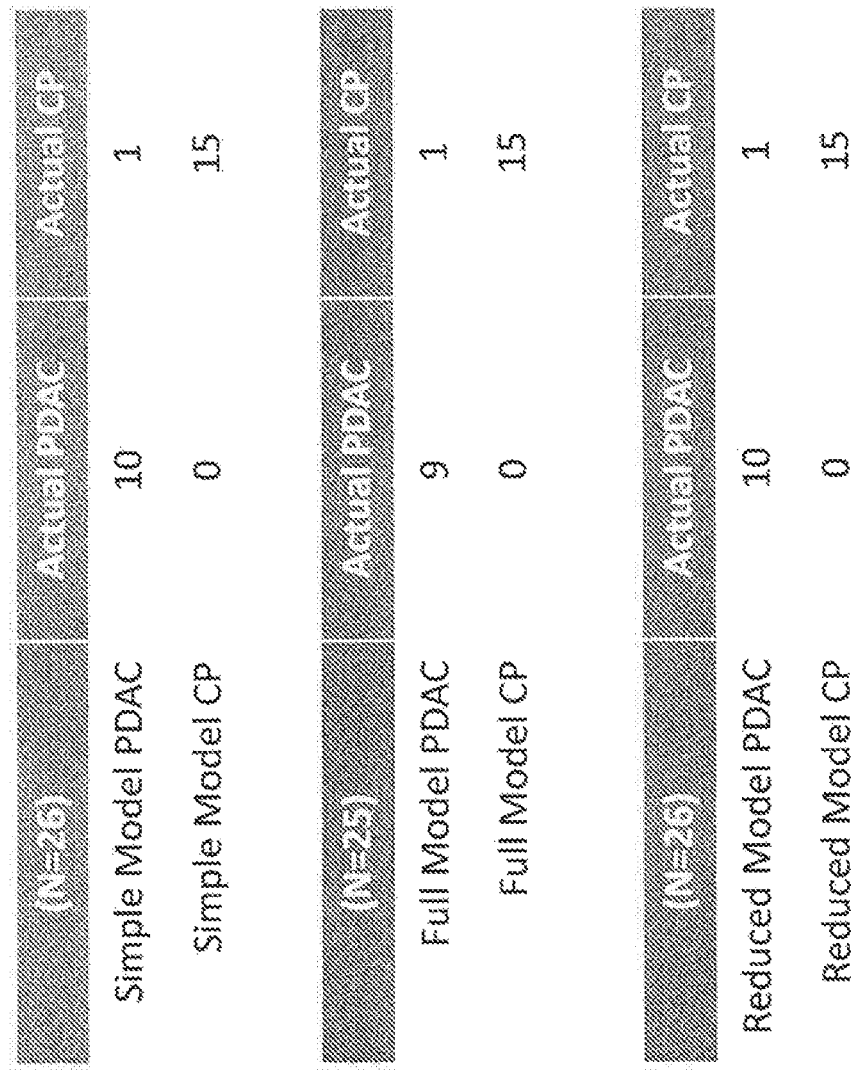
FIG. 5. Assessing the ability of the LDA+ModT+6 Full Model, Simple Model, and Reduced Model to correctly distinguish between PDAC and CP in samples that were determined to by cytologically atypical.

An analysis was also performed to determine how well the Simple, Full, and Reduced Models could distinguish between PDAC and CP in samples that were determined to exhibit atypical cytology. These samples were later resolved as either PDAC or CP based on histological assessment. As shown in FIG. 5, all models performed well in terms of the ability to distinguish between the PDAC and CP samples.

Example 2 miRInform Pancreas (MP) can detect PDAC specimens with 95% specificity and 82% sensitivity. However, in certain contexts it is important to have greater sensitivity or to have an attached measure of confidence that will stratify MP calls into high confidence and low confidence results. In this report we describe how such a test can be implemented.
Methodology The original MP test was developed based on building a model on 95 FFPE samples. The classification algorithm for MP is based on linear discriminate analysis that integrates the expression values from 6 miRNAs. FIG. 6 captures the performance of MP without adjustment by a potential reflex test or additional QC procedures. These results are based on the independent validation set of 184 FNA samples, and sets expectations for unbiased performance estimates. Future consideration of a reflex test (or associated measures of confidence) should be compared against these baseline results.

One observation from the predictive performance of MP is the negative predictive value (NPV) estimate. Any additional interpretation or modification of MP must mitigate the false negative rate, FNR. Basically, the FNR is comparable to the true negative rate, TNR, thus creating a low NPV. In order to distinguish TNs from FNs (TNs=true negatives; FNs=false negatives), inventors performed differential expression analysis on the TN (n=19) and FN (n=30) samples (see TN and FN from previous slide).

The differential expression analysis is designed to find one single diff pair (two miRNAs used in conjunction to produce a single expression value) to distinguish TNs from FNs. That analysis focuses only on the subset of miRNAs that are contained in MP. Both parametric and non-parametric tests were examined, but there seemed to be insufficient signal for parametric tests, and the results were relatively well correlated between parametric and non-parametric tests. An alternative strategy is to look for more than 1 diff pair to distinguish between TNs and FNs. That is done in the context of a tree classification algorithm although other classification algorithms can be used.

Figure 7:
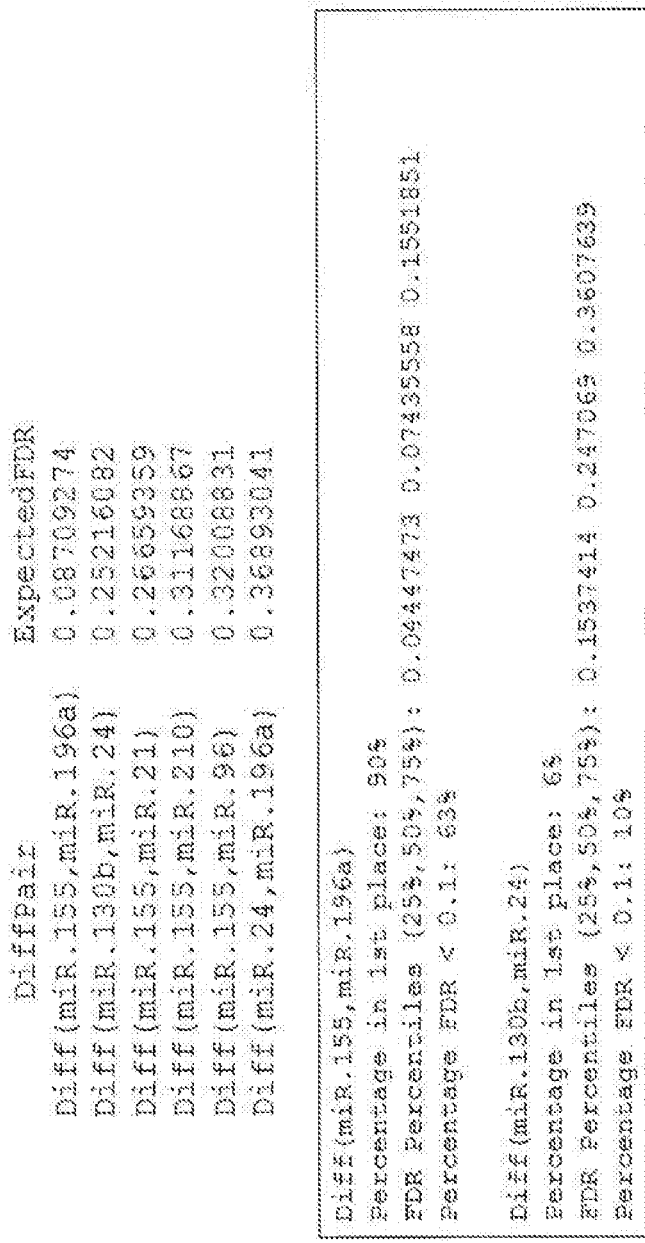
FIG. 7. The top diff pairs are shown sorted by the TriMean of the simulated Wilcox-test FDR estimates (ExpectedFDR). The false discovery rates (FDRs) are conservative because of the combinatorial nature of the pairings and subsequent hypothesis testing—the p-values are adjusted for all possible pairings. Results are based on 10 replications of 10-fold cross validation (100 total samplings). The replicated CV is balanced in the sense that equal numbers of TN and FN are removed. The bottom box shows basic statistics of the FDR estimates and how often the labeled diff pair is the top ranked candidate in addition to the percentage of sampled runs where the FDR is less than 10%.

Both the differential expression analysis and models to predict TNs (as opposed to FNs) are evaluated under replicated cross-validation. In particular, inventors chose 10 replications of 10-fold cross-validation producing 100 replications of all results. That is done to help mitigate bias in the performance estimates and to look at the stability of the results.
Results FIG. 7 shows the top discriminators of TNs and FNs based on all possible pairings of all 11 miRNAs run in the panel. The results show the top pairs are predominately composed of miR-155 which suggests that miR-155 would be an excellent component of discriminating TNs and FNs. However, miR-155 data is not as complete (in other studies outside of the FNA validation study) as, say, the $2^{nd}$ ranked pair, Diff(miR-130b, miR-24). That particular diffpair is composed of two miRNAs that are in the original MP model but paired with different miRNAs. Therefore, it would not require extra experimental work for evaluation and can easily be calculated as part of the standard test. The issue is that the ExpectedFDR value (the trimean of the false discovery rate or FDR based on 10 replications of 10 fold cross validation) is not as good (not as low) as the top pair. This suggests that the top candidates still have a high probability of being a false positive. Setting this issue aside inventors examined Diff(miR-130b, miR-24) more closely.

Figure 8:
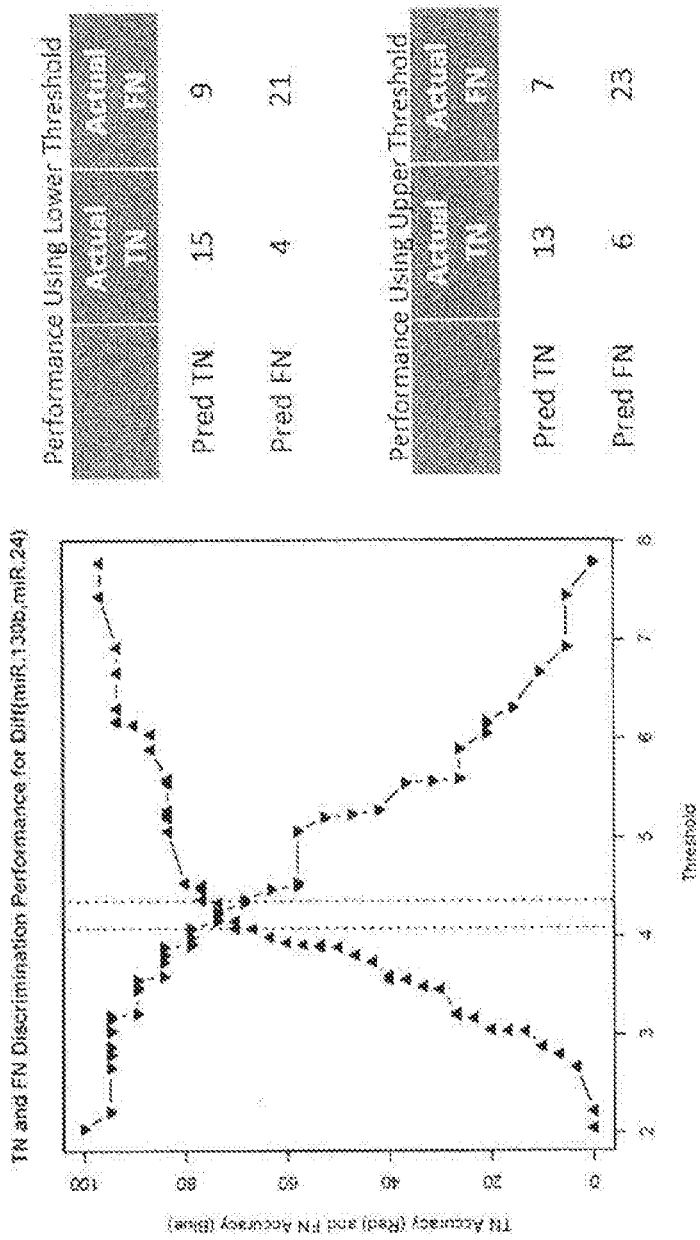
FIG. 8. The plot shows the expected performance on the FNA sample set using the Diff(miR-130b, miR-24) pair. The vertical lines capture 95% of the thresholds determined from replicated CV. The 2×2 tables show the performance at the lower and upper thresholds. The lower threshold is 4.08 while the upper threshold is 4.36. The data suggested here suggests maximum possible performance as we are training/testing on the same data. The right set of 2×2 tables show the performance estimates at the two vertical dashed lines. Specifically, the top box shows the results at the lower threshold (left dashed line) and the bottom box shows the results at the upper threshold (right dashed line). Both thresholds have very similar estimates for overall accuracy, and the 95% confidence intervals strongly overlap (data not shown). See mam text for more information.

In order to visualize predictive accuracy of the candidate Diff(miR-130b, miR-24), inventors examined accuracy estimates associated with predicting TNs and FNs. FIG. 8 shows the estimated accuracy of the diff pair, Diff(miR-130b, miR-24), (y-axis) at predicting TNs (down triangles) and FNs (up triangles) as a function of the threshold (x-axis). As the threshold is adjusted, the predictive performance increases (decreases) if the number of samples correctly classified increases (decreases). The vertical dashed lines represent the 2, 5 and 97.5 percentiles of the estimates for the optimal threshold. In other words, the optimal threshold is captured between the vertical lines with 95% confidence. The two boxes on the right hand side show the performance of the diff pair using the lower 95% threshold (top box) and the upper 95% threshold (lower box). Note that these results are only for the TNs and FNs, and not for all 184 samples in the study. Importantly, the results between the two thresholds are quite similar as is also evident by the relatively narrow range of the 95% range of the thresholds.

Using the upper and lower thresholds for Diff(miR-130b, miR-24), inventors look at overall predictive performance stratified by call status (Sec FIG. 9). The left box shows the results using the lower 95% threshold, and the right box shows the upper 95% threshold. In either case, the results are very similar. The results from the figure are generated as follows. The samples are classified $1^{st}$ by MP. The results of MP are then stratified by the results of Diff(miR-130b, miR-24). We observe the samples that are above the threshold (lower parts of both boxes) lending to be enriched for high confident calls. That is, we have good sensitivity and specificity for samples that have Diff(miR-130b, miR-24) >Threshold where Threshold can be the upper or lower 95% thresholds derived from the previous slide. In contrast, samples below either threshold tend to be equally balanced for true positives (TPs) and FNs. In the end, Samples classified that are >=the thresholds are likely higher confident calls that will likely improve the NPV. However, fewer samples are available so the 95% CI are now wider (data not shown), but the lower bound of the 95% CI of sensitivity and NPV are generally greater than the point estimates from the population as a whole.

Inventors considered the results of the following experiment; 1) If the call is PDAC according to MP, then the sample is called PDAC 2) If the call is Benign according to MP, the reflex test, Diff(miR-130b, miR-24), classifies specimens as either PDAC (above the threshold) or Benign (below the threshold). In this case, inventors have a range of thresholds from our simulation so a sample is classified based on the call from all 100 simulations (10 replicates of 10 fold cross-validation). All samples that do not have the same call of PDAC or Benign by the reflex test for all 100 simulated runs, the sample is automatically classified incorrectly. The left side of FIG. 10 shows that most samples are classified consistently, but there is an expected hit in specificity as inventors are in effect taking calls that were originally classified as Benign and now evaluating with a reflex test. One can only expect this to increase the FPR (decrease specificity), but the overall accuracy increases as we classify more PDAC samples correctly than incorrectly classifying Benign samples. The right side of FIG. 10 shows the overall performance using the reflex test with MP. Note that the total number of samples Is still 184—the same number considered for the FNA validation. This should be compared to FIG. 6 where the results are shown without the reflex test. There is no independent test set for the reflex test so we are training and testing on the same data set which can lead to biased performance estimates. This is mitigated by calling all samples within the 95% threshold range as incorrect thereby decreasing overall performance. In other words, all samples classified in the gray zone spanned by the 95% threshold range will only penalize the overall performance of the test.

FIG. 11 juxtaposes the performance of MP with the reflex test (left hand side) and without the reflex test (right hand side). As explained in the previous figure, only samples consistently classified as either PDAC or Benign by the reflex test will be marked as accurately classified. In contrast to the previous figure, all samples that were PDAC by cytology are excluded from this analysis so the total specimens considered for analysis is much less than 184.

Inventors performed an additional analysis where all samples that were PDAC or Suspicious by cytology are excluded from this analysis. We evaluated this population because samples that were Suspicious by Cytology tended to be PDAC samples. This would be another clinically relevant application of the test. FIG. 12 shows performance of MP with (left hand side) and without (right hand side) the reflex test. As explained in the previous figure, only samples consistently classified as either PDAC or Benign by tire reflex test will be accurately classified. In general, we see an increase in overall accuracy including the reflex test as we now tend to call more PDAC samples correctly with the cost of a reduction in specificity.

Inventors evaluated the performance of MP when used in conjunction with Cytology. That means a sample is classified as PDAC if either Cytology or MP classifies the specimen as PDAC. Otherwise, the specimen is classified as Benign. The term 'Conjunction' implies an either/or relationship of Cytology and MP.

FIG. 13 shows performance using this strategy with (left hand side) and without (right hand side) the reflex test. The end result is a test that is very accurate because of the excellent sensitivity of Cytology and the excellent specificity of MP. The problem with this strategy is that the FPR will increase because Cytology tends to call some samples PDAC even though they are Benign.

The analysis above provides support that the reflex test improves sensitivity at the risk of reducing specificity. If the focus is sensitivity, then Diff(miR-130b, miR-24) can be used. If your focus is specificity, then do not use Diff(miR-130b, miR-24). An alternate strategy is to use Diff(miR-130b, miR-24) as a concurrent test to stratify results into high quality results and low quality results (See FIG. 9). With that strategy in mind about 2/3 of the specimens are classified very accurately while 1/3 of the specimens are likely to be excluded from the high confidence results. Two more notes about test results: overall accuracy estimates will increase with Diff(miR-130b, miR-24) as it focuses on increased sensitivity and there is a higher prevalence of PDAC samples; pay close attention to the lower 95% CI of Sens, Spec, PPV and NPV.

Figure 14:
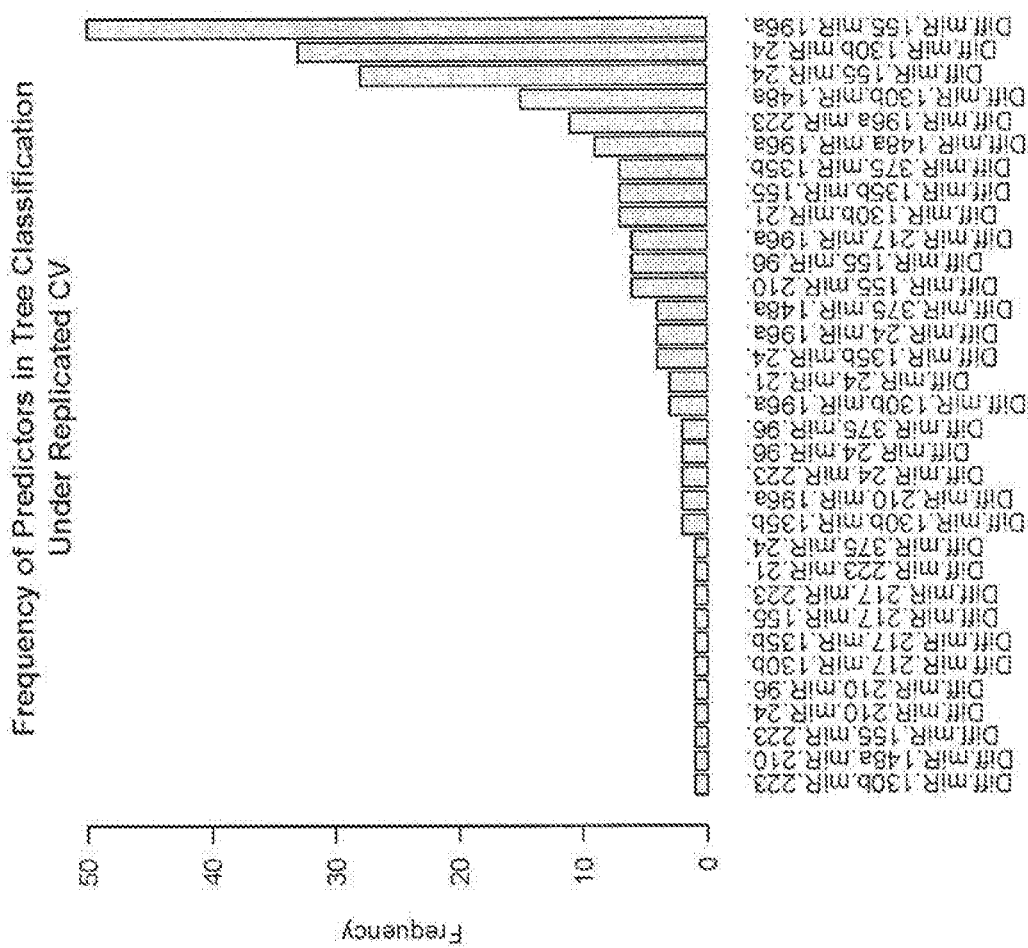
FIG. 14. The frequency plot shows how often a given diff pair is selected by the tree classifier based on the assumption of having only 3 nodes in the tree (2 diff pair predictors). First, a full tree is generated, and then pruned to 3 nodes. The results are correlated with the Wilcox test results (See FIG. 7). The feature selection is nested within CV.
Figure 15:
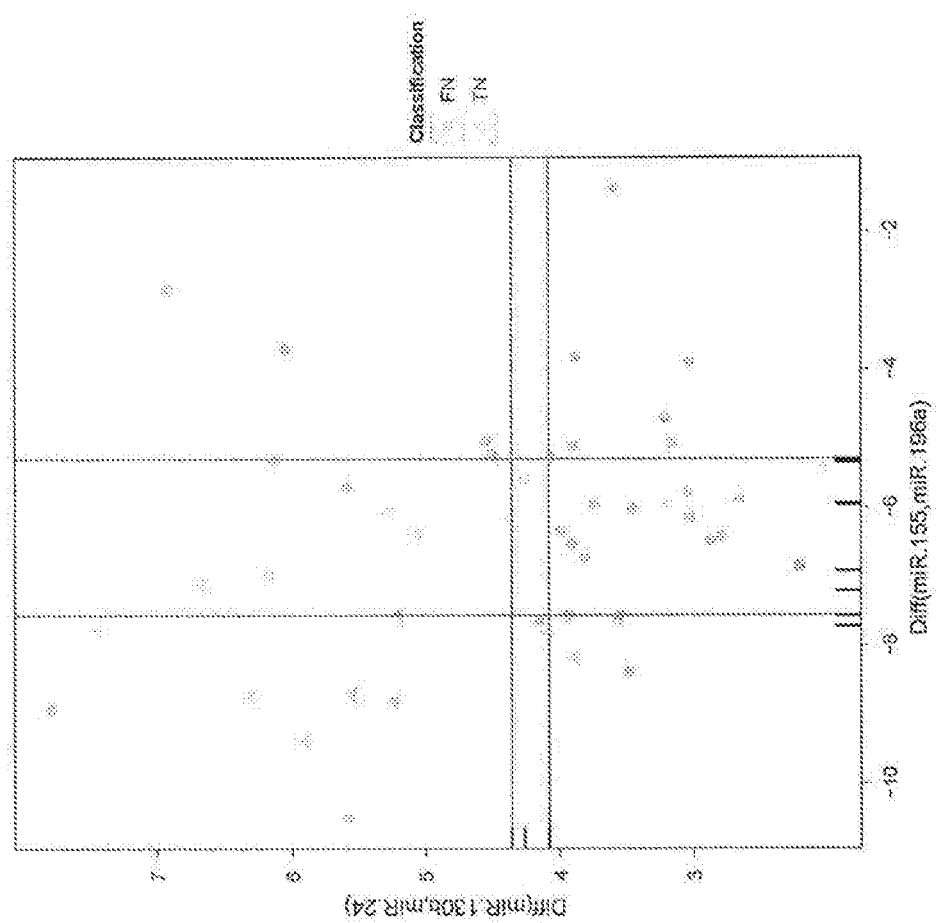
FIG. 15. The figure shows the top 2 diff pairs for the tree classification results by frequency selection (Sec FIG. 14). The horizontal and vertical lines cover the threshold distribution for 95% of the iterations in the simulation for Diff(miR-130b, miR-24) (horizontal lines) and Diff(miR-155, miR-196a) (vertical lines). Samples are shaped by classification status where circles are FNs and trianbles are TNs. The regions of uncertainty would be areas delimited by the 95% ranges.

Inventors results outlined above were focused on Diff (miR-130b, miR-24). At this point, inventors will now investigate how the application of a more complex reflex test could affect patient classification results. Specifically, the inventors considered a classification tree based on two diff pairs. As per our previous evaluation strategy, inventors will evaluate the classification results (diff pair selection and tree construction) using 10 replicates of 10-fold cross-validation in order to derive a distribution of results. This analysis was performed in order to see if inventors can improve performance using 2 diff pairs instead of just Diff(miR-130b, miR-24). FIG. 14 shows how often a given diff pair was selected to be in a classification tree that discriminates TN and FN. A diff pair that is selected more frequently than others is likely to have more discriminatory power associated with it. FIG. 15 shows the projection of the TNs and FNs projected into the space spanned by the top two diff pairs. One can see tire TNs tend to be clustered in the upper left quadrant while the FNs are predominately in the lower right. However, in the case of the top predictor, Diff(miR-155, miR-196a), the decision thresholds spanned by the two vertical lines are quite wide which leads to poor overall predictive performance. The FN accuracy is 59.33%, the TN accuracy is 44.21% and the overall accuracy is 53.47%. The performance estimates are low and can likely be improved by increasing the sample size. In sum, Diff(miR.155, miR.196a) has among the strongest p-value estimates by the Wilcox-test, but the threshold Is unstable because the 95% range is wide. Diff(miR.130b, miR.24) has a weaker p-value, but more consistent thresholding because the 95% is narrow.

Example 3

Biomarker Performance

Figure 16:
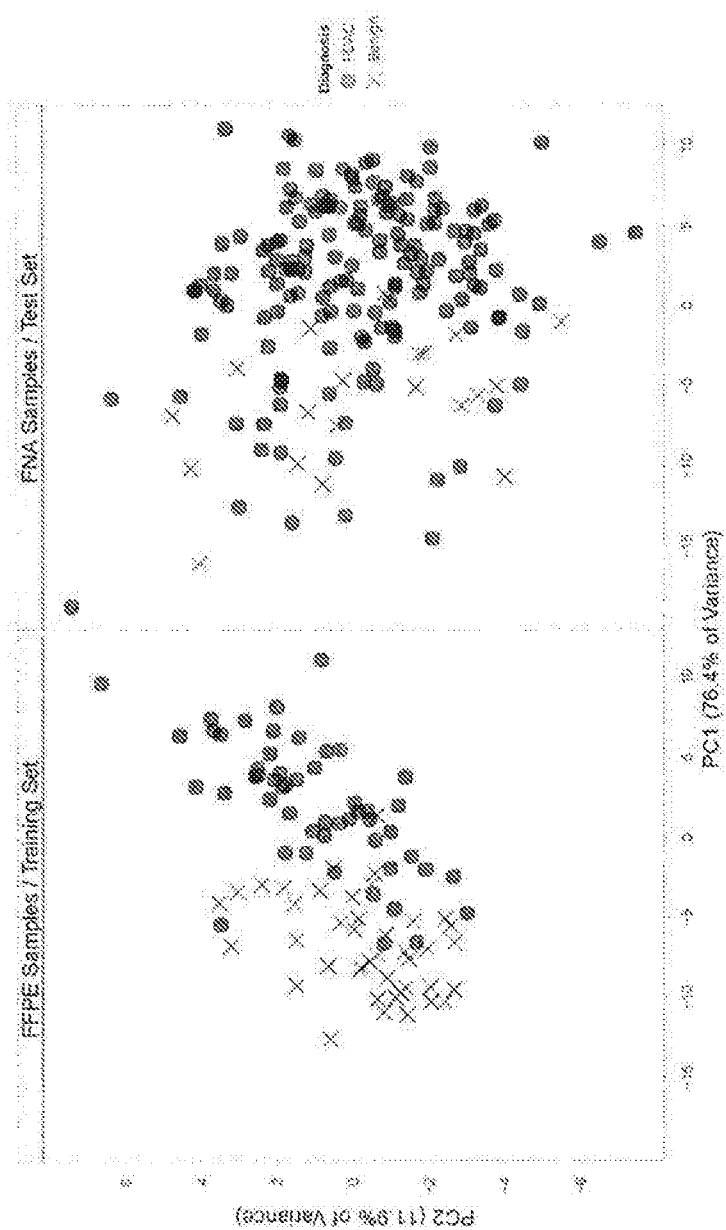
FIG. 16. Final Diagnosis Drives Most of the Variance in the Diffspace of the Merged Training and Test Sets. The figure shows principal component analysis (PCA) applied to the expression values of the 6 DiffPairs composing MP stratified by sample type with the FFPE samples in the left panel and FNA samples in the right panel. The final diagnosis drives most of the 1st principal component (x-axis) while both final diagnosis and sample type drive most of the 2nd principal component (y-axis). The markers are shaped by final diagnosis with PDAC samples as circles and Benign samples as Xs.
Figure 17:
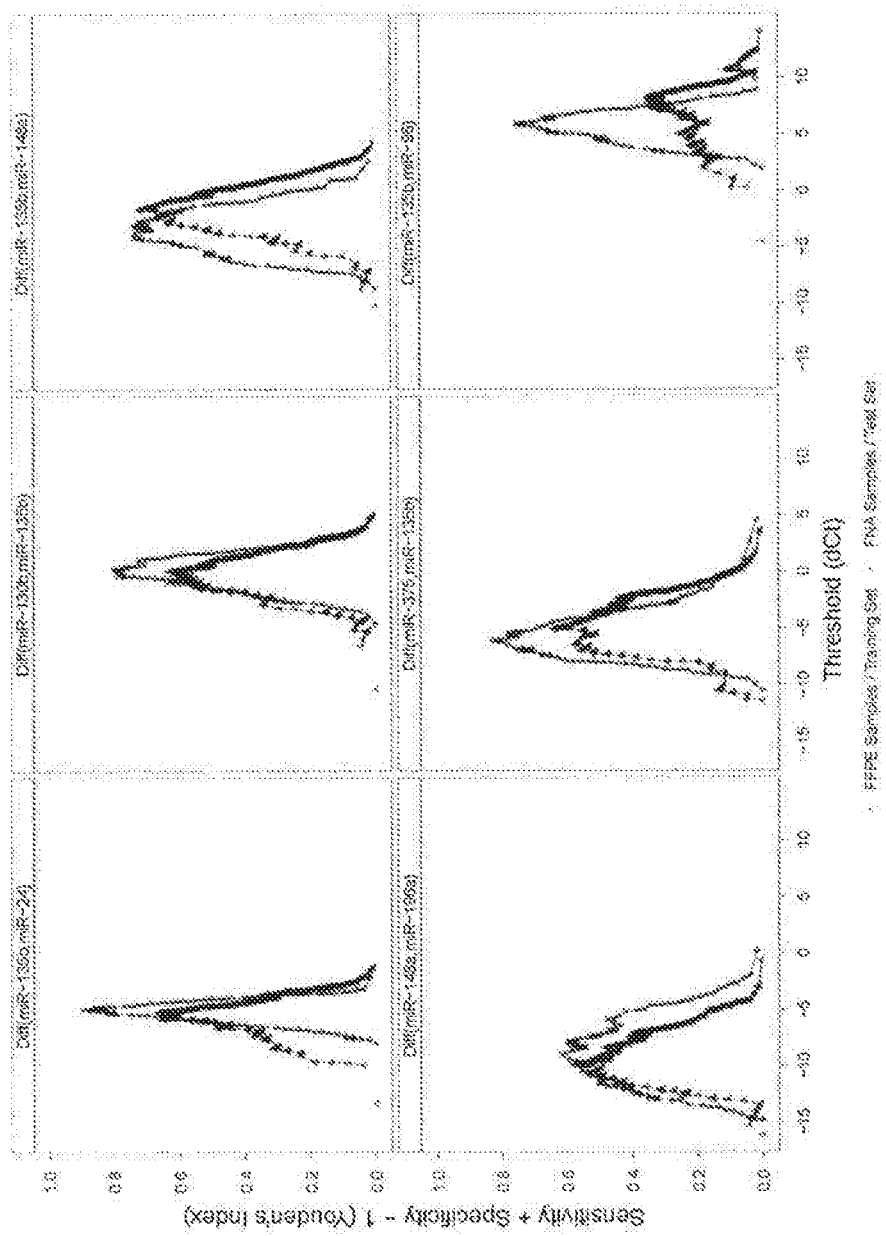
FIG. 17. Biomarker expression values are mostly consistent between sample types. Youden's Index (y-axis) summarizes the predictive performance of each DiffPair (biomarker) used in MP by panel. In order for the model to successfully migrate between sample types, the point of maximum performance (maximum Youden's Index) should be aligned between the training set (FFPE—circles plus lines) and test set (FNA—triangles plus lines). A deviation in alignment between curves would lead to differences in performance estimates between sample types. Note that the performance of Diff(miR-135b, miR-96) has the worst translated performance between sample types, but it was the 2nd least important predictor by weight in MP. The most important predictor, Diff(miR-135b, miR-24) was relatively well aligned between the training and test sets.

Here we discuss the predictive performance of the individual biomarkers as opposed to the predictive model (See Table 2, Table 3 and Table 4 for raw expression values and model scores for the 184 specimens used in the final analysis; in Tables 2-4 the sequential numerical identifiers in the leftmost column refers to the same specimen across tables). First we looked at the inherent ability of tire diff pairs in the model to separate Benign and PDAC samples in both the FFPE (training data) and FNA (test data) samples. This is easily visualized with principal component analysis (PCA) (See FIG. 16). PCA analysis is an unsupervised method of visualization that spatially orients points (samples in this case) such that samples with similar expression values are in closer proximity. In other words, the PDAC samples are clustered together and the Benign samples are clustered together because the underlying expression values in the signature capture sufficient information to separate the classes. Note this analysis is not based on the model built on top of the underlying diff pair expression values, and this method does not use class membership. Next we looked at biomarker expression individually. In order to capture the translation of univariate predictive performance of each DiffPair in MP test, we plotted Youden's Index (sensitivity plus specificity minus 1) for each DiffPair as a function of threshold (See FIG. 17). In general, all marker pairs showed relatively consistent behavior between sample types except Diff(miR-135b, miR-96). As expected, the univariate predictive performance decreased between sample types, but, critically, the thresholds of maximum performance were particularly well aligned between sample types except for Diff(miR-135b, miR-96) and, to a lesser extent, Diff(miR-135b, miR-148a). In aggregate, the DiffPair normalization procedure along with robust biomarkers (as measured in the DiffSpace) allowed the model to maintain high performance in an alternate sample type.

Model Performance

Figure 18:
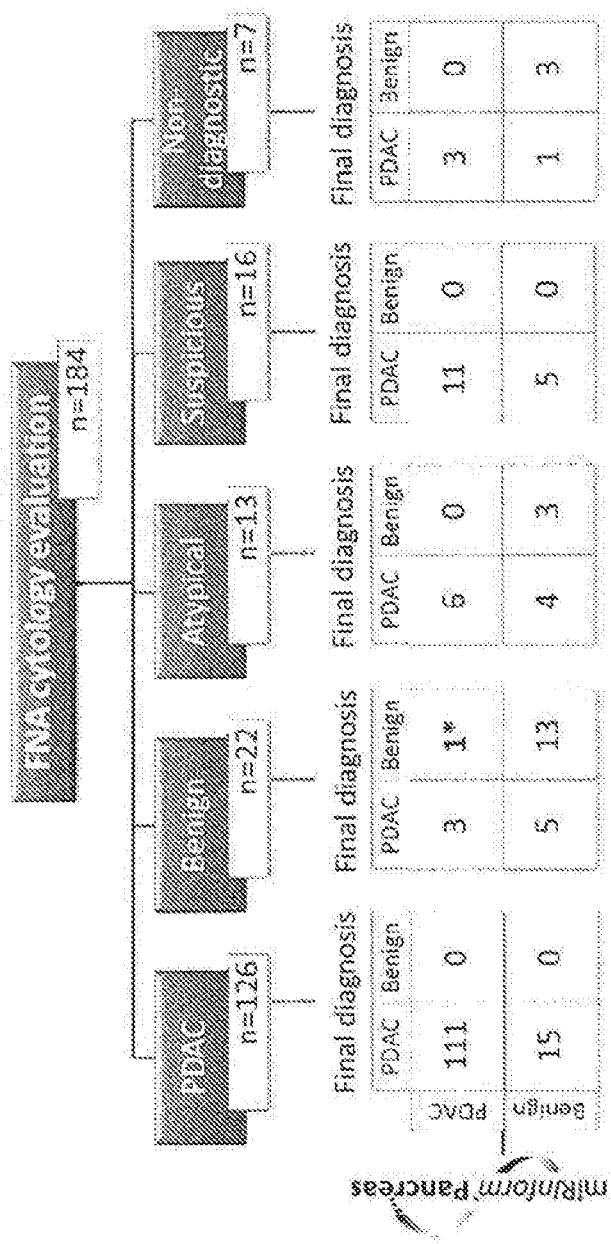
FIG. 18. Classification performance of MP stratified by Cytology.
Figure 19:
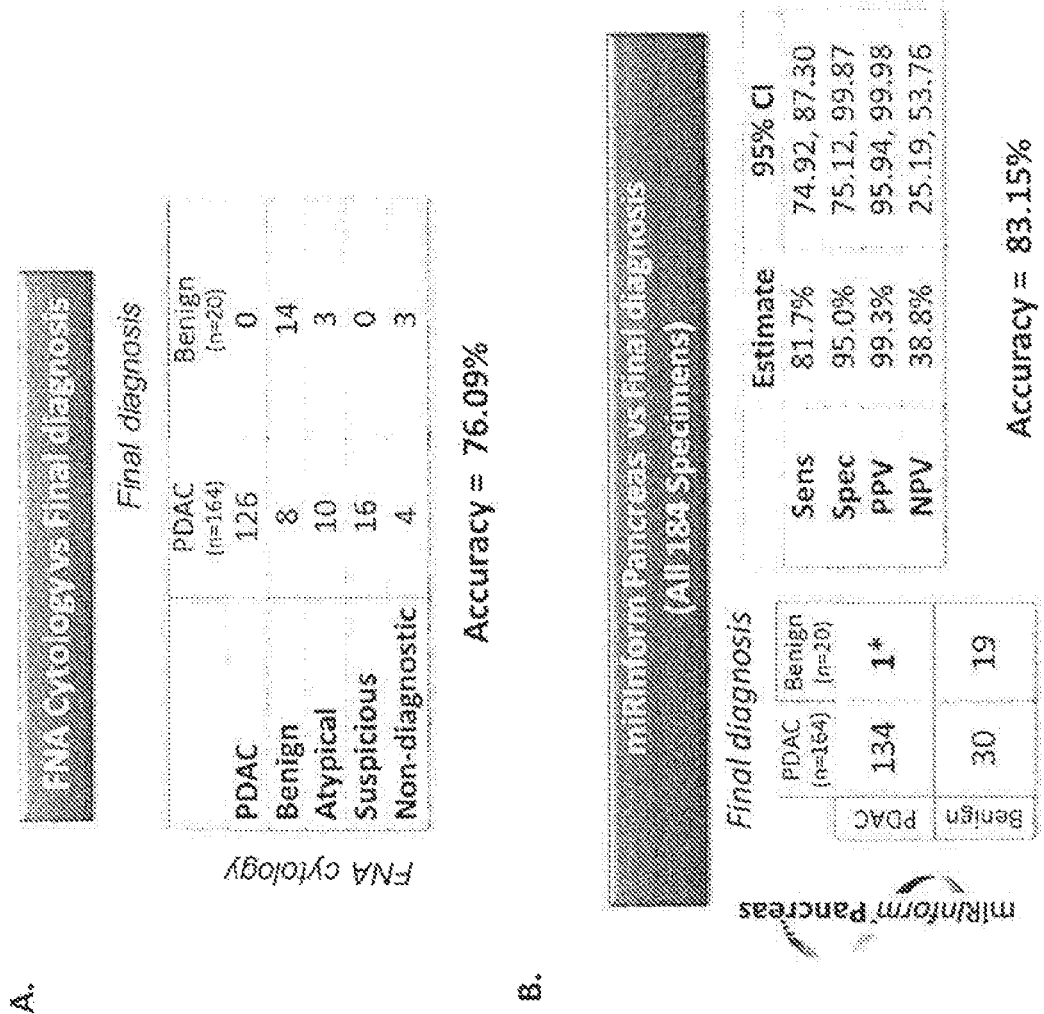
FIG. 19. Overall diagnostic performance of FNA cytology alone (A) and the MP test alone (B) for 184 FNA specimens using Final diagnosis as the gold standard.

First we interrogated the performance of FNA cytology alone on 184 FNA specimens. Among these samples, a cytological diagnosis of PDAC was established in 126 cases, benign in 22 cases, atypical in 13 cases, suspicious for adenocarcinoma in 16 cases, and non-diagnostic in 7 cases (FIG. 18). The accuracy of cytological PDAC call was 100%, while a benign cytology call was accurate 63.4% of the time (14/22 specimens), for an overall accuracy of 76.09% (FIG. 19A). Note that the estimate for overall accuracy assumes that all FNA cytology calls other than PDAC or benign are miscalls. Since this analysis was completed, one of those patients has developed symptoms of progressive pancreatic disease (weight loss, mass infiltration into duodenum, etc.). This patient is currently being followed to obtain a more definitive diagnosis. If this patient develops pancreatic cancer, the accuracy of FNA benign cytology will decrease to 59.09%. There were 36 specimens in the category of inconclusive cytology, which could not be categorized as PDAC or benign using cytology alone. Following the routine preoperative management algorithm these patients will undergo a repeat FNA procedure with a hope of obtaining diagnostic specimen.

Subsequently, we evaluated the performance of the MP test on the same patient population (See FIG. 18). In the group of 126 PDAC specimens by FNA cytology, the MP test accurately identified 111/126 specimens (88.09%) as PDAC. Within the group of 22 benign specimens by FNA cytology, the MP accurately identified 13 out of 14 true benign specimens as well as 3 out of 8 true PDAC specimens which were missed by cytology. The one patient which is currently progressing toward pancreatic cancer, was identified as PDAC by MP. In addition, in the group of 36 patients with inconclusive cytology (cytology was neither PDAC nor benign) the test was able to provide a confirmatory diagnosis of PDAC for 20/30 (66.67%) patients with PDAC, and confirm benign in 6/6 patients (100%). Overall, the test accurately classified 134 PDAC specimens and 19 benign specimens, for an overall accuracy of 83.15% (See FIG. 19).

We also interrogated the performance of FNA cytology alone on 184 FNA specimens. Among these samples, a cytological diagnosis of PDAC was established in 126 cases, benign in 22 cases, atypical in 13 cases, suspicious for adenocarcinoma in 16 cases, and non-diagnostic in 7 cases. The accuracy of cytological PDAC call was 100%, while a benign cytology call was accurate 63.4% of the time (14/22 specimens), for an overall accuracy of 76.09% (FIG. 20A). Note that the estimate for overall accuracy assumes that all FNA cytology calls other than PDAC or benign are miscalls. Since this analysis was completed, one of those patients has developed symptoms of progressive pancreatic disease (weight loss, mass infiltration into duodenum, etc.). This patient is currently being followed to obtain a more definitive diagnosis. If this patient develops pancreatic cancer, the accuracy of FNA benign cytology will decrease to 59.09%. There were 36 specimens in the category of inconclusive cytology, which could not be categorized as PDAC or benign using cytology alone. Following the routine preoperative management algorithm these patients will undergo a repeat FNA procedure with a hope of obtaining diagnostic specimen.

Figure 20:
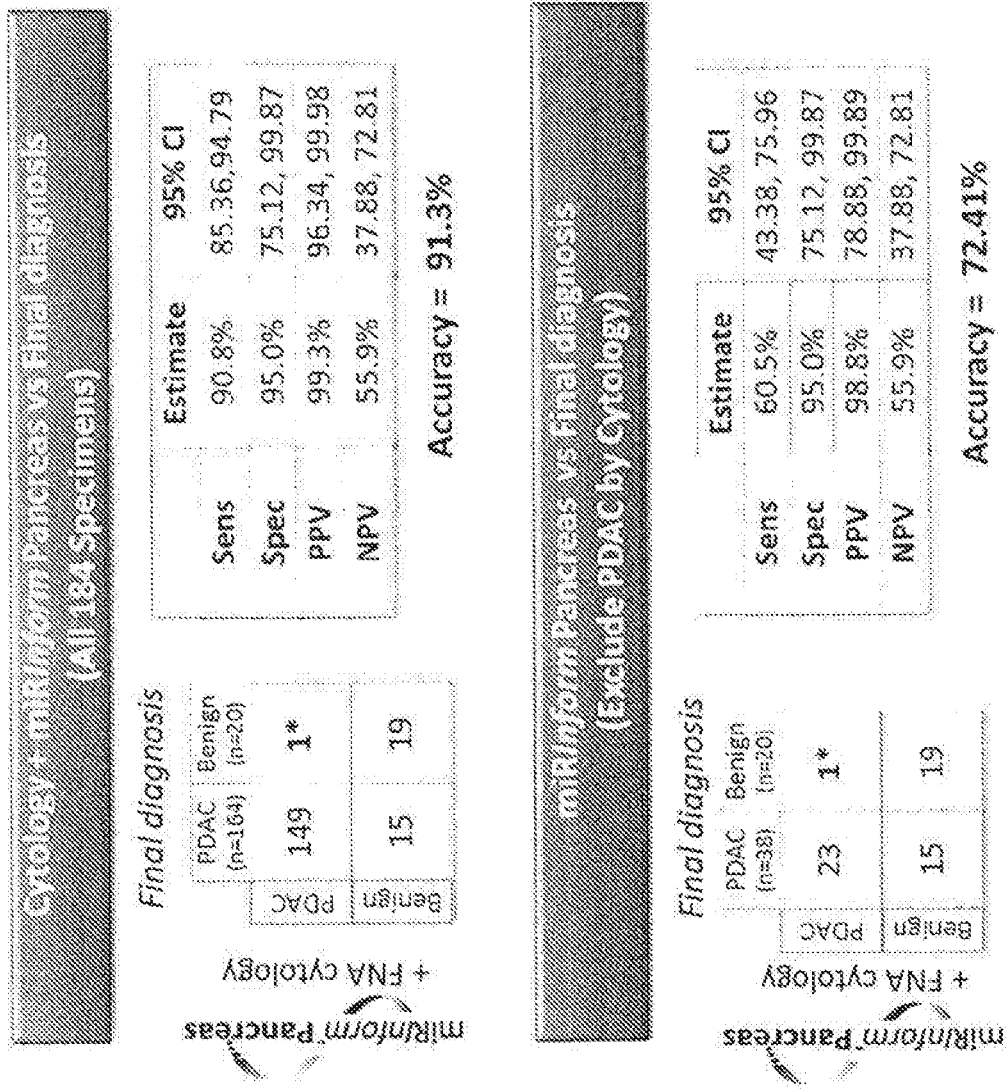
FIG. 20. (A) Overall diagnostic performance of FNA cytology combined with the MP test for 184 FNA specimens using Final diagnosis as a gold standard. In this context, a sample is predicted as PDAC if either cytology or MP classifies a specimen as PDAC. Otherwise, the sample is predicted as Benign. (B) Diagnostic performance of FNA cytology combined with the MP test on the 58 specimens in the benign and inconclusive cytology category (exclude PDAC by cytology) using Final diagnosis as gold standard.

Subsequently, we evaluated tire performance of the MP test on the same patient population. In the group of 126 PDAC specimens by FNA cytology, the MP test accurately identified 111/126 specimens (88.09%) as PDAC. Within the group of 22 benign specimens by FNA cytology, MP accurately identified 13 out of 14 true benign specimens as well as 3 out of 8 true PDAC specimens which were missed by cytology. The one patient which is currently progressing toward pancreatic cancer was identified as PDAC by MP. In addition, in the group of 36 patients with inconclusive cytology (cytology was neither PDAC nor benign) the test was able to provide a confirmatory diagnosis of PDAC for 20/30 (66.67%) patients with PDAC, and confirm benign in 6/6 patients (100%). Overall, the test accurately classified 134 PDAC specimens and 19 benign specimens, for an overall accuracy of 83.15% (FIG. 20).

The performance of the MP test in conjunction with FNA cytology on the 184 FNA specimens was evaluated using following assumptions; an FNA specimen was determined to be PDAC if either FNA cytology or MP reported it as PDAC. Otherwise, the specimen was classified as benign.

This approach allowed us to combine the best features of these two diagnostic tools: superior accuracy of malignant FNA cytology and the high specificity and PPV of MP in the benign and inconclusive FNA cytology specimens. As a result a total of 149 out of 164 PDAC specimens and 19 out of 20 benign specimens were accurately classified, resulting in an increase of the diagnostic accuracy to 91.3% from 76.09% for FNA cytology alone (See FIG. 19). An important and clinically relevant application of MP is classification of samples that are presumably benign based on cytological diagnosis of benign, as well as classification of specimens with inconclusive cytology calls. In this context (excluding all specimens called PDAC by cytology), the overall accuracy of MP is 72.41% as compared to 24.14% for FNA cytology alone. In addition to resolving 3 out of 8 false negative calls in the benign by cytology group, MP enabled accurate identification of 20/30 PDAC specimens and all benign specimens in the group of specimens inconclusive by cytology (See FIG. 19B).

TABLE 2

|  | miR-217 | miR-375 | miR-130b | miR-135b | miR-148a | miR-155 | miR-210 | miR-24 | miR-196a | miR-223 | miR-96 | miR-21 |
|---|---|---|---|---|---|---|---|---|---|---|---|---|
| 1 | 38.90 | 27.03 | 30.61 | 28.82 | 28.84 | 34.20 | 26.85 | 25.64 | 35.74 | 28.54 | 41.25 | 24.39 |
| 2 | 38.39 | 31.73 | 29.92 | 29.78 | 28.99 | 32.72 | 26.39 | 24.88 | 35.76 | 24.42 | 34.89 | 23.02 |
| 3 | 38.85 | 33.90 | 33.30 | 37.90 | 32.54 | 37.78 | 30.91 | 29.70 | 39.16 | 28.21 | 38.81 | 28.34 |
| 4 | 36.56 | 28.42 | 32.16 | 36.28 | 30.86 | 30.94 | 27.61 | 25.98 | 37.92 | 30.30 | 40.49 | 24.17 |
| 5 | 27.61 | 21.04 | 22.89 | 24.03 | 22.33 | 26.92 | 21.98 | 20.26 | 31.68 | 19.88 | 27.13 | 18.27 |
| 6 | 30.67 | 24.62 | 30.28 | 35.43 | 27.34 | 35.62 | 30.32 | 27.07 | 40.32 | 29.17 | 35.68 | 26.32 |
| 7 | 39.44 | 23.44 | 24.94 | 24.29 | 24.56 | 27.78 | 23.88 | 20.99 | 31.49 | 20.20 | 28.50 | 17.79 |
| 8 | 27.99 | 21.26 | 26.13 | 28.62 | 24.11 | 28.62 | 24.62 | 22.22 | 33.72 | 21.95 | 31.61 | 20.74 |
| 9 | 27.53 | 20.57 | 24.40 | 32.00 | 22.55 | 29.31 | 23.80 | 22.36 | 34.68 | 21.63 | 30.49 | 20.88 |
| 10 | 34.40 | 22.32 | 25.94 | 25.80 | 25.77 | 27.35 | 22.23 | 21.15 | 34.50 | 22.78 | 32.23 | 19.74 |
| 11 | 28.25 | 21.42 | 24.55 | 25.08 | 22.75 | 27.73 | 23.85 | 20.65 | 33.78 | 19.93 | 30.09 | 18.57 |
| 12 | 39.39 | 21.58 | 24.85 | 23.67 | 24.77 | 25.62 | 20.94 | 19.32 | 29.45 | 19.48 | 29.85 | 17.12 |
| 13 | NA | 31.68 | 36.66 | 33.21 | 35.00 | 38.16 | 31.04 | 30.55 | 39.57 | 33.34 | 40.71 | 28.37 |
| 14 | 36.46 | 22.00 | 25.99 | 25.48 | 23.75 | 27.96 | 24.72 | 21.00 | 33.03 | 22.10 | 30.68 | 18.48 |
| 15 | 37.68 | 27.53 | 28.17 | 28.05 | 27.56 | 32.55 | 27.52 | 25.39 | 35.52 | 24.32 | 32.10 | 21.39 |
| 16 | 24.08 | 18.98 | 24.02 | 27.60 | 20.70 | 29.60 | 25.87 | 21.22 | 36.02 | 22.41 | 30.20 | 19.60 |
| 17 | 37.88 | 26.27 | 25.59 | 28.26 | 26.25 | 29.22 | 23.76 | 21.67 | 35.75 | 21.47 | 30.97 | 20.06 |
| 18 | 28.29 | 21.54 | 27.50 | 29.04 | 25.06 | 30.60 | 25.61 | 23.13 | 36.77 | 22.64 | 35.23 | 21.25 |
| 19 | 30.23 | 21.54 | 25.68 | 23.72 | 25.31 | 28.68 | 24.20 | 20.42 | 31.82 | 21.37 | 32.13 | 18.91 |
| 20 | 28.52 | 21.04 | 24.94 | 31.51 | 24.33 | 28.81 | 23.86 | 21.13 | 35.54 | 19.35 | 33.48 | 21.27 |
| 21 | 34.88 | 28.10 | 32.68 | 29.40 | 30.75 | 34.20 | 28.31 | 26.50 | 37.56 | 27.06 | 36.93 | NA |
| 22 | 38.72 | 24.67 | 29.66 | 28.03 | 28.28 | 31.03 | 27.54 | 23.51 | 36.51 | 24.94 | 37.54 | NA |
| 23 | 36.10 | 27.34 | 31.71 | 28.62 | 29.65 | 33.48 | 28.37 | 25.78 | 37.05 | 27.40 | 37.36 | NA |
| 24 | 34.90 | 23.30 | 24.83 | 23.55 | 24.39 | 25.70 | 21.78 | 19.60 | 29.07 | 18.67 | 32.21 | NA |
| 25 | 36.36 | 22.72 | 26.16 | 23.79 | 25.23 | 28.55 | 22.63 | 21.28 | 35.11 | 23.62 | 33.43 | NA |
| 26 | 23.65 | 18.05 | 22.05 | 26.19 | 19.52 | 25.23 | 22.30 | 19.17 | 31.72 | 18.18 | 29.08 | NA |
| 27 | 31.12 | 20.92 | 23.84 | 23.59 | 23.88 | 25.25 | 21.63 | 19.29 | 33.38 | 18.78 | 31.82 | NA |
| 28 | 32.14 | 19.30 | 24.11 | 20.59 | 23.03 | 25.15 | 21.77 | 18.07 | 28.68 | 18.82 | 30.37 | NA |
| 29 | 33.99 | 24.04 | 22.40 | 25.29 | 22.62 | 23.74 | 20.26 | 18.41 | 30.09 | 16.50 | 28.18 | NA |
| 30 | 27.15 | 21.03 | 23.09 | 23.61 | 22.94 | 23.96 | 21.48 | 19.10 | 27.34 | 19.68 | 32.84 | NA |
| 31 | 25.99 | 19.72 | 25.17 | 26.33 | 21.99 | 29.11 | 25.48 | 21.23 | 36.67 | 22.46 | 31.31 | NA |
| 32 | 35.61 | 21.68 | 27.04 | 24.61 | 25.87 | 28.21 | 24.70 | 23.27 | 35.40 | 20.94 | 32.73 | NA |
| 33 | 25.16 | 20.24 | 24.49 | 20.68 | 21.87 | 25.07 | 21.06 | 18.55 | 29.64 | 18.65 | 30.16 | NA |
| 34 | 34.08 | 21.26 | 22.26 | 23.64 | 23.18 | 25.36 | 20.81 | 19.08 | 30.98 | 15.64 | 29.09 | NA |
| 35 | 35.96 | 21.34 | 25.91 | 26.12 | 25.06 | 27.80 | 21.66 | 20.80 | 35.39 | 20.89 | 31.67 | 19.89 |
| 36 | 36.89 | 21.38 | 25.90 | 24.81 | 25.92 | 28.10 | 22.48 | 20.55 | 31.01 | 21.62 | 32.22 | 20.10 |
| 37 | 36.61 | 23.47 | 24.26 | 25.24 | 23.29 | 27.01 | 22.51 | 20.14 | 29.72 | 17.02 | 29.10 | 17.05 |
| 38 | 33.07 | 24.51 | 29.87 | 29.42 | 29.05 | 33.40 | 26.81 | 24.13 | 33.87 | 24.55 | 33.59 | 24.00 |
| 39 | 38.60 | 23.18 | 28.96 | 27.68 | 26.84 | 31.84 | 26.10 | 24.24 | 37.70 | 24.06 | 35.13 | 22.99 |
| 40 | 30.78 | 21.95 | 25.45 | 30.32 | 25.62 | 28.71 | 23.06 | 21.29 | 36.35 | 21.27 | 32.75 | 20.39 |
| 41 | 26.17 | 19.93 | 23.45 | 26.92 | 22.26 | 28.19 | 22.19 | 20.25 | 34.14 | 18.57 | 29.84 | 18.91 |
| 42 | 27.16 | 20.01 | 25.32 | 23.81 | 22.97 | 27.08 | 21.89 | 20.32 | 30.98 | 21.18 | 32.95 | 18.36 |
| 43 | 40.00 | 22.76 | 26.12 | 30.41 | 25.83 | 31.78 | 23.63 | 23.09 | 35.68 | 22.38 | 33.36 | 21.06 |
| 44 | 33.43 | 18.97 | 27.38 | 22.57 | 23.69 | 27.30 | 22.05 | 19.72 | 30.89 | 22.94 | 33.17 | 17.66 |
| 45 | 24.90 | 19.21 | 24.46 | 25.93 | 21.28 | 25.90 | 22.13 | 20.12 | 31.16 | 21.75 | 32.92 | 18.73 |
| 46 | 32.10 | 26.92 | 30.73 | 30.46 | 28.39 | 34.86 | 29.68 | 27.53 | 37.79 | 28.72 | 38.48 | 23.62 |
| 47 | 33.17 | 23.37 | 23.56 | 24.32 | 23.57 | 27.74 | 21.27 | 19.67 | 30.59 | 18.33 | 30.63 | 18.13 |
| 48 | 28.10 | 19.16 | 23.46 | 22.91 | 23.11 | 25.68 | 21.24 | 17.90 | 31.21 | 19.10 | 28.86 | 17.01 |
| 49 | 38.03 | 23.57 | 27.71 | 26.31 | 26.24 | 29.75 | 22.47 | 21.05 | 32.64 | 24.77 | 33.62 | 19.05 |
| 50 | 35.62 | 24.54 | 26.50 | 30.02 | 26.81 | 30.58 | 24.23 | 23.04 | 36.61 | 23.71 | 33.39 | 21.06 |
| 51 | NA | 31.31 | 31.35 | 41.66 | 31.56 | 37.38 | 29.15 | 28.30 | 43.17 | 29.35 | 37.16 | 26.09 |
| 52 | 34.98 | 19.73 | 25.74 | 25.40 | 25.20 | 27.12 | 23.08 | 20.42 | 29.43 | 22.69 | 32.50 | 19.48 |
| 53 | 29.50 | 22.07 | 28.39 | 27.83 | 24.51 | 31.60 | 26.72 | 23.61 | 36.65 | 27.24 | 37.42 | 21.31 |
| 54 | 34.76 | 20.72 | 24.96 | 22.78 | 21.77 | 29.08 | 24.03 | 20.37 | 29.52 | 22.63 | 30.24 | 17.76 |
| 55 | 31.48 | 19.96 | 24.18 | 24.79 | 24.15 | 26.26 | 20.93 | 19.03 | 30.13 | 19.24 | 29.56 | 17.77 |
| 56 | 38.79 | 24.92 | 27.35 | 26.65 | 25.89 | 31.09 | 25.08 | 23.03 | 32.90 | 25.64 | 32.10 | 21.52 |
| 57 | NA | 29.94 | 36.08 | 36.40 | 33.53 | 38.69 | 31.78 | 30.03 | 42.39 | 33.87 | 44.09 | 27.58 |
| 58 | 36.26 | 21.67 | 25.77 | 23.80 | 24.07 | 26.69 | 20.89 | 18.98 | 30.38 | 20.44 | 30.88 | 16.93 |
| 59 | 30.13 | 23.54 | 29.64 | 34.89 | 26.14 | 34.72 | 29.25 | 26.08 | 42.29 | 29.31 | 37.86 | 24.82 |
| 60 | 31.80 | 21.11 | 26.63 | 25.08 | 24.69 | 29.50 | 24.23 | 20.49 | 35.45 | 23.67 | 33.85 | 17.93 |
| 61 | 36.31 | 22.43 | 26.18 | 24.54 | 25.22 | 26.93 | 22.04 | 19.32 | 34.61 | 17.82 | 32.95 | 18.08 |
| 62 | 31.72 | 21.06 | 24.37 | 28.47 | 24.44 | 27.81 | 23.06 | 20.89 | 36.21 | 22.61 | 32.65 | 19.53 |
| 63 | NA | 25.36 | 31.42 | 30.20 | 29.73 | 35.89 | 27.33 | 26.07 | 42.38 | 29.41 | 39.19 | 23.90 |
| 64 | 41.69 | 29.52 | 30.84 | 26.06 | 29.63 | 34.95 | 26.24 | 23.26 | 37.30 | 27.09 | 35.30 | 21.74 |
| 65 | 37.42 | 23.26 | 30.96 | 34.13 | 28.38 | 30.57 | 29.03 | 25.39 | 41.07 | 28.25 | 35.63 | 23.80 |

TABLE 2-continued

|  | miR-217 | miR-375 | miR-130b | miR-135b | miR-148a | miR-155 | miR-210 | miR-24 | miR-196a | miR-223 | miR-96 | miR-21 |
|---|---|---|---|---|---|---|---|---|---|---|---|---|
| 66 | NA | 28.80 | 31.79 | 31.75 | 30.40 | 34.80 | 29.96 | 26.85 | 38.50 | 29.64 | 35.15 | 23.45 |
| 67 | 29.15 | 19.61 | 22.69 | 23.86 | 22.55 | 24.98 | 21.16 | 18.71 | 29.88 | 16.40 | 28.45 | NA |
| 68 | 31.34 | 20.20 | 25.09 | 21.97 | 24.01 | 25.67 | 21.01 | 18.62 | 29.62 | 18.33 | 29.97 | NA |
| 69 | 35.03 | 22.08 | 25.69 | 27.25 | 23.19 | 28.49 | 24.58 | 21.44 | 34.06 | 20.31 | 30.96 | NA |
| 70 | 35.34 | 22.69 | 23.32 | 23.02 | 23.51 | 25.12 | 20.41 | 18.64 | 28.62 | 16.81 | 28.02 | NA |
| 71 | 27.22 | 19.93 | 26.18 | 25.97 | 23.21 | 26.73 | 23.91 | 21.34 | 32.77 | 22.33 | 33.16 | NA |
| 72 | 33.87 | 23.61 | 25.45 | 24.73 | 24.08 | 28.08 | 23.45 | 21.21 | 30.97 | 19.30 | 28.74 | NA |
| 73 | 39.38 | 23.81 | 29.21 | 25.73 | 27.81 | 28.13 | 24.97 | 22.93 | 33.97 | 22.97 | 35.29 | NA |
| 74 | 36.50 | 20.52 | 25.72 | 23.23 | 25.32 | 26.04 | 21.07 | 19.63 | 29.69 | 21.11 | 33.40 | NA |
| 75 | 33.56 | 21.79 | 26.69 | 23.11 | 24.92 | 27.73 | 23.77 | 21.13 | 31.98 | 22.42 | 32.13 | 18.37 |
| 76 | 38.27 | 24.20 | 26.74 | 28.93 | 25.11 | 29.87 | 24.72 | 22.20 | 34.92 | 22.13 | 31.79 | 20.63 |
| 77 | 35.69 | 22.74 | 25.61 | 23.38 | 24.18 | 27.12 | 21.88 | 19.54 | 33.65 | 18.74 | 30.44 | 18.08 |
| 78 | 35.84 | 21.34 | 28.08 | 23.06 | 25.98 | 28.31 | 24.09 | 21.42 | 30.66 | 22.26 | 33.29 | 19.33 |
| 79 | 35.83 | 22.48 | 24.60 | 21.94 | 24.24 | 28.26 | 20.99 | 19.52 | 30.84 | 20.74 | 32.48 | 17.16 |
| 80 | 33.35 | 21.92 | 23.62 | 22.71 | 23.28 | 26.02 | 20.18 | 19.05 | 31.33 | 18.87 | 30.77 | 15.98 |
| 81 | 36.79 | 24.50 | 28.00 | 27.72 | 26.28 | 30.23 | 25.00 | 21.86 | 35.55 | 22.97 | 37.61 | 20.47 |
| 82 | NA | 25.29 | 33.40 | 32.70 | 32.39 | 32.22 | 33.73 | 25.95 | 39.98 | NA | 43.22 | 26.40 |
| 83 | 37.47 | 21.82 | 27.77 | 25.01 | 26.76 | 30.19 | 22.58 | 21.38 | 35.70 | 24.60 | 36.76 | 19.34 |
| 84 | 40.05 | 22.02 | 27.19 | 27.12 | 25.30 | 29.65 | 25.46 | 21.96 | 38.45 | 23.49 | 37.70 | 21.13 |
| 85 | 35.89 | 21.11 | 26.56 | 24.18 | 25.65 | 27.49 | 23.50 | 20.31 | 34.48 | 21.98 | 34.90 | 19.54 |
| 86 | 40.42 | 25.15 | 26.78 | 23.89 | 27.56 | 31.18 | 25.90 | 22.82 | 35.89 | 21.69 | 37.99 | 21.73 |
| 87 | 37.19 | 24.64 | 25.38 | 24.33 | 26.52 | 29.83 | 23.15 | 21.32 | 40.48 | 22.05 | 35.91 | 21.05 |
| 88 | NA | 32.39 | 27.64 | 28.70 | 31.52 | 27.18 | 26.63 | 21.69 | 38.92 | NA | 37.37 | 21.25 |
| 89 | 38.84 | 25.08 | 27.80 | 27.45 | 28.17 | 28.40 | 26.53 | 22.22 | 35.43 | NA | 35.33 | 21.01 |
| 90 | 42.21 | 23.36 | 30.19 | 27.05 | 29.73 | 30.01 | 26.16 | 21.97 | 42.19 | NA | 39.02 | 22.91 |
| 91 | 39.38 | 23.37 | 28.15 | 28.92 | 28.53 | 32.01 | 25.13 | 24.20 | 35.78 | NA | 36.33 | 22.33 |
| 92 | 28.78 | 24.52 | 30.12 | 33.34 | 29.42 | 32.19 | 30.11 | 23.45 | 39.31 | NA | 39.39 | 23.61 |
| 93 | 32.25 | 22.62 | 28.64 | 30.58 | 27.32 | 32.53 | 27.94 | 24.75 | 40.72 | NA | 37.31 | 24.74 |
| 94 | 29.62 | 24.12 | 30.50 | 29.19 | 29.43 | 30.46 | 30.49 | 22.71 | 39.39 | NA | 41.51 | 23.18 |
| 95 | 39.58 | 24.72 | 31.76 | 29.38 | 32.37 | 29.76 | 30.53 | 22.87 | 36.50 | NA | 41.72 | 23.10 |
| 96 | 37.52 | 26.77 | 28.86 | 25.78 | 30.28 | 27.09 | 29.20 | 20.69 | 33.30 | NA | 36.88 | 20.74 |
| 97 | 27.52 | 21.33 | 23.45 | 23.29 | 22.75 | 25.59 | 20.88 | 19.05 | 29.42 | 15.73 | 29.44 | NA |
| 98 | 35.63 | 23.75 | 27.64 | 25.72 | 25.98 | 27.84 | 22.53 | 21.08 | 32.19 | 21.33 | 34.16 | NA |
| 99 | 34.57 | 21.26 | 25.85 | 22.94 | 24.00 | 26.59 | 23.09 | 19.73 | 32.35 | 16.87 | 32.27 | NA |
| 100 | 36.25 | 22.91 | 25.64 | 21.91 | 24.79 | 24.29 | 22.45 | 18.27 | 32.52 | 18.30 | 31.12 | NA |
| 101 | 36.55 | 20.56 | 26.08 | 24.83 | 25.00 | 27.31 | 22.12 | 19.95 | 34.10 | 21.11 | 32.22 | NA |
| 102 | 27.84 | 21.15 | 24.67 | 22.88 | 24.01 | 26.08 | 21.02 | 19.69 | 32.75 | 18.21 | 30.16 | NA |
| 103 | 37.26 | 24.30 | 26.93 | 27.92 | 27.41 | 27.29 | 24.41 | 22.29 | 32.41 | 19.20 | 32.71 | NA |
| 104 | 36.12 | 22.59 | 26.12 | 24.05 | 26.63 | 27.51 | 23.47 | 21.00 | 30.71 | 18.89 | 32.83 | NA |
| 105 | 36.27 | 22.99 | 25.40 | 24.89 | 24.84 | 25.72 | 22.04 | 19.11 | 31.40 | 20.28 | 31.90 | NA |
| 106 | 38.04 | 22.67 | 25.90 | 29.78 | 25.76 | 27.63 | 23.66 | 21.39 | 32.86 | 18.34 | 33.13 | NA |
| 107 | 26.90 | 20.97 | 24.16 | 21.85 | 22.78 | 25.63 | 21.06 | 18.96 | 29.33 | 16.53 | 32.10 | NA |
| 108 | 27.47 | 19.97 | 24.76 | 22.44 | 22.47 | 26.39 | 21.26 | 18.56 | 28.90 | 17.69 | 31.93 | NA |
| 109 | 34.92 | 22.06 | 27.32 | 26.98 | 26.78 | 27.38 | 23.86 | 21.40 | 31.03 | 18.86 | 33.42 | NA |
| 110 | 37.04 | 22.09 | 27.63 | 25.26 | 25.47 | 30.08 | 25.73 | 22.28 | 34.86 | 20.88 | 33.17 | 19.01 |
| 111 | 36.04 | 21.99 | 26.25 | 23.90 | 25.44 | 29.84 | 23.69 | 21.08 | 32.23 | 21.77 | 33.22 | 17.65 |
| 112 | 35.65 | 22.70 | 26.27 | 24.18 | 25.47 | 28.90 | 23.61 | 20.85 | 31.05 | 21.71 | 33.43 | 17.64 |
| 113 | 25.91 | 19.61 | 24.28 | 30.16 | 22.15 | 29.90 | 24.90 | 21.62 | 35.79 | 19.51 | 32.71 | 21.14 |
| 114 | 28.12 | 22.54 | 26.94 | 24.50 | 24.13 | 29.08 | 24.18 | 21.95 | 32.52 | 20.64 | 34.88 | 18.92 |
| 115 | 30.47 | 23.01 | 25.68 | 30.96 | 25.30 | 30.15 | 24.05 | 22.65 | 36.31 | 20.64 | 33.93 | 21.43 |
| 116 | 38.23 | 25.26 | 27.28 | 31.68 | 26.63 | 31.18 | 26.09 | 24.11 | 36.25 | 21.96 | 33.78 | 20.54 |
| 117 | 29.82 | 22.76 | 22.56 | 26.89 | 23.15 | 27.73 | 21.70 | 20.34 | 34.58 | 18.02 | 30.51 | 18.58 |
| 118 | 31.61 | 20.61 | 23.31 | 24.13 | 23.67 | 28.22 | 22.39 | 20.13 | 33.45 | 18.52 | 30.68 | 18.27 |
| 119 | 40.60 | 24.27 | 26.37 | 27.15 | 25.68 | 29.88 | 23.43 | 21.82 | 35.58 | 20.28 | 33.51 | 20.56 |
| 120 | 31.56 | 21.20 | 24.47 | 22.96 | 25.56 | 28.39 | 21.59 | 19.93 | 33.50 | 19.86 | 31.86 | 19.04 |
| 121 | 35.97 | 24.55 | 26.31 | 23.05 | 25.95 | 28.20 | 21.69 | 19.77 | 33.30 | 22.44 | 33.73 | 17.62 |
| 122 | 34.28 | 16.90 | 23.46 | 24.16 | 24.27 | 27.96 | 20.70 | 19.38 | 27.77 | 21.67 | 30.98 | 19.62 |
| 123 | 28.54 | 21.23 | 25.32 | 24.53 | 25.11 | 27.89 | 23.04 | 19.88 | 35.55 | 19.29 | 33.13 | 18.70 |
| 124 | 34.98 | 23.06 | 26.11 | 24.89 | 26.80 | 27.49 | 21.22 | 20.13 | 31.50 | 20.28 | 35.11 | 20.04 |
| 125 | 32.38 | 20.49 | 25.38 | 26.79 | 26.88 | 28.56 | 23.23 | 20.71 | 31.20 | 20.93 | 34.02 | 20.37 |
| 126 | 32.45 | 22.19 | 27.31 | 29.16 | 25.69 | 31.50 | 25.71 | 23.23 | 36.77 | 23.24 | 34.33 | 22.77 |
| 127 | 26.99 | 20.82 | 24.91 | 24.43 | 23.66 | 27.67 | 21.79 | 19.24 | 31.28 | 19.71 | 32.04 | 18.58 |
| 128 | 27.28 | 21.02 | 24.89 | 25.38 | 23.81 | 27.51 | 22.74 | 19.50 | 32.09 | 19.70 | 32.15 | 19.72 |
| 129 | 37.66 | 23.76 | 28.06 | 26.55 | 28.48 | 30.21 | 23.46 | 21.94 | 33.54 | 22.32 | 35.20 | 21.24 |
| 130 | 30.17 | 21.56 | 27.47 | 26.75 | 25.36 | 28.94 | 24.03 | 21.80 | 32.10 | 22.75 | 33.94 | 20.24 |
| 131 | 35.77 | 21.59 | 25.96 | 24.52 | 23.59 | 28.11 | 21.92 | 19.03 | 30.96 | 19.34 | 32.97 | 18.75 |
| 132 | NA | 27.37 | 31.47 | 33.19 | 32.54 | 36.36 | 27.21 | 27.27 | 42.37 | 28.59 | 37.61 | 25.94 |
| 133 | NA | 27.05 | 31.58 | 31.00 | 29.36 | 36.43 | 29.88 | 27.10 | 41.81 | 28.41 | 36.90 | 23.53 |
| 134 | 43.61 | 26.80 | 28.12 | 28.56 | 29.01 | 31.34 | 25.54 | 23.53 | 36.00 | 22.42 | 34.46 | 21.75 |
| 135 | 32.24 | 23.95 | 29.95 | 30.52 | 28.07 | 30.43 | 27.82 | 24.39 | 39.15 | 26.45 | 37.57 | NA |
| 136 | 32.54 | 24.48 | 30.47 | 27.59 | 28.18 | 32.43 | 26.47 | 24.33 | 35.55 | 28.55 | 36.58 | NA |
| 137 | 34.47 | 21.25 | 26.76 | 26.84 | 26.63 | 28.13 | 23.96 | 21.14 | 33.29 | 21.00 | 33.61 | NA |
| 138 | 35.92 | 28.78 | 31.09 | 28.14 | 30.38 | 33.67 | 27.59 | 24.77 | 37.20 | 25.70 | 37.43 | NA |
| 139 | 29.41 | 18.81 | 24.77 | 25.79 | 24.75 | 28.10 | 23.45 | 20.67 | 34.38 | 20.15 | 31.72 | NA |
| 140 | 43.18 | 28.18 | 32.81 | 33.62 | 30.65 | 35.99 | 31.60 | 27.53 | 42.05 | 25.28 | 40.58 | NA |
| 141 | 31.59 | 18.86 | 23.94 | 24.09 | 24.83 | 27.17 | 22.08 | 19.47 | 33.66 | 19.15 | 32.31 | NA |
| 142 | 35.40 | 28.98 | 34.26 | 34.00 | 32.38 | 38.13 | 31.96 | 29.06 | 42.78 | 30.03 | 42.69 | NA |
| 143 | 29.19 | 23.32 | 29.60 | 33.41 | 26.28 | 34.44 | 28.34 | 25.86 | 40.39 | 27.39 | 39.99 | 25.48 |

TABLE 2-continued

|  | miR-217 | miR-375 | miR-130b | miR-135b | miR-148a | miR-155 | miR-210 | miR-24 | miR-196a | miR-223 | miR-96 | miR-21 |
|---|---|---|---|---|---|---|---|---|---|---|---|---|
| 144 | 35.98 | 19.62 | 23.95 | 21.97 | 23.67 | 26.38 | 20.28 | 19.45 | 34.28 | 18.45 | 29.95 | NA |
| 145 | 31.02 | 21.68 | 24.89 | 21.78 | 24.23 | 25.36 | 22.07 | 18.60 | 28.47 | 19.43 | 31.41 | 16.68 |
| 146 | 42.14 | 24.12 | 29.33 | 25.17 | 25.58 | 31.18 | 26.00 | 23.76 | 34.30 | 24.23 | 34.71 | 19.94 |
| 147 | 36.67 | 23.74 | 23.69 | 27.36 | 23.76 | 22.79 | 21.79 | 17.80 | 32.17 | 16.24 | 32.32 | 18.11 |
| 148 | 28.82 | 21.68 | 27.90 | 29.61 | 25.60 | 30.95 | 26.76 | 24.34 | 38.59 | 24.38 | 37.80 | 23.23 |
| 149 | 31.13 | 19.82 | 25.31 | 25.44 | 24.29 | 27.39 | 23.23 | 21.09 | 32.34 | 19.73 | 31.01 | 18.78 |
| 150 | 30.77 | 23.64 | 25.75 | 26.08 | 22.91 | 26.49 | 24.14 | 19.44 | 35.23 | 15.35 | 33.50 | 18.20 |
| 151 | 33.76 | 21.76 | 25.06 | 22.02 | 23.35 | 26.91 | 20.07 | 18.75 | 32.43 | 19.39 | 32.76 | 16.43 |
| 152 | 39.75 | 24.94 | 30.40 | 27.59 | 30.18 | 30.91 | 24.78 | 24.33 | 34.99 | 26.39 | 38.42 | 22.46 |
| 153 | 35.18 | 22.39 | 25.30 | 22.14 | 24.71 | 25.16 | 20.81 | 18.97 | 29.68 | 17.03 | 32.03 | NA |
| 154 | 35.35 | 22.32 | 28.48 | 27.26 | 27.32 | 30.01 | 23.83 | 22.26 | 36.95 | 23.57 | 37.96 | 21.17 |
| 155 | 32.12 | 20.58 | 25.08 | 23.94 | 23.11 | 26.40 | 21.60 | 19.86 | 35.34 | 20.81 | 32.74 | 17.49 |
| 156 | 38.28 | 24.79 | 31.57 | 29.34 | 30.64 | 37.14 | 26.32 | 25.14 | 38.98 | 30.62 | 41.50 | 23.29 |
| 157 | 33.21 | 24.93 | 32.22 | 35.70 | 28.67 | 37.67 | 29.71 | 27.15 | 44.04 | 29.96 | 42.93 | 25.72 |
| 158 | 38.07 | 23.90 | 28.01 | 25.66 | 27.91 | 28.29 | 22.07 | 20.57 | 34.09 | 21.58 | 36.72 | 19.78 |
| 159 | 37.48 | 26.04 | 28.05 | 25.87 | 26.53 | 30.61 | 24.01 | 21.31 | 33.42 | 19.41 | 36.37 | 20.56 |
| 160 | 30.51 | 21.30 | 25.60 | 23.64 | 24.24 | 27.25 | 21.48 | 19.60 | 30.37 | 21.53 | 33.40 | 17.43 |
| 161 | 28.28 | 20.39 | 25.36 | 24.94 | 23.46 | 26.89 | 22.38 | 19.81 | 29.19 | 18.72 | 32.26 | 17.78 |
| 162 | 30.74 | 21.95 | 23.84 | 21.65 | 24.39 | 25.81 | 23.31 | 18.69 | 28.05 | 21.65 | 30.77 | NA |
| 163 | 32.41 | 18.45 | 23.05 | 25.26 | 21.73 | 26.76 | 21.32 | 19.16 | 30.59 | 18.32 | 29.21 | 17.63 |
| 164 | 34.48 | 20.97 | 25.12 | 21.85 | 23.15 | 25.63 | 22.82 | 18.53 | 29.58 | 19.73 | 30.32 | 16.99 |
| 165 | 33.54 | 26.73 | 30.30 | 32.34 | 29.28 | 35.29 | 28.44 | 27.14 | 40.78 | 28.44 | 35.82 | 25.83 |
| 166 | 27.59 | 20.71 | 24.72 | 28.66 | 22.89 | 27.28 | 22.85 | 20.64 | 35.09 | 19.81 | 29.75 | 18.97 |
| 167 | 35.78 | 26.03 | 27.68 | 26.23 | 26.72 | 32.42 | 25.97 | 22.64 | 38.16 | 23.62 | 33.17 | 20.80 |
| 168 | 31.84 | 21.04 | 23.87 | 22.48 | 22.42 | 25.45 | 21.02 | 18.10 | 27.96 | 18.66 | 29.52 | 15.62 |
| 169 | 35.47 | 22.63 | 25.98 | 22.76 | 23.98 | 27.60 | 21.08 | 18.20 | 30.08 | 22.51 | 30.01 | 16.41 |
| 170 | 26.98 | 21.47 | 25.99 | 24.57 | 23.94 | 29.27 | 22.41 | 19.92 | 33.18 | 20.85 | 33.48 | 18.05 |
| 171 | 34.20 | 20.50 | 24.31 | 24.65 | 22.65 | 29.13 | 22.86 | 20.52 | 33.06 | 19.77 | 30.25 | 17.40 |
| 172 | 24.20 | 19.33 | 25.43 | 27.59 | 23.00 | 28.31 | 22.98 | 20.23 | 35.88 | 18.12 | 35.35 | 19.97 |
| 173 | 26.26 | 21.56 | 25.87 | 25.12 | 23.03 | 29.77 | 23.95 | 20.28 | 35.48 | 22.48 | 33.11 | 17.49 |
| 174 | 33.20 | 22.56 | 27.46 | 24.50 | 25.35 | 29.13 | 22.98 | 20.19 | 33.35 | 21.55 | 34.57 | 18.48 |
| 175 | 35.39 | 21.23 | 26.91 | 22.77 | 25.16 | 27.37 | 22.13 | 19.99 | 29.50 | 21.48 | 34.28 | 18.89 |
| 176 | 37.21 | 24.73 | 27.09 | 25.35 | 27.28 | 30.60 | 22.97 | 21.43 | 31.97 | 19.90 | 37.27 | 20.04 |
| 177 | 25.34 | 19.38 | 24.32 | 23.89 | 21.19 | 28.46 | 23.98 | 19.36 | 32.85 | 18.77 | 33.17 | 18.13 |
| 178 | 30.81 | 26.71 | 30.11 | 31.71 | 27.21 | 30.47 | 30.68 | 27.24 | 41.79 | 26.96 | 38.28 | 24.17 |
| 179 | 28.33 | 20.54 | 24.51 | 21.55 | 23.26 | 25.80 | 20.82 | 18.35 | 29.11 | 18.20 | 29.19 | NA |
| 180 | 40.05 | 26.58 | 28.71 | 33.86 | 27.46 | 32.28 | 25.62 | 24.23 | 37.59 | 22.74 | 34.10 | 22.54 |
| 181 | 36.88 | 22.13 | 25.82 | 22.12 | 25.46 | 26.47 | 20.43 | 19.12 | 26.03 | 19.35 | 32.54 | 17.32 |
| 182 | 38.10 | 28.22 | 31.98 | 31.00 | 29.67 | 35.26 | 31.10 | 27.45 | 40.76 | 29.22 | 39.44 | 23.80 |
| 183 | 35.99 | 19.85 | 24.79 | 21.19 | 24.29 | 26.18 | 21.59 | 19.15 | 29.35 | 18.50 | 30.45 | NA |
| 184 | 29.94 | 21.20 | 25.00 | 21.10 | 24.96 | 26.99 | 20.51 | 19.05 | 27.90 | 19.76 | 30.66 | NA |

TABLE 3

|  | Diff(miR-135b, miR-24) | Diff(miR-130b, miR-135b) | Diff(miR-135b, miR-148a) | Diff(miR-148a, miR-196a) | Diff(miR-375, miR-135b) | Diff(miR-135b, miR-96) | Diff(miR-130b, miR-24) |
|---|---|---|---|---|---|---|---|
| 1 | 3.18 | 1.79 | −0.02 | −6.90 | −1.79 | −12.43 | 4.96 |
| 2 | 4.91 | 0.14 | 0.79 | −6.78 | 1.95 | −5.11 | 5.04 |
| 3 | 8.20 | −4.61 | 5.37 | −6.62 | −4.00 | −0.91 | 3.59 |
| 4 | 10.29 | −4.12 | 5.42 | −7.06 | −7.86 | −4.21 | 6.18 |
| 5 | 3.77 | −1.14 | 1.71 | −9.36 | −2.99 | −3.09 | 2.63 |
| 6 | 8.36 | −5.14 | 8.09 | −12.98 | −10.81 | −0.26 | 3.22 |
| 7 | 3.30 | 0.65 | −0.28 | −6.92 | −0.85 | −4.21 | 3.95 |
| 8 | 6.40 | −2.49 | 4.51 | −9.61 | −7.36 | −2.99 | 3.91 |
| 9 | 9.64 | −7.59 | 9.44 | −12.12 | −11.42 | 1.50 | 2.05 |
| 10 | 4.65 | 0.14 | 0.03 | −8.73 | −3.49 | −6.43 | 4.79 |
| 11 | 4.43 | −0.53 | 2.33 | −11.02 | −3.66 | −5.01 | 3.89 |
| 12 | 4.35 | 1.18 | −1.10 | −4.68 | −2.08 | −6.18 | 5.53 |
| 13 | 2.66 | 3.45 | −1.78 | −4.57 | −1.53 | −7.50 | 6.11 |
| 14 | 4.48 | 0.51 | 1.73 | −9.28 | −3.48 | −5.20 | 4.99 |
| 15 | 2.66 | 0.12 | 0.49 | −7.95 | −0.52 | −4.05 | 2.78 |
| 16 | 6.37 | −3.58 | 6.89 | −15.32 | −8.61 | −2.60 | 2.79 |
| 17 | 6.59 | −2.68 | 2.01 | −9.50 | −1.99 | −2.71 | 3.92 |
| 18 | 5.91 | −1.54 | 3.98 | −11.71 | −7.50 | −6.19 | 4.37 |
| 19 | 3.31 | 1.96 | −1.59 | −6.51 | −2.18 | −8.41 | 5.27 |
| 20 | 10.38 | −6.57 | 7.18 | −11.21 | −10.47 | −1.97 | 3.81 |
| 21 | 2.90 | 3.27 | −1.34 | −6.82 | −1.31 | −7.52 | 6.18 |
| 22 | 4.52 | 1.63 | −0.25 | −8.23 | −3.36 | −9.51 | 6.15 |
| 23 | 2.84 | 3.09 | −1.03 | −7.41 | −1.28 | −8.75 | 5.93 |
| 24 | 3.96 | 1.27 | −0.84 | −4.68 | −0.25 | −8.66 | 5.23 |
| 25 | 2.52 | 2.36 | −1.44 | −9.88 | −1.07 | −9.64 | 4.88 |
| 26 | 7.02 | −4.14 | 6.66 | −12.20 | −8.14 | −2.89 | 2.88 |
| 27 | 4.30 | 0.25 | −0.29 | −9.50 | −2.68 | −8.22 | 4.55 |
| 28 | 2.52 | 3.52 | −2.44 | −5.65 | −1.29 | −9.78 | 6.04 |

TABLE 3-continued

| | Diff(miR-135b, miR-24) | Diff(miR-130b, miR-135b) | Diff(miR-135b, miR-148a) | Diff(miR-148a, miR-196a) | Diff(miR-375, miR-135b) | Diff(miR-135b, miR-96) | Diff(miR-130b, miR-24) |
|---|---|---|---|---|---|---|---|
| 29 | 6.88 | −2.89 | 2.67 | −1.25 | −2.89 | −9.23 | 3.99 |
| 30 | 4.51 | −0.52 | 0.67 | −4.40 | −2.58 | −9.23 | 3.99 |
| 31 | 5.10 | −1.16 | 4.34 | −14.68 | −6.61 | −4.98 | 3.94 |
| 32 | 1.34 | 2.43 | −1.26 | −9.53 | −2.93 | −8.12 | 3.77 |
| 33 | 2.14 | 3.80 | −1.19 | −7.77 | −0.44 | −9.48 | 5.94 |
| 34 | 4.56 | −1.38 | 0.46 | −7.80 | −2.38 | −5.45 | 3.18 |
| 35 | 5.32 | −0.21 | 1.06 | −10.33 | −4.79 | −5.54 | 5.11 |
| 36 | 4.26 | 1.09 | −1.11 | −5.09 | −3.44 | −7.40 | 5.35 |
| 37 | 5.10 | −0.98 | 1.95 | −6.43 | −1.77 | −3.86 | 4.12 |
| 38 | 5.29 | 0.44 | 0.38 | −4.82 | −4.91 | −4.17 | 5.73 |
| 39 | 3.45 | 1.27 | 0.85 | −10.87 | −4.50 | −7.44 | 4.72 |
| 40 | 9.03 | −4.88 | 4.70 | −10.73 | −8.38 | −2.43 | 4.16 |
| 41 | 6.66 | −3.47 | 4.66 | −11.88 | −6.98 | −2.92 | 3.19 |
| 42 | 3.49 | 1.51 | 0.84 | −8.01 | −3.80 | −9.14 | 5.00 |
| 43 | 7.32 | −4.28 | 4.58 | −9.85 | −7.65 | −2.95 | 3.04 |
| 44 | 2.85 | 4.80 | −1.12 | −7.20 | −3.60 | −10.60 | 7.66 |
| 45 | 5.81 | −1.47 | 4.65 | −9.87 | −6.72 | −6.99 | 4.34 |
| 46 | 2.93 | 0.27 | 2.06 | −9.40 | −3.54 | −8.03 | 3.20 |
| 47 | 4.65 | −0.76 | 0.75 | −7.02 | −0.95 | −6.31 | 3.88 |
| 48 | 5.01 | 0.55 | −0.20 | −8.10 | −3.75 | −5.95 | 5.56 |
| 49 | 5.26 | 1.40 | 0.07 | −6.39 | −2.74 | −7.31 | 6.66 |
| 50 | 6.97 | −3.51 | 3.21 | −9.80 | −5.48 | −3.37 | 3.46 |
| 51 | 13.36 | −10.32 | 10.10 | −11.62 | −10.35 | 4.50 | 3.05 |
| 52 | 4.99 | 0.33 | 0.20 | −4.23 | −5.67 | −7.09 | 5.32 |
| 53 | 4.22 | 0.55 | 3.33 | −12.15 | −5.76 | −9.58 | 4.78 |
| 54 | 2.41 | 2.18 | 1.02 | −7.75 | −2.07 | −7.46 | 4.59 |
| 55 | 5.77 | −0.62 | 0.65 | −5.99 | −4.83 | −4.77 | 5.15 |
| 56 | 3.62 | 0.71 | 0.76 | −7.01 | −1.72 | −5.46 | 4.33 |
| 57 | 6.37 | −0.32 | 2.87 | −8.86 | −6.46 | −7.69 | 6.05 |
| 58 | 4.82 | 1.96 | −0.27 | −6.31 | −2.13 | −7.07 | 6.79 |
| 59 | 8.81 | −5.25 | 8.75 | −16.15 | −11.35 | −2.97 | 3.56 |
| 60 | 4.59 | 1.55 | 0.39 | −10.76 | −3.98 | −8.77 | 6.14 |
| 61 | 5.22 | 1.64 | −0.68 | −9.39 | −2.10 | −8.41 | 6.86 |
| 62 | 7.59 | −4.10 | 4.03 | −11.77 | −7.41 | −4.18 | 3.49 |
| 63 | 4.12 | 1.22 | 0.47 | −12.65 | −4.84 | −8.99 | 5.34 |
| 64 | 2.80 | 4.78 | −3.57 | −7.67 | 3.46 | −9.24 | 7.58 |
| 65 | 8.74 | −3.17 | 5.76 | −12.69 | −10.87 | −1.49 | 5.57 |
| 66 | 4.90 | 0.04 | 1.35 | −8.10 | −2.94 | −3.40 | 4.94 |
| 67 | 5.15 | −1.17 | 1.31 | −7.33 | −4.25 | −4.59 | 3.98 |
| 68 | 3.34 | 3.13 | −2.04 | −5.61 | −1.77 | −8.01 | 6.47 |
| 69 | 5.81 | −1.56 | 4.06 | −10.86 | −5.17 | −3.71 | 4.25 |
| 70 | 4.38 | 0.30 | −0.49 | −5.11 | −0.33 | −5.00 | 4.68 |
| 71 | 4.63 | 0.21 | 2.76 | −9.55 | −6.04 | −7.19 | 4.84 |
| 72 | 3.52 | 0.71 | 0.65 | −6.89 | −1.13 | −4.01 | 4.24 |
| 73 | 2.80 | 3.48 | −2.08 | −6.17 | −1.91 | −9.56 | 6.28 |
| 74 | 3.59 | 2.49 | −2.09 | −4.37 | −2.71 | −10.17 | 6.08 |
| 75 | 1.99 | 3.58 | −1.81 | −7.06 | −1.32 | −9.01 | 5.56 |
| 76 | 6.74 | −2.19 | 3.82 | −9.80 | −4.73 | −2.86 | 4.54 |
| 77 | 3.84 | 2.23 | −0.79 | −9.47 | −0.64 | −7.05 | 6.07 |
| 78 | 1.64 | 5.02 | −2.92 | −4.67 | −1.72 | −10.23 | 6.66 |
| 79 | 2.42 | 2.66 | −2.29 | −6.61 | 0.54 | −10.53 | 5.08 |
| 80 | 3.67 | 0.91 | −0.56 | −8.05 | −0.79 | −8.06 | 4.58 |
| 81 | 5.85 | 0.29 | 1.44 | −9.27 | −3.22 | −9.90 | 6.14 |
| 82 | 6.75 | 0.70 | 0.32 | −7.59 | −7.41 | −10.51 | 7.45 |
| 83 | 3.63 | 2.76 | −1.75 | −8.94 | −3.19 | −11.75 | 6.39 |
| 84 | 5.16 | 0.07 | 1.82 | −13.15 | −5.10 | −10.58 | 5.23 |
| 85 | 3.87 | 2.38 | −1.47 | −8.83 | −3.07 | −10.72 | 6.25 |
| 86 | 1.07 | 2.89 | −3.67 | −8.33 | 1.26 | −14.10 | 3.96 |
| 87 | 3.00 | 1.05 | −2.19 | −13.96 | 0.31 | −11.58 | 4.05 |
| 88 | 7.01 | −1.06 | −2.82 | −7.40 | 3.69 | −8.67 | 5.95 |
| 89 | 5.23 | 0.35 | −0.72 | −7.26 | −2.37 | −7.88 | 5.58 |
| 90 | 5.09 | 3.14 | −2.68 | −12.46 | −3.69 | −11.97 | 8.23 |
| 91 | 4.72 | −0.77 | 0.39 | −7.25 | −5.55 | −7.40 | 3.95 |
| 92 | 9.90 | −3.22 | 3.92 | −9.89 | −8.82 | −6.04 | 6.67 |
| 93 | 5.83 | −1.94 | 3.26 | −13.40 | −7.97 | −6.73 | 3.89 |
| 94 | 6.48 | 1.31 | −0.24 | −9.96 | −5.07 | −12.32 | 7.79 |
| 95 | 6.51 | 2.38 | −2.99 | −4.13 | −4.66 | −12.33 | 8.89 |
| 96 | 5.09 | 3.08 | −4.50 | −3.01 | 0.99 | −11.10 | 8.17 |
| 97 | 4.23 | 0.17 | 0.54 | −6.67 | −1.96 | −6.16 | 4.40 |
| 98 | 4.63 | 1.92 | −0.26 | −6.21 | −1.96 | −8.44 | 6.56 |
| 99 | 3.21 | 2.91 | −1.06 | −8.35 | −1.68 | −9.33 | 6.13 |
| 100 | 3.63 | 3.73 | −2.88 | −7.73 | 1.01 | −9.21 | 7.36 |
| 101 | 4.87 | 1.25 | −0.18 | −9.10 | −4.27 | −7.40 | 6.13 |
| 102 | 3.19 | 1.78 | −1.13 | −8.74 | −1.74 | −7.27 | 4.98 |
| 103 | 5.63 | −0.99 | 0.51 | −5.00 | −3.62 | −4.79 | 4.64 |
| 104 | 3.05 | 2.07 | −2.58 | −4.08 | −1.45 | −8.78 | 5.12 |
| 105 | 5.78 | 0.50 | 0.05 | −6.56 | −1.90 | −7.01 | 6.28 |

TABLE 3-continued

| | Diff(miR-135b, miR-24) | Diff(miR-130b, miR-135b) | Diff(miR-135b, miR-148a) | Diff(miR-148a, miR-196a) | Diff(miR-375, miR-135b) | Diff(miR-135b, miR-96) | Diff(miR-130b, miR-24) |
|---|---|---|---|---|---|---|---|
| 106 | 8.40 | −3.89 | 4.03 | −7.11 | −7.11 | −3.34 | 4.51 |
| 107 | 2.89 | 2.31 | −0.93 | −6.55 | −0.88 | −10.25 | 5.20 |
| 108 | 3.88 | 2.32 | −0.03 | −6.43 | −2.47 | −9.49 | 6.20 |
| 109 | 5.58 | 0.34 | 0.20 | −4.25 | −4.92 | −6.44 | 5.92 |
| 110 | 2.98 | 2.37 | −0.21 | −9.39 | −3.17 | −7.91 | 5.35 |
| 111 | 2.82 | 2.35 | −1.54 | −6.79 | −1.91 | −9.32 | 5.17 |
| 112 | 3.33 | 2.09 | −1.29 | −5.59 | −1.48 | −9.26 | 5.42 |
| 113 | 8.54 | −5.88 | 8.01 | −13.63 | −10.55 | −2.55 | 2.67 |
| 114 | 2.55 | 2.44 | 0.37 | −8.39 | −1.97 | −10.38 | 4.99 |
| 115 | 8.31 | −5.28 | 5.67 | −11.01 | −7.95 | −2.96 | 3.03 |
| 116 | 7.56 | −4.40 | 5.05 | −9.62 | −6.42 | −2.10 | 3.16 |
| 117 | 6.55 | −4.33 | 3.74 | −11.44 | −4.13 | −3.62 | 2.22 |
| 118 | 4.00 | −0.82 | 0.46 | −9.78 | −3.52 | −6.55 | 3.18 |
| 119 | 5.33 | −0.78 | 1.47 | −9.90 | −2.88 | −6.36 | 4.55 |
| 120 | 3.03 | 1.51 | −2.60 | −7.94 | −1.76 | −8.89 | 4.54 |
| 121 | 3.28 | 3.26 | −2.90 | −7.35 | 1.50 | −10.67 | 6.54 |
| 122 | 4.78 | −0.70 | −0.11 | −3.50 | −7.26 | −6.83 | 4.08 |
| 123 | 4.65 | 0.79 | −0.59 | −10.43 | −3.30 | −8.60 | 5.44 |
| 124 | 4.76 | 1.22 | −1.91 | −4.69 | −1.83 | −10.22 | 5.98 |
| 125 | 6.07 | −1.41 | −0.09 | −4.33 | −6.30 | −7.24 | 4.67 |
| 126 | 5.92 | −1.85 | 3.47 | −11.08 | −6.97 | −5.17 | 4.08 |
| 127 | 5.19 | 0.48 | 0.77 | −7.62 | −3.61 | −7.61 | 5.66 |
| 128 | 5.88 | −0.49 | 1.57 | −8.28 | −4.36 | −6.77 | 5.39 |
| 129 | 4.60 | 1.51 | −1.94 | −5.06 | −2.79 | −8.66 | 6.12 |
| 130 | 4.96 | 0.72 | 1.39 | −6.74 | −5.19 | −9.18 | 5.67 |
| 131 | 5.49 | 1.44 | 0.92 | −7.36 | −2.93 | −8.45 | 6.93 |
| 132 | 5.92 | −1.72 | 0.65 | −9.83 | −5.83 | −4.42 | 4.20 |
| 133 | 3.90 | 0.58 | 1.63 | −12.45 | −3.95 | −5.91 | 4.48 |
| 134 | 5.03 | −0.44 | −0.45 | −7.00 | −1.75 | −5.90 | 4.59 |
| 135 | 6.13 | −0.58 | 2.45 | −11.08 | −6.57 | −7.04 | 5.55 |
| 136 | 3.26 | 2.88 | −0.58 | −7.37 | −3.11 | −8.99 | 6.14 |
| 137 | 5.70 | −0.08 | 0.21 | −6.66 | −5.59 | −6.77 | 5.62 |
| 138 | 3.36 | 2.95 | −2.24 | −6.83 | 0.64 | −9.30 | 6.32 |
| 139 | 5.12 | −1.02 | 1.04 | −9.63 | −6.98 | −5.93 | 4.11 |
| 140 | 6.09 | −0.81 | 2.96 | −11.40 | −5.44 | −6.97 | 5.28 |
| 141 | 4.62 | −0.15 | −0.74 | −8.83 | −5.23 | −8.22 | 4.47 |
| 142 | 4.95 | 0.25 | 1.63 | −10.41 | −5.03 | −8.68 | 5.20 |
| 143 | 7.55 | −3.81 | 7.14 | −14.12 | −10.09 | −6.57 | 3.74 |
| 144 | 2.52 | 1.97 | −1.70 | −10.60 | −2.36 | −7.98 | 4.50 |
| 145 | 3.17 | 3.11 | −2.45 | −4.24 | −0.10 | −9.64 | 6.28 |
| 146 | 1.40 | 4.16 | −0.42 | −8.72 | −1.05 | −9.54 | 5.56 |
| 147 | 9.56 | −3.67 | 3.60 | −8.42 | −3.62 | −4.96 | 5.89 |
| 148 | 5.27 | −1.71 | 4.01 | −12.99 | −7.93 | −8.19 | 3.56 |
| 149 | 4.35 | −0.12 | 1.14 | −8.05 | −5.62 | −5.57 | 4.23 |
| 150 | 6.63 | −0.32 | 3.16 | −12.32 | −2.44 | −7.43 | 6.31 |
| 151 | 3.27 | 3.03 | −1.33 | −9.08 | −0.26 | −10.74 | 6.31 |
| 152 | 3.26 | 2.81 | −2.59 | −4.81 | −2.65 | −10.83 | 6.07 |
| 153 | 3.17 | 3.16 | −2.57 | −4.96 | 0.25 | −9.89 | 6.33 |
| 154 | 5.00 | 1.22 | −0.06 | −9.63 | −4.94 | −10.70 | 6.22 |
| 155 | 4.09 | 1.14 | 0.84 | −12.23 | −3.36 | −8.79 | 5.23 |
| 156 | 4.19 | 2.23 | −1.30 | −8.34 | −4.55 | −12.16 | 6.43 |
| 157 | 8.54 | −3.48 | 7.02 | −15.36 | −10.77 | −7.24 | 5.06 |
| 158 | 5.09 | 2.35 | −2.25 | −6.18 | −1.75 | −11.07 | 7.44 |
| 159 | 4.57 | 2.18 | −0.66 | −6.89 | 0.17 | −10.49 | 6.75 |
| 160 | 4.05 | 1.95 | −0.59 | −6.13 | −2.35 | −9.75 | 6.00 |
| 161 | 5.14 | 0.42 | 1.49 | −5.74 | −4.56 | −7.31 | 5.55 |
| 162 | 2.97 | 2.19 | −2.74 | −3.66 | 0.30 | −9.11 | 5.16 |
| 163 | 6.10 | −2.21 | 3.53 | −8.86 | −6.81 | −3.95 | 3.89 |
| 164 | 3.32 | 3.27 | −1.30 | −6.43 | −0.89 | −8.46 | 6.59 |
| 165 | 5.19 | −2.04 | 3.06 | −11.50 | −5.61 | −3.49 | 3.15 |
| 166 | 8.02 | −3.94 | 5.78 | −12.21 | −7.95 | −1.09 | 4.08 |
| 167 | 3.58 | 1.45 | −0.49 | −11.45 | −0.19 | −6.94 | 5.04 |
| 168 | 4.38 | 1.40 | 0.06 | −5.53 | −1.44 | −7.04 | 5.77 |
| 169 | 4.56 | 3.22 | −1.21 | −6.11 | −0.13 | −7.25 | 7.78 |
| 170 | 4.65 | 1.42 | 0.63 | −9.24 | −3.10 | −8.91 | 6.07 |
| 171 | 4.13 | −0.34 | 1.99 | −10.40 | −4.15 | −5.60 | 3.79 |
| 172 | 7.36 | −2.15 | 4.59 | −12.88 | −8.26 | −7.76 | 5.20 |
| 173 | 4.84 | 0.75 | 2.10 | −12.45 | −3.56 | −7.99 | 5.59 |
| 174 | 4.30 | 2.96 | −0.85 | −8.01 | −1.94 | −10.07 | 7.27 |
| 175 | 2.79 | 4.13 | −2.38 | −4.34 | −1.54 | −11.51 | 6.92 |
| 176 | 3.93 | 1.73 | −1.92 | −4.70 | −0.62 | −11.92 | 5.66 |
| 177 | 4.53 | 0.43 | 2.70 | −11.67 | −4.51 | −9.28 | 4.96 |
| 178 | 4.47 | −1.60 | 4.50 | −14.58 | −5.00 | −6.58 | 2.87 |
| 179 | 3.20 | 2.96 | −1.71 | −5.85 | −1.01 | −7.64 | 6.16 |
| 180 | 9.63 | −5.15 | 6.40 | −10.12 | −7.28 | −0.24 | 4.48 |
| 181 | 3.00 | 3.70 | −3.34 | −0.57 | 0.01 | −10.42 | 6.69 |
| 182 | 3.56 | 0.98 | 1.33 | −11.09 | −2.78 | −8.44 | 4.53 |

TABLE 3-continued

| | Diff(miR-135b, miR-24) | Diff(miR-130b, miR-135b) | Diff(miR-135b, miR-148a) | Diff(miR-148a, miR-196a) | Diff(miR-375, miR-135b) | Diff(miR-135b, miR-96) | Diff(miR-130b, miR-24) |
|---|---|---|---|---|---|---|---|
| 183 | 2.05 | 3.60 | −3.10 | −5.06 | −1.34 | −9.26 | 5.65 |
| 184 | 2.05 | 3.90 | −3.86 | −2.94 | 0.10 | −9.57 | 5.95 |

TABLE 4

| | miRInformPancreasScore | miRInformPancreasCall | Cytology | Truth | CalledCorrectly |
|---|---|---|---|---|---|
| 1 | 1.00 | PDAC | NonDiagnostic | PDAC | TRUE |
| 2 | 0.98 | PDAC | Atypical | PDAC | TRUE |
| 3 | 0.00 | Benign | Atypical | PDAC | FALSE |
| 4 | 0.00 | Benign | Benign | Benign | TRUE |
| 5 | 1.00 | PDAC | Benign | Benign | FALSE |
| 6 | 0.00 | Benign | Benign | PDAC | FALSE |
| 7 | 1.00 | PDAC | Atypical | PDAC | TRUE |
| 8 | 0.05 | Benign | PDAC | PDAC | FALSE |
| 9 | 0.00 | Benign | NonDiagnostic | Benign | TRUE |
| 10 | 0.99 | PDAC | PDAC | PDAC | TRUE |
| 11 | 0.93 | PDAC | NonDiagnostic | PDAC | TRUE |
| 12 | 1.00 | PDAC | Benign | PDAC | TRUE |
| 13 | 1.00 | PDAC | Suspicious | PDAC | TRUE |
| 14 | 0.92 | PDAC | PDAC | PDAC | TRUE |
| 15 | 1.00 | PDAC | Benign | PDAC | TRUE |
| 16 | 0.00 | Benign | Benign | PDAC | FALSE |
| 17 | 0.12 | Benign | NonDiagnostic | PDAC | FALSE |
| 18 | 0.05 | Benign | Benign | Benign | TRUE |
| 19 | 1.00 | PDAC | Suspicious | PDAC | TRUE |
| 20 | 0.00 | Benign | Benign | PDAC | FALSE |
| 21 | 1.00 | PDAC | PDAC | PDAC | TRUE |
| 22 | 0.99 | PDAC | PDAC | PDAC | TRUE |
| 23 | 1.00 | PDAC | PDAC | PDAC | TRUE |
| 24 | 1.00 | PDAC | PDAC | PDAC | TRUE |
| 25 | 1.00 | PDAC | Suspicious | PDAC | TRUE |
| 26 | 0.00 | Benign | PDAC | PDAC | FALSE |
| 27 | 1.00 | PDAC | PDAC | PDAC | TRUE |
| 28 | 1.00 | PDAC | Suspicious | PDAC | TRUE |
| 29 | 0.19 | Benign | PDAC | PDAC | FALSE |
| 30 | 1.00 | PDAC | PDAC | PDAC | TRUE |
| 31 | 0.02 | Benign | PDAC | PDAC | FALSE |
| 32 | 1.00 | PDAC | PDAC | PDAC | TRUE |
| 33 | 1.00 | PDAC | PDAC | PDAC | TRUE |
| 34 | 1.00 | PDAC | PDAC | PDAC | TRUE |
| 35 | 0.51 | PDAC | PDAC | PDAC | TRUE |
| 36 | 1.00 | PDAC | PDAC | PDAC | TRUE |
| 37 | 0.99 | PDAC | PDAC | PDAC | TRUE |
| 38 | 0.98 | PDAC | PDAC | PDAC | TRUE |
| 39 | 1.00 | PDAC | PDAC | PDAC | TRUE |
| 40 | 0.00 | Benign | Suspicious | PDAC | FALSE |
| 41 | 0.01 | Benign | Benign | Benign | TRUE |
| 42 | 1.00 | PDAC | Suspicious | PDAC | TRUE |
| 43 | 0.03 | Benign | Suspicious | PDAC | FALSE |
| 44 | 1.00 | PDAC | PDAC | PDAC | TRUE |
| 45 | 0.24 | Benign | PDAC | PDAC | FALSE |
| 46 | 1.00 | PDAC | PDAC | PDAC | TRUE |
| 47 | 1.00 | PDAC | PDAC | PDAC | TRUE |
| 48 | 0.95 | PDAC | PDAC | PDAC | TRUE |
| 49 | 0.88 | PDAC | PDAC | PDAC | TRUE |
| 50 | 0.07 | Benign | PDAC | PDAC | FALSE |
| 51 | 0.00 | Benign | PDAC | PDAC | FALSE |
| 52 | 1.00 | PDAC | PDAC | PDAC | TRUE |
| 53 | 0.83 | PDAC | PDAC | PDAC | TRUE |
| 54 | 1.00 | PDAC | Suspicious | PDAC | TRUE |
| 55 | 0.95 | PDAC | PDAC | PDAC | TRUE |
| 56 | 1.00 | PDAC | PDAC | PDAC | TRUE |
| 57 | 0.06 | Benign | PDAC | PDAC | FALSE |
| 58 | 0.95 | PDAC | PDAC | PDAC | TRUE |
| 59 | 0.00 | Benign | Benign | PDAC | FALSE |
| 60 | 0.75 | PDAC | PDAC | PDAC | TRUE |
| 61 | 0.50 | PDAC | PDAC | PDAC | TRUE |
| 62 | 0.00 | Benign | Suspicious | PDAC | FALSE |
| 63 | 0.99 | PDAC | PDAC | PDAC | TRUE |
| 64 | 1.00 | PDAC | PDAC | PDAC | TRUE |
| 65 | 0.00 | Benign | NonDiagnostic | Benign | TRUE |
| 66 | 0.89 | PDAC | PDAC | PDAC | TRUE |
| 67 | 0.99 | PDAC | PDAC | PDAC | TRUE |

TABLE 4-continued

|  | miRInformPancreasScore | miRInformPancreasCall | Cytology | Truth | CalledCorrectly |
|---|---|---|---|---|---|
| 68 | 1.00 | PDAC | PDAC | PDAC | TRUE |
| 69 | 0.05 | Benign | Benign | Benign | TRUE |
| 70 | 1.00 | PDAC | PDAC | PDAC | TRUE |
| 71 | 0.91 | PDAC | PDAC | PDAC | TRUE |
| 72 | 1.00 | PDAC | PDAC | PDAC | TRUE |
| 73 | 1.00 | PDAC | PDAC | PDAC | TRUE |
| 74 | 1.00 | PDAC | PDAC | PDAC | TRUE |
| 75 | 1.00 | PDAC | PDAC | PDAC | TRUE |
| 76 | 0.01 | Benign | PDAC | PDAC | FALSE |
| 77 | 0.98 | PDAC | PDAC | PDAC | TRUE |
| 78 | 1.00 | PDAC | PDAC | PDAC | TRUE |
| 79 | 1.00 | PDAC | PDAC | PDAC | TRUE |
| 80 | 1.00 | PDAC | PDAC | PDAC | TRUE |
| 81 | 0.30 | Benign | PDAC | PDAC | FALSE |
| 82 | 0.02 | Benign | Benign | Benign | TRUE |
| 83 | 1.00 | PDAC | PDAC | PDAC | TRUE |
| 84 | 0.30 | Benign | Atypical | Benign | TRUE |
| 85 | 1.00 | PDAC | PDAC | PDAC | TRUE |
| 86 | 1.00 | PDAC | PDAC | PDAC | TRUE |
| 87 | 1.00 | PDAC | PDAC | PDAC | TRUE |
| 88 | 0.67 | PDAC | PDAC | PDAC | TRUE |
| 89 | 0.99 | PDAC | PDAC | PDAC | TRUE |
| 90 | 0.51 | PDAC | PDAC | PDAC | TRUE |
| 91 | 1.00 | PDAC | PDAC | PDAC | TRUE |
| 92 | 0.00 | Benign | Benign | Benign | TRUE |
| 93 | 0.14 | Benign | Benign | Benign | TRUE |
| 94 | 0.01 | Benign | PDAC | PDAC | FALSE |
| 95 | 0.68 | PDAC | PDAC | PDAC | TRUE |
| 96 | 1.00 | PDAC | PDAC | PDAC | TRUE |
| 97 | 1.00 | PDAC | PDAC | PDAC | TRUE |
| 98 | 0.99 | PDAC | PDAC | PDAC | TRUE |
| 99 | 1.00 | PDAC | Atypical | PDAC | TRUE |
| 100 | 1.00 | PDAC | PDAC | PDAC | TRUE |
| 101 | 0.87 | PDAC | Atypical | PDAC | TRUE |
| 102 | 1.00 | PDAC | PDAC | PDAC | TRUE |
| 103 | 0.99 | PDAC | PDAC | PDAC | TRUE |
| 104 | 1.00 | PDAC | PDAC | PDAC | TRUE |
| 105 | 0.78 | PDAC | PDAC | PDAC | TRUE |
| 106 | 0.00 | Benign | Suspicious | PDAC | FALSE |
| 107 | 1.00 | PDAC | PDAC | PDAC | TRUE |
| 108 | 1.00 | PDAC | PDAC | PDAC | TRUE |
| 109 | 0.99 | PDAC | PDAC | PDAC | TRUE |
| 110 | 1.00 | PDAC | PDAC | PDAC | TRUE |
| 111 | 1.00 | PDAC | Suspicious | PDAC | TRUE |
| 112 | 1.00 | PDAC | PDAC | PDAC | TRUE |
| 113 | 0.00 | Benign | Atypical | PDAC | FALSE |
| 114 | 1.00 | PDAC | NonDiagnostic | PDAC | TRUE |
| 115 | 0.00 | Benign | Atypical | PDAC | FALSE |
| 116 | 0.01 | Benign | PDAC | PDAC | FALSE |
| 117 | 0.26 | Benign | Benign | PDAC | FALSE |
| 118 | 1.00 | PDAC | Benign | PDAC | TRUE |
| 119 | 0.80 | PDAC | PDAC | PDAC | TRUE |
| 120 | 1.00 | PDAC | Atypical | PDAC | TRUE |
| 121 | 1.00 | PDAC | PDAC | PDAC | TRUE |
| 122 | 1.00 | PDAC | PDAC | PDAC | TRUE |
| 123 | 0.96 | PDAC | PDAC | PDAC | TRUE |
| 124 | 1.00 | PDAC | PDAC | PDAC | TRUE |
| 125 | 1.00 | PDAC | PDAC | PDAC | TRUE |
| 126 | 0.14 | Benign | PDAC | PDAC | FALSE |
| 127 | 0.94 | PDAC | PDAC | PDAC | TRUE |
| 128 | 0.53 | PDAC | PDAC | PDAC | TRUE |
| 129 | 1.00 | PDAC | PDAC | PDAC | TRUE |
| 130 | 0.99 | PDAC | PDAC | PDAC | TRUE |
| 131 | 0.49 | Benign | PDAC | PDAC | FALSE |
| 132 | 0.95 | PDAC | PDAC | PDAC | TRUE |
| 133 | 0.98 | PDAC | Suspicious | PDAC | TRUE |
| 134 | 1.00 | PDAC | PDAC | PDAC | TRUE |
| 135 | 0.03 | Benign | Atypical | Benign | TRUE |
| 136 | 1.00 | PDAC | PDAC | PDAC | TRUE |
| 137 | 0.94 | PDAC | PDAC | PDAC | TRUE |
| 138 | 1.00 | PDAC | PDAC | PDAC | TRUE |
| 139 | 0.97 | PDAC | PDAC | PDAC | TRUE |
| 140 | 0.10 | Benign | Benign | Benign | TRUE |
| 141 | 1.00 | PDAC | PDAC | PDAC | TRUE |
| 142 | 0.95 | PDAC | PDAC | PDAC | TRUE |
| 143 | 0.00 | Benign | Atypical | PDAC | FALSE |
| 144 | 1.00 | PDAC | PDAC | PDAC | TRUE |
| 145 | 1.00 | PDAC | Suspicious | PDAC | TRUE |

TABLE 4-continued

| | miRInformPancreasScore | miRInformPancreasCall | Cytology | Truth | CalledCorrectly |
|---|---|---|---|---|---|
| 146 | 1.00 | PDAC | PDAC | PDAC | TRUE |
| 147 | 0.00 | Benign | Benign | Benign | TRUE |
| 148 | 0.47 | Benign | Benign | Benign | TRUE |
| 149 | 1.00 | PDAC | Atypical | PDAC | TRUE |
| 150 | 0.00 | Benign | Atypical | Benign | TRUE |
| 151 | 1.00 | PDAC | PDAC | PDAC | TRUE |
| 152 | 1.00 | PDAC | PDAC | PDAC | TRUE |
| 153 | 1.00 | PDAC | PDAC | PDAC | TRUE |
| 154 | 0.91 | PDAC | PDAC | PDAC | TRUE |
| 155 | 0.91 | PDAC | PDAC | PDAC | TRUE |
| 156 | 1.00 | PDAC | PDAC | PDAC | TRUE |
| 157 | 0.00 | Benign | Benign | Benign | TRUE |
| 158 | 0.99 | PDAC | PDAC | PDAC | TRUE |
| 159 | 0.99 | PDAC | PDAC | PDAC | TRUE |
| 160 | 1.00 | PDAC | PDAC | PDAC | TRUE |
| 161 | 0.98 | PDAC | PDAC | PDAC | TRUE |
| 162 | 1.00 | PDAC | PDAC | PDAC | TRUE |
| 163 | 0.40 | Benign | PDAC | PDAC | FALSE |
| 164 | 1.00 | PDAC | Suspicious | PDAC | TRUE |
| 165 | 0.82 | PDAC | PDAC | PDAC | TRUE |
| 166 | 0.00 | Benign | Benign | Benign | TRUE |
| 167 | 0.99 | PDAC | PDAC | PDAC | TRUE |
| 168 | 1.00 | PDAC | PDAC | PDAC | TRUE |
| 169 | 0.92 | PDAC | PDAC | PDAC | TRUE |
| 170 | 0.91 | PDAC | PDAC | PDAC | TRUE |
| 171 | 0.99 | PDAC | Suspicious | PDAC | TRUE |
| 172 | 0.00 | Benign | Benign | Benign | TRUE |
| 173 | 0.17 | Benign | Suspicious | PDAC | FALSE |
| 174 | 0.97 | PDAC | PDAC | PDAC | TRUE |
| 175 | 1.00 | PDAC | PDAC | PDAC | TRUE |
| 176 | 1.00 | PDAC | PDAC | PDAC | TRUE |
| 177 | 0.78 | PDAC | PDAC | PDAC | TRUE |
| 178 | 0.88 | PDAC | PDAC | PDAC | TRUE |
| 179 | 1.00 | PDAC | PDAC | PDAC | TRUE |
| 180 | 0.00 | Benign | NonDiagnostic | Benign | TRUE |
| 181 | 1.00 | PDAC | PDAC | PDAC | TRUE |
| 182 | 1.00 | PDAC | PDAC | PDAC | TRUE |
| 183 | 1.00 | PDAC | PDAC | PDAC | TRUE |
| 184 | 1.00 | PDAC | PDAC | PDAC | TRUE |

REFERENCES

The following references, to the extent that they provide exemplary procedural or other details supplementary to those set forth herein, are specifically incorporated herein by reference.

U.S. Pat. No. 4,337,063
U.S. Pat. No. 4,404,289
U.S. Pat. No. 4,405,711
U.S. Pat. No. 4,659,774
U.S. Pat. No. 4,682,195
U.S. Pat. No. 4,683,202
U.S. Pat. No. 4,704,362
U.S. Pat. No. 4,816,571
U.S. Pat. No. 4,959,463
U.S. Pat. No. 5,141,813
U.S. Pat. No. 5,143,854
U.S. Pat. No. 5,202,231
U.S. Pat. No. 5,214,136
U.S. Pat. No. 5,221,619
U.S. Pat. No. 5,223,618
U.S. Pat. No. 5,242,974
U.S. Pat. No. 5,264,566
U.S. Pat. No. 5,268,486
U.S. Pat. No. 5,288,644
U.S. Pat. No. 5,324,633
U.S. Pat. No. 5,378,825
U.S. Pat. No. 5,384,261
U.S. Pat. No. 5,405,783
U.S. Pat. No. 5,412,087
U.S. Pat. No. 5,424,186
U.S. Pat. No. 5,428,148
U.S. Pat. No. 5,429,807
U.S. Pat. No. 5,432,049
U.S. Pat. No. 5,436,327
U.S. Pat. No. 5,445,934
U.S. Pat. No. 5,446,137
U.S. Pat. No. 5,466,786
U.S. Pat. No. 5,468,613
U.S. Pat. No. 5,470,710
U.S. Pat. No. 5,470,967
U.S. Pat. No. 5,472,672
U.S. Pat. No. 5,480,980
U.S. Pat. No. 5,492,806
U.S. Pat. No. 5,503,980
U.S. Pat. No. 5,510,270
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,574,146
U.S. Pat. No. 5,580,726
U.S. Pat. No. 5,580,732

U.S. Pat. No. 5,583,013
U.S. Pat. No. 5,593,839
U.S. Pat. No. 5,599,672
U.S. Pat. No. 5,599,695
U.S. Pat. No. 5,602,240
U.S. Pat. No. 5,602,244
U.S. Pat. No. 5,610,287
U.S. Pat. No. 5,610,289
U.S. Pat. No. 5,614,617
U.S. Pat. No. 5,623,070
U.S. Pat. No. 5,624,711
U.S. Pat. No. 5,631,134
U.S. Pat. No. 5,637,683
U.S. Pat. No. 5,639,603
U.S. Pat. No. 5,645,897
U.S. Pat. No. 5,652,099
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,670,663
U.S. Pat. No. 5,672,697
U.S. Pat. No. 5,677,195
U.S. Pat. No. 5,681,947
U.S. Pat. No. 5,695,940
U.S. Pat. No. 5,700,637
U.S. Pat. No. 5,700,922
U.S. Pat. No. 5,705,629
U.S. Pat. No. 5,708,153
U.S. Pat. No. 5,708,154
U.S. Pat. No. 5,714,606
U.S. Pat. No. 5,728,525
U.S. Pat. No. 5,744,305
U.S. Pat. No. 5,763,167
U.S. Pat. No. 5,770,358
U.S. Pat. No. 5,777,092
U.S. Pat. No. 5,789,162
U.S. Pat. No. 5,792,847
U.S. Pat. No. 5,800,992
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,856,174
U.S. Pat. No. 5,858,988
U.S. Pat. No. 5,859,221
U.S. Pat. No. 5,871,928
U.S. Pat. No. 5,872,232
U.S. Pat. No. 5,876,932
U.S. Pat. No. 5,886,165
U.S. Pat. No. 5,919,626
U.S. Pat. No. 5,922,591
U.S. Pat. No. 6,004,755
U.S. Pat. No. 6,040,193
U.S. Pat. No. 6,087,102
U.S. Pat. No. 6,251,666
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Pat. No. 6,723,509
U.S. patent application Ser. No. 09/545,207
U.S. patent application Ser. No. 10/667,126
U.S. patent application Ser. No. 11/141,707

U.S. Patent Prov. Appn. Ser. No. 60/575,743
U.S. Patent Prov. Appn. Ser. No. 60/649,584
Ambros, *Cell*, 107(7):823-826, 2001.
Beaucage, and Lyer, *Tetrahedron*, 48:2223-2311, 1992.
Brennecke et al., *Cell*, 113:25-36, 2003.
Calin et al., *Proc. Natl. Acad. Sci*. USA. 99:15524-15529, 2002.
Carrington et al., *Science*, 301(5631):336-338, 2003.
Cummins et al., In: *IRT: Nucleosides and nucleosides*, La Jolla Calif., 72, 1996.
Denli et al., *Trends Biochem. Sci.*, 28:196, 2003.
Didenko, *Biotechniques*, 31(5): 1106-16, 1118, 1120-1, 2001.
Emptage et al., *Neuron*, 2001 Jan. 29(1):197-208, 2001.
EP 266,032
EP 373 203
EP 785 280
EP 799 897
Esquela-Kerscher and Slack, *Nat Rev Cancer*, 6(4):259-269, 2006.
Fodor et al., *Science*, 251:767-777, 1991.
Freelove and Walling, *Am. Fam. Physician*, 73(3):485-492, 2006.
Froehler et al., *Nucleic Acids Res.*, 14(13):5399-5407, 1986.
Gillam et al., *J. Biol. Chem.*, 253:2532, 1978.
Gillam et al., *Nucleic Acids Res.*, 6:2973, 1979.
Griffey et al., *J Mass Spectrum*, 32(3):305-13, 1997.
He et al., *Proc. Natl. Acad. Sci.* USA, 102(52):19075-19080, 2005.
Itakura and Riggs, *Science*, 209:1401-1405, 1980.
Itakura et al., *J. Biol. Chem*, 250:4592, 1975.
Jemal et al., *CA Cancer J Clin.*, 56(2): 106-130, 2006.
Khorana, *Science*, 203, 614, 1979.
Klostermeier and Millar, *Biopolymers*, 61(3):159-79, 2001-2002.
Kornberg and Baker, In: *DNA Replication*, 2d Ed., Freeman, San Francisco, 1992.
Lagos-Quintana et al., *Science*, 294(5543):853-858, 2001.
Lau et al., *Science*, 294(5543):858-862, 2001.
Lee and Ambros, *Science;* 294(5543):862-864, 2001.
Lee et al., *EMBO J.* 21:4663-70, 2002.
Lu et al., *Nature*, 435(7043):834-838, 2005.
Monti et al., *Virchows Arch.*, 445(3):236-247, 2004.
Olsen et al., *Dev. Biol*, 216:671, 1999.
Sambrook et al., In: *DNA microaarays: a molecular cloning manual.* Cold Spring Harbor Laboratory Press, Cold Spring Harbor, N.Y., 2003.
Sambrook et al., In: *Molecular cloning: a laboratory manual,* $2^{nd}$ Ed., Cold Spring Harbor Laboratory Press. Cold Spring Harbor, N.Y., 1989.
Sambrook et al., In; *Molecular cloning: a laboratory manual* $3^{rd}$ Ed., Cold Spring Harbor Laboratory Press, Cold Spring Harbor, N.Y., 2001.
Seggerson et al., *Dev. Biol*, 243:215, 2002.
U.K. Patent 8 803 000
U.K. Patent 1,529,202
WO 0168255
WO 03020898
WO 03022421
WO 03023058
WO 03029485
WO 03040410
WO 03053586
WO 03066906
WO 03067217
WO 03076928
WO 03087297

WO 03091426
WO 03093810
WO 03100448A1
WO 04020085
WO 04027093
WO 09923256
WO 09936760
WO 93/17126
WO 95/11995
WO 95/21265
WO 95/21944

WO 95/35505
WO 96/31622
WO 97/10365
WO 97/27317
WO 9743450
WO 99/35505
WO0138580
WO03100012
Yeo et al., *Curr. Prob. Cancer,* 26:176-275, 2002.
Xu et al., *Curr. Biol.,* 13:790-795, 2003.

What is claimed is:

1. A method of producing amplified, labeled miRNA molecules from a pancreatic sample from a subject, the method comprising:
   contacting the pancreatic sample from the subject with primers specific for a group of microRNAs consisting of up to 11 different labeled miRNAs that include at least miR-135b and at least 4 of the following miRNAs: miR148a, miR-130b, miR-196a, miR-24, miR-375, and miR-96,
   wherein miR-217 is not one of the up to 11 different miRNAs; and
   reacting the sample with the primers under conditions to amplify the labeled microRNA molecules using polymerase chain reaction to produce the amplified, labeled miRNA molecules.

2. The method of claim 1, wherein the group of microRNAs consists of up to 7 different labeled miRNA molecules.

3. The method of claim 1, wherein the pancreatic sample is a biopsy.

4. The method of claim 3, wherein the biopsy is surgical resection or a fine needle aspirate.

5. The method of claim 1, further comprising obtaining a sample from the subject.

6. The method of claim 1, further comprising labeling the miRNA molecules from a pancreatic sample prior to reacting the sample with the primers.

* * * * *

SEQUENCE LISTING

<160> NUMBER OF SEQ ID NOS: 12

<210> SEQ ID NO 1
<211> LENGTH: 21
<212> TYPE: RNA
<213> ORGANISM: Homo sapiens

<400> SEQUENCE: 1
uagguaguuu cauguuguug g             21

<210> SEQ ID NO 2
<211> LENGTH: 22
<212> TYPE: RNA
<213> ORGANISM: Homo sapiens

<400> SEQUENCE: 2
cugugcgugu gacagcggcu ga            22

<210> SEQ ID NO 3
<211> LENGTH: 23
<212> TYPE: RNA
<213> ORGANISM: Homo sapiens

<400> SEQUENCE: 3
uacugcauca ggaacugauu gga           23

<210> SEQ ID NO 4
<211> LENGTH: 22
<212> TYPE: RNA
<213> ORGANISM: Homo sapiens

<400> SEQUENCE: 4
uuuguucguu cggcucgcgu ga            22

<210> SEQ ID NO 5
<211> LENGTH: 22
<212> TYPE: RNA
<213> ORGANISM: Homo sapiens

<400> SEQUENCE: 5
cagugcaaug augaaagggc au            22

<210> SEQ ID NO 6
<211> LENGTH: 22
<212> TYPE: RNA
<213> ORGANISM: Homo sapiens

<400> SEQUENCE: 6
uauggcuuuu cauuccuaug ug            22

<210> SEQ ID NO 7
<211> LENGTH: 22

```
<212> TYPE: RNA
<213> ORGANISM: Homo sapiens

<400> SEQUENCE: 7
ucagugcacu acagaacuuu gu                                              22

<210> SEQ ID NO 8
<211> LENGTH: 22
<212> TYPE: RNA
<213> ORGANISM: Homo sapiens

<400> SEQUENCE: 8
uuaaugcuaa ucgugauagg gg                                              22

<210> SEQ ID NO 9
<211> LENGTH: 21
<212> TYPE: RNA
<213> ORGANISM: Homo sapiens

<400> SEQUENCE: 9
ugucaguuug ucaaauaccc c                                               21

<210> SEQ ID NO 10
<211> LENGTH: 22
<212> TYPE: RNA
<213> ORGANISM: Homo sapiens

<400> SEQUENCE: 10
uuuggcacua gcacauuuuu gc                                              22

<210> SEQ ID NO 11
<211> LENGTH: 22
<212> TYPE: RNA
<213> ORGANISM: Homo sapiens

<400> SEQUENCE: 11
uggcucaguu cagcaggaac ag                                              22

<210> SEQ ID NO 12
<211> LENGTH: 22
<212> TYPE: RNA
<213> ORGANISM: Homo sapiens

<400> SEQUENCE: 12
uagcuuauca gacugauguu ga                                              22
```